United States Patent
Littman et al.

(10) Patent No.: US 10,301,629 B2
(45) Date of Patent: May 28, 2019

(54) STRUCTURE, MANUFACTURING AND USES OF HUMAN-DERIVED CELL-PERMEABLE PEPTIDES CONJUGATED WITH SPECIFIC BIOLOGICALLY ACTIVE CARGO PEPTIDES

(71) Applicant: Portage Pharmaceuticals Ltd., Douglas (IM)

(72) Inventors: Bruce H. Littman, Stonington, CT (US); John F. Thompson, Warwick, RI (US); Frank W. Marcoux, Stonington, CT (US)

(73) Assignee: PORTAGE PHARMACEUTICALS LTD. (CA)

( * ) Notice: Subject to any disclaimer, the term of this patent is extended or adjusted under 35 U.S.C. 154(b) by 20 days.

(21) Appl. No.: 14/897,450

(22) PCT Filed: Jun. 11, 2014

(86) PCT No.: PCT/IB2014/002029
§ 371 (c)(1),
(2) Date: Dec. 10, 2015

(87) PCT Pub. No.: WO2015/025217
PCT Pub. Date: Feb. 26, 2015

(65) Prior Publication Data
US 2016/0136293 A1  May 19, 2016

Related U.S. Application Data
(60) Provisional application No. 61/833,819, filed on Jun. 11, 2013.

(51) Int. Cl.
| | | |
|---|---|---|
| A61K 38/00 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| C07K 16/00 | (2006.01) | |
| C07K 17/00 | (2006.01) | |
| A61K 38/55 | (2006.01) | |
| C07K 14/81 | (2006.01) | |
| C12N 15/113 | (2010.01) | |
| A61K 38/17 | (2006.01) | |
| A61K 38/45 | (2006.01) | |

(Continued)

(52) U.S. Cl.
CPC ...... *C12N 15/1137* (2013.01); *A61K 38/1709* (2013.01); *A61K 38/45* (2013.01); *A61K 38/465* (2013.01); *A61K 38/47* (2013.01); *A61K 38/482* (2013.01); *A61K 38/51* (2013.01); *A61K 39/05* (2013.01); *A61K 47/645* (2017.08); *C07K 14/4702* (2013.01); *C12N 9/12* (2013.01); *C12N 9/16* (2013.01); *C12N 9/2402* (2013.01); *C12N 9/6424* (2013.01); *C12N 9/88* (2013.01); *C07K 2319/01* (2013.01); *C07K 2319/10* (2013.01); *C12N 2310/3513* (2013.01); *C12Y 207/1101* (2013.01); *C12Y 301/06013* (2013.01); *C12Y 302/01045* (2013.01); *C12Y 302/01076* (2013.01); *C12Y 304/21093* (2013.01); *C12Y 406/01002* (2013.01)

(58) Field of Classification Search
None
See application file for complete search history.

(56) References Cited

U.S. PATENT DOCUMENTS

| | | |
|---|---|---|
| 7,968,512 B2 | 6/2011 | Crisanti |
| 8,623,833 B2 | 1/2014 | Rothbard et al. |

(Continued)

FOREIGN PATENT DOCUMENTS

| | | |
|---|---|---|
| JP | A-2001-514858 | 9/2001 |
| JP | A-2008-508364 | 3/2008 |

(Continued)

OTHER PUBLICATIONS

Prochiantz A "Cell Permeable Peptides and Messenger PRoteins, from a Serendipitous Observation to a New Signaling Mechanism" p. 239-244. Handbook of Cell-Penetrating Peptides, Second Edition. Ed. Ulo Langel. Published 2006.*
Apostolopoulos et.al. "Delivery of tumor associated antigens to antigen presenting cells using penetratin induces potent immune responses," Vaccine 24:3191-202, 2006.
Appledorn et.al., "Adenovirus Vector-Induced Innate Inflammatory Mediators, Mapk Signaling, As Well As Adaptive Immune Responses Are Dependent upon Both TLR2 and TLR9 in Vivo," J Immunol 181:2134-44, 2008.
Batchu et.al., "Protein transduction of dendritic cells for Ny-Eso-1-based . immunotherapy of myeloma," Cancer Res. 65:10041-49, 2005.

(Continued)

*Primary Examiner* — Zachary J Miknis
(74) *Attorney, Agent, or Firm* — Perkins Coie LLP

(57) ABSTRACT

Embodiments disclosed herein provide compositions for conjugates, including fusion proteins, and methods of using them to treat a variety of conditions. In some embodiments, the conjugates and/or fusion proteins incorporate a 60-amino acid human homeodomain (e.g., peptides derived from human HOX genes), to translocate functional and regulatory peptides and proteins or other biologically active molecules such as nucleic acids, which are not naturally associated with the human homeodomain, across cell and nuclear membranes to intended sites of action without provoking an unwanted immune response that may reduce exposure to the conjugate and/or result in a clinical adverse event. In further embodiments, disclosed conjugates and fusion proteins can pass through the blood-brain barrier to allow entry into the CNS. In various embodiments, the disclosed compositions are suitable for delivery into a cell (i) the expression product of a gene of interest and/or (ii) novel peptides or polynucleotides to regulate gene function.

3 Claims, 19 Drawing Sheets

Specification includes a Sequence Listing.

(51) Int. Cl.
| | |
|---|---|
| A61K 38/46 | (2006.01) |
| A61K 38/47 | (2006.01) |
| A61K 38/48 | (2006.01) |
| A61K 38/51 | (2006.01) |
| A61K 39/05 | (2006.01) |
| C07K 14/47 | (2006.01) |
| C12N 9/12 | (2006.01) |
| C12N 9/16 | (2006.01) |
| C12N 9/24 | (2006.01) |
| C12N 9/64 | (2006.01) |
| C12N 9/88 | (2006.01) |
| A61K 47/64 | (2017.01) |

(56) References Cited

U.S. PATENT DOCUMENTS

| | | | |
|---|---|---|---|
| 8,735,340 | B2 | 5/2014 | Crisanti |
| 2004/0037821 | A1* | 2/2004 | Crisanti ............... A61K 48/00 424/94.61 |
| 2008/0015137 | A1* | 1/2008 | Chook ................. C07K 14/47 514/21.2 |
| 2010/0190691 | A1 | 7/2010 | Epenetos et al. |
| 2011/0256168 | A1* | 10/2011 | Crisanti ........... A61K 47/48238 424/193.1 |
| 2012/0244136 | A1* | 9/2012 | Robbins ................. C07K 7/06 424/94.3 |

FOREIGN PATENT DOCUMENTS

| | | |
|---|---|---|
| JP | A-2008-535512 | 9/2008 |
| JP | A-2011-519558 | 7/2011 |
| KR | 20110026071 | 3/2011 |
| WO | WO 1998/007859 | 2/1998 |
| WO | WO 2013/158819 | 10/2013 |
| WO | WO 2013158819 A2 * | 10/2013 ............ C12N 5/0645 |

OTHER PUBLICATIONS

Brooks, et al., "Cell-penetrating peptides: Application in vaccine delivery," Biochimica et Biophysica Acta 1805:25-34, 2010.
C. Avignolo et al. "Internalization via Antennapedia protein transduction domain of an scFv antibody toward c-Myc protein," Faseb J. 22:1237-45, 2008.
Cantile et al., "The Hox genes network in uro-Genital Cancers: mechanisms and potential therapeutic implications," Curr Med Chem. (2011) vol. 18, no. 32, pp. 4872-84.
Cardone, Monica! et al., "Correction of Hunter syndrome in the Mpsii mouse model by AAV2/8-mediated gene delivery," Hum. Mol. Genet. 15(7):1225-36, 2006.
Carey et al., "An Amino-terminal Fragment of GAL4 Binds Dna as a Dimer," J Mol Biol 209:423-432, 1989.
Frick, M., "The Tuberculosis Vaccines Pipeline," Jun. 2013.
Gogoi et al., "A versatile method for the preparation of conjugates of peptides with Dna/Pha/analog by employing chemo-selctive click reaction in water," Nucleic Acids Res. (2007) vol. 35, no. 21, p. 139.
Griveau et al., "Silencing of MiR-21 by locked nucleic acid-lipid nanocapsule complexes sensitize human glioblastoma cells to radiation-dinduced cell death," Int J Pharm. (2013) vol. 454, no. 2, pp. 765-74.
Harding, C.V. et al., "Regulation of antigen presentation by Mycobacterim tuberculosis: a roll for Toll-like receptors," Nat Rev Microbiol. 8(4):296-307, 2010.
Huntington Study Group authors, "Unified Huntington's Disease Rating Scale: Reliability and Consistency," Movement Disorders 11(2):136-142, 1996.
Jacobson S, et al. "Determining consequences of retinal membrane guanylyl cyclase (RetGC1) deficiency in human Leber congenital amaurosis en route to therapy: residual cone-photoreceptor vision correlates with biochemical properties of the mutants," Human Molecular Genetics 22(1):168-83, 2013.

Kim et al., "Introduction of soluble proteins into the MHC class I pathway by conjugation to an HIV tat peptide," J. Immunol. 159:1666-68, 1997.
Lal et al. "Polycystin-1 C-terminal tail associates with β-catenin and inhibits canonical Wnt Signaling," Hum. Mol. Genet. 17(20):3105-17, Oct. 15, 2008.
Lu et al., "TAP-independent presentation of CTL epitopes by Trojan antigens," J. Immunol. 166:7063-7071, 2001.
May M.J. et al. "Selective inhibition of NF-κB activation by a peptide that blocks the interaction of NEMO with the IκB kinase complex," Science 289:1550-54, Sep. 1, 2000.
Park et al., "The kinase PDK1 integrates T cell antigen receptor and CD28 coreceptor signaling to induce NF-kappaB and activate T cells," Nat Immunol. 10(2)158-166, Feb. 2009.
PCT/IB2014/002029 International Search Report dated Jul. 28, 2015.
Pooga et al., "Cell penetrating PNA constructs regulate galanin receptor levels and modify pain transmission in vivo," Nat Biotechnol. (1998) vol. 16, No. 9, pp. 857-861.
Redfern et.al. "Toll-Like Receptor Expression and Activation in Mice with Experimental Dry Eye," Invest. Ophthalmol. Vis. Sci. 54(2):1554-63, Feb. 28, 2013.
Rowland, R. and McShane, "Tuberculosis Vaccines in Clinical Trials," Expert Rev Vaccines 10(5):645-58, 2011.
Scheller et.al., "Human cytomegalovirus protein pp65: an efficient protein carrier system into human dendritic cells," Gene Ther. 15:318-325, 2008.
Schutze-Redelmeier et al., "Introduction of exogenous antigens into the MHC class I processing and presentation pathway by Drosophila antennapedia homeodomain primes cytotoxic T cells in vivo," J. Immunol. 157(2):650-55, Jul. 15, 1996.
Smaill et.al., "A Human Type 5 Adenovirus—Based Tuberculosis Vaccine Induces Robust T Cell Responses in Humans Despite Preexisting Anti-Adenovirus Immunity," Sci. Transl. Med. 5, 205: 1-11, 2013.
Strickland I. and Ghosh S. "Use of cell permeable NBD peptides for suppression of inflammation," Ann. Rheum. Dis. 65(Suppl 3):iii75-iii82, 2006.
Tameris et.al., "Safety and efficacy of MVA85A, a new tuberculosis vaccine, in infants previously vaccinated with BCG: a randomised, placebo-controlled phase 2b trial," The Lancet 381:1021-1028, 2013.
Tchilian et. al., "Immunization with different formulations Mycobacterium tuberculosis antigen 85A induces immune responses with different specificity and protective efficacy," Vaccine 31:4624-31, 2013.
Viehl et.al., "Tat mammaglobin fusion protein transduced dendritic cells stimulate mammaglobin-specific CD4 and CD8 T cells," Breast Cancer Res. Treat.91:271-78, 2005.
Wang D et al., "Characterization of an MPS I-H knock-in mouse that carries a nonsense mutation analogous to the human IDUA-W402X mutation," Molecular Genetics and Metabolism 99:62-71, 2010.
Wraith, J. E. et al., "Mucopolysaccharidosis type II (Hunter syndrome): a clinical review and recommendations for treatment in the era of enzyme replacement therapy," Europ. J. Pediat. 167: 267-277, 2008.
Littman et al., "Efficacy of PPL-003 and the Role of NFκB Activation in a Rat Model of Dry Eye Disease," Invest. Ophthalmol. Vis.Sci. 57(12):407 (Sep. 2016).
Rosenbaum et al., "Efficacy of PPL-003 and Inhibition of NFκB Activation in a Rabbit Mycobacterial Antigen-Induced Uveitis Model," Invest. Ophthalmol. Vis.Sci. 57(12):1896 (Sep. 2016).
Extended European Search Report dated Feb. 13, 2017 for European Application No. 14838596.6.
Kong et al., "The third helix of the murine Hoxc8 homeodomain facilitates protein transduction in mammalian cells," Biochemical and Biophysical Research Communications. 377:161-164 (Oct. 1, 2008).
Lee et al., "Human HOXA5 homeodomain enhances protein transduction and its application to vascular inflammation," Biochemical and Biophysical Research Communications. 410:312-316 (May 30, 2011).

(56) References Cited

OTHER PUBLICATIONS

Milletti, "Cell-penetrating peptides: classes, origin, and current landscape," Drug Discovery Today. 17(15-16):850-60 (Aug. 1, 2012).

Balayssac et al., "Comparison of Penetratin and Other Homeodomain-Derived Cell-Penetrating Peptides: Interaction in a Membrane-Mimicking Environment and Cellular Uptake Efficiency," Biochemistry 45:1408-1420 (Jan. 10, 2006).

GenBank[online], Accession No. NP_776272, Mar. 24, 2012 uploaded, [retrieved on Jul. 13, 2018], Definition: homeobox protein Hox-C12 [*Homo sapiens*].

GenBank[online], Accession No. NP_115485, Apr. 18, 2013 uploaded, [retrieved on Jul. 13, 2018], Definition: homeobox protein orthopedia [*Homo sapiens*].

GenBank[online], Accession No. NP_067016, Jan. 7, 2013 uploaded, [retrieved on Jul. 13, 2018], Definition: homeobox protein Hox-D12 [*Homo sapiens*].

GenBank[online], Accession No. NP_00182446, Jan. 12, 2013 uploaded, [retrieved on Jul. 13, 2018], Definition: T-cell leukemia homeobox protein 1 isoform 2 [*Homo sapiens*].

\* cited by examiner

Translation Map
His-TEV-PPL-002

```
  1  ATGGGCCCATCACCACCACCATCACAGCGCTGCAGAAAATCTGTACTTTCAGAGCCGTAAG
  1   M  G  H  H  H  H  H  H  S  A  A  E  N  L  Y  F  Q  S  R  K
 61  AAGCGTAAACCGTATTCCAAACTGGCAACTGGCCGGAGTTGGAAGGTGAGTTCCTGGTTAAC
 21   K  R  K  P  Y  S  K  L  L  A  B  L  E  G  E  F  L  V  N
121  GAATTCATTACCCGTCAGCGTCGCCGTTCGGAAGCTGAGCGGATCGCCTGAACCTGTCTGACCAA
 41   E  F  I  T  R  Q  R  R  R  B  L  S  D  R  L  N  L  S  D  Q
181  CAAGTGAAAATCTGGTTTCAGAATCGTCGTATGAAGAAAAAGCGCCTCGCTGACCGCGGTTG
 61   Q  V  K  I  W  F  Q  N  R  R  M  K  K  K  R  L  L  T  A  L
241  GACTGGAGCTGGCTGCAGACGGAAG
 81   D  W  S  W  L  Q  T  E
```

6x HIS

TEV Cleavage

SEQ ID NO:113

His-TEV-PPL-002
GC Percentage: 51.568%

*FIG. 6*

Translation Map
His-TEV-PPL-002

```
  1 ATGGCTCATCACCATCACCATCACAGCGCAGCGGAGAACTTGTATTTCAAGCCCGTAAG
  1  M  A  H  H  H  H  H  H  S  A  A  E  N  L  Y  F  Q  A  R  K
                  6x HIS                              TEV Cleavage 61 AAACGTAAACCGTACACCAAGCAGCAAATTGCGGAGCTGGAGAATGAATTCCTGGTCAAT
 21  K  R  K  P  Y  T  K  Q  Q  I  A  E  L  E  N  E  F  L  V  N 121 GAATTCATCAACCGTCAGAAGCGTCAAAGAAGCGCAAAGAACTGGAACTGCCGACCAG
 41  E  F  I  N  R  Q  K  R  E  E  L  S  Q  R  L  N  L  S  D  Q 181 CAAGTGAAAATCTGGTTCAAAAACCGTCGCATGAAGAAGAAACGTGTTGTTACGGCGCTG
 61  Q  V  K  I  W  F  Q  N  R  R  M  K  K  K  R  V  V  T  A  L

241 GATTGGAGCTGGCTGCAGACCGAG
 81  D  W  S  W  L  Q  T  E
```

His-TEV-PPL-003
GC Percentage: 48.780%

*FIG. 7*

STRUCTURE, MANUFACTURING AND USES OF HUMAN-DERIVED CELL-PERMEABLE PEPTIDES CONJUGATED WITH SPECIFIC BIOLOGICALLY ACTIVE CARGO PEPTIDES

PRIORITY CLAIM

This application is a 35 USC § 371 U.S. National Stage Application of International Patent Application No. PCT/IB14/02029, filed Jun. 11, 2014, entitled "Structure, Manufacturing and Uses of Human-Derived Cell-Permeable Peptides Conjugated with Specific Biologically Active Cargo Peptides," which claims priority to U.S. provisional patent application Ser. No. 61/833,819 filed Jun. 11, 2013, the entire contents of which are incorporated herein by reference and relied upon.

TECHNICAL FIELD

The embodiments disclosed herein relate generally to compositions and methods for treating a variety of conditions or diseases through administration of cell permeable peptide conjugates, particularly, but not exclusively, in the form of a fusion protein or protein/nucleic acid complex utilizing peptides derived from the amino acid homeodomain sequences coded for by human homeobox (HOX) genes and other human genes containing a homeodomain with cell permeabilizing properties. More particularly, the embodiments relate to a delivery system comprising a human homeodomain or variant or portion thereof, linked to one or more functional or regulatory peptides or proteins. These peptides facilitate entry into tissues, cells and the nucleus of cells thus allowing the fusion protein or conjugate containing a biologically active second region or "cargo" to reach its site of action for therapeutic purposes.

BACKGROUND

In diseases with manifestations due to aberrant gene function or deficient function, genes may be regulated through the direct delivery of biologically active molecules, such as nucleic acids, peptides and proteins, to their intracellular and intranuclear sites of action to influence gene expression either directly or indirectly through interference with transcription, translation or transcription factor production and action and also missing or defective protein products may be replaced to provide these types of molecules in individuals with germ-line or somatic mutations. The direct replacement of biologically important proteins in genetically deficient individuals is hampered by both (i) the inability of these proteins to reach intracellular sites and tissue sites such as the central nervous system (CNS) where they normally function and (ii) by the immunogenicity of these proteins.

SUMMARY

The embodiments disclosed herein together with a range of modifications provide compositions for conjugates, including fusion proteins, and methods of using them to treat a variety of conditions. The conjugates or fusion proteins incorporate a human HOX gene-derived 60 amino acid sequence or variant, or other human homeodomain sequence or variant or portion thereof to translocate functional and regulatory molecules, which are not naturally associated with the human homeodomain or variant or portion thereof, across cell and nuclear membranes to their intended sites of action without provoking an unwanted immune response that may reduce exposure and/or effectiveness of the conjugate, or which may produce an adverse clinical event. Further, such conjugates and fusion proteins also allow entry into the CNS by facilitating passage through the blood-brain barrier and then entry into cells in the CNS, such as microglia and neurons; they also allow for engagement of these functional or regulatory molecules to their intracytoplasmic and intranuclear targets. The ability to deliver directly into a cell (i) the expression product of a gene of interest or (ii) novel molecules able to regulate gene function has wide applicability in the medical field.

In addition to facilitating delivery of biologically active molecules to local (topical) and systemic intracellular and intranuclear targets, peptide sequences from human HOX genes also facilitate transport across the blood-brain barrier thus providing for CNS intracellular exposure to molecules containing these HOX gene sequences. Exploiting the technology's application of delivery of treatments across what are currently barriers to the delivery of drugs (such as the blood brain barrier), systemic administration can target cancers of the central nervous system by delivering drugs across the blood brain barrier. Examples of such applications are HOX gene derived peptides conjugated with adriamycin, doxorubicin or monoclonal antibodies directed at cancer cell targets such as Her2 (e.g., trastuzumab) for treatment of brain metastasized Her2 positive breast cancer. In addition, anti-bacterial and anti-viral agents that otherwise do not achieve therapeutic levels in the CNS are able to penetrate the blood brain barrier and successfully treat intracellular and extracellular bacterial and viral CNS infections in animal models.

In one embodiment, the conjugate comprises a first region, having a sequence described in any of SEQ ID Nos. 1-19 or variant or portion thereof, conjugated to a second region not naturally associated with the first region, wherein the second region is a polypeptide having a sequence set forth in any one of SEQ ID Nos. 20, 23, 26, 30, 33, 36, 39, 42, 45, 48, 51, 54, 57, 60, 63, 66, 69, and 72 or a variant or variant or portion thereof. In one embodiment, the first region is derived from the human gene.

In one embodiment the conjugate comprises:
(a) a first region comprising a 60-amino acid domain or variant portion thereof of one of two HOX genes, HOX C12 and HOX D12; and
(b) a second region not naturally associated with the first region; and wherein at least the first region is non-denatured.

According to one embodiment, the second region may comprise a nucleic acid. This may be associated via the specific 1,3 dipolar Huisgen cycloaddition reaction known as 'click-reaction' between azide and alkyne groups and is employed for the synthesis of peptide-oligonucleotide conjugates. Alternatively, this embodiment may be seen as a protein/nucleic acid complex where the second region may comprise a nucleic acid binding domain, capable of binding nucleic acids as part of the complex.

According to another embodiment, the first and second regions are associated via the specific 1,3 dipolar Huisgen cycloaddition reaction (i.e., 'click-reaction'), wherein the oligonucleotides act as miRNAs or antagonists to miRNAs in order to affect gene expression. These oligonucleotides may comprise DNA, RNA, LNA (locked nucleic acid), PNA (peptide nucleic acid) or other nucleic acids.

According to a further embodiment, the first and second regions are connected via standard peptide bonds wherein nucleobases are attached to a peptide backbone rather than to a phosphodiester backbone. Some or all of these nucleobases are capable of hybridizing to other nucleic acids in the cell and affecting gene expression. These nucleobases may be PNA, γPNA or contain other side chains with similar properties.

In yet another embodiment, peptide or peptide-nucleic acid conjugates can be used to affect the activity of miRNAs including, but not limited to, antagonizing miRNA-132 for inhibition of the Ras pathway and cancer, antagonizing miR-21 for inhibiting cancer or the NF-κB pathway and inflammation, or affecting the function of other miRNAs and pathways that may have detrimental and/or undesirable effects on health.

According to a further embodiment the conjugate is in the form of a fusion protein. In this embodiment, the second region is a functional or regulatory protein.

In another embodiment a conjugate can comprise:
(a) a first region comprising a human homeodomain with cell permeabilizing capabilities linked to
(b) a second region not naturally associated with the first region comprising a protein such as a functional enzyme.

In another embodiment a composition comprises a conjugate or fusion protein that may take any of the following forms: an inhalable composition; an eye drop or other ophthalmic composition for local or injectable use; an enema; a topical composition; or an injectable composition, including an injectable implant for sustained release.

Another embodiment disclosed is a method comprising steps that permit a conjugate or fusion protein containing one or more biologically active peptides or proteins to be translocated to cells of the CNS.

Other embodiments comprise methods to prevent immunogenicity of otherwise antigenic proteins delivered as conjugates or fusion proteins to their intended cytosolic or nuclear sites of action.

These and other embodiments will be disclosed in further detail below.

BRIEF DESCRIPTION OF THE DRAWINGS

FIG. 6 shows an exemplary sequence for plasmid pJ411:129925, showing a 6 HIS leader, with a transition sequence of SAA followed by the TEV cleavage site (ENLYFQS) (SEQ. ID No. 81) to produce SEQ. ID No. 21 (also referred to as PPL-002) with the appropriate N-terminus.

FIG. 7 shows an exemplary sequence for plasmid pJ411:129926, showing a 6 HIS leader, with a transition sequence of SAA followed by the TEV cleavage site (ENLYFQS) (SEQ. ID No. 81) to produce SEQ ID No. 22 (also referred to as PPL-003) with the appropriate N-terminus.

DETAILED DESCRIPTION

The human HOX genes and other homeodomain coding genes are important in embryonic development and include small regions homologous to the gene antennapedia (Antp) but where the majority of amino acids are included in uniquely human sequences that facilitate their function. The protein sequence of antennapedia is characterized by the presence of a 60-amino acid motif (homeodomain) that binds to specific DNA target elements. The Antp homeodomain (see U.S. Pat. No. 7,968,512) and much smaller sequences from the Antp gene have been shown to facilitate the entry of biologically active ("cargo") peptides into tissues and cells to reach their site of action for therapeutic purposes.

While the homeodomain and smaller regions of Antp can be used to translocate proteins, including functional and regulatory proteins in vitro and in animal models, peptide sequences from human HOX genes and certain other human homeodomain sequences can also facilitate transport of biologically active molecules such as peptides, proteins and nucleotides to their intracellular and intranuclear sites of action (i) without provoking an unwanted immune response that may reduce exposure and/or effectiveness of the conjugate or may produce an adverse event, and (ii) with greater efficiency than Antp conjugates and fusion proteins. The ability to deliver biologically active molecules including the expression product of a gene of interest directly into a cell has wide applicability, particularly in the medical field. HOX and other human homeodomain peptides are also able to translocate nucleic acids. This is especially advantageous for applications utilizing a mechanism of gene regulation.

Figure 1:
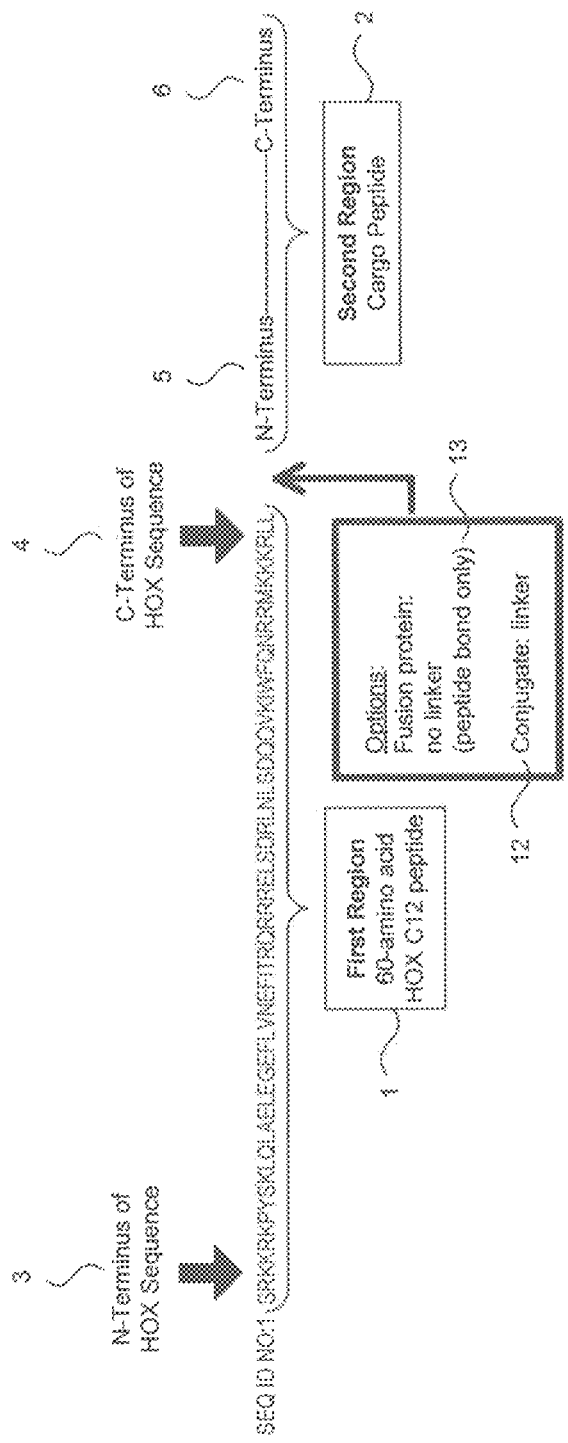
FIG. 1 shows an exemplary 60-amino acid human HOX C12 homeodomain (first region) or variant or portion thereof at the N-terminus of a Cargo peptide.
Figure 2:
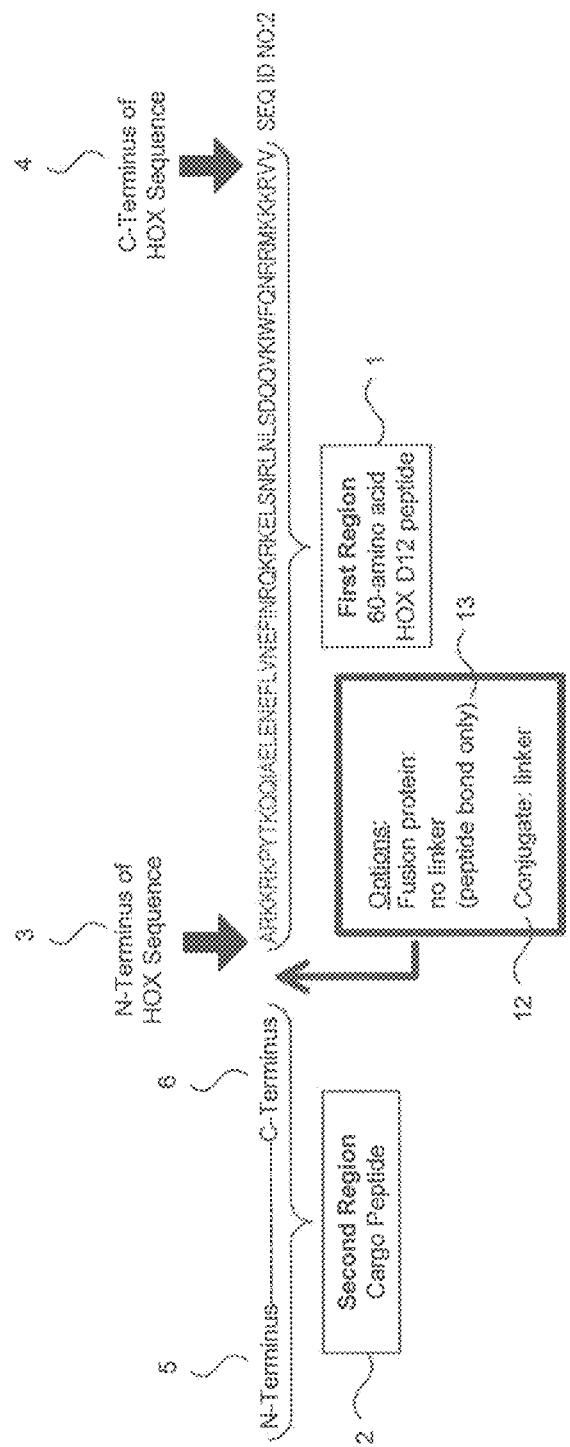
FIG. 2 shows an exemplary cargo peptide (second region) at the N-terminus of 60-amino acid human HOX D12 homeodomain or variant or portion thereof.
Figure 3A:
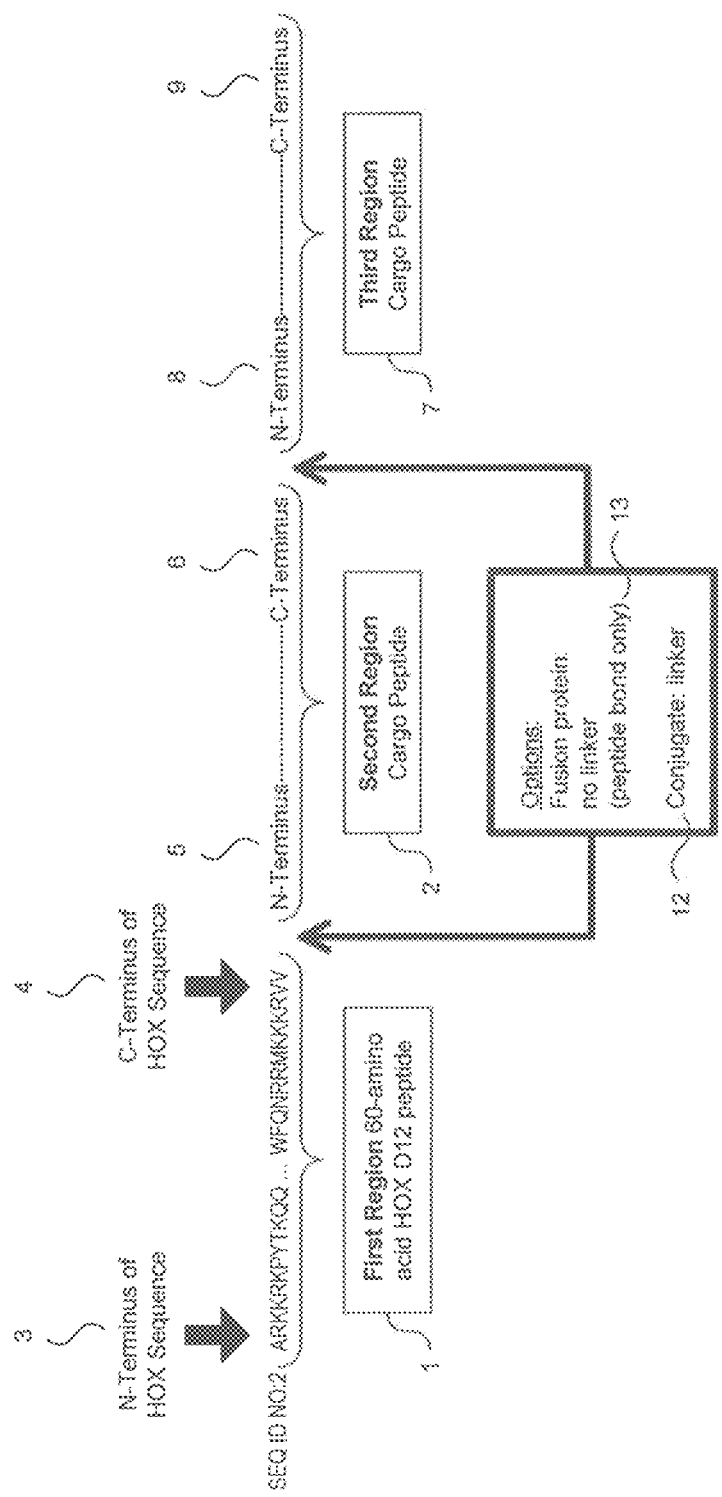
FIG. 3a shows an exemplary 60-amino acid human HOX D12 homeodomain (first region) or variant or portion thereof at its C-terminus with Cargo peptides (second and third regions), where the third region may be used to target the entire structure to specific tissues or cell types.
Figure 3B:
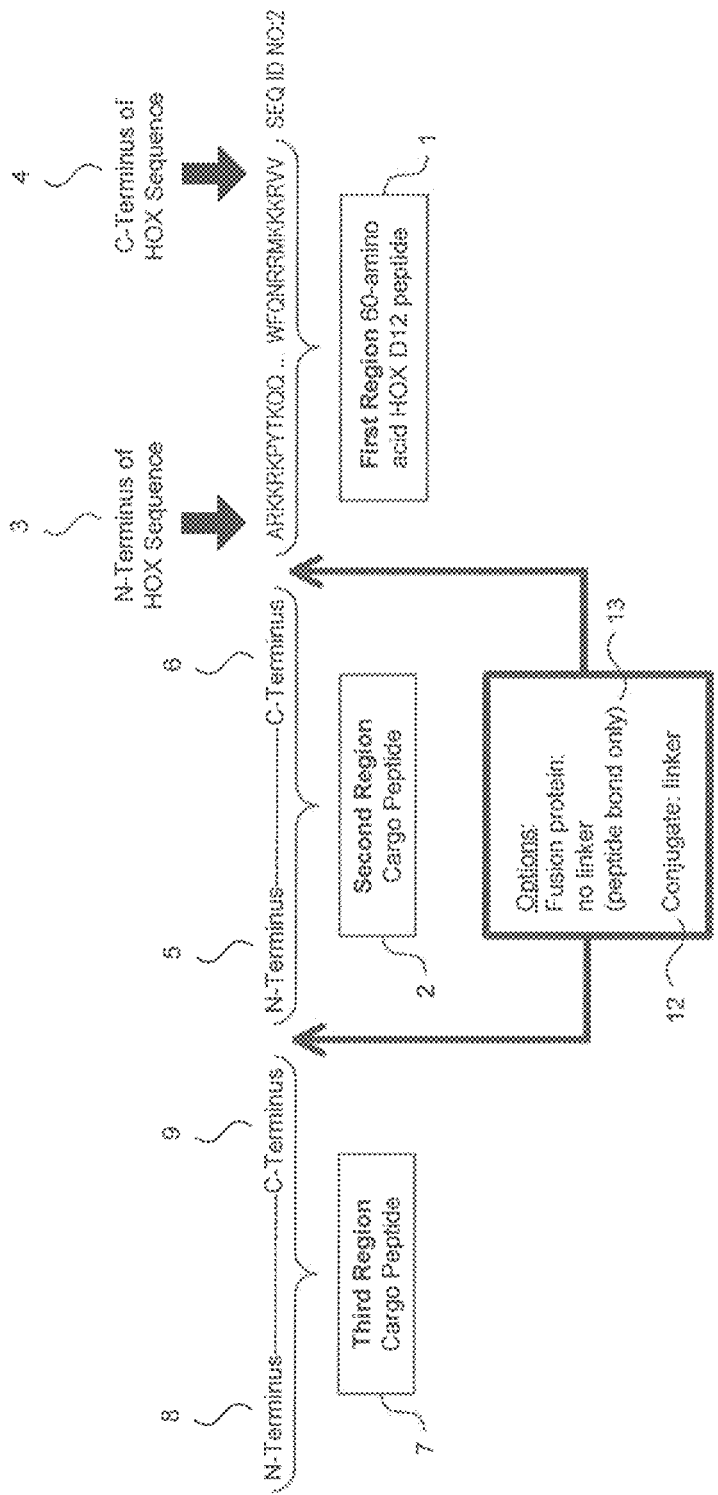
FIG. 3b shows an exemplary 60-amino acid human HOX D12 homeodomain (first region) or variant or portion thereof at its N-terminus with Cargo peptides (second and third regions), where the third region may be used to target the entire structure to specific tissues or cell type.

Several of the disclosed embodiments and their modifications relate to novel conjugates, which may take the form of fusion proteins, each comprising a 60-amino acid peptide or variant or portion thereof (1 e.g. as shown in FIG. 1) derived from human HOX genes or from other human genes containing a homeodomain with cell permeabilizing properties, linked (e.g. 12 or 13 as shown in FIG. 1) to a second region (2): at least one of the biologically active "cargo" peptides disclosed herein. FIG. 1 shows one embodiment comprising the 60-amino acid human HOX C12 homeodomain ("first region") (1) linked on its C-terminus (4) to the N-terminus (5) of a biologically-active cargo peptide ("second region") (2). FIG. 2 shows an alternative embodiment comprising the 60-amino acid human HOX D12 homeodomain ("first region") (1) is linked on its N-terminus (3) to the C-terminus (6) of a biologically-active cargo peptide ("second region") (2). The links in both embodiments may be a simple peptide bond (13) or a linker sequence known in the art (12) provided that function of the fusion protein or conjugate is not compromised by its addition.

The term "compromised" refers to reduced function of the conjugate embodiments as reflected in reduced efficacy of treatment for any of the outcomes discussed herein, e.g., compromised function could be reflected in an attenuated reduction in immunogenicity as compared to the reduction in immunogenicity observed with (1) the conjugate in the form of a fusion protein, or (2) the conjugate comprising an alternative linker.

Cargo peptides include both small synthetic peptides and larger proteins such as antibodies or the binding regions of antibodies into cells for therapeutic purposes. (Schutze-Redelmeier M-P et al. "Introduction of exogenous antigens into the MHC class 1 processing and presentation pathway by *Drosophila* antennapedia homeodomain primes cytotoxic T cells in vivo. *J. Imunol.* 157(2):650-55, Jul. 15, 1996; M. J. May et al. "Selective inhibition of NF-κB activation by a peptide that blocks the interaction of NEMO with the IκB kinase complex" *Science* 289:1550-54, Sep. 1, 2000; I Strickland and S Ghosh. "Use of cell permeable NBD peptides for suppression of inflammation" *Ann. Rheum. Dis.* 65(Suppl 3):iii75-iii82, 2006; C. Avignolo et al. "Internalization via Antennapedia protein transduction domain of an scFv antibody toward c-Myc protein" *FASEB J.* 22:1237-45, 2008.)

The terms "peptide(s)," "protein(s)," and "polypeptide(s)" are used synonymously.

The term "human homeodomain" refers to (1) human HOX-derived homeodomains such as the HOX C12 and HOX D12 sequences shown in Table 3 as SEQ ID No. 1 and SEQ ID No. 2, respectively, or variants or portions thereof; and (2) any other human homeodomain that has cell permeabilizing activity, such as SEQ ID Nos. 3 through 19, or variants or portions thereof.

The phrase "not naturally associated with" means that entire sequence of the conjugate or fusion protein is not found in nature, and that the entire sequence is not encoded for by a single gene found in nature.

The phrase "operably linked" means that the first and second region are linked such that the second region is able to translocate a cell membrane. Such linkage may be produced via application of "click" chemistry methods or other methods known in the art or may be incorporated as a fusion protein with a peptide bond between regions.

A person of ordinary skill in the molecular biology/biotechnology art would appreciate that numerous variations of the sequences shown in Tables 3 and 4 would fall within the embodiments disclosed herein. As used herein, homology refers to identity or near identity of nucleotide or amino acid sequences. As is understood in the art, nucleotide mismatches can occur at the third or wobble base in the codon without causing amino acid substitutions in the translated polypeptide sequence. Also, minor nucleotide modifications (e.g., substitutions, insertions or deletions) in certain regions of the gene sequence can be tolerated whenever such modifications result in changes in amino acid sequence that do not alter functionality of the final gene product. Homologs of specific DNA sequences may be identified by those skilled in the art using the test of cross-hybridization of nucleic acids under conditions of stringency as is well understood m the art (as described in Hames et al., *Nucleic Acid Hybridisation*, (1985) IRL Press, Oxford, UK). Extent of homology is often measured in terms of percentage of identity between the sequences compared.

The term "variant" refers to a polypeptide or protein that differs from a reference polypeptide or protein, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides and proteins of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's or protein's biological functional activity, certain amino acid sequence substitutions can be made in a polypeptide or protein sequence and nevertheless obtain a polypeptide or protein with like properties.

Amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gin, His), (Asp: Glu, Cys, Ser), (Gln: Asn), (Glu: Asp), (Gly: Ala), (His: Asn, Gin), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure, therefore, consider functional or biological equivalents of a polypeptide or protein as set forth above. In particular, embodiments of the polypeptides and proteins can include variants having about 50%, 60%, 70%, 80%, 90%, and 95% sequence identity to the polypeptide and protein of interest.

"Identity," as known in the art, is a relationship between two or more polypeptide or protein sequences, as determined by comparing the sequences. In the art, "identity" also refers to the degree of sequence relatedness between polypeptides or proteins, as determined by the match between strings of such sequences. "Identity" can be readily calculated by known bioinformational methods.

First Region:

The first region of the conjugate or fusion protein embodiments disclosed may comprise a natural or synthetic 60-amino acid peptide or variant or portion thereof derived from the HOX C12 or HOX D12 gene or any other human homeodomain that has cell permeabilizing activity, such as SEQ ID Nos. 3 through 19, or variants or portions thereof.

In one embodiment, the HOX C12 (SEQ ID No. 1) amino acid sequence is:

SRKKRKPYSKLQLAELEGEFLVNEFITRQRRRELSDRLNLSDQQVK

IWFQNRRMKKKRLL

In a another embodiment, the HOX D12 (SEQ ID No. 2) amino acid sequence is:

ARKKRKPYTKQQIAELENEFLVNEFINRQKRKELSNRLNLSDQQVK

IWFQNRRMKKKRVV

Alternatively, other embodiments will include any one of 17 additional human 60-amino acid homeodomain sequences or variants or portions thereof with permeabilizing properties to allow for intracellular and intranuclear delivery of conjugates and fusion proteins. Further, these additional sequences each provide for CNS penetration of molecules that otherwise would not penetrate the blood brain barrier. Examples of amino acid sequences of these conjugates and fusion proteins with HOX C12 and HOX D12 homeodomains in the first region are shown in Table 3 (SEQ ID Nos. 21-22, 24-25, 27-28, 31-32, 34-35, 37-38, 40-41, 43-44, 46-47, 49-50, 52-53, 55-56, 58-59, 61-62, 64-65, 67-68. 70-71, and 73-74, or variants or portions thereof) and any of the other human homeodomains or variants or portions thereof (SEQ ID Nos. 3-19) and variations on these sequences may be substituted for either of the HOX C12 and D12 homeodomains. Each of the human homeodomain sequences is less than 50% identical to the 60-amino acid Antp sequence and thus is structurally distinct and has unique human properties. Additionally, because all of the homeodomain sequences shown in the table are of human origin they will not be antigenic in humans. Each of the human homeodomain sequences is listed below in Table 3 along with the abbreviation of the name of the human gene from which it is derived (SEQ ID Nos. 1 through 19). Cargo sequences may or may not be of human origin depending on their intended function.

In addition synthetic variants may be used provided that they retain the ability to translocate the membrane. Synthetic variants will generally differ from the naturally-occurring proteins by substitution, particularly conservative substitution. The phrase "conservative amino acid changes" herein means replacing an amino acid from one of the amino acid groups, namely hydrophobic, polar, acidic or basic, with an amino acid from within the same group. An example of such a change is the replacement of valine by methionine and vice versa. Other examples of conservative substitutions may be seen by reference to Table 1 below:

TABLE 1

Conservative Amino Acid Substitutions.

| ALIPHATIC | Non-polar | GAP | ILV |
|---|---|---|---|
| | Polar-uncharged | CSTM | NQ |
| | Polar-charged | DE | RK |
| AROMATIC | | | HFWY |
| OTHER | | | N |

Such variants may be synthesized directly or prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed to make the encoded protein. These methods are only illustrative of the numerous standard techniques known in the art for manipulation of DNA sequences and other known techniques may also be used. Variants that retain at least 50% sequence identity with the claimed 60-amino acid sequences or variants or portions thereof derived from HOX-C12 and HOX-D12 will likely maintain their cell permeability characteristics and retain their human characteristics resulting in low immunogenicity potential. The ability of a naturally occurring or synthetic HOX sequence to translocate the membrane may be tested by routine methods known in the art. Any polynucleotide which encodes the amino acid of SEQ ID Nos. 1-19 (Table 3) or variant or portion thereof can be used in a fusion protein or conjugate herein.

Second Region Peptides or Proteins:

The second region of the conjugate or fusion protein embodiments disclosed may comprise any peptide or protein sequence not naturally associated with the first region. The gene encoding the first region may or may not also encode the second region. The second region also may or may not be from the same species as the first region, but the first and second regions will be present in the conjugate or fusion protein embodiments in a manner different from the natural situation.

The second region of the fusion protein or conjugate embodiments may be a peptide or protein of any length as long as it is biologically active on its target when included in the fusion protein or conjugate.

Second Region Nucleic Acids:

The second region may include any nucleic acid that may be therapeutically active. In one embodiment, the nucleic acid can be DNA or RNA. In another embodiment, the nucleic acid is an oligonucleotide or a PNA.

In one embodiment, the second region may include any peptide nucleic acid such as PNAs in which nucleobases replace standard amino acids and the second region may be therapeutically active, including acting via antagonizing or activating miRNAs, in order to affect gene expression or other biological process.

In another embodiment, the second region may include any peptide nucleic acid such as PNAs and wherein the second region may be therapeutically active, including acting via antagonizing or activating mRNAs, by activating or repressing splicing or translation in order to affect gene expression or other biological process.

In certain embodiments comprising a protein/nucleic acid complex, the complex can further comprise a nucleic acid or PNA as part of the second region that, when inside a cell, binds to a RISC complex or an miRNA. For example, binding to miR132 miRNA may inhibit cancer or NF-κB. Such binding to an miRNA molecule can form a stable complex, wherein the miRNA molecule can become incapable of affecting the expression of genes as would normally be the case for an unbound miRNA.

In some embodiments comprising a protein/nucleic acid complex, the complex can further comprise a nucleic acid or PNA as part of the second region that, when inside a cell, binds to genomic DNA. For example, binding to DNA at transcription factor binding sites may prevent transcription factor binding and/or activity and thus affect gene transcription.

In further embodiments comprising a protein/nucleic acid complex, the complex can further comprise a nucleic acid, LNA or PNA as part of the second region that, when inside a cell, binds to an mRNA. For example, binding to DYRK1b mRNA can down-regulate DYRK1b expression and/or translation.

In additional embodiments comprising a protein/nucleic acid complex, the complex can further comprise a nucleic acid (or DNA) binding domain as part of the second region. In one embodiment, the nucleic acid binding domain may serve to mediate the specific, high affinity and non-covalent interaction of the protein component with the nucleic acid or PNA component.

The nucleic acid binding domain may be an RNA or DNA binding domain, e.g., the DNA binding domain of a transcription factor, particularly a yeast or human transcription factor. For example, a GAL4-derivable domain, mediates the selective binding of the protein to the DNA sequence CGGAGGACAGTCCTCCG (Cavey et al *J Mol Biol* 209: 423, 1989). Further, the DNA binding domain consists of GAL4 amino acids 2 to 147. A DNA binding domain may bind to single-stranded or to a double-stranded DNA on the second domain.

Other applications for the conjugate or fusion protein embodiments disclosed include development of antibacterial and antiviral measures. For example, HOX gene-derived or other human homeodomain-derived cell permeable peptides may be used to transport in the cytoplasm of infected cells recombinant antibodies, naturally occurring innate immunity effecter molecules or DNA binding molecules and which destroy bacteria, parasites or interfere with a crucial step of bacterial or viral replication.

Suitable peptides and proteins include those that are of therapeutic and/or diagnostic application such as, but are not limited to: cytokines, chemokines, hormones, antibodies, engineered immunoglobulin-like molecules, a single chain antibody, conjugates, enzymes, immune co-stimulatory molecules, immunomodulatory molecules, anti-sense RNA, a transdominant negative mutant of a target protein, a toxin, such as endotoxin A, Colicin A, d-endotoxin, diphtheria toxin, *Bacillus* anthrox toxin, Cholera toxin, Pertussis toxin, *E. coli* toxins, Shigatoxin or a Shiga-like toxin, a conditional toxin, an antigen, a tumor suppressor protein and growth factors, membrane proteins, vasoactive proteins and peptides, anti-viral proteins and ribozymes, and derivatives. When included, such coding sequences may be typically operatively linked to a suitable promoter, which may be a promoter driving expression of a ribozyme(s), or a different promoter or promoters.

One or more embodiments may provide a pharmaceutical composition for treating an individual by gene therapy in animals or humans, wherein the composition comprises a therapeutically effective amount of the conjugate or fusion protein. Typically, a physician will determine the actual dosage which will be most suitable for an individual subject and it will vary with the age, weight and response of the particular individual.

Fusion protein or conjugate embodiments delivering one or more therapeutic molecules such as genes or proteins may be used alone or in combination with other treatments or components of the treatment. Diseases which may be treated include, but are not limited to: cancer, neurological diseases, inherited diseases, heart disease, stroke, arthritis, viral and bacterial infections, and diseases of the immune system. Suitable therapeutic genes include those coding for tumor suppressor proteins, enzymes, pro-drug activating enzymes, immunomodulatory molecules, antibodies, engineered immunoglobulin-like molecules, conjugates, hormones, membrane proteins, vasoactive proteins or peptides, cytokines, chemokines, anti-viral proteins, antisense RNA and ribozymes.

The conjugate may also contain one or more cytokine-encoding nucleic acids or cytokines. Suitable cytokines and growth factors include but are not limited to: ApoE, ApoSAA, BDNF, Cardiotrophin-1, EGF, ENA-78, Eotaxin, Eotaxin-2. Exodus-2, FGF-acidic, FGF-basic, fibroblast growth factor-10 (Marshall 1998 Nature Biotechnology 16: 129). FLT3 ligand (Kimura et al. (1997), Fractalkine (CX3C), GDNF, G-CSF, GM-CSF, GF-[beta]1, insulin, IFN-[gamma], IGF-I IGF-II, IL-1[alpha], IL-1[beta], IL-2, IL-3. IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin [alpha], Inhibin [beta], IP-10, keratinocyte growth factor-2 (KGF-2), KGF, Leptin, LIF, Lymphotactin, Mullerian inhibitory substance, monocyte colony inhibitory factor, monocyte attractant protein (Marshall 1998 ibid), M-CSF, MDC (67 a.a.), MDC (69 a.a.), MCP-1 (MCAF), MCP-2, MCP-3, MCP4, MDC (67 a.a), MDC (69 a.a.), MIG, MIP-1[alpha], MIP-1[beta], MIP-3[alpha], MIP-3 [beta], MIP4, myeloid progenitor inhibitor factor-1 (MPIF-1), NAP-2, Neurturin, Nerve growth factor, [beta]-NGF, NT-3, NT-4, Oncostatin M, PDGF-AA, PDGF-AB, PDGF-BB, PF-4, RANTES, SDF1 [alpha], SDF1[beta], SCF, SCGF, stem cell factor (SCF), TARC, TGF-[alpha], TGF-[beta], TGF-[beta]2, TGF-[beta]3, tumor necrosis factor (TNF), TNF-[alpha], TNF-[beta], TNF-1, TPO, VEGF, GCP-2 GRO/IMGSA, GRO-[beta], GRO-[gamma], HCC1, and 1-309. It is also contemplated that homologous cytokines and growth factors can be used as cargo in suitable animal systems for research or veterinary applications.

The fusion protein or conjugate embodiments disclosed may comprise further suitable domains known to those skilled in the art. For example, an endoplasmic reticulum retention signal functions to affect the intracellular routing of the internalized conjugate or protein/nucleic acid complex. A suitable endoplasmic retention signal may be a mammalian endoplasmic reticulum retention signal.

Also present may be a translocation domain which serves to enhance nucleic acid or protein escape from the cellular vesicle system and thus to augment nucleic acid transfer by this route. This domain may serve to reduce or avoid lysosomal degradation after internalization of the protein/nucleic acid into the target cell. Suitable translocation domains are derivable from toxins, particularly bacterial toxins, such as exotoxin A, Colicin A, d-endotoxin, diphtheria toxin, *Bacillus* anthrax toxin, Cholera toxin, Perussis toxin, *E. coli* toxin toxins, Shigatoxin or Shiga-like toxin.

The first binding domain may be modified to target cell sites other than the nucleus.

Additionally, or alternatively, a target cell-specific binding domain recognizing a cell surface structure may be present, such as a receptor protein or surface antigen on the target cell.

The term "conjugate" or "conjugates" herein comprises a category of structures, including fusion proteins, in which the first region, a 60-amino acid human homeodomain sequence or variant or portion thereof, is conjugated directly via a peptide bond or other type of bond including both covalent and non-covalent bonds. Conjugates may include a linker region that connects the homeodomain sequence to a second region, a functional or regulatory peptide or protein ("cargo" peptide) that is not naturally associated with the first region. Any of a wide variety of linkers (short, connecting sequences) known in the art may be utilized to form the conjugate provided that function of the conjugate is not compromised by its addition. Thus, translocation of the second region is enabled through a cellular or nuclear membrane. For example, see a wide variety of linkers known in the art in Chen et al. "Fusion protein linkers: property, design and functionality." Advanced Drug Delivery Reviews. http://dx.doi.org/10.1016/J.addr.2012.09.039. In alternative embodiments the term "fusion protein" is used to refer to a particular subcategory of conjugate that exists when no such linkers are used to form the conjugate and the domains are linked entirely by peptide bonds.

The first (HOX or other human homeodomain) region and second (cargo) regions may be linked by a cleavable linker region this may be any region suitable for this purpose provided the function of the conjugate is not compromised by its addition. The cleavable linker region is a protease cleavable linker, although other linkers, cleavable for example by small molecules, may be used. These include Met-X sites, cleavable by cyanogen bromide, Asn-Gly, cleavable by hydroxylamine, Asp-Pro, cleavable by weak acid and Trp-X cleavable by, inter alia, NBS-skatole. Protease cleavage sites require milder cleavage conditions and are found in, for example, factor Xa, thrombin and collagenase. Any of these may be used. The precise sequences are available in the art and the skilled person will have no difficulty in selecting a suitable cleavage site. By way of example, the protease cleavage region targeted by Factor Xa is I E G R. The protease cleavage region targeted by Enterokinase is D D D D K (SEQ. ID No. 84). The protease cleavage region targeted by Thrombin is L V P R G (SEQ. ID No. 85). The cleavable linker region may be one that is targeted by endocellular proteases. Linkers may not be required for function but linkers may be included between first and second regions to allow targeted release of the second region without compromising function or to enhance biological activity of the second region with linker cleavage.

TABLE 2

| showing partial listing of linkers known in the art, adapted from Chen et al., 2012. |
|---|
| $(GGGGS)_n$, where n = 1, 2, 3, or 4 (SEQ ID No: 86) |
| $(Gly)_n$, where n = 6 or 8 (SEQ ID No: 87) |
| $(EAAAK)_n$ where n = 1-3 (SEQ ID No: 88) |
| $A(EAAAK)_4ALEA(EAAAK)_4$ A (SEQ ID No: 89) |
| PAPAP (SEQ ID No: 90) |
| AEAAAKEAAAKA (SEQ ID No: 91) |
| $(Ala\text{-}Pro)_n$ where n = 10-34 aa (SEQ ID No: 92) |
| VSQTSKLTR↓AETVFPDV (SEQ ID No: 93) |
| PLG↓LWAc (SEQ ID No: 94) |
| RVL↓AEA (SEQ ID No: 95); |
| EDVVCC↓SMSY (SEQ ID No: 96); |
| GGIEGR↓GS (SEQ ID No: 97) |
| TRHRQPR↓GWE (SEQ ID No: 98); |
| AGNRVRR↓SVG (SEQ ID No: 99); |
| RRRRRRR↓R↓R(SEQ ID No: 100) |
| GFLG↓ (SEQ ID No: 101) |

↓= cleavable at this location

The embodiments disclosed allow for potent therapeutic action, including efficient translocation into intracellular and intranuclear sites of action of any of a number of identified peptides for the specified therapeutic treatments, wherein (i) the CNS is a target tissue; and (ii) regardless of the target tissue, such translocation does not provoke an unwanted immune response that may reduce the exposure and/or effectiveness of the conjugate or produce an adverse or undesirable clinical event. The biologically-active peptide of the "second region" is not naturally associated with the human homeodomain sequence or variant or portion thereof (the "first region") before they are joined.

Further, in a variety of embodiments the conjugate or fusion protein may comprise a third region also comprising a cargo peptide. FIGS. 3*a* and 3*b* show alternative embodiments comprising the 60-amino acid human homeodomain ("first region," shown abbreviated here) and an additional cargo protein that may target the fusion protein or conjugate to its cellular site of action. In FIG. 3*a*, the human HOX D12 homeodomain on the left (1), is linked on its C-terminus (4) to the N-terminus (5) of a biologically-active cargo peptide of interest ("second region") (2), while a third cargo peptide of interest ("third region") (7) is linked on its N-terminus (8) to the C-terminus (6) of the "second region" (2). This third region may remain linked or fused via peptide bonds to the entire fusion protein or may be designed for removal after uptake or binding to specific sites in targeted tissues.

FIG. 3*b* shows an alternative embodiment, with the human HOX D12 homeodomain on the right (1), linked through its N-terminus (3) to the C-terminus (6) of the second region (2), while a third region cargo peptide (7) is linked through the N-terminus (5) of the second region (2). The links may be simple peptide bonds (13) or a linker sequences known in the art (12), or a combination of both, provided that the function of the conjugate is not compromised by the addition of a linker sequence. A second cargo peptide ("third region") (7) may target the conjugate or fusion protein to its cellular site of action. See Example 2.

Conjugate and fusion protein embodiments herein may be produced in accordance with any of the standard molecular biology techniques described in the literature. See, for example, Ausubel et al. (2002) *Short Protocols in Molecular Biology: A Compendium of Methods from Current Protocols in Molecular Biology*, 5th Ed. John Wiley & Sons. Manufacturing methods including purification methods that may be used are also disclosed in U.S. Pat. No. 7,968,512, the entirety of which is incorporated herein by reference.

"Expression vectors" or "plasmids" (used interchangeably herein) may be used for producing conjugates or components thereof to introduce heterologous DNA into host cells, either for expression or replication. Selection by the artisan of the appropriate vector will depend on its intended use, i.e. (DNA amplification or DNA expression), the size of the DNA to be inserted into the vector, and the host cell to be transformed with the vector. Each vector contains various components depending on its intended use, which comprise one or more of: an origin of replication, one or more marker genes, an enhancer element, a promoter, a transcription termination sequence and a signal sequence.

Sources of nucleic acid may be ascertained by reference to published literature or databanks provided by organizations such as NCBI or EMBL. Identification of sequences of interest may be accomplished by using BLAST, BLAT, or other homology search algorithms. Further, nucleic acid encoding the desired first or second region may be obtained from academic or commercial sources where such sources are willing to provide the material or by synthesizing or cloning the appropriate sequence where only the sequence data are available. Generally, this may be done by reference to literature sources which describe the cloning of the gene in question. Alternatively, where limited sequence data are available or where it is desired to express a nucleic acid homologous or otherwise related to a known nucleic acid, exemplary nucleic acids can be characterized as those nucleotide sequences which hybridize to the nucleic acid sequences known in the art.

The phrase "stringency of hybridization" refers to conditions under which polynucleic acids hybrids are stable. Such conditions are evident to those of ordinary skill in the art. Also as understood by persons skilled in the art, the stability of hybrids is reflected in the melting temperature ($T_m$) of the hybrid which decreases approximately 1 to 1.5[deg.] C. with every 1% decrease in sequence homology. In general, the stability of a hybrid is a function of sodium ion concentration and temperature. The hybridization reaction typically is performed under conditions of higher stringency, followed by washes of varying stringency.

As used herein, the phrase "high stringency" refers to conditions that permit hybridization of only those nucleic acid sequences that form stable hybrids in 1 M Na+ at 65-68[deg.] C. High stringency conditions can be provided, for example, by hybridization in an aqueous solution containing 6*SSC, 5* Denhardt's, 1% SDS (sodium dodecyl sulphate), 0.1 Na+ pyrophosphate and 0.1 mg/ml denatured salmon sperm DNA as nonspecific competitor. Following hybridization, high stringency washing may be done in several steps, with a final wash (about 30 minutes) at the hybridization temperature in 0.2-0.1*SSC, 0.1% SDS.

The phrase "moderate stringency" refers to conditions equivalent to hybridization in the above described solution, except that the temperature is at about 60-62[deg.] C. In that case the final wash is performed at the hybridization temperature in 1*SSC, 0.1% SDS.

Low stringency refers to conditions equivalent to hybridization in the above described solution at about 50-52[deg.] C. In that case, the final wash is performed at the hybridization temperature in 2*SSC, 0.1% SDS.

It is understood that these conditions may be adapted and duplicated using a variety of buffers, e.g., formamide-based buffers, and temperatures. Denhardt's solution and SSC are well known to those of skill in the art as are other suitable hybridization buffers (see, e.g. Sambrook, et al., eds. (1989) *Molecular Cloning: A Laboratory Manual*, Cold Spring Harbor Laboratory Press, New York or Ausubel, et al., eds. (1990) *Current Protocols in Molecular Biology*, John Wiley & Sons, Inc.). Optimal hybridization conditions must be determined empirically, as the length and the GC content of the probe also play a role.

In one embodiment, the conjugate or fusion protein may be produced through use of an expression vector comprising the nucleic acid sequence and a promoter for recombinant synthesis in, for example, plant cells (including algae), in bacteria such as *E. coli*, or in eukaryotic cells such as Chinese Hamster Ovary (CHO) cells or yeast cells.

In another embodiment, a host cell is transformed with the expression vector.

In yet another embodiment a nucleic acid sequence encodes the conjugate or fusion protein for the purposes of synthesis and manufacture by recombinant technology.

In some embodiments, the conjugate or fusion protein is non-denatured, meaning it may exist in its native state, the form in which the protein occurs in the intact cell in its three-dimensional structure.

The term "non-denatured" may also, but need not, imply a specific non-denaturing step. Denaturing alters the three-dimensional shape of the protein molecule without rupture of its peptide bonds; disulfide bonds may be ruptured, or certain groups in the protein may be chemically modified if such processes are also accompanied by changes in its overall three-dimensional structure.

In other embodiments, the conjugate or fusion protein is renatured, a process by which the denatured protein is returned to its original conformation prior to denaturation. For peptides, reversible denaturation is generally brought about by disulfide reducing agents and urea, and for nucleic acid, by heat and salts.

In one embodiment, the first region is at the N-terminus of the second region. In another embodiment the first region is at the C-terminus of the second region.

Purification methods known in the art may be used in the process of preparing conjugates and fusion proteins according to the embodiments disclosed, for example, as described in Zachariou, M. (2010) *Affinity Chromatoqraphy: Methods and Protocols*, 2nd Ed. Totoua, N.J.: Humana Press. The conjugate or fusion protein can be obtained from bacterial or eukaryotic cell lysates, as denaturing reagents, small changes in pH, and differences in osmolarity may have an effect on the translocation properties of the peptides. Conditions for obtaining and purifying the human homeodomain peptides, including HOX-derived peptides are disclosed herein.

The ability of HOX peptide-conjugates to translocate across the cell surface membrane may be dependent on the conformation of the recombinant proteins. For example, translocation of the polypeptide by using either bacteria cell extracts or purified proteins exposed to small amounts of detergent (ionic and non-ionic) or denaturating agents (urea or guanidinuim) may prevent or inhibit translocation. This conformation-dependent property may be preserved by purifying the HOX peptide-conjugate or other human homeodomain conjugate under native conditions.

In one embodiment, both the first (the human homeodomain or variant or portion thereof) and second (biologically active peptide or protein) regions are purified from a bacterial lysate. In other embodiments, the conjugate or fusion protein is purified from a plant cell lysate. In yet another embodiment, the conjugate or fusion protein is purified from an eukaryotic cell lysate, culture medium or fermentation broth.

One embodiment is a method for preparing a conjugate or fusion protein, comprising:
(a) culturing the host cell under conditions which provide for the expression of the conjugate from the expression vector within the host cell; and
(b) recovering the conjugate, which recovery comprises
   (i) fusing an amino acid tail or other specific ligand to the conjugate, which tail is capable of binding to at least one substrate and not to another substrate, and wherein the conjugate or fusion protein is caused to bind via the tail to at least one substrate, and wherein components of the host cell do not bind to this substrate, and
   (ii) putting into contact the conjugate and remaining components of the host cell with the other substrate such that the conjugate is not bound and the remaining components of the host cell are bound to the other substrate.

Another embodiment is a method for preparing a conjugate or fusion protein comprising:
(i) culturing a host cell, transformed with an expression vector comprising nucleic acid, operably linked to a promoter, encoding a fusion protein where
   (a) a first region comprises the HOX peptide or other human homeodomain peptide; and
   (b) a second region not naturally associated with the first region comprises a peptide or protein, under conditions which provide for expression of the fusion protein from the expression vector within the host cell; and
(ii) recovering the fusion protein, which method comprises fusing an amino acid tail or other ligand to the conjugate, which tail is capable of binding to at least one substrate and not to another substrate, and wherein the conjugate is caused to bind via the tail to at least one substrate such that components of the host cell do not bind to this substrate; and the conjugate is contacted with the other substrate such that the conjugate is not bound and remaining components of the host cell are bound to the other substrate.

In another embodiment as part of the affinity purification process, the embodiments include the use of a tail or ligand that is attached to the conjugate or fusion protein; this allows for both positive and negative purification steps.

For all combined first and second region sequences, additional amino acid sequences can be added to either the amino or carboxy termini in order to facilitate purification. Such sequences may include FLAG-tags (DYKDDDDK) (SEQ ID No. 102), myc-tags (EQKLISEEDL) (SEQ ID No. 103), His-tags (such as HHHHHH, HHHHHHGS (SEQ ID No. 104), the latter utilizing a GS linker, see FIGS. 4 and 5), and other similar tags known to those in the art. In addition, ligands such as the biotin-acceptor protein (GLN-DIFEAQKIEWHE) (SEQ ID No. 105) together with the active BirA protein may be used. For sequences that include an N-terminal initiating methionine, if a N-terminal purification domain is added the methionine will be on the N-terminal of the purification domain instead of at the N-terminal of the human homeodomain peptide first region.

For any tag, a peptide linker known in the art may be used and removed after purification with a specific protease.

Figure 4:
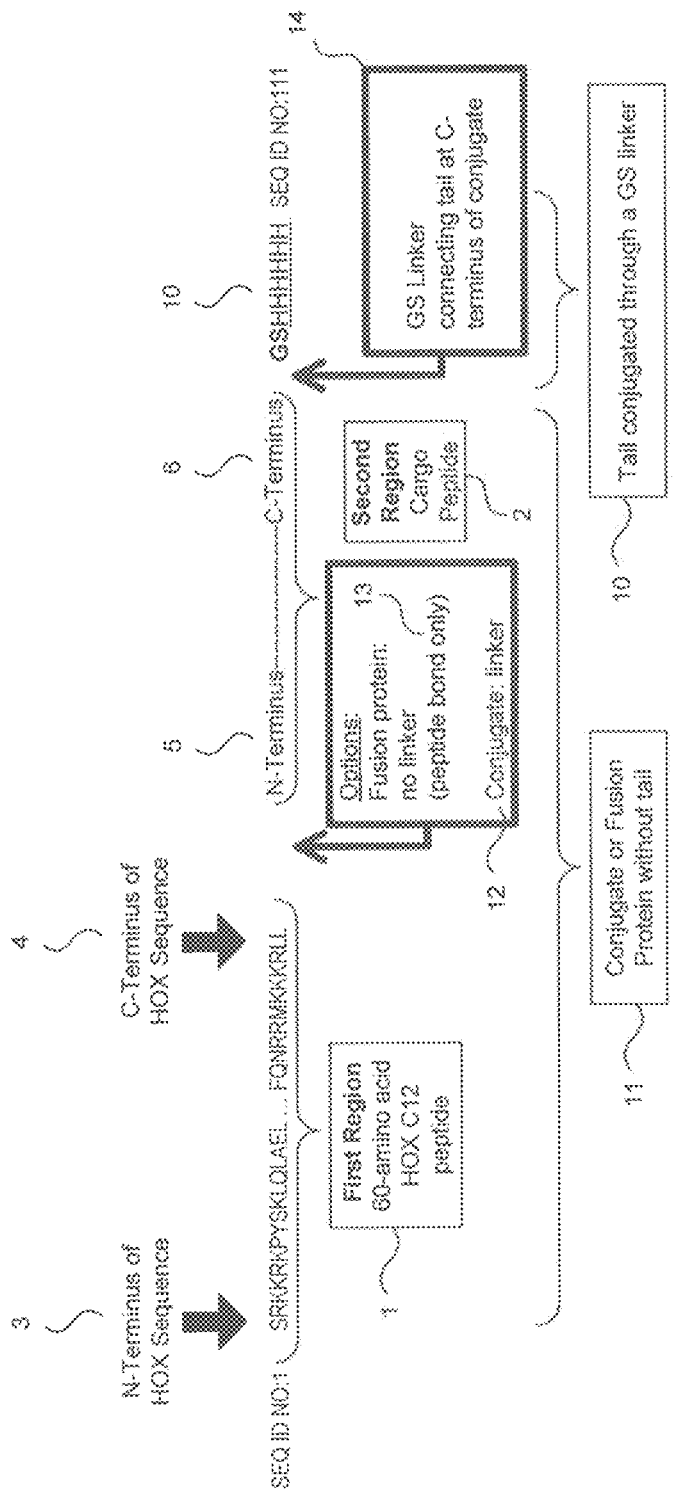
FIG. 4 shows an exemplary 60-amino acid human HOX C12 homeodomain (first region) or variant or portion thereof at the N-terminus of a Cargo peptide (second region), and His-tail conjugated to C-terminus through GS linker.

In one embodiment, the amino acid tail or ligand is fused to the C-terminus of the conjugate. For example, FIG. 4 shows an embodiment comprising a biologically-active cargo peptide (2), linked on its C-terminus (6) through either a peptide bond (13) or a linker sequence known in the art (12) to the N-terminus (3) of the human homeodomain "first region" shown abbreviated here (1). A GS linker (14) is shown attaching a His-tag ("tail") to the C-terminus (6) of the cargo peptide (2). Any linker may be used provided it does not compromise the function of the conjugate.

In one embodiment, the immobilized substrate is a nickel or cobalt column, avidin column, or an antibody column with affinity for the amino acid tail. In another embodiment, the conjugate's amino acid tail is serially brought into contact with at least two immobilized substrates with which the tail has affinity, in which case the nickel or cobalt column and/or avidin and/or antibody may be used in any order.

In another embodiment, the method of purifying a conjugate comprises fusing an amino acid tail or ligand to the conjugate or fusion protein, which tail is capable of binding to at least one substrate while impurities bind only to a second substrate; the conjugate is contacted with the other substrate such that the conjugate is not bound and remaining impurities are bound to the other substrate.

According to another embodiment, a method for producing and purifying a conjugate or fusion protein comprising the 60-amino acid human homeodomain or variant or portion thereof and a biologically-active peptide or protein comprises culturing the host cell for the expression of the conjugate or fusion protein from the expression vector and subsequently recovering the conjugate or fusion protein using affinity purification techniques known in the art.

When the second region is a DNA binding domain, a complex with nucleic acid may be formed by mixing the conjugate formed with the nucleic acid.

Further embodiments include pharmaceutical compositions comprising the conjugates or fusion proteins of the embodiments disclosed herein, and methods of use of the conjugates or fusion proteins in the preparation of a medicament for the treatment of a disease.

In one embodiment, a conjugate or fusion protein comprises a biologically active peptide or protein that is a functional enzyme, linked to the human homeodomain or variant or portion thereof.

Other embodiments comprise any of a variety of formulations for treating conditions or diseases identified.

Upstream Production of SEQ ID No. 21 and SEQ ID No. 22.

A bacterial expression construct was generated for two homeobox candidate proteins PPL-002 (SEQ ID No. 21, Table 3) and PPL-003 (SEQ ID No. 22, Table 3) capable of regulated expression of the target protein with a TEV cleavable N-terminal His tag in the T7 vector system. The T7 expression system is suitable for producing material for animal efficacy studies; however, other expression vectors/system are also contemplated and are known by one of ordinary skill in the molecular biology/biotechnology art.

Synthetically-created, codon-optimized gene sequences were cloned into the vector for inducible expression of the selected protein with kanamycin selection. The DNA and corresponding amino acid sequences for homeobox proteins PPL-002 (e.g., plasmid pJ411:129925) and PPL-003 (e.g., pJ411:129926) are shown in FIG. 6 and FIG. 7, respectively. Each expressed protein contains a 6 HIS leader, with a transition sequence of SAA, followed by the TEV cleavage site (ENLYFQS) to produce the PPL-002 or PPL-003 sequence with the appropriate N terminus.

Upon transformation into DH5a, six clones for each construct were tested for presence of the insert by restriction digest. The synthesized DNA sequence was sequenced for confirmation. Verified expression constructs for each protein were used to transform bacterial strain E. coli BL21 (DE3), a commercially available strain from Invitrogen/Thermo Fisher Scientific (Waltham, Mass., USA), and a PD glycerol cell stock was prepared for each best expressing clone.

Preliminary expression optimization studies were performed in shake flask cultures. Upon moving to small scale fermenters, further optimization of cell growth was performed. Early oxygen supplementation and a pH set point of about 7.1 were shown to be optimal. Induction temperature was optimized at about 18° C.

Composition embodiments disclosed herein may comprise a pharmaceutically acceptable carrier, diluent or excipient. The term "pharmaceutically acceptable carrier diluent or excipient" refers to any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition.

The choice of pharmaceutically acceptable carrier, excipient or diluent may be selected based on the formulation and the intended route of administration, as well as standard pharmaceutical practice. Such compositions may comprise any agents that may aid, regulate, release or increase entry into the body compartment, tissue, intracellular or intranuclear target site, such as binder(s), lubricant(s), suspending agent(s), coating agent(s), solubilizing agent(s), or other agents. An injectable implant for the sustained release of the protein may also be used to obtain prolonged exposure and action. The term "sustained release" refers to formulations from which the conjugate is released at a slow rate allowing for a longer period of exposure at active concentrations.

The compositions comprising one or more conjugates or fusion proteins disclosed herein can be administered, depending on condition to be treated or other considerations, in any number of ways, for example without limitation, by any one or more of the following: (1) inhalation; (2) in the form of a suppository or pessary; (3) in the form of a topical lotion, solution, cream, ointment or dusting powder; (4) by use of a skin patch; (5) orally in the form of tablets containing excipients such as starch or lactose, or in capsules or ovules either alone or in admixture with excipients, or in the form of elixirs, solutions or suspensions containing flavoring or coloring agents; (6) injected parenterally, for example intracavernosally, intravenously, intramuscularly or subcutaneously; (7) for ophthalmic diseases, they may be formulated as eye drops or for intraocular injection; (8) for parenteral administration, they may be in the form of a sterile aqueous solution or injectable implant which may contain other substances, for example, with adequate salt or monosaccharide content to make the solution isotonic with blood or substances that allow slow release; and (9) for buccal or sublingual administration the compositions may be administered in the form of tablets or lozenges which can be formulated in a conventional manner.

In one embodiment, the conjugate comprises:
a first region comprising a structure derived from (1) the human HOX genes, or (2) other human genes having a sequence described in any of SEQ ID Nos. 1-19, wherein 1-20, 1-15, or 1-10 amino acid residues are substituted, deleted, added, and/or inserted; and
a second region is a functional or regulatory polypeptide or protein not naturally associated with the first region. In various embodiments, the second region is selected from the group consisting of NBD peptide, PC1 CTT-derived p200, PC1 CTT-derived p21, glucocerebrosidase, alpha-L-iduronidase, iduronidate-2-sulfatase, retinal membrane guanylyl cyclase, the zinc finger peptide construct, ZF6×Hunt-Kox-1, the zinc finger peptide construct, ZF12×Hunt-Kox-1, and the zinc finger peptide construct, ZF18×Hunt-Kox-1.

In one embodiment, the conjugate comprises:
a first region comprising a structure derived from (1) the human HOX genes, or (2) other human genes having a sequence described in any of SEQ ID Nos. 1-19, wherein 1-20, 1-15, or 1-10 amino acid residues are substituted, deleted, added, and/or inserted and wherein said amino acid has (i) has human homeodomain activity; and (ii) maintains the cell permeabilizing activity of the helical regions of the human HOX genes or other human genes containing a homeodomain with cell permeabilizing properties; and
a second region is a functional or regulatory polypeptide or protein not naturally associated with the first region. In various embodiments the second region is selected from the group consisting of NBD peptide, PC1 CTT-derived p200, PC1 CTT-derived p21, glucocerebrosidase, alpha-L-iduronidase, iduronidate-2-sulfatase, retinal membrane guanylyl cyclase, the zinc finger peptide construct, ZF6×Hunt-Kox-1, the zinc finger peptide construct, ZF12×Hunt-Kox-1, and the zinc finger peptide construct, ZF18×Hunt-Kox-1.

In one embodiment, the active concentration of fusion protein or conjugate in cell culture is less than about 115 µM, less than about 100 µM, less than about 90 µM, less than about 80 µM, less than about 70 µM, less than about 65 µM, less than about 60 µM, less than about 55 µM, less than about 50 µM, less than about 45 µM, less than about 40 µM, less than about 35 µM, less than about 30 µM, less than about 25 µM, less than about 20 µM, less than about 15 µM, less than about 10 µM, less than about 5 µM, or less than about 1 µM for example, less than about 1 µM to about 3 µM, less than about 1 µM to about 6 µM, less than about 1 µM to about 8 µM, less than about 1 µM to about 15 µM, less than about 1 µM to about 25 µM, less than about 1 µM to about 50 µM, less than about 1 µM to about 70 µM, less than about 1 µM to about 85 µM, less than about 1 µM to about 110 µM, less than about 10 µM to about 110 µM, less than about 15 µM to about 70 µM, less than about 15 µM to about 60 µM, less than about 20 µM to about 55 µM, or less than about 25 µM to about 45 µM.

In other embodiments, the dosage delivered (daily or as required) in mouse models (per 20 g mouse) through (1) an intravenous (i.v.) or intraperitoneal (i.p.) injection, (2) a topical formulation, or (3) an inhaled formulation is at least 500 µg, at least 450 µg, at least 400 µg, at least 350 µg, at least 300 µg, at least 250 µg, at least 200 µg, at least 150 µg, at least 100 µg, at least 80 µg, at least 70 µg, at least 60 µg, at least 50 µg, at least 40 µg, at least 30 µg, at least 20 µg, at least 10 µg, or at least 1 µg, for example, about 1 µg to about 500 µg, about 10 µg to about 450 µg, about 20 µg to about 400 µg about 30 µg to about 350 µg, about 30 µg to about 200 µg, about 30 µg to about 100 µg, about 40 µg to about 300 µg, about 40 µg to about 200 µg, about 50 µg to about 100 µg, about 50 µg to about 90 µg, about 55 µg to about 85 µg, about 60 µg to about 80 µg, about 60 µg to about 100 µg; about 1 µg to about 200 µg; about 1 µg to about 100 µg, about 1 µg to about 90 µg, about 1 µg to about 80 µg, about 1 µg to about 70 µg, about 1 to about 60 µg, about 1 to about 50 µg, about 1 to about 40 µg, about 1 to about 30 µg, about 1 to about 20 µg, about 1 to about 15 µg, about 1 to about 12 µg, about 1 to about 10 µg, about 1 to about 8 µg about 1 to about 6 µg, about 1 to about 4 µg, or about 1 to about 3 µg.

In other embodiments, the dosage delivered (daily or as required) through an intravenous (i.v.) or intraperitoneal (i.p.) injection in a mouse model is at least 100 mg/kg, less than about 80 mg/kg, less than about 45 mg/kg, less than about 40 mg/kg, less than about 30 mg/kg, less than about 25 mg/kg, less than about 20 mg/kg, less than about 15 mg/kg, less than about 12 mg/kg, less than about 10 mg/kg, less than about 8 mg/kg, less than about 4 mg/kg, less than about 2 mg/kg, or less than about 1 mg/kg, for example, less than about 1 mg/kg to about 50 mg/kg, about 5 mg/kg to about 40 mg/kg, about 8 mg/kg to about 30 mg/kg, about 10 mg/kg to about 20 mg/kg, or about 12 mg/kg to about 15 mg/kg, about 8 mg/kg to about 12 mg/kg, about 5 mg/kg to about 9 mg/kg, about 3 mg/kg to about 6 mg/kg, about 2 mg/kg to about 5 mg/kg, about 2 mg/kg to about 4 mg/kg, about 1 mg/kg to about 3 mg/kg, about 1 mg/kg to about 2.0 mg/kg.

In other embodiments, the dosage delivered (daily or as required) through an inhaled formulation in humans (70 kg weight) is at least about 600 mg, at least about 500 mg, at least about 450 mg, at least about 400 mg, at least about 350 mg, at least about 300 mg, at least about 250 mg, at least about 200 mg, at least about 150 mg, at least about 125 mg, at least about 100 mg, at least about 75 mg, at least about 50 mg, at least about 25 mg, at least about 20 mg, at least about 15 mg, at least about 10 mg, at least about 5 mg, at least about 1 mg, at least about 500 µg, at least about 450 µg, at least about 400 µg, at least about 350 µg, at least about 300 µg, at least about 250 µg, at least about 200 µg, at least about 150 µg, at least about 100 µg, at least about 80 µg, at least about 70 µg, at least about 60 µg, at least about 50 µg, at least about 40 µg, at least about 30 µg, at least about 20 µg, at least about 10 µg, or at least about 1 µg, for example, between about 1 µg to about 750 µg; about 1 µg to about 500 µg, about 10 µg to about 450 µg, about 20 µg to about 400 µg about 30 µg to about 350 µg, about 30 µg to about 200 µg, about 30 µg to about 100 µg, about 40 µg to about 300 µg, about 40 µg to about 200 µg, about 50 µg to about 100 µg, about 50 µg to about 90 µg, about 55 µg to about 85 µg, about 60 µg to about 80 µg, about 60 µg to about 100 µg; about 1 µg to about 200 µg; about 1 µg to about 100 µg, about 1 µg to about 90 µg, about 1 µg to about 80 µg, about 1 µg to about 70 µg, about 1 to about 60 µg, about 1 to about 50 µg, about 1 to about 40 µg, about 1 to about 30 µg, about 1 to about 20 µg, about 1 to about 15 µg, about 1 to about 12 µg, about 1 to about 10 µg, about 1 to about 8 µg about 1 to about 6 µg, about 1 to about 4 µg, about 1 µg to about 3 µg, about 1 µg to about 1 mg, about 1 µg to about 2 mg, about 1 µg to about 5 mg; about 1 µg to about 10 mg; about 1 mg to about 10 mg, about 1 mg to about 15 mg; about 2 mg to about 20 mg, about 3 mg to about 30 mg, about 4 mg to about 40 mg, about 5 mg to about 50 mg, about 5 mg to about 80 mg, about 5 mg to about 110 mg, about 10 mg to about 150 mg, about 10 mg to about 80 mg, about 20 mg to about 70 mg, about 20 mg to about 60 mg, about 30 mg to about 60 mg, about 120 mg to about 190 mg, about 130 mg to about 180 mg, about 130 mg to about 200 mg, about 140 mg to about 250 mg, about 180 mg to about 300 mg, about 190 mg to about 350 mg, about 220 mg to about 400 mg, about 250 mg to about 425 mg, about 280 mg to about 460 mg, about 300 mg to about 480 mg, about 350 mg to about 490 mg, about 380 mg to about 550 mg, about 400 mg to about 580 mg, about 480 mg to about 590 mg, or about 520 mg to about 600 mg.

In other embodiments, the dosage delivered (daily or as required) through topical formulation in humans and in mouse models is less than about 5% wt/vol, less than about 4.5% wt/vol, less than about 3.5% wt/vol, less than about 2.5% wt/vol, less than about 1.5% wt/vol, less than about 0.5% wt/vol, less than about 0.4% wt/vol, less than about 0.3% wt/vol, less than about 0.2%, less than about 0.1% wt/vol, less than about 0.09% wt/vol, less than about 0.08% wt/vol, less than about 0.07% wt/vol, less than about 0.06% wt/vol, less than about 0.05% wt/vol, less than about 0.04% wt/vol, less than about 0.03% wt/vol, less than about 0.02% wt/vol, less than about 0.01% wt/vol, less than about 0.008% wt/vol, less than about 0.006% wt/vol, less than about 0.004% wt/vol, or less than about 0.002% wt/vol, for example between about 0.002% wt/vol and about 5% wt/vol, about 0.01% wt/vol and about 4% wt/vol, about 0.05% wt/vol and about 3% wt/vol, about 0.02% wt/vol and about 2.5% wt/vol, about 0.03% wt/vol and about 2% wt/vol, about 0.05% wt/vol and about 1% wt/vol, about 0.06% wt/vol and about 0.9% wt/vol, about 0.07% wt/vol and about 0.6% wt/vol, about 0.08% wt/vol and about 0.4% wt/vol, about 0.09% wt/vol and about 0.2% wt/vol or about 0.09 wt/vol and about 0.1% wt/vol.

In other embodiments the dosage delivered (daily or as required) through a topical formulation in humans (70 kg weight) is less than about 70 µg, less than about 50 µg, less than about 45 µg, less than about 40 µg, less than about 30 µg, less than about 25 µg, less than about 20 µg, less than about 15 µg, less than about 12 µg, less than about 10 µg, less than about 8 µg, less than about 4 µg, less than about 2 µg, or less than about 1 µg, for example, about 1 µg to about 50 µg, about 5 µg to about 40 µg, about 8 µg to about 30 µg, about 10 µg to about 20 µg, or about 12 µg to about 15 µg, about 8 µg to about 12 µg, about 5 µg to about 9, about 3 µg to about 6 µg, about 2 µg to about 5 µg, or less than about 1 µg to about 3 µg.

In another embodiment, the systemic dosage delivered (daily or as required) through an intravenous, subcutaneous or intramuscular injection or an injectable implant for sustained release formulations in humans is less than about 100 mg/kg, less than about 80 mg/kg, less than about 45 mg/kg, less than about 40 mg/kg, less than about 30 mg/kg, less than about 25 mg/kg, less than about 20 mg/kg, less than about 15 mg/kg, less than about 12 mg/kg, less than about 10 mg/kg, less than about 8 mg/kg, less than about 4 mg/kg, less than about 2 mg/kg, less than about 1 mg/kg, less than about 0.1 mg/kg, or less than about 0.01 mg/kg, for example, less than about 0.01 mg/kg to about 50 mg/kg, less than about 5 mg/kg to about 40 mg/kg, less than about 8 mg/kg to about 30 mg/kg, less than about 10 mg/kg to about 20 mg/kg, or less than about 12 mg/kg to about 15 mg/kg, less than about 8 mg/kg to about 12 mg/kg, less than about 5 mg/kg to about 9 mg/kg, less than about 3 mg/kg to about 6 mg/kg, less than about 2 mg/kg to about 5 mg/kg, less than about 2 mg/kg to about 4 mg/kg, less than about 1 mg/kg to about 3 mg/kg, less than about 0.2 mg/kg to about 2.0 mg/kg, less than about 0.1 mg/kg to about 1.5 mg/kg, or less than about 0.01 mg/kg to about 2.00 mg/kg.

In other embodiments, the dosage delivered (daily or as required) to humans (based on 70 kg weight) through any formulation other than an intravenous, subcutaneous, or intramuscular injection or injectable implant for the sustained release, inhaled or topical formulation is at least about 600 mg, at least about 500 mg, at least about 450 mg, at least about 400 mg, at least about 350 mg, at least about 300 mg, at least about 250 mg, at least about 200 mg, at least about 150 mg, at least about 125 mg, at least about 100 mg, at least about 75 mg, at least about 50 mg, at least about 25 mg, at least about 20 mg, at least about 15 mg, at least about 10 mg, at least about 5 mg, at least about 1 mg, at least about 500 µg, at least about 450 µg, at least about 400 µg, at least about 350 µg, at least about 300 µg, at least about 250 µg, at least about 200 µg, at least about 150 µg, at least about 100 µg, at least about 80 µg, at least about 70 µg, at least about 60 µg, at least about 50 µg, at least about 40 µg, at least about 30 µg, at least about 20 µg, at least about 10 µg, or at least about 1 µg, for example, between about 1 µg to about 750 µg; about 1 µg to about 500 µg, about 10 µg to about 450 µg, about 20 µg to about 400 µg about 30 µg to about 350 µg, about 30 µg to about 200 µg, about 30 µg to about 100 µg, about 40 µg to about 300 µg, about 40 µg to about 200 µg, about 50 µg to about 100 µg, about 50 µg to about 90 µg, about 55 µg to about 85 µg, about 60 µg to about 80 µg, about 60 µg to about 100 µg; about 1 µg to about 200 µg; about 1 µg to about 100 µg, about 1 µg to about 90 µg, about 1 µg to about 80 µg, about 1 µg to about 70 µg, about 1 to about 60 µg, about 1 to about 50 µg, about 1 to about 40 µg, about 1 to about 30 µg, about 1 to about 20 µg, about 1 to about 15 µg, about 1 to about 12 µg, about 1 to about 10 µg, about 1 to about 8 µg about 1 to about 6 µg, about 1 to about 4 µg, about 1 µg to about 3 µg, about 1 µg to about 1 mg, about 1 µg to about 2 mg, about 1 µg to about 5 mg; about 1 µg to about 10 mg; about 1 mg to about 10 mg, about 1 mg to about 15 mg; about 2 mg to about 20 mg, about 3 mg to about 30 mg, about 4 mg to about 40 mg, about 5 mg to about 50 mg, about 5 mg to about 80 mg, about 5 mg to about 110 mg, about 10 mg to about 150 mg, about 10 mg to about 80 mg, about 20 mg to about 70 mg, about 20 mg to about 60 mg, about 30 mg to about 60 mg, about 120 mg to about 190 mg, about 130 mg to about 180 mg, about 130 mg to about 200 mg, about 140 mg to about 250 mg, about 180 mg to about 300 mg, about 190 mg to about 350 mg, about 220 mg to about 400 mg, about 250 mg to about 425 mg, about 280 mg to about 460 mg, about 300 mg to about 480 mg, about 350 mg to about 490 mg, about 380 mg to about 550 mg, about 400 mg to about 580 mg, about 480 mg to about 590 mg, or about 520 mg to about 600 mg.

In one embodiment, the formulation is administered systemically or locally (e.g. intraocular injection, enema formulation, inhalation) at intervals of 6 hours, 12 hours, daily or every other day or on a weekly or monthly basis to elicit the desired benefit or otherwise provide a therapeutic effect. In another embodiment, the formulation is administered as required to elicit the desired benefit or otherwise provide a therapeutic effect.

In another embodiment, the improvement in post-myocardial infarction (MI) cardiac output will be assessed by ultrasound. In another embodiment, the improvement in post-stroke neurological function will be assessed by determining the percent of patients with a NIHSS of less than 17 one month after presentation. In another embodiment, immunogenicity of the human homeodomain or variant or portion thereof conjugates or fusion proteins will be assessed by determining the incorporation of 3H-thymidine by lymphocytes. In another embodiment, immunogenicity of the human homeodomain or variant or portion thereof conjugates or fusion proteins will be assessed by determining the level of specific antibodies produced by the recipient animal or human. In another embodiment, the extent of ischemia-reperfusion injury will be assessed using known histopathology techniques to examine the area of necrotic tissue in a stroke model. In yet another embodiment, the GAG accumulation will be assessed using known histopathology techniques. In another embodiment behavioral and motor deficits in a mouse model of Huntington's Disease will be assessed using published methods evaluating grip strength in the forepaws and balance ability on a rotorod balance beam. In other embodiments each outcome will be assessed by known methods.

In one embodiment, upon treatment of one or more human or animal subjects with any of the fusion protein or conjugate embodiments disclosed, the subject(s) will exhibit one or more of the following outcomes:

(a) a reduction in shortness of breath or difficulty breathing;
(b) a reduction in cytokine production;
(c) a reduction of TNF-α concentration in blood;
(d) a reduction of IL-1 concentration in blood;
(e) a reduction of IL-6 concentration in blood;
(f) a reduction in bronchoalveolar lavage fluid (BALF) inflammatory cell numbers;
(g) a reduction in BALF cytokine levels (e.g. TNF-α, IL-1, IL-6, IL-8);
(h) Improvement of pulmonary function (e.g. FEV1);
(i) Improvement in functional (including exercise) capacity;
(j) a reduction in exacerbations of COPD requiring emergent care or hospitalization;
(k) restoration of tear secretion towards normal levels;
(l) a reduction in hair loss;
(m) an increase in hair growth;
(n) a reduction in the area of necrotic brain tissue by MRI;
(o) a reduction in C-reactive protein (CRP);
(p) a reduction in acute mortality (i.e., at one month);
(q) an improvement in post-myocardial infarction (MI) cardiac output as measured by ultrasound;
(r) an improvement in post-stroke neurological function as measured by the determining the percent of patients with a NIHSS of less than 17 one month after presentation;
(s) an inhibition in kidney growth;
(t) reduced allergic responses and infusion reactions to the 60-amino acid human homeodomain (or variant or portion thereof) conjugates or fusion proteins compared to previous treatments with the cargo second region alone;
(u) reduced anti-cargo peptide specific antibody levels;
(v) a reduction in the accumulation of a GCase substrate, glycosylceramide;
(w) a reduction in the urinary excretion of dermatan sulfate;
(x) a reduction in the urinary excretion of heparan sulfate;
(y) restoration of electroretinogram (ERG) function;
(z) restoration of visual acuity as determined through standard clinical methodology;
(aa) normalization or improvement in motor deficits, as assessed using the Unified Huntington's Disease Rating Scale (UHDRS) Total Motor Score; and/or other clinically validated scoring methods;
(bb) normalization of skeletal development as assessed by standard growth and development pediatric techniques;
(cc) normalization of brain development as assessed by standard pediatric techniques;
(dd) a reduced progression of renal cyst size and number assessed by MRI;
(ee) an increase in the level of anti-inflammatory interleukin-10 (IL-10) in blood;
(ff) an increase in the level of anti-inflammatory interleukin-10 (IL-10) in BALF;
(gg) a reduction in the level of IP-10 in blood;
(hh) a reduction in the level of IP-10 in BALF; and/or
(ii) a reduction in amyloid A protein (SAA) in blood;

(jj) a reduction in mouse Kc or human IL-8 in blood or BALF;
(kk) a reduction in GM-CSF in blood or BALF;
(ll) prevention of an increase in graded vitreous haze and/or graded anterior chamber cells;
(mm) prevention of deterioration of visual acuity;
(nn) reduced tumor cell growth and/or reduced tumor growth;
(oo) reduced expression of DYRK1b; and/or
(pp) reduced activation of NF-κB regulated genes.

In another embodiment, the patient will be treated over a period, for example, of about 1 day through the lifetime of the patient, over a period of about 1 day to about 200 weeks, about 1 day to about 100 weeks, about 1 day to about 80 weeks, about 1 day to about 50 weeks, about 1 day to about 40 weeks, about 1 day to about 20 weeks, about 1 day to about 15 weeks, about 1 day to about 12 weeks, about 1 day to about 10 weeks, about 1 day to about 5 weeks, about 1 week to about 4 weeks, about 2 weeks to about 3 weeks, about 1 day to about 2 weeks, about 1 week, about 1 to 5 days, about 1 to 3 days, or about 1 to 2 days.

In another embodiment comprising a fusion protein or conjugate formulation utilized in any of the proposed studies in the examples provided, in other research and treatment, including animal research for human and animal applications, and veterinary treatment, the treatment group members, or the treatment group(s) will exhibit one or more of the following outcomes, each compared to baseline or control, unless otherwise indicated:
(a) an inhibition of NF-κB transcriptional activity;
(b) a reduction in cytokine production;
(c) an inhibition of TNF-α concentration in blood;
(d) an inhibition of IL-1 concentration in blood;
(e) an inhibition of IL-6 concentration in blood;
(f) a reduction in bronchoalveolar lavage fluid (BALF) inflammatory cell numbers;
(g) a reduction in bronchoalveolar lavage fluid (BALF) cytokine levels (e.g. TNF-α, IL-1, IL-6, IL-8);
(h) a reduction in goblet cell infiltration in the epithelial cornea;
(i) an attenuation of the loss of goblet cells in the conjunctiva;
(j) reduced lymph-angiogenesis;
(k) restoration of tear secretion towards normal levels;
(l) a reduction in hair loss or an increase in hair growth;
(m) a reduction in the area of necrotic brain tissue as assess with MRI;
(n) a reduction in C-reactive protein (CRP);
(o) a reduction in acute mortality (i.e., at one month);
(p) an improvement in post-myocardial infarction (MI) cardiac output as measured by ultrasound;
(q) an improvement in post-stroke neurological function as measured by the percent of patients with a NIHSS of less than 17 one month after presentation;
(r) an inhibition in kidney growth;
(s) an attenuated change in concentration of osteocalcin in blood, as compared to the change elicited by treatment with the human homeodomain-p200 fusion protein or conjugate, e.g. HOX C12-p200 or HOX D12-p200;
(t) reduced allergic responses and infusion reactions to the 60-amino acid human homeodomain (or variant or portion thereof) conjugates or fusion proteins, as assessed through incorporation of 3H-thymidine by lymphocytes;
(u) a reduction in anti-cargo peptide specific antibody levels
(v) a reduction in the accumulation of a GCase substrate, glycosylceramide;
(w) a reduction in the accumulation of α-synuclein/ubiquitin aggregates in the brain;
(x) a reduction in the urinary excretion of dermatan sulfate;
(y) a reduction in the urinary excretion of heparan sulfate;
(z) a reduction in dermatan sulfate as determined through histopathology;
(aa) a reduction in heparan sulfate as determined through histopathology;
(bb) restoration of electroretinogram (ERG) function;
(cc) restoration of visual acuity as determined through standard clinical methodology;
(dd) a reduction or repression of the mutant Huntingtin gene expression in the HD murine model;
(ee) normalization or improvement in motor deficits in patients, as assessed using the Unified Huntington's Disease Rating Scale (UHDRS) Total Motor Score;
(ff) normalization or improvement in motor deficits in mice as assessed using published methods evaluating grip strength in the forepaws and balance ability on a rotorod balance beam;
(gg) a reduction in neuronal loss and/or reduced striatal cell volume as assessed by molecular methods and histological analysis in the HD murine model;
(hh) an increase in the level of anti-inflammatory interleukin-10 (IL-10) in blood;
(ii) an increase in the level of anti-inflammatory interleukin-10 (IL-10) in BALF;
(jj) a reduction in the level of IP-10 in blood;
(kk) a reduction in the level of IP-10 in BALF;
(l) a reduction in serum amyloid A protein (SAA) in blood;
(mm) a reduction in or human IL-8 in blood or BALF;
(nn) a reduction in GM-CSF in blood or BALF;
(oo) prevention of an increase in graded vitreous haze and/or graded anterior chamber cells;
(pp) prevention of deterioration of visual acuity;
(qq) reduced tumor cell growth and/or reduced tumor growth;
(rr) reduced expression of DYRK1b; and/or
(ss) reduced activation of NF-κB regulated genes.

In another embodiment, the treatment with a formulation comprising a fusion protein and/or conjugate embodiment disclosed in clinical studies will extend over a period, for example, of about 1 day to about 52 weeks, about 1 day to about 26 weeks, about 1 day to about 16 weeks, about 1 day to about 12 weeks, about 1 day to about 10 weeks, about 1 day to about 5 weeks, about 1 week to about 4 weeks, about 2 weeks to about 3 weeks, about 1 day to about 2 weeks, about 1 week, about 1 to 6 days, about 1 to 4 days, or about 1 to 2 days.

In another embodiment, upon treatment with a formulation comprising a fusion protein and/or conjugate embodiments disclosed, the (1) patient(s) or (2) treatment group(s) as disclosed in the studies in the examples, including experimental animals such as mice in animal models, exhibit one or more of the following outcomes compared to controls:
(a) an inhibition in NF-κB transcriptional activity of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(b) a reduction in cytokine production and/or concentration in blood and/or BALF of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(c) a reduction of TNF-α concentration in blood and/or BALF of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(d) a reduction of IL-1 concentration in blood and/or BALF of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(e) a reduction of IL-6 concentration in blood and/or BALF of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(f) a reduction in bronchoalveolar lavage fluid (BALF) inflammatory cell numbers of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(g) a reduction in bronchoalveolar lavage fluid (BALF) cytokines (e.g., TNF-α, IL-1, IL-6, IL-8) of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(h) a reduction in goblet cell infiltration in the epithelial cornea of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(i) an attenuation of the loss of goblet cells in the conjunctiva of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(j) reduced lymph-angiogenesis of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(k) restoration of tear secretion towards normal levels as measured by the Schirmer test, with an increase in Schirmer wetting of more than 20 mm, more than 15 mm, more than 10 mm, more than 5 mm, for example between 5 mm and 20 mm, 10 mm and 20 mm, 5 mm and 15 mm, 5 mm and 10 mm or 15 mm to 20 mm (actual % change or median % change compared to baseline or control);

(l) a reduction in hair loss or an increase in hair growth of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(m) a reduction in the area of necrotic brain tissue of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(n) a reduction in serum C-reactive protein (CRP) of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(o) a reduction in acute mortality (i.e., at one month) of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(p) an improvement in post-myocardial infarction (MI) cardiac output, as measured by ultrasound, of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control)

(q) an improvement in post-stroke neurological function as measured by the percent of patients with a NIHSS of less than 17, one month after presentation, of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(r) an inhibition in kidney growth of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(s) an attenuated change in concentration of osteocalcin using the HOX C12-p21, HOX D12-p21, or other p21-containing fusion protein or conjugate in blood comprising a human homeodomain with cell membrane permeabilizing properties of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to the change elicited by treatment with, e.g., the HOX C12-p200 fusion protein or conjugate or other p200-containing fusion protein or conjugate comprising a human homeodomain with cell membrane permeabilizing properties);

(t) reduced allergic responses and infusion reactions of the 60-amino acid human homeodomain (or variant or portion thereof) conjugates or fusion proteins compared to their cargo proteins alone, as assessed through incorporation of 3H-thymidine by lymphocytes of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change from baseline or control);

(u) a reduction in anti-cargo peptide specific antibody levels after treatment with 60-amino acid human homeodomain (or variant or portion thereof) conjugates or fusion proteins compared to treatment with their cargo proteins alone, of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change from baseline or control);

(v) reduction in the accumulation of a GCase substrate, glycosylceramide of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(w) reduction in the accumulation of α-synuclein/ubiquitin aggregates in the brain of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(x) reduction in the urinary excretion of dermatan sulfate of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(y) reduction in the urinary excretion of heparan sulfate of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(z) reduction in dermatan sulfate as determined through histopathology of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(aa) reduction in heparan sulfate as determined through histopathology of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(bb) the restoration of electroretinogram (ERG) function of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(cc) the restoration of visual acuity as determined through standard clinical methodology of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(dd) a reduction or repression of the mutant Huntingtin gene expression in the HD murine model of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(ee) normalization or improvement in motor deficits in patients, as assessed using the Unified Huntington's Disease Rating Scale (UHDRS) Total Motor Score by an absolute amount of at least about 4 points, at least about 3 points, at least about 2 points, at least about 1.5 points, at least about 1 point, at least about 0.5 point, at least about 0.4 point, at least about 0.3 point, or at least about 0.2 point, for example about 0.5 to about 2 points, about 1 to about 2 points, or about 1.5 to about 2.5 points, and/or an improvement in total motor score of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, about 10% to about 80%, about 10% to about 30%, about 10% to about 20%, about 20% to about 40%, about 30% to about 50% (compared to baseline and untreated control groups);

(ff) normalization or improvement in motor deficits in mice as assessed using published methods evaluating grip strength in the forepaws and balance ability on a rotorod balance beam of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, about 10% to about 80%, about 10% to about 30%, about 10% to about 20%, about 20% to about 40%, about 30% to about 50% (compared to baseline and untreated control groups);

(gg) a reduction in neuronal loss and/or reduced striatal cell volume as assessed by molecular methods and histological analysis in the HD murine model of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(hh) an increase in IL-10 in plasma (blood) and/or BALF of at least about 3,000%, at least about 2,000%, at least about 1,000%, at least about 500%, at least about 380%, at least about 360%, at least about 340%, at least about 320%, at least about 300%, at least about 280%, at least about 260%, at least about 240%, at least about 220%, at least about 200%, at least about 180%, at least about 160%, at least about 140%, at least about 120%, at least about 110%, at least about 100%, at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 400% to about 500%, about 450% to about 500%, about 420% to about 480%, about 300% to about 450%, about 350% to about 430%, about 320% to about 380%, about 200% to about 350%, about 250% to about 330%, about 220% to about 280%, about 100% to about 250%, about 150% to about 230%, about 120% to about 180%, about 50% to about 150%, about 60% to about 130%, about 80% to about 110%, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(ii) an increase in IL-10 in blood or BALF to least about 300 pg/mL, to at least about 400 pg/mL, to least about 500 pg/mL, to least about 600 pg/mL, to least about 800 pg/mL, to least about 1000 pg/mL, to least about 1200 pg/mL, to least about 1400 pg/mL, to least about 1600 pg/mL, to least about 1800 pg/mL, to least about 2000 pg/mL, to least about 2200 pg/mL, to least about 2400 pg/mL, to least about 2600 pg/mL, to least about 2800 pg/mL, to least about 3000 pg/mL, to at least about 4000 pg/ml, for example, about 300 mg/mL to about 3900 pg/mL, about 380 pg/mL to about 2900 pg/mL, about 400 pg/mL to about 2800 pg/mL, about 450 pg/mL to about 2500 pg/mL, about 500 pg/mL to about 2400 pg/mL, about 800 pg/mL to about 3000 pg/mL, about 900 pg/mL to about 2900 pg/mL, about 1200 pg/mL to about 2900 pg/mL, about 1400 pg/mL to about 2900 pg/mL, about 1800 pg/mL to about 2900 pg/mL, about 2000 pg/mL to about 2900 pg/mL, about 2200 pg/mL to about 2900 pg/mL, about 2200 pg/mL to about 3000 pg/mL, about 2500 pg/mL to about 3000 pg/mL, or about 2500 pg/mL to about 3000 pg/mL.

(jj) a reduction in the level of IP-10 in blood and BALF to at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control), (kk) a reduction in serum amyloid A protein (SAA) in blood (plasma) of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(ll) a reduction in Mouse Kc or human IL-8 in blood and/or BALF of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(mm); a reduction in GM-CSF in blood or BALF of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

(nn) prevention of a clinically significant increase in graded vitreous haze and/or graded anterior chamber cells based on commonly accepted clinical criteria known to those expert in the field.

(oo) prevention of deterioration of a clinically significant change in visual acuity based on commonly used and accepted criteria known to those expert in the field;

(pp) reduced tumor cell growth and/or reduced tumor growth of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control); and/or (rr) reduced expression of DYRK1b of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control); and/or (ss) reduced activation of NF-κB regulated genes of at least about 99%, at least about 95%, at least about 90%, at least about 80%, at least about 70%, at least about 60%, at least about 50%, at least about 40%, at least about 35%, at least about 30%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control).

According to the embodiments disclosed and their modifications, the conjugates or fusion proteins may be used alone or in combination with other treatments or components of other treatments. Diseases and disorders or conditions that may be treated include, but are not limited to: cancer, inflammation or inflammatory disease, dermatological disorders, fever, cardiovascular effects, hemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumor growth, invasion and spread, angiogenesis, metastases, malignant, ascites and malignant pleural effusion; cerebral ischemia, ischemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosciersosis, cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumor immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration: inhibition or activation of follicle-stimulating hormone (modulation of fertility); chemotactic/chemokinetic activity (e.g. for mobilizing specific cell types to sites of injury or infection); haemostatic and thrombolytic activity (e.g. for treating hemophilia and stroke); antiinflammatory activity (for treating e.g. septic shock or Crohn's disease); as antimicrobials: modulators of e.g. metabolism or behavior; as analgesics; treating specific deficiency disorders; in treatment of e.g. psoriasis, in human or veterinary medicine; macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scieritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumor cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

TABLE 3

Peptide Sequence Identities.

| Sequence ID No | Descriptor or Gene from which the Sequence was Derived | Sequence |
| --- | --- | --- |
| 1 | HOX C12 | SRKKRKPYSKLQLAELEGEFLVNEFITRQRRRELSD RLNLSDQQVKIWFQNRRMKKKRLL |
| 2 | HOX D12 | ARKKRKPYTKQQIAELENEFLVNEFINRQKRKELSN RLNLSDQQVKIWFQNRRMKKKRVV |
| 3 | OTP | QKRHRTRFTPAQLNELERSFAKTHYPDIFMREELAL RIGLTESRVQVWFQNRRAKWKKRK |
| 4 | TLX1 | KKKPRTSFTRLQICELEKRFHRQKYLASAERAALAK ALKMTDAQVKTWFQNRRTKWRRQT |
| 5 | TLX3 | RKKPRTSFSRVQICELEKRFHRQKYLASAERAALAK SLKMTDAQVKTWFQNRRTKWRRQT |
| 6 | TLX2 | RKKPRTSFSRSQVLELERRFLRQKYLASAERAALAK ALRMTDAQVKTWFQNRRTKWRRQT |
| 7 | NKX6-1 | RKHTRPTFSGQQIFALEKTFEQTKYLAGPERARLAY SLGMTESQVKVWFQNRRTKWRKKH |
| 8 | NKX6-2 | KKHSRPTFSGQQIFALEKTFEQTKYLAGPERARLAY SLGMTESQVKVWFQNRRTKWRKRH |
| 9 | NKX6-3 | KKHTRPTFTGHQIFALEKTFEQTKYLAGPERARLAY SLGMTESQVKVWFQNRRTKWRKKS |
| 10 | NKX3-2 | KKRSRAAFSHAQVFELERRFNHQRYLSGPERADLA ASLKLTETQVKIWFQNRRYKTKRRQ |
| 11 | BARHL1 | PRKARTAFTDHQLAQLERSFERQKYLSVQDRMELA ASLNLTDTQVKTWYQNRRTKWKRQT |
| 12 | BARHL2 | PRKARTAFSDHQLNQLERSFERQKYLSVQDRMDLA AALNLTDTQVKTWYQNRRTKWKRQT |
| 13 | BARX1 | GRRSRTVFTELQLMGLEKRFEKQKYLSTPDRIDLAE SLGLSQLQVKTWYQNRRMKWKKIV |
| 14 | BARX2 | PRRSRTIFTELQLMGLEKKFQKQKYLSTPDRLDLAQ SLGLTQLQVKTWYQNRRMKWKKMV |
| 15 | BSX | RRKARTVFSDSQLSGLEKRFEIQRYLSTPERVELAT ALSLSETQVKTWFQNRRMKHKKQL |
| 16 | DLX2 | VRKPRTIYSSFQLAALQRRFQKTQYLALPERAELAA SLGLTQTQVKIWFQNRRSKFKKMW |
| 17 | DLX3 | VRKPRTIYSSYQLAALQRRFQKAQYLALPERAELA AQLGLTQTQVKIWFQNRRSKFKKLY |
| 18 | DBX1 | GMLRRAVFSDVQRKALEKMFQKQKYISKPDRKKL AAKLGLKDSQVKIWFQNRRMKWRNSK |
| 19 | DBX2 | GILRRAVFSEDQRKALEKMFQKQKYISKTDRKKLAI NLGLKESQVKIWFQNRRMKWRNSK |
| 20 | NEMO binding domain ("NBD") (second region peptide only) | TALDWSWLQTE |

TABLE 3-continued

Peptide Sequence Identities.

| Sequence ID No | Descriptor or Gene from which the Sequence was Derived | Sequence |
|---|---|---|
| 21 | HOX C12-NBD (Entire sequence: combined SEQ ID Nos. 1 and 20) | SRKKRKPYSKLQLAELEGEFLVNEFITRQRRRELSDRLNLSDQQVKIWFQNRRMKKKRLLTALDWSWLQTE |
| 22 | HOX D12-NBD (Entire sequence: combined SEQ ID Nos. 2 and 20) | ARKKRKPYTKQQIAELENEFLVNEFINRQKRKELSNRLNLSDQQVKIWFQNRRMKKKRVVTALDWSWLQTE |
| 23 | p200 peptide derived from the PC1 CTT (second region peptide only) | VILRWRYHALRGELYRPAWEPQDYEMVELFLRRLRLWMGLSKVKEFRHKVRFEGMEPLPSRSSRGSKVSPDVPPPSAGSDASHPSTSSSQLDGLSVSLGRLGTRCEPEPSRLQAVFEALLTQFDRLNQATEDVYQLEQQLHSLQGRRSSRAPAGSSRGPSPGLRPALPSRLARASRGVDLATGPSRTPLRAKNKVHPSST |
| 24 | HOX C12-p200 (Entire sequence: combined SEQ ID Nos. 1 and 23, also showing initiating methionine residue) | MSRKKRKPYSKLQLAELEGEFLVNEFITRQRRRELSDRLNLSDQQVKIWFQNRRMKKKRLLVILRWRYHALRGELYRPAWEPQDYEMVELFLRRLRLWMGLSKVKEFRHKVRFEGMEPLPSRSSRGSKVSPDVPPPSAGSDASHPSTSSSQLDGLSVSLGRLGTRCEPEPSRLQAVFEALLTQFDRLNQATEDVYQLEQQLHSLQGRRSSRAPAGSSRGPSPGLRPALPSRLARASRGVDLATGPSRTPLRAKNKVHPSST |
| 25 | HOX D12-p200 (Entire sequence: combined SEQ ID Nos. 2 and 23, also showing initiating methionine residue) | MARKKRKPYTKQQIAELENEFLVNEFINRQKRKELSNRLNLSDQQVKIWFQNRRMKKKRVVVILRWRYHALRGELYRPAWEPQDYEMVELFLRRLRLWMGLSKVKEFRHKVRFEGMEPLPSRSSRGSKVSPDVPPPSAGSDASHPSTSSSQLDGLSVSLGRLGTRCEPEPSRLQAVFEALLTQFDRLNQATEDVYQLEQQLHSLQGRRSSRAPAGSSRGPSPGLRPALPSRLARASRGVDLATGPSRTPLRAKNKVHPSST |
| 26 | p21 peptide (alternate second region peptide for PKD structures) | IRRIRLWMGLSKVKEFRHKVR |
| 27 | HOX C12-p21 (Entire sequence: combined SEQ ID Nos. 1 and 26, also showing initiating methionine residue) | MSRKKRKPYSKLQLAELEGEFLVNEFITRQRRRELSDRLNLSDQQVKIWFQNRRMKKKRLLIRRIRLWMGLSKVKEFRHKVR |
| 28 | HOX D12-p21 (Entire sequence: combined SEQ ID Nos. 2 and 26, also showing initiating methionine residue) | MARKKRKPYTKQQIAELENEFLVNEFINRQKRKELSNRLNLSDQQVKIWFQNRRMKKKRVVIRRIRLWMGLSKVKEFRHKVR |

TABLE 3-continued

Peptide Sequence Identities.

| Sequence ID No | Descriptor or Gene from which the Sequence was Derived | Sequence |
|---|---|---|
| 29 | VRQ397- (noncompetitive V2 receptor antagonist. that can be linked to protein structures for targeting p21 and p200 containing HOX or Human Homeodomain fusion peptides) | CRAVKY |
| 30 | glucocerbrosi-daseamino acid sequence ("GCase") (second region peptide only) | ARPCIPKSFGYSSVVCVCNATYCDSFDPPTFPALGTF SRYESTRSGRRMELSMGPIQANHTGTGLLLTLQPEQ KFQKVKGFGGAMTDAAALNILALSPPAQNLLLKSY FSEEGIGYNIIRVPMASCDFSIRTYTYADTPDDFQLH NFSLPEEDTKLKIPLIHRALQLAQRPVSLLASPWTSP TWLKTNGAVNGKGSLKGQPGDIYHQTWARYFVKF LDAYAEHKLQFWAVTAENEPSAGLLSGYPFQCLGF TPEHQRDFIARDLGPTLANSTHHNVRLLMLDDQRL LLPHWAKVVLTDPEAAKYVHGIAVHWYLDFLAPA KATLGETHRLFPNTMLFASEACVGSKFWEQSVRLG SWDRGMQYSHSIITNLLYHVVGWTDWNLALNPEG GPNWVRNFVDSPIIVDITKDTFYKQPMFYHLGHFSK FIPEGSQRVGLVASQKNDLDAVALMHPDGSAVVV VLNRSSKDVPLTIKDPAVGFLETISPGYSIHTYLWRR Q |
| 31 | HOX C12-GCase (Entire sequence: combined SEQ ID Nos. 1 and 30, also showing initiating methionine residue) | MSRKKRKPYSKLQLAELEGEFLVNEFITRQRRRELS DRLNLSDQQVKIWFQNRRMKKKRLLARPCIPKSFG YSSVVCVCNATYCDSFDPPTFPALGTFSRYESTRSG RRMELSMGPIQANHTGTGLLLTLQPEQKFQKVKGF GGAMTDAAALNILALSPPAQNLLLKSYFSEEGIGYN IIRVPMASCDFSIRTYTYADTPDDFQLHNFSLPEEDT KLKIPLIHRALQLAQRPVSLLASPWTSPTWLKTNGA VNGKGSLKGQPGDIYHQTWARYFVKFLDAYAEHK LQFWAVTAENEPSAGLLSGYPFQCLGFTPEHQRDFI ARDLGPTLANSTHHNVRLLMLDDQRLLLPHWAKV VLTDPEAAKYVHGIAVHWYLDFLAPAKATLGETH RLFPNTMLFASEACVGSKFWEQSVRLGSWDRGMQ YSHSIITNLLYHVVGWTDWNLALNPEGGPNWVRN FVDSPIIVDITKDTFYKQPMFYHLGHFSKFIPEGSQR VGLVASQKNDLDAVALMHPDGSAVVVVLNRSSKD VPLTIKDPAVGFLETISPGYSIHTYLWRRQ |
| 32 | HOX D12-GC ase (Entire sequence: combined SEQ ID Nos. 2 and 30, also showing initiating methionine residue) | MARKKRKPYTKQQIAELENEFLVNEFINRQKRKEL SNRLNLSDQQVKIWFQNRRMKKKRVVARPCIPKSF GYSSVVCVCNATYCDSFDPPTFPALGTFSRYESTRS GRRMELSMGPIQANHTGTGLLLTLQPEQKFQKVKG FGGAMTDAAALNILALSPPAQNLLLKSYFSEEGIGY NIIRVPMASCDFSIRTYTYADTPDDFQLHNFSLPEED TKLKIPLIHRALQLAQRPVSLLASPWTSPTWLKTNG AVNGKGSLKGQPGDIYHQTWARYFVKFLDAYAEH KLQFWAVTAENEPSAGLLSGYPFQCLGFTPEHQRD FIARDLGPTLANSTHHNVRLLMLDDQRLLLPHWAK VVLTDPEAAKYVHGIAVHWYLDFLAPAKATLGET HRLFPNTMLFASEACVGSKFWEQSVRLGSWDRGM QYSHSIITNLLYHVVGWTDWNLALNPEGGPNWVR NFVDSPIIVDITKDTFYKQPMFYHLGHFSKFIPEGSQ RVGLVASQKNDLDAVALMHPDGSAVVVVLNRSSK DVPLTIKDPAVGFLETISPGYSIHTYLWRRQ |
| 33 | RetGC-1 (second region peptide only) | AVFTVGVLGPWACDPIFSRARPDLAARLAAARLNR DPGLAGGPRFEVALLPEPCRTPGSLGAVSSALARVS GLVGPVNPAACRPAELLAEEAGIALVPWGCPWTQA EGTTAPAVTPAADALYALLRAFGWARVALVTAPQ DLWVEAGRSLSTALRARGLPVASVTSMEPLDLSGA REALRKVRDGPRVTAVIMVMHSVLLGGEEQRYLL EAAEELGLTDGSLVFLPFDTIHYALSPGPEALAALA |

TABLE 3-continued

Peptide Sequence Identities.

| Sequence ID No | Descriptor or Gene from which the Sequence was Derived | Sequence |
|---|---|---|
| | | NSSQLRRAHDAVLTLTRHCPSEGSVLDSLRRAQER RELPSDLNLQQVSPLFGTIYDAVFLLARGVAEARAA AGGRWVSGAAVARHIRDAQVPGFCGDLGGDEEPP FVLLDTDAAGDRLFATYMLDPARGSFLSAGTRMHF PRGGSAPGPDPSCWFDPNNICGGGLEPGLVFLGFLL VVGMGLAGAFLAHYVRHRLLHMQMVSGPNKIILT VDDITFLHPHGGTSRKVAQGSRSSLGARSMSDIRSG PSQHLDSPNIGVYEGDRVWLKKFPGDQHIAIRPATK TAFSKLQELRHENVALYLGLFLARGAEGPAALWEG NLAVVSEHCTRGSLQDLLAQREIKLDWMFKSSLLL DLIKGIRYLHHRGVAHGRLKSRNCIVDGRFVLKITD HGHGRLLEAQKVLPEPPRAEDQLWTAPELLRDPAL ERRGTLAGDVFSLAIIMQEVVCRSAPYAMLELTPEE VVQRVRSPPPLCRPLVSMDQAPVECILLMKQCWAE QPELRPSMDHTFDLFKNINKGRKTNIIDSMLRMLEQ YSSNLEDLIRERTEELELEKQKTDRLLTQMLPPSVA EALKTGTPVEPEYFEQVTLYFSDIVGFTTISAMSEPI EVVDLLNDLYTLFDAIIGSHDVYKVETIGDAYMVA SGLPQRNGQRHAAEIANMSLDILSAVGTFRMRHMP EVPVRIRIGLHSGPCVAGVVGLTMPRYCLFGDTVN TASRMESTGLPYRIHVNLSTVGILRALDSGYQVELR GRTELKGKGAEDTFWLVGRRGFNKPIPKPPDLQPG SSNHGISLQEIPPERRRKLEKARPGQFS |
| 34 | HOX C12-RetGC-1 (Entire sequence: combined SEQ ID Nos. 1 and 33, also showing initiating methionine residue) | MSRKKRKPYSKLQLAELEGEFLVNEFITRQRRRELS DRLNLSDQQVKIWFQNRRMKKKRLLAVFTVGVLG PWACDPIFSRARPDLAARLAAARLNRDPGLAGGPR FEVALLPEPCRTPGSLGAVSSALARVSGLVGPVNPA ACRPAELLAEEAGIALVPWGCPWTQAEGTTAPAVT PAADALYALLRAFGWARVALVTAPQDLWVEAGRS LSTALRARGLPVASVTSMEPLDLSGAREALRKVRD GPRVTAVIMVMHSVLLGGEEQRYLLEAAEELGLTD GSLVFLPFDTIHYALSPGPEALAALANSSQLRRAHD AVLTLTRHCPSEGSVLDSLRRAQERRELPSDLNLQQ VSPLFGTIYDAVFLLARGVAEARAAAGGRWVSGA AVARHIRDAQVPGFCGDLGGDEEPPFVLLDTDAAG DRLFATYMLDPARGSFLSAGTRMHFPRGGSAPGPD PSCWFDPNNICGGGLEPGLVFLGFLLVVGMGLAGA FLAHYVRHRLLHMQMVSGPNKIILTVDDITFLHPHG GTSRKVAQGSRSSLGARSMSDIRSGPSQHLDSPNIG VYEGDRVWLKKFPGDQHIAIRPATKTAFSKLQELR HENVALYLGLFLARGAEGPAALWEGNLAVVSEHC TRGSLQDLLAQREIKLDWMFKSSLLLDLIKGIRYLH HRGVAHGRLKSRNCIVDGRFVLKITDHGHGRLLEA QKVLPEPPRAEDQLWTAPELLRDPALERRGTLAGD VFSLAIIMQEVVCRSAPYAMLELTPEEVVQRVRSPP PLCRPLVSMDQAPVECILLMKQCWAEQPELRPSMD HTFDLFKNINKGRKTNIIDSMLRMLEQYSSNLEDLI RERTEELELEKQKTDRLLTQMLPPSVAEALKTGTPV EPEYFEQVTLYFSDIVGFTTISAMSEPIEVVDLLNDL YTLFDAIIGSHDVYKVETIGDAYMVASGLPQRNGQ RHAAEIANMSLDILSAVGTFRMRHMPEVPVRIRIGL HSGPCVAGVVGLTMPRYCLFGDTVNTASRMESTG LPYRIHVNLSTVGILRALDSGYQVELRGRTELKGKG AEDTFWLVGRRGFNKPIPKPPDLQPGSSNHGISLQEI PPERRRKLEKARPGQFS |
| 35 | HOX D12-RetGC-1 (Entire sequence: combined SEQ ID Nos. 2 and 33, also showing initiating methionine residue) | MARKKRKPYTKQQIAELENEFLVNEFINRQKRKEL SNRLNLSDQQVKIWFQNRRMKKKRVVAVFTVGVL GPWACDPIFSRARPDLAARLAAARLNRDPGLAGGP RFEVALLPEPCRTPGSLGAVSSALARVSGLVGPVNP AACRPAELLAEEAGIALVPWGCPWTQAEGTTAPAV TPAADALYALLRAFGWARVALVTAPQDLWVEAGR SLSTALRARGLPVASVTSMEPLDLSGAREALRKVR DGPRVTAVIMVMHSVLLGGEEQRYLLEAAEELGLT DGSLVFLPFDTIHYALSPGPEALAALANSSQLRRAH DAVLTLTRHCPSEGSVLDSLRRAQERRELPSDLNLQ QVSPLFGTIYDAVFLLARGVAEARAAAGGRWVSG AAVARHIRDAQVPGFCGDLGGDEEPPFVLLDTDAA GDRLFATYMLDPARGSFLSAGTRMHFPRGGSAPGP DPSCWFDPNNICGGGLEPGLVFLGFLLVVGMGLAG AFLAHYVRHRLLHMQMVSGPNKIILTVDDITFLHPH GGTSRKVAQGSRSSLGARSMSDIRSGPSQHLDSPNI |

TABLE 3-continued

Peptide Sequence Identities.

| Sequence ID No | Descriptor or Gene from which the Sequence was Derived | Sequence |
|---|---|---|
| | | GVYEGDRVWLKKFPGDQHIAIRPATKTAFSKLQEL RHENVALYLGLFLARGAEGPAALWEGNLAVVSEH CTRGSLQDLLAQREIKLDWMFKSSLLLDLIKGIRYL HHRGVAHGRLKSRNCIVDGRFVLKITDHGHGRLLE AQKVLPEPPRAEDQLWTAPELLRDPALERRGTLAG DVFSLAIIMQEVVCRSAPYAMLELTPEEVVQRVRSP PPLCRPLVSMDQAPVECILLMKQCWAEQPELRPSM DHTFDLFKNINKGRKTNIIDSMLRMLEQYSSNLEDL IRERTEELELEKQKTDRLLTQMLPPSVAEALKTGTP VEPEYFEQVTLYFSDIVGFTTISAMSEPIEVVDLLND LYTLFDAIIGSHDVYKVETIGDAYMVASGLPQRNG QRHAAEIANMSLDILSAVGTFRMRHMPEVPVRIRIG LHSGPCVAGVVGLTMPRYCLFGDTVNTASRMEST GLPYRIHVNLSTVGILRALDSGYQVELRGRTELKGK GAEDTFWLVGRRGFNKPIPKPPDLQPGSSNHGISLQ EIPPERRRKLEKARPGQFS |
| 36 | ZF6xHunt-Kox-1 (second region peptide only) showing 6 zinc finger repeats | TGAERPFQCRICMRNFSQRATLQRHIRTHTGEKPFA CDICGRKFAQRATLQRHTKIHTGSERPFQCRICMRN FSQRATLQRHIRTHTGEKPFACDICGRKFAQRATLQ RHTKIHTGSERPFQCRICMRNFSQRATLQRHIRTHT GEKPFACDICGRKFAQRATLQRHTKIHLRQKDGGG GSGGGGSGGGGSQLVSSLSPQHSAVTQGIIKNKEG MDAKSLTAWSRTLVTFKDVFVDFTREEWKLLDTA QQIVYRNVMLENYKNLVSLGYQLTKPDVILRLEKG EEPWLVEREIHQETHPDSETAFEIKSSV |
| 37 | HOX C12-ZF6xHunt-Kox-1 (Entire sequence: combined SEQ ID Nos. 1 and 36, also showing initiating methionine residue) | MSRKKRKPYSKLQLAELEGEFLVNEFITRQRRRELS DRLNLSDQQVKIWFQNRRMKKKRLLTGAERPFQC RICMRNFSQRATLQRHIRTHTGEKPFACDICGRKFA QRATLQRHTKIHTGSERPFQCRICMRNFSQRATLQR HIRTHTGEKPFACDICGRKFAQRATLQRHTKIHTGS ERPFQCRICMRNFSQRATLQRHIRTHTGEKPFACDI CGRKFAQRATLQRHTKIHLRQKDGGGGSGGGGSG GGGSQLVSSLSPQHSAVTQGIIKNKEGMDAKSLTA WSRTLVTFKDVFVDFTREEWKLLDTAQQIVYRNV MLENYKNLVSLGYQLTKPDVILRLEKGEEPWLVER EIHQETHPDSETAFEIKSSV |
| 38 | HOX D12-ZF6xHunt-Kox-1 (Entire sequence: combined SEQ ID Nos. 2 and 36, also showing initiating methionine residue) | MARKKRKPYTKQQIAELENEFLVNEFINRQKRKEL SNRLNLSDQQVKIWFQNRRMKKKRVVTGAERPFQ CRICMRNFSQRATLQRHIRTHTGEKPFACDICGRKF AQRATLQRHTKIHTGSERPFQCRICMRNFSQRATLQ RHIRTHTGEKPFACDICGRKFAQRATLQRHTKIHTG SERPFQCRICMRNFSQRATLQRHIRTHTGEKPFACDI CGRKFAQRATLQRHTKIHLRQKDGGGGSGGGGSG GGGSQLVSSLSPQHSAVTQGIIKNKEGMDAKSLTA WSRTLVTFKDVFVDFTREEWKLLDTAQQIVYRNV MLENYKNLVSLGYQLTKPDVILRLEKGEEPWLVER EIHQETHPDSETAFEIKSSV |
| 39 | ZF12xHunt-Kox-1 (second region peptide only) showing 12 zinc finger repeats | TGAERPFQCRICMRNFSQRATLQRHIRTHTGEKPFA CDICGRKFAQRATLQRHTKIHTGSERPFQCRICMRN FSQRATLQRHIRTHTGEKPFACDICGRKFAQRATLQ RHTKIHTGSERPFQCRICMRNFSQRATLQRHIRTHT GEKPFACDICGRKFAQRATLQRHTKIHLRQKDGGG GSGGGGSQLVGTAERPFQCRICMRNFSQRA TLQRHIRTHTGEKPFACDICGRKFAQRATLQRHTKI HTGSERPFQCRICMRNFSQRATLQRHIRTHTGEKPF ACDICGRKFAQRATLQRHTKIHTGSERPFQCRICMR NFSQRATLQRHIRTHTGEKPFACDICGRKFAQRATL QRHTKIHLRQKDGGGGSGGGGSGGGGSQLVSSLSP QHSAVTQGIIKNKEGMDAKSLTAWSRTLVTFKDVF VDFTREEWKLLDTAQQIVYRNVMLENYKNLVSLG YQLTKPDVILRLEKGEEPWLVEREIHQETHPDSETA FEIKSSV |
| 40 | HOX C12-ZF12xHunt-Kox-1 (entire sequence, combined SEQ ID Nos. 1 and | MSRKKRKPYSKLQLAELEGEFLVNEFITRQRRRELS DRLNLSDQQVKIWFQNRRMKKKRLLTGAERPFQC RICMRNFSQRATLQRHIRTHTGEKPFACDICGRKFA QRATLQRHTKIHTGSERPFQCRICMRNFSQRATLQR HIRTHTGEKPFACDICGRKFAQRATLQRHTKIHTGS ERPFQCRICMRNFSQRATLQRHIRTHTGEKPFACDI |

TABLE 3-continued

Peptide Sequence Identities.

| Sequence ID No | Descriptor or Gene from which the Sequence was Derived | Sequence |
|---|---|---|
| | 39, also showing initiating methionine residue) | CGRKFAQRATLQRHTKIHLRQKDGGGGSGGGGSG GGGSQLVGTAERPFQCRICMRNFSQRATLQRHIRTH TGEKPFACDICGRKFAQRATLQRHTKIHTGSERPFQ CRICMRNFSQRATLQRHIRTHTGEKPFACDICGRKF AQRATLQRHTKIHTGSERPFQCRICMRNFSQRATLQ RHIRTHTGEKPFACDICGRKFAQRATLQRHTKIHLR QKDGGGGSGGGGSGGGGSQLVSSLSPQHSAVTQGI IKNKEGMDAKSLTAWSRTLVTFKDVFVDFTREEW KLLDTAQQIVYRNVMLENYKNLVSLGYQLTKPDVI LRLEKGEEPWLVEREIHQETHPDSETAFEIKSSV |
| 41 | HOX D12-ZF12xHunt-Kox-1 (entire sequence, combined SEQ ID Nos. 2 and 39, also showing initiating methionine residue) | MARKKRKPYTKQQIAELENEFLVNEFINRQKRKEL SNRLNLSDQQVKIWFQNRRMKKKRVVTGAERPFQ CRICMRNFSQRATLQRHIRTHTGEKPFACDICGRKF AQRATLQRHTKIHTGSERPFQCRICMRNFSQRATLQ RHIRTHTGEKPFACDICGRKFAQRATLQRHTKIHTG SERPFQCRICMRNFSQRATLQRHIRTHTGEKPFACDI CGRKFAQRATLQRHTKIHLRQKDGGGGSGGGGSG GGGSQLVGTAERPFQCRICMRNFSQRATLQRHIRTH TGEKPFACDICGRKFAQRATLQRHTKIHTGSERPFQ CRICMRNFSQRATLQRHIRTHTGEKPFACDICGRKF AQRATLQRHTKIHTGSERPFQCRICMRNFSQRATLQ RHIRTHTGEKPFACDICGRKFAQRATLQRHTKIHLR QKDGGGGSGGGGSGGGGSQLVSSLSPQHSAVTQGI IKNKEGMDAKSLTAWSRTLVTFKDVFVDFTREEW KLLDTAQQIVYRNVMLENYKNLVSLGYQLTKPDVI LRLEKGEEPWLVEREIHQETHPDSETAFEIKSSV |
| 42 | ZF18xHunt-Kox-1 (second region peptide only) showing 18 zinc finger repeats | TGAERPFQCRICMRNFSQRATLQRHIRTHTGEKPFA CDICGRKFAQRATLQRHTKIHTGSERPFQCRICMRN FSQRATLQRHIRTHTGEKPFACDICGRKFAQRATLQ RHTKIHTGSERPFQCRICMRNFSQRATLQRHIRTHT GEKPFACDICGRKFAQRATLQRHTKIHLRQKDGGG GSGGGGSGGGGSQLVGTAERPFQCRICMRNFSQRA TLQRHIRTHTGEKPFACDICGRKFAQRATLQRHTKI HTGSERPFQCRICMRNFSQRATLQRHIRTHTGEKPF ACDICGRKFAQRATLQRHTKIHTGSERPFQCRICMR NFSQRATLQRHIRTHTGEKPFACDICGRKFAQRATL QRHTKIHLRQKDGGGGSGGGGSGGGGSQLVGTAE RPFQCRICMRNFSQRATLQRHIRTHTGEKPFACDIC GRKFAQRATLQRHTKIHTGSERPFQCRICMRNFSQR ATLQRHIRTHTGEKPFACDICGRKFAQRATLQRHTK IHTGSERPFQCRICMRNFSQRATLQRHIRTHTGEKPF ACDICGRKFAQRATLQRHTKIHLRQKDGGGGSGGG GSGGGGSQLVSSLSPQHSAVTQGIIKNKEGMDAKS LTAWSRTLVTFKDVFVDFTREEWKLLDTAQQIVYR NVMLENYKNLVSLGYQLTKPDVILRLEKGEEPWLV EREIHQETHPDSETAFEIKSSV |
| 43 | HOX C12-ZF18xHunt-Kox-1 (entire sequence, combined SEQ ID Nos. 1 and 42, also showing initiating methionine residue) | MSRKKRKPYSKLQLAELEGEFLVNEFITRQRRRELS DRLNLSDQQVKIWFQNRRMKKKRLLTGAERPFQC RICMRNFSQRATLQRHIRTHTGEKPFACDICGRKFA QRATLQRHTKIHTGSERPFQCRICMRNFSQRATLQR HIRTHTGEKPFACDICGRKFAQRATLQRHTKIHTGS ERPFQCRICMRNFSQRATLQRHIRTHTGEKPFACDI CGRKFAQRATLQRHTKIHLRQKDGGGGSGGGGSG GGGSQLVGTAERPFQCRICMRNFSQRATLQRHIRTH TGEKPFACDICGRKFAQRATLQRHTKIHTGSERPFQ CRICMRNFSQRATLQRHIRTHTGEKPFACDICGRKF AQRATLQRHTKIHTGSERPFQCRICMRNFSQRATLQ RHIRTHTGEKPFACDICGRKFAQRATLQRHTKIHLR QKDGGGGSGGGGSGGGGSQLVGTAERPFQCRICM RNFSQRATLQRHIRTHTGEKPFACDICGRKFAQRAT LQRHTKIHTGSERPFQCRICMRNFSQRATLQRHIRT HTGEKPFACDICGRKFAQRATLQRHTKIHTGSERPF QCRICMRNFSQRATLQRHIRTHTGEKPFACDICGRK FAQRATLQRHTKIHLRQKDGGGGSGGGGSGGGGS QLVSSLSPQHSAVTQGIIKNKEGMDAKSLTAWSRT LVTFKDVFVDFTREEWKLLDTAQQIVYRNVMLEN YKNLVSLGYQLTKPDVILRLEKGEEPWLVEREIHQE THPDSETAFEIKSSV |

TABLE 3-continued

Peptide Sequence Identities.

| Sequence ID No | Descriptor or Gene from which the Sequence was Derived | Sequence |
|---|---|---|
| 44 | HOX D12-ZF12xHunt-Kox-1 (entire sequence, combined SEQ ID Nos. 2 and 42, also showing initiating methionine residue) | MARKKRKPYTKQQIAELENEFLVNEFINRQKRKEL SNRLNLSDQQVKIWFQNRRMKKKRVVTGAERPFQ CRICMRNFSQRATLQRHIRTHTGEKPFACDICGRKF AQRATLQRHTKIHTGSERPFQCRICMRNFSQRATLQ RHIRTHTGEKPFACDICGRKFAQRATLQRHTKIHTG SERPFQCRICMRNFSQRATLQRHIRTHTGEKPFACDI CGRKFAQRATLQRHTKIHLRQKDGGGGSGGGGSG GGGSQLVGTAERPFQCRICMRNFSQRATLQRHIRTH TGEKPFACDICGRKFAQRATLQRHTKIHTGSERPFQ CRICMRNFSQRATLQRHIRTHTGEKPFACDICGRKF AQRATLQRHTKIHTGSERPFQCRICMRNFSQRATLQ RHIRTHTGEKPFACDICGRKFAQRATLQRHTKIHLR QKDGGGGSGGGGSGGGGSQLVGTAERPFQCRICM RNFSQRATLQRHIRTHTGEKPFACDICGRKFAQRAT LQRHTKIHTGSERPFQCRICMRNFSQRATLQRHIRT HTGEKPFACDICGRKFAQRATLQRHTKIHTGSERPF QCRICMRNFSQRATLQRHIRTHTGEKPFACDICGRK FAQRATLQRHTKIHLRQKDGGGGSGGGGSGGGGS QLVSSLSPQHSAVTQGIIKNKEGMDAKSLTAWSRT LVTFKDVFVDFTREEWKLLDTAQQIVYRNVMLEN YKNLVSLGYQLTKPDVILRLEKGEEPWLVEREIHQE THPDSETAFEIKSSV |
| 45 | Alpha-L-iduronidase (second region 653 amino acid second region peptide including the 27 amino acid signal sequence) | MRPLRPRAALLALLASLLAAPPVAPAEAPHLVHVD AARALWPLRRFWRSTGFCPPLPHSQADQYVLSWD QQLNLAYVGAVPHRGIKQVRTHWLLELVTTRGST GRGLSYNFTHLDGYLDLLRENQLLPGFELMGSASG HFTDFEDKQQVFEWKDLVSSLARRYIGRYGLAHVS KWNFETWNEPDHHDFDNVSMTMQGFLNYYDACS EGLRAASPALRLGGPGDSFHTPPRSPLSWGLLRHCH DGTNFFTGEAGVRLDYISLHRKGARSSISILEQEKV VAQQIRQLFPKFADTPIYNDEADPLVGWSLPQPWR ADVTYAAMVVKVIAQHQNLLLANTTSAFPYALLS NDNAFLSYHPHPFAQRTLTARFQVNNTRPPHVQLL RKPVLTAMGLLALLDEEQLWAEVSQAGTVLDSNH TVGVLASAHRPQGPADAWRAAVLIYASDDTRAHP NRSVAVTLRLRGVPPGPGLVYVTRYLDNGLCSPDG EWRRLGRPVFPTAEQFRRMRAAEDPVAAAPRPLPA GGRLTLRPALRLPSLLLVHVCARPEKPPGQVTRLRA LPLTQGQLVLVWSDEHVGSKCLWTYEIQFSQDGKA YTPVSRKPSTFNLFVFSPDTGAVSGSYRVRALDYW ARPGPFSDPVPYLEVPVPRGPPSPGNP |
| 46 | HOX C12-Alpha-L-iduronidase (Entire sequence, combined SEQ ID Nos. 1 and 45, also showing initiating methionine residue | MSRKKRKPYSKLQLAELEGEFLVNEFITRQRRRELS DRLNLSDQQVKIWFQNRRMKKKRLLMRPLRPRAA LLALLASLLAAPPVAPAEAPHLVHVDAARALWPLR RFWRSTGFCPPLPHSQADQYVLSWDQQLNLAYVG AVPHRGIKQVRTHWLLELVTTRGSTGRGLSYNFTH LDGYLDLLRENQLLPGFELMGSASGHFTDFEDKQQ VFEWKDLVSSLARRYIGRYGLAHVSKWNFETWNE PDHHDFDNVSMTMQGFLNYYDACSEGLRAASPAL RLGGPGDSFHTPPRSPLSWGLLRHCHDGTNFFTGEA GVRLDYISLHRKGARSSISILEQEKVVAQQIRQLFPK FADTPIYNDEADPLVGWSLPQPWRADVTYAAMVV KVIAQHQNLLLANTTSAFPYALLSNDNAFLSYHPHP FAQRTLTARFQVNNTRPPHVQLLRKPVLTAMGLLA LLDEEQLWAEVSQAGTVLDSNHTVGVLASAHRPQ GPADAWRAAVLIYASDDTRAHPNRSVAVTLRLRG VPPGPGLVYVTRYLDNGLCSPDGEWRRLGRPVFPT AEQFRRMRAAEDPVAAAPRPLPAGGRLTLRPALRL PSLLLVHVCARPEKPPGQVTRLRALPLTQGQLVLV WSDEHVGSKCLWTYEIQFSQDGKAYTPVSRKPSTF NLFVFSPDTGAVSGSYRVRALDYWARPGPFSDPVP YLEVPVPRGPPSPGNP |
| 47 | HOX D12-Alpha-L-iduronidase (Entire sequence, combined SEQ ID Nos. 2 and 45, also | MARKKRKPYTKQQIAELENEFLVNEFINRQKRKEL SNRLNLSDQQVKIWFQNRRMKKKRVVMRPLRPRA ALLALLASLLAAPPVAPAEAPHLVHVDAARALWPL RRFWRSTGFCPPLPHSQADQYVLSWDQQLNLAYV GAVPHRGIKQVRTHWLLELVTTRGSTGRGLSYNFT HLDGYLDLLRENQLLPGFELMGSASGHFTDFEDKQ QVFEWKDLVSSLARRYIGRYGLAHVSKWNFETWN EPDHHDFDNVSMTMQGFLNYYDACSEGLRAASPA |

TABLE 3-continued

Peptide Sequence Identities.

| Sequence ID No | Descriptor or Gene from which the Sequence was Derived | Sequence |
| --- | --- | --- |
| | showing initiating methionine residue | LRLGGPGDSFHTPPRSPLSWGLLRHCHDGTNFFTGE AGVRLDYISLHRKGARSSISILEQEKVVAQQIRQLFP KFADTPIYNDEADPLVGWSLPQPWRADVTYAAMV VKVIAQHQNLLLANTTSAFPYALLSNDNAFLSYHP HPFAQRTLTARFQVNNTRPPHVQLLRKPVLTAMGL LALLDEEQLWAEVSQAGTVLDSNHTVGVLASAHR PQGPADAWRAAVLIYASDDTRAHPNRSVAVTLRLR GVPPGPGLVYVTRYLDNGLCSPDGEWRRLGRPVFP TAEQFRRMRAAEDPVAAAPRPLPAGGRLTLRPALR LPSLLLVHVCARPEKPPGQVTRLRALPLTQGQLVLV WSDEHVGSKCLWTYEIQFSQDGKAYTPVSRKPSTF NLFVFSPDTGAVSGSYRVRALDYWARPGPFSDPVP YLEVPVPRGPPSPGNP |
| 48 | Iduronate-2-sulfatase (second region 550 amino acid sequence including the 25 amino acid signal sequence) | MPPPRTGRGLLWLGLVLSSVCVALGSETQANSTTD ALNVLLIIVDDLRPSLGCYGDKLVRSPNIDQLASHS LLFQNAFAQQAVCAPSRVSFLTGRRPDTTRLYDFNS YWRVHAGNFSTIPQYFKENGYVTMSVGKVFHPGIS SNHTDDSPYSWSFPPYHPSSEKYENTKTCRGPDGEL HANLLCPVDVLDVPEGTLPDKQSTEQAIQLLEKMK TSASPFFLAVGYHKPHIPFRYPKEFQKLYPLENITLA PDPEVPDGLPPVAYNPWMDIRQREDVQALNISVPY GPIPVDFQRKIRQSYFASVSYLDTQVGRLLSALDDL QLANSTIIAFTSDHGWALGEHGEWAKYSNFDVATH VPLIFYVPGRTASLPEAGEKLFPYLDPFDSASQLMEP GRQSMDLVELVSLFPTLAGLAGLQVPPRCPVPSFHV ELCREGKNLLKHFRFRDLEEDPYLPGNPRELIAYSQ YPRPSDIPQWNSDKPSLKDIKIMGYSIRTIDYRYTV WVGFNPDEFLANFSDIHAGELYFVDSDPLQDHNMY NDSQGGDLFQLLMP |
| 49 | HOX C12-Iduronate-2-sulfatase (Entire sequence, combined SEQ ID nos. 1 and 48, also showing initiating methionine) | MSRKKRKPYSKLQLAELEGEFLVNEFITRQRRRELS DRLNLSDQQVKIWFQNRRMKKKRLLMPPPRTGRG LLWLGLVLSSVCVALGSETQANSTTDALNVLLIIVD DLRPSLGCYGDKLVRSPNIDQLASHSLLFQNAFAQQ AVCAPSRVSFLTGRRPDTTRLYDFNSYWRVHAGNF STIPQYFKENGYVTMSVGKVFHPGISSNHTDDSPYS WSFPPYHPSSEKYENTKTCRGPDGELHANLLCPVD VLDVPEGTLPDKQSTEQAIQLLEKMKTSASPFFLAV GYHKPHIPFRYPKEFQKLYPLENITLAPDPEVPDGLP PVAYNPWMDIRQREDVQALNISVPYGPIPVDFQRKI RQSYFASVSYLDTQVGRLLSALDDLQLANSTIIAFT SDHGWALGEHGEWAKYSNFDVATHVPLIFYVPGR TASLPEAGEKLFPYLDPFDSASQLMEPGRQSMDLV ELVSLFPTLAGLAGLQVPPRCPVPSFHVELCREGKN LLKHFRFRDLEEDPYLPGNPRELIAYSQYPRPSDIPQ WNSDKPSLKDIKIMGYSIRTIDYRYTVWVGFNPDEF LANFSDIHAGELYFVDSDPLQDHNMYNDSQGGDLF QLLMP |
| 50 | HOX D12-Iduronate-2-sulfatase (Entire sequence, combined SEQ ID nos. 2 and 48, also showing initiating methionine) | MARKKRKPYTKQQIAELENEFLVNEFINRQKRKEL SNRLNLSDQQVKIWFQNRRMKKKRVVMPPPRTGR GLLWLGLVLSSVCVALGSETQANSTTDALNVLLIIV DDLRPSLGCYGDKLVRSPNIDQLASHSLLFQNAFAQ QAVCAPSRVSFLTGRRPDTTRLYDFNSYWRVHAGN FSTIPQYFKENGYVTMSVGKVFHPGISSNHTDDSPY SWSFPPYHPSSEKYENTKTCRGPDGELHANLLCPV DVLDVPEGTLPDKQSTEQAIQLLEKMKTSASPFFLA VGYHKPHIPFRYPKEFQKLYPLENITLAPDPEVPDG LPPVAYNPWMDIRQREDVQALNISVPYGPIPVDFQR KIRQSYFASVSYLDTQVGRLLSALDDLQLANSTIIAF TSDHGWALGEHGEWAKYSNFDVATHVPLIFYVPG RTASLPEAGEKLFPYLDPFDSASQLMEPGRQSMDL VELVSLFPTLAGLAGLQVPPRCPVPSFHVELCREGK NLLKHFRFRDLEEDPYLPGNPRELIAYSQYPRPSDIP QWNSDKPSLKDIKIMGYSIRTIDYRYTVWVGFNPD EFLANFSDIHAGELYFVDSDPLQDHNMYNDSQGGD LFQLLMP |
| 51 | Peptide One of Four spanning the Ag85A 99-118 | ETFLTSELPGWLQAN |

TABLE 3-continued

Peptide Sequence Identities.

| Sequence ID No | Descriptor or Gene from which the Sequence was Derived | Sequence |
|---|---|---|
| | Epitope (second region 15 amino acid sequence, TB Vaccine) | |
| 52 | HOX C12-Ag85A 99-118 Epitope Peptide One of Four (Entire sequence, combined SEQ ID nos. 1 and 51, TB Vaccine) | SRKKRKPYSKLQLAELEGEFLVNEFITRQRRR TABLE 3-continued Peptide Sequence Identities.

| Sequence ID No | Descriptor or Gene from which the Sequence was Derived | Sequence |
|---|---|---|
| 58 | HOX C12-Ag85A 99-118 Epitope, Peptide Three of Four (Entire sequence, combined SEQ ID nos. 1 and 57, TB Vaccine) | SRKKRKPYSKLQLAELEGEFLVNEFITRQRRRELSD RLNLSDQQVKIWFQNRRMKKKRLLWLQANRHVKP TGSAV |
| 59 | HOX D12-Ag85A 99-118 Epitope, Peptide Three of Four (Entire sequence, combined SEQ ID nos. 2 and 57, TB Vaccine) | ARKKRKPYTKQQIAELENEFLVNEFINRQKRKELSN RLNLSDQQVKIWFQNRRMKKKRVVWLQANRHVK PTGSAV |
| 60 | Peptide Four of Four spanning the Ag85A 99-118 epitope (second region 15 amino acid sequence, TB Vaccine) | RHVKPTGSAVVGLSM |
| 61 | HOX C12-Ag85A 99-118 Epitope, Peptide Four of Four (Entire sequence, combined SEQ ID nos. 1 and 60, TB Vaccine) | SRKKRKPYSKLQLAELEGEFLVNEFITRQRRRELSD RLNLSDQQVKIWFQNRRMKKKRLLRHVKPTGSAV VGLSM |
| 62 | HOX D12-Ag85A 99-118 Epitope, Peptide Four of Four (Entire sequence, combined SEQ ID nos. 2 and 60, TB Vaccine) | ARKKRKPYTKQQIAELENEFLVNEFINRQKRKELSN RLNLSDQQVKIWFQNRRMKKKRVVRHVKPTGSAV VGLSM |
| 63 | Peptide One of Three spanning the Ag85A 70-78 epitope (second region 15 amino acid sequence, TB Vaccine) | QSGLSVVMPVGGQSS |
| 64 | HOX C12-Ag85A 70-78 Epitope, Peptide One | SRKKRKPYSKLQLAELEGEFLVNEFITRQRRRELSD RLNLSDQQVKIWFQNRRMKKKRLLQSGLSVVMPV GGQSS |

TABLE 3-continued

Peptide Sequence Identities.

| Sequence ID No | Descriptor or Gene from which the Sequence was Derived | Sequence |
|---|---|---|
| | of Three (Entire sequence, combined SEQ ID nos. 1 and 63, TB Vaccine) | |
| 65 | HOX D12-Ag85A 70-78 Epitope, Peptide One of Three (Entire sequence, combined SEQ ID nos. 2 and 63, TB Vaccine) | ARKKRKPYTKQQIAELENEFLVNEFINRQKRKELSN RLNLSDQQVKIWFQNRRMKKKRVVQSGLSVVMPV GGQSS |
| 66 | Peptide Two of Three spanning the Ag85A 70-78 Epitope (second region 15 amino acid sequence, TB Vaccine) | VVMPVGGQSSFYSDW |
| 67 | HOX C12-Ag85A 70-78 Epitope, Peptide Two of Three (Entire sequence, combined SEQ ID nos. 1 and 66, TB Vaccine) | SRKKRKPYSKLQLAELEGEFLVNEFITRQRRRELSD RLNLSDQQVKIWFQNRRMKKKRLLVVMPVGGQSS FYSDW |
| 68 | HOX D12-Ag85A 70-78 Epitope, Peptide Two of Three (Entire sequence, combined SEQ ID nos. 2 and 66, TB Vaccine) | ARKKRKPYTKQQIAELENEFLVNEFINRQKRKELSN RLNLSDQQVKIWFQNRRMKKKRVVVVMPVGGQSS FYSDW |
| 69 | Peptide Three of Three spanning the Ag85A 70-78 Epitope (second region 15 amino acid sequence, TB Vaccine) | GGQSSFYSDWYQPAC |
| 70 | HOX C12-Ag85A 70-78 Epitope, Peptide Three of Three (Entire sequence, combined SEQ ID nos. 1 and | SRKKRKPYSKLQLAELEGEFLVNEFITRQRRRELSD RLNLSDQQVKIWFQNRRMKKKRLLGGQSSFYSDW YQPAC |

TABLE 3-continued

Peptide Sequence Identities.

| Sequence ID No | Descriptor or Gene from which the Sequence was Derived | Sequence |
|---|---|---|
| | 69, TB Vaccine) | |
| 71 | HOX D12-Ag85A 70-78 Epitope, Peptide Three of Three (Entire sequence, combined SEQ ID nos. 2 and 69, TB Vaccine) | ARKKRKPYTKQQIAELENEFLVNEFINRQKRKELSN RLNLSDQQVKIWFQNRRMKKKRVVGGQSSFYSDW YQPAC |
| 72 | Ag85A Epitope (second region cargo) | AFSRPGLP VEYLQVPSPS MGRDIKVQFQ SGGANSPALY LLDGLRAQDD FSGWDINTPA FEWYDQSGLS VVMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA |
| 73 | HOX C12-Ag85A (Entire sequence, combined SEQ ID nos. 1 and 72, TB Vaccine) | SRKKRKPYSKLQLAELEGEFLVNEFITRQRRRELSD RLNLSDQQVKIWFQNRRMKKKRLL AFSRPGLP VEYLQVPSPS MGRDIKVQFQ SGGANSPALY LLDGLRAQDD FSGWDINTPA FEWYDQSGLS VVMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA |
| 74 | HOX D12-Ag85A (Entire sequence, combined SEQ ID nos. 2 and 72, TB Vaccine) | ARKKRKPYTKQQIAELENEFLVNEFINRQKRKELSN RLNLSDQQVKIWFQNRRMKKKRVV AFSRPGLP VEYLQVPSPS MGRDIKVQFQ SGGANSPALY LLDGLRAQDD FSGWDINTPA FEWYDQSGLS VVMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA |

Various features and embodiments and select modifications will now be described by way of non-limiting examples. In all examples where an initiating methionine is included in a complete sequence to allow recombinant synthesis, the initiating methionine may be removed during purification to derive the active product with the indicated human homeodomain sequence. References to sequence numbers for complete conjugates in paragraphs describing their use are referring to the conjugate after removal of the initiating methionine.

Example 1

Conjugates or fusion peptides or proteins comprised of the 60-amino acid human homeodomain and the cargo NBD peptide that inhibits NF-κB transcription factor generation are examples of embodiments that regulate gene expression through interference with protein-protein interactions.

In one embodiment, the HOX C12 amino acid sequence first region is SEQ ID No. 1:

SRKKRKPYSKLQLAELEGEFLVNEFITRQRRRELSDRLNLSDQQVKIWF QNRRMKKKRLL

In another embodiment, the HOX D12 amino acid sequence first region is SEQ ID No. 2:

ARKKRKPYTKQQIAELENEFLVNEFINRQKRKELSNRLNLSDQQVKIWF QNRRMKKKRVV

In these two embodiments, this first region is linked via a simple peptide bond or, alternatively, a linker known in the art, (See Table 2), to the NF-κB essential modifier (NEMO), abbreviated NBD, for NEMO binding domain, the "cargo" peptide. Any linker may be used provided its addition does not compromise the function of the conjugate. The NBD amino acid sequence is SEQ ID No. 20, the second region:

TALDWSWLQTE and the entire fusion protein sequence embodiment incorporating the HOX C12 first region (SEQ ID No. 1), containing only a peptide bond linking the two regions, is:

```
                                           SEQ ID No. 21
SRKKRKPYSKLQLAELEGEFLVNEFITRQRRRELSDRLNLSDQQVKIWFQ
NRRMKKKRLLTALDWSWLQTE
```

The entire fusion protein sequence embodiment incorporating the HOX D12 first region (SEQ ID No. 2), containing only a peptide bond linking the two regions, is:

```
SEQ ID No. 22:
ARKKRKPYTKQQIAELENEFLVNEFINRQKRKELSNRLNLSDQQVKIWFQ
NRRMKKKRWTALDWSWLQTE
```

The size of each of SEQ ID Nos 21 and 22 allows the entire fusion protein to be produced synthetically. If it is produced through recombinant synthesis SEQ ID Nos. 21 and 22, or variants or portions thereof may include an N-terminal methionine. Linkers are not required for function but linkers may be included in alternative embodiments between the first and second regions provided they do not compromise function of the conjugate. To that end, any linker known in the art (see, e.g., Table 2) may be used to produce embodiments of this conjugate, and would alter SEQ ID Nos. 21 and 22, at least in part, to the extent that the linker sequence would bridge these first and second regions.

Figure 5:
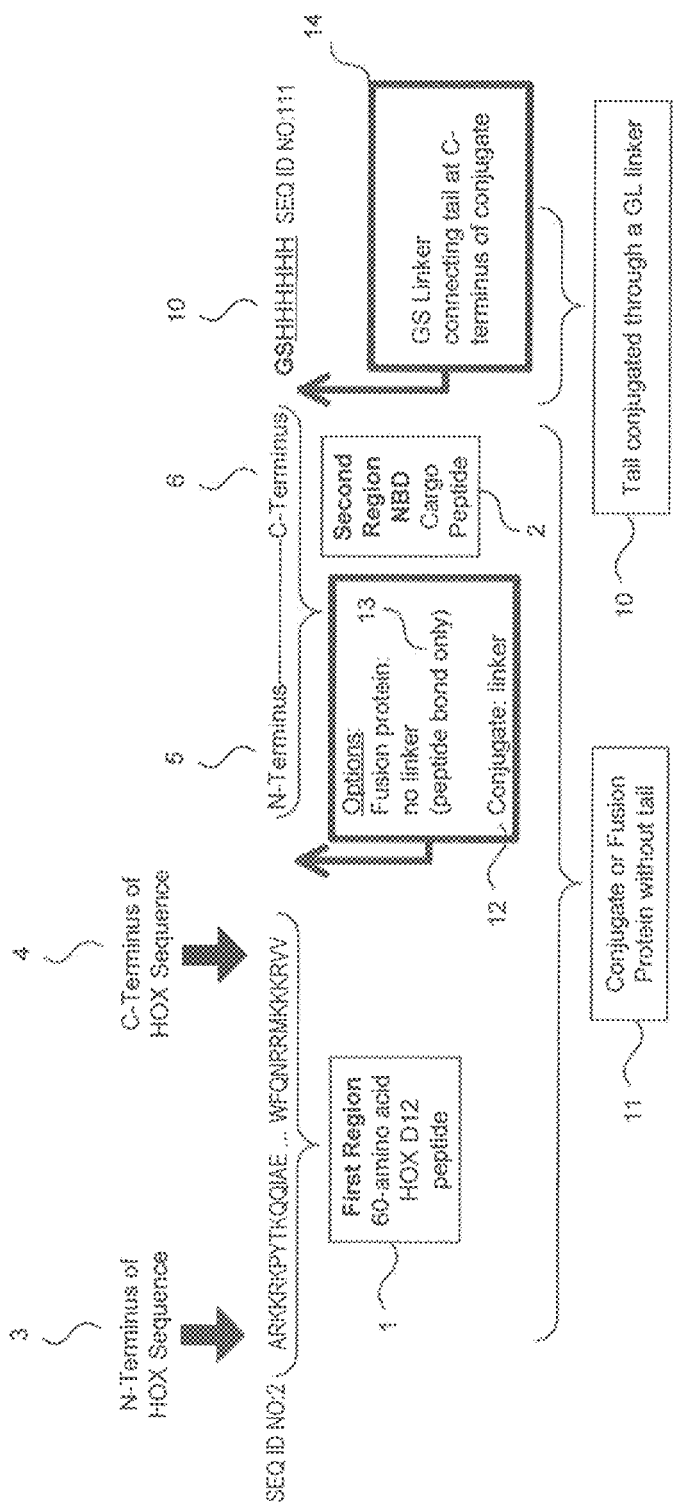
FIG. 5 shows an exemplary 60-amino acid human HOX D12 homeodomain (first region) or variant or portion thereof at N-terminus of NBD Cargo peptide (second region), and His-tail conjugated to C-terminus through GS linker.

In still further embodiments, additional amino acid sequences ("tails") can be added to either the amino or carboxy termini in order to facilitate purification. Such sequences may include FLAG-tags (DYKDDDDK) (SEQ ID No. 102), myc-tags (EQKLISEEDL) (SEQ ID No. 103), His-tags (HHHHHH) (SEQ ID No. 80), and other similar tags known to those in the art. Such tags may or may not include linkers. In addition, ligands such as the biotin-acceptor protein (GLNDIFEAQKIEWHE) (SEQ ID No. 105) together with the active BirA protein may be used. For sequences that include an N-terminal initiating methionine, if a N-terminal purification domain is added the methionine will be on the N-terminal of the purification domain instead of at the N-terminal of the human homeodomain peptide first region. FIG. 5 shows one embodiment in which the HOX D12 homeodomain is conjugated to the NBD cargo peptide, and is further conjugated to a His-tag through a GS linker.

In various embodiments, SEQ ID Nos. 21 and 22 or a portion thereof may be formulated for systemic or local delivery for the treatment of inflammatory diseases. Embodiments of local delivery include examples such as an inhaled liquid or dry powder formulation for chronic obstructive lung disease (COPD), a colonic enema formulation for ulcerative colitis or Crohn's disease (inflammatory bowel disease) with colonic and/or rectal inment, an eye drop formulation for inflammatory eye diseases such as dry eyes (keratoconjuntivitis sicca), uveitis and scleritis and topical ointment and cream formulations for inflammatory and autoimmune skin diseases such as psoriasis and alopecia areata. Systemic formulations include intravenous, subcutaneous and intramuscular injection and injectable implant formulations for sustained release for the treatment of chronic inflammatory diseases such as rheumatoid arthritis, ulcerative colitis, Crohn's disease, psoriasis, etc., and acute inflammatory conditions such as inflammatory atherosclerotic plaque instability for the prevention of acute myocardial infarction (coronary artery thrombosis) and stroke, prevention of ischemia-reperfusion injury in stroke and myocardial infarction (reduced infarct size and improved function) and in organ transplant patients (improved organ function). To the extent that activation of NF-κB inflammatory pathways are involved in the pathogenesis and progression of certain cancers, as reported widely in the literature, for example, in colon, lung and some skin cancers, systemic administration includes treatment of cancer.

SEQ ID No. 21 (labeled PPL-002 in the studies described) and SEQ ID No. 22 (labeled PPL-003 in the studies described) were chemically synthesized and their respective physical and biological properties were characterized and compared to two Antennapedia-based cell permeable membrane constructs with the same 11-amino acid NEMO binding domain (NBD) cargo (SEQ ID No. 20) that has been previously described (M. J. May et al. "Selective inhibition of NF-κB activation by a peptide that blocks the interaction of NEMO with the IκB kinase complex" *Science* 289:1550-54, Sep. 1, 2000; I Strickland and S Ghosh. "Use of cell permeable NBD peptides for suppression of inflammation" *Ann. Rheum. Dis.* 65(Suppl 3):iii75-iii82, 2006). One of these fusion peptides utilizes an N-terminal 17-amino acid sequence from the Antennapedia homeodomain and the 11-amino acid NBD peptide at its C-terminal end and was labeled PPL-004 in these studies. The other Antennapedia-based construct is a fusion peptide combining the 60 amino acid homeodomain of Antennapedia with the same 11-amino acid NBD cargo and is labeled PPL-001 in these studies.

Physical Characteristics:

SEQ ID No. 22, (PPL-003), differed in its solubility and salt interactions compared to SEQ ID No. 21 (PPL-002) that make it better suited for pharmaceutical development. It also differed in these characteristics compared to the published Antennapedia based NBD peptide (PPL-004) and the other Antennapedia based NBD peptide, PPL-001.

PPL-001, PPL-002 and PPL-004 peptides are soluble in water; however, they did not demonstrate solubility in salt containing buffers such a those commonly used as pharmaceutical vehicles or formulations. In 10 mM Tris buffered saline, pH 7.4, which is conventionally used pharmaceutical administration, PPL-003 was soluble as a clear solution even at the highest concentration tested, 5 mg/mL (0.566 mM), while PPL-002 (1 mg/mL) formed a cloudy solution possibly due to salt interactions with the charged groups on the peptide. The Antennapedia-based NBD peptides (PPL-001 and PPL-004) were also insoluble in this buffered saline solution. Using 1 mM arginine, 0.01% and 0.1% Tween 20 or adding histidine to Tris buffered saline and using citrate buffered solutions did not improve the solubility characteristics of PPL-001, PPL-002 or PPL-004. The different solubility characteristics of PPL-003 compared to PPL-002 and the Antennapedia-based peptides was not predicted on the basis of structural differences. In addition only PPL-003 could be completely dissolved at 5 mg/mL in phosphate buffered physiological saline solutions at pH 7.4.

We tested the ability of certain embodiments of the human HOX C12 or HOX D12 homeodomain-NBD permeabilizing peptides (fusion proteins) disclosed to inhibit NF-κB activation and the formation of cytokines such as tumor necrosis factor alpha (TNF-α) when it is preincubated with cells prior to stimulation with endotoxin using techniques known in the art. We conducted in vitro studies utilizing embodiments comprising SEQ ID No. 21 and/or No. 22, or a portion thereof in which TNF-α-stimulated NF-κB transcriptional activities were measured and where endotoxin-stimulated cytokine production was studied.

Embodiments of the NBD cargo peptide conjugated to the human HOX C12 or HOX D12 homeodomain (SEQ ID Nos. 21 and/or 22 or variant or portion thereof) were active in both of these in vitro assays at various concentrations between about 50 µM to about 200 µM, and TNF-α-stimulated NF-κB transcriptional activity and/or cytokine production was measured by known methods and compared to the control group.

In Vitro Activity Using NF-κB Luciferase Reporter Cell Lines:

An in vitro assay measuring the inhibition of NF-κB activation utilizing a TNF-α stimulated human embryonic kidney cell line (HEK 293) and an endotoxin (LPS) stimulated murine macrophage-like cell line (RAW 264.7), both with an NF-κB luciferase reporter gene, were utilized to measure the bioactivity of embodiments of cell permeable peptides with the NBD cargo (Park et al. Phosphoinositide-dependent kinase 1 integrates T cell receptor and CD28 co-receptor signaling to effect NF-κB induction and T cell activation. *Nat Immunol.* 10(2):158-166, February 2009). (FIGS. 8a and 8b.)

Figures 8A, 8B:
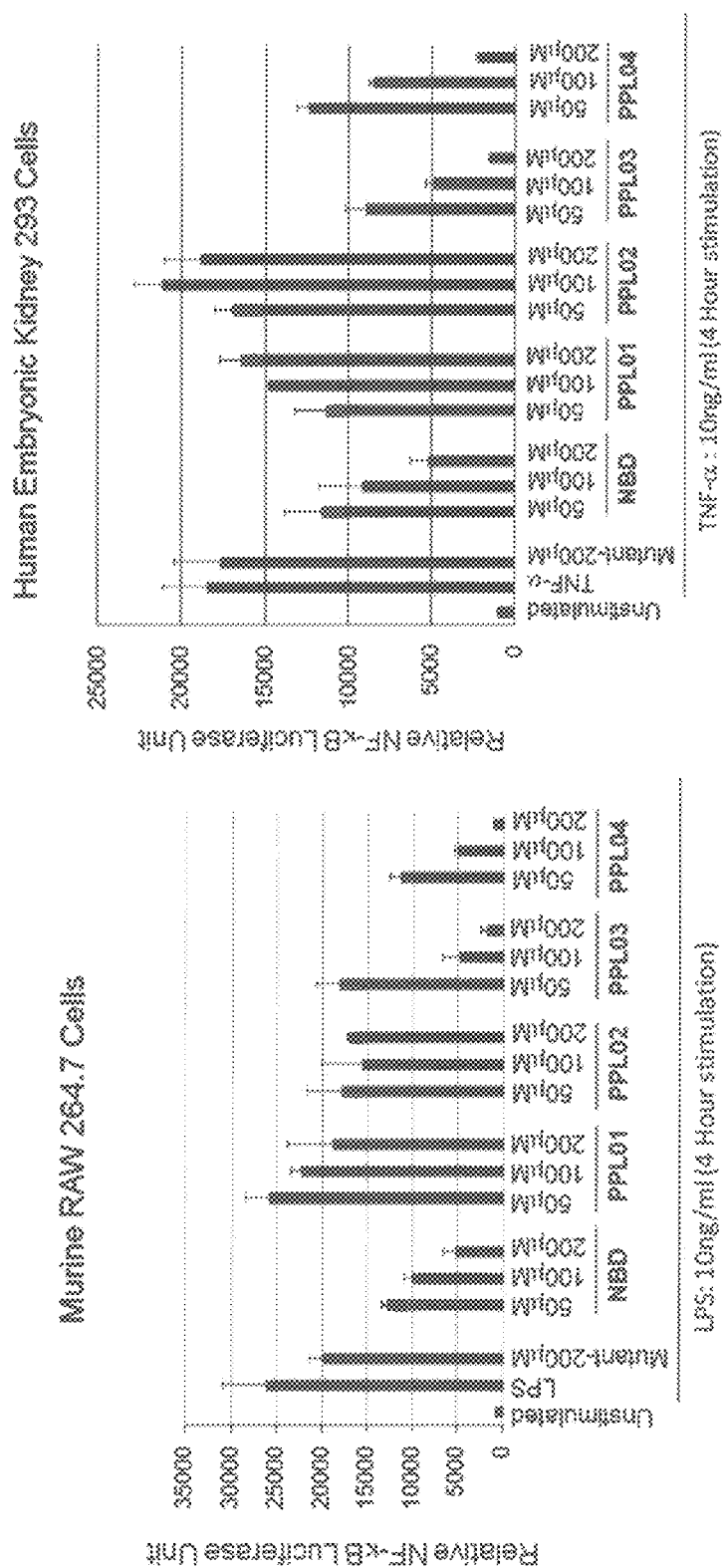
FIG. 8a shows inhibition of NF-κB activation in murine RAW 264.7 cells (LPS 4-hour stimulation). Error bars represent SEM.
FIG. 8b shows inhibition of NF-κB activation in Human Embryonic Kidney (HEK) 293 cells (TNF-α 4-hour stimulation). Error bars represent SEM.
Figure 9:
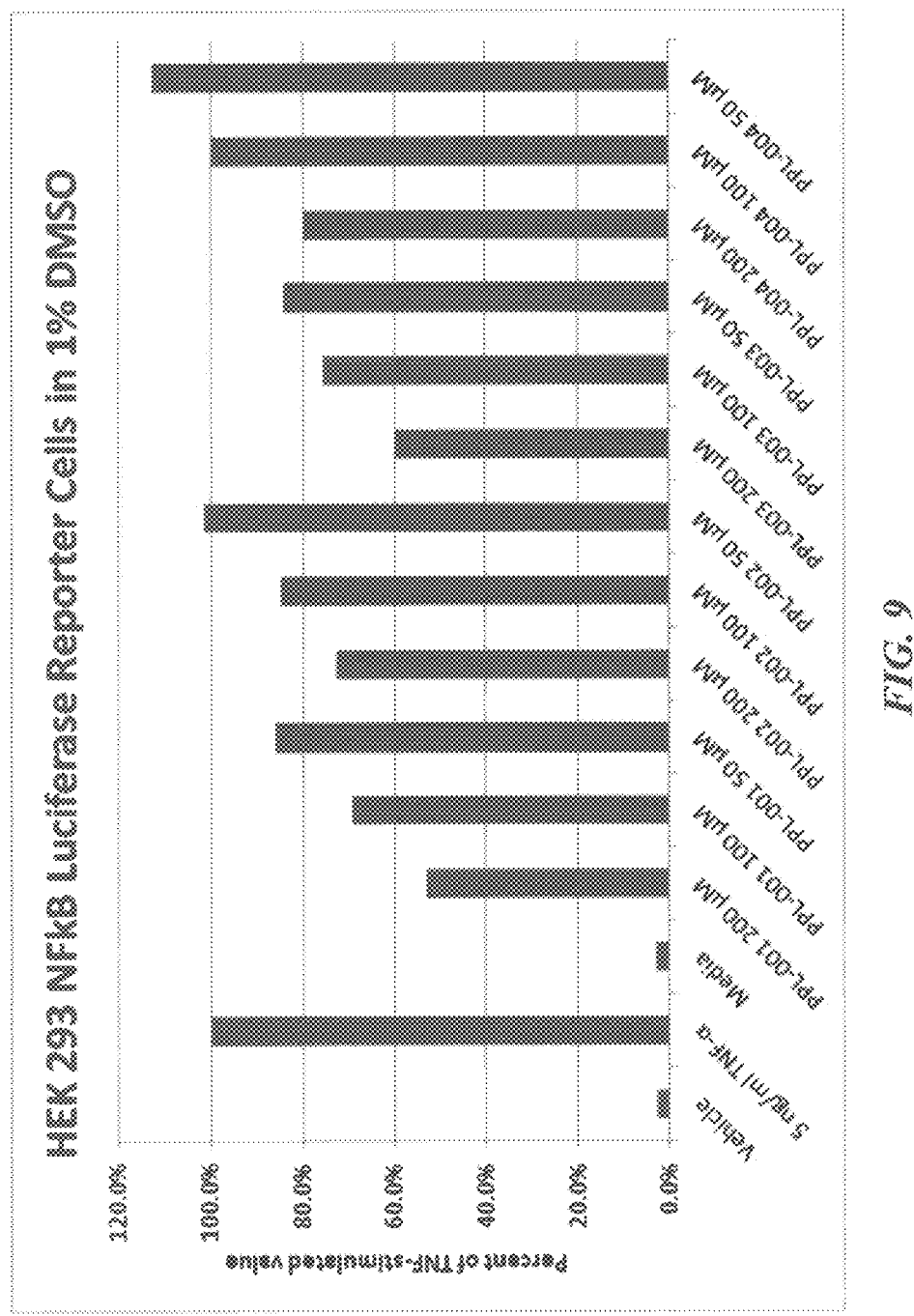
FIG. 9 shows inhibition of TNF-α-stimulated NF-κB activation in HEK 293 NF-κB Luciferase Reporter Cells by NBD cargo containing cell permeable peptides

KEY to FIGS. 8a, 8b and 9:

| | |
|---|---|
| Unstimulated or Vehicle | Cells without endotoxin (LPS) or TNF-α stimulation |
| LPS | Cells stimulated with endotoxin (LPS) 10 ng/mL or human TNF-α at 10 ng/mL for 4 hours following a 3-hour incubation with control buffer |
| Mutant: 200 micromolar | Cells stimulated with endotoxin (LPS) 10 ng/mL or human TNF-α at 10 ng/mL for 4 hours following a 3-hour incubation with the NBD mutant inactive peptide |
| NBD | Cells stimulated with endotoxin (LPS) 10 ng/mL or human TNF-α at 10 ng/mL for 4 hours following a 30-hour incubation with commercially purchased peptide with a 17-amino acid Antennapedia-based homeodomain sequence and a C-terminal 11-amino acid NBD sequence (SEQ ID No. 020 is the NBD portion) |
| PPL-001 | Cells stimulated with endotoxin (LPS) 10 ng/mL or human TNF-α at 10 ng/mL for 4 hours following a 3-hour incubation with a Portage Pharmaceuticals-produced peptide with a 60-amino acid Antennapedia-based homeodomain sequence and a C-terminal 11-amino acid NBD sequence (SEQ ID No. 020). |
| PPL-002 (SEQ ID No. 21) | Cells stimulated with endotoxin (LPS) 10 ng/mL or human TNF-α at 10 ng/mL for 4 hours following a 3-hour incubation with a Portage Pharmaceuticals-produced peptide with a 60-amino acid human HOX-C12 homeodomain sequence (SEQ ID No. 001) and a C-terminal 11-amino acid NBD sequence (SEQ ID No. 020) |
| PPL-003 (SEQ ID No. 22) | Cells stimulated with endotoxin (LPS) 10 ng/mL or human TNF-α at 10 ng/mL for 4 hours following a 3-hour incubation with a Portage Pharmaceuticals-produced peptide with a 60-amino acid human HOX-D12 homeodomain sequence (SEQ ID 002) and a C-terminal 11-amino acid NBD sequence (SEQ ID 020). |

In initial experiments these peptides were first dissolved in DMSO and then diluted in phosphate buffered saline prior to addition to complete tissue culture medium containing the NF-κB luciferase reporter cell lines. In these studies PPL-003 was found to have activity similar to PPL-004 and a commercially available version of PPL-004 with the identical structure. In one test, a control mutant peptide with a change in the NBD sequence rendering it unable to bind to the NBD target sequence was inactive demonstrating the specificity of the test for the NBD sequence used as cargo.

When the final concentration of DMSO was adjusted to 1% for all peptides and their ability to inhibit human TNF-α-stimulated (5 ng/ml) NF-κB activation was measured using HEK 293 cells, there was a clear dose-response for all peptides. However, PPL-003 appeared to be more potent than the others at the same and lowest 50 micromolar concentration. FIG. 9 reports the luciferase signal as a percent of the TNF-α-stimulated cells with no peptide pretreatment.

In the rodent-systemic intravenous endotoxin challenge model, mice were pretreated using systemic intravenous (i.v.) or intraperitoneal (i.p.) administration of an embodiment formulations comprising the NBD cargo peptide conjugated to a human HOX C12 or HOX D12 homeodomain (SEQ ID Nos. 21 and/or 22) as described below and in future studies at a dose per 20 g mouse of 1 µg to at least 2,000 µg or more. Multiple inflammatory and anti-inflammatory cytokines and the acute phase protein, serum amyloid A (SAA) were measured in blood and results compared to the vehicle negative control group and to a dexamethasone pretreated positive control group.

Figure 10:
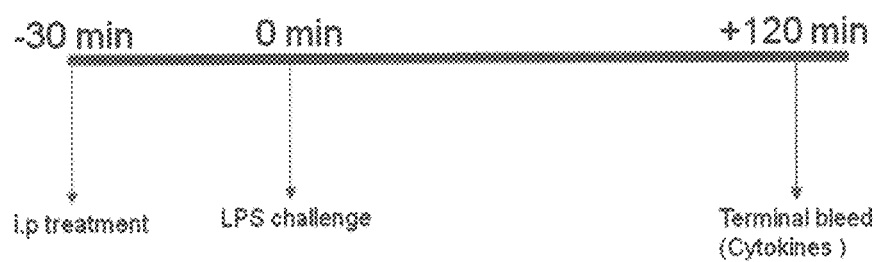
FIG. 10: Timeline for determining in vivo activity of NBD cargo-containing cell permeable peptides: Mice were pretreated with peptides, challenged by injection of lipopolysaccharide (LPS) and blood samples were taken for cytokine assays at the indicated times

In Vivo Activity of NBD Cargo-Containing Cell Permeable Peptides:

Initial studies were conducted in mice pretreated by i.p. injection of peptides at a dose of 500 micrograms (pg) per mouse (10 mg/kg) or dexamethasone (3 mg/kg) 30 minutes prior to challenge by injection of endotoxin (LPS) at a dose of 50 micrograms/kg. The ability of peptide pretreatment to inhibit the inflammatory cytokine response or stimulate the anti-inflammatory cytokine response to LPS was determined 2 hours after LPS injection (FIG. 10).

Figure 11B:
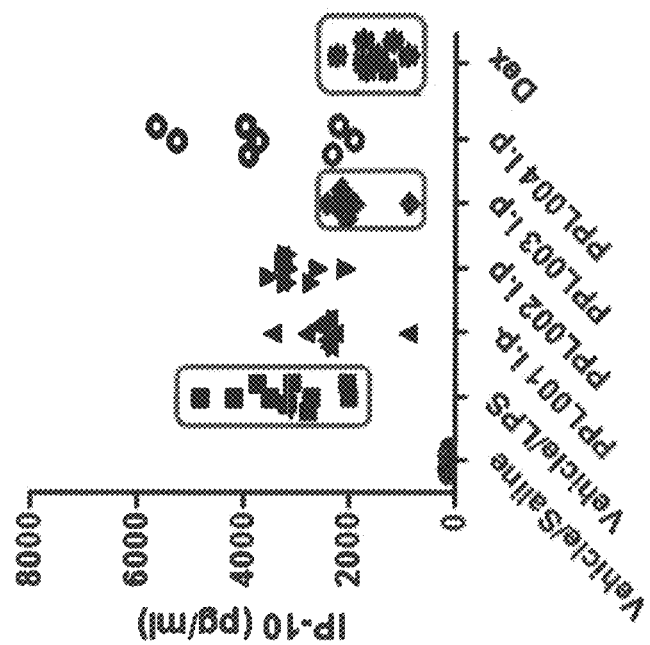
FIG. 11b shows IP-10 response following LPS injection and peptide or dexamethasone (Dex) pretreatment. Each datapoint represents the value for a single mouse.
Figure 11A:
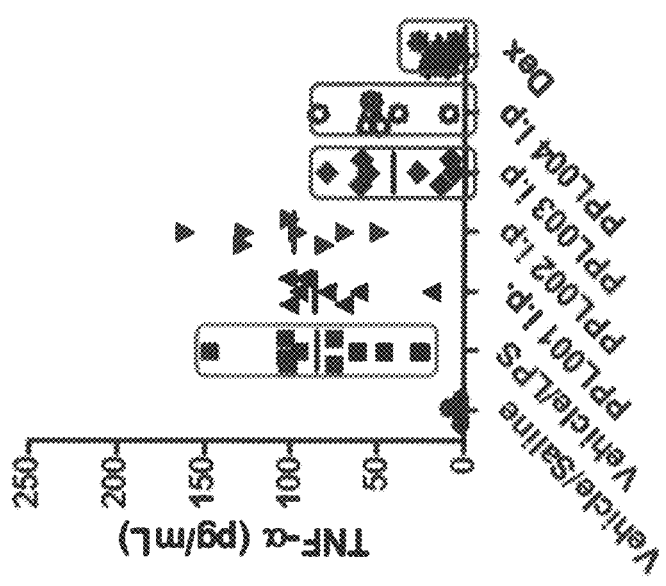
FIG. 11a shows TNF-α response following LPS injection and peptide or dexamethasone (Dex) pretreatment. Each datapoint represents the value for a single mouse.

Cytokine levels in mouse plasma two hours after LPS injection were reduced in mice treated with NBD-containing peptides. (FIGS. 11a and 11b) For example, levels of TNF-α and IP-10 (CXCL 10) were convincingly reduced by pretreatment with PPL-003 with some mice demonstrating reduced levels of these cytokines similar to the dexamethasone-treated group. Interestingly PPL-003 was differentiated from PPL-004 with respect to their abilities to reduce the IP-10 response. While IP-10 levels were reduced by i.p. pretreatment with PPL-003 to levels similar to those measured after dexamethasone treatment, there was no effect of PPL-004 i.p. pretreatment on IP-10 plasma levels. These selective effects on specific cytokines may have important implications for PPL-003 as a therapeutic agent for inflammatory diseases.

Figure 12:
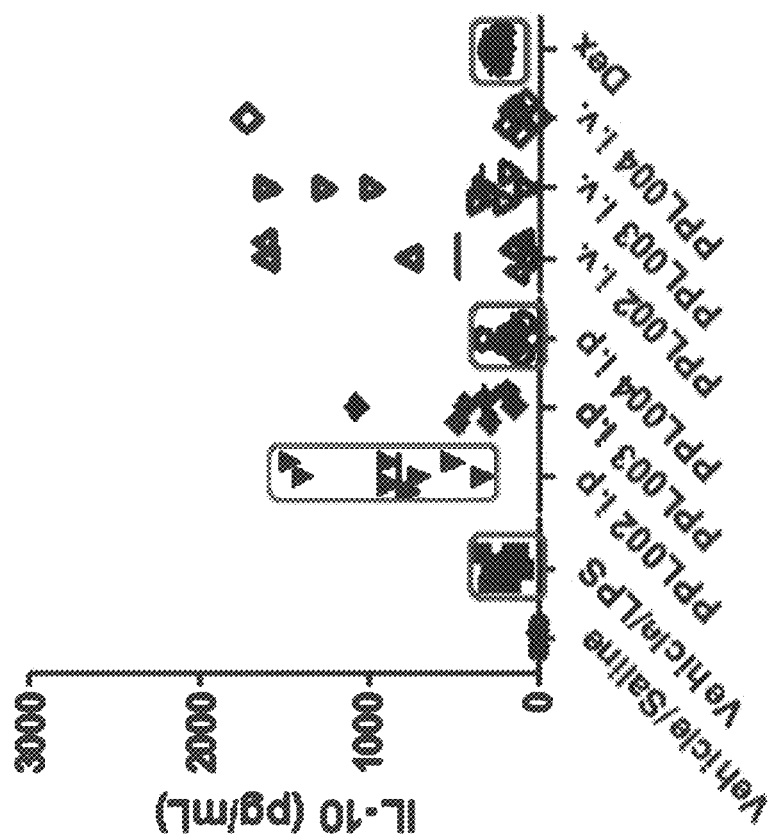
FIG. 12 shows IL-10 response following LPS injection and peptide or dexamethasone (Dex) pretreatment. Each datapoint represents the value for a single mouse.

Pretreatment with PPL-002 and PPL-003 embodiments also lead to increased levels of the anti-inflammatory cytokine Interleukin-10 (IL-10). Peptides were dosed both i.p. and i.v. at 500 micrograms per mouse (10 mg/kg) 30 minutes prior to challenge by injection of endotoxin (LPS) at a dose of 50 micrograms/kg. Dexamethasone dosed i.p. at 3 mg/kg had no effect on IL-10 levels while PPL-002 (SEQ ID No. 21) i.p. pretreatment led to a significant increase in IL-10 ($p<0.01$). PPL-002 (SEQ ID No. 21) and PPL-003 (SEQ ID No. 22) embodiment i.v. pretreatments also increased IL-10 levels. Interestingly this ability to increase IL-10 levels after LPS challenge was not seen in mice pretreated with PPL-004, the published NBD cell permeable peptide with an N-terminal 17-amino acid sequence from the Antennapedia homeodomain and the 11-amino acid NBD peptide at its C-terminal end (FIG. 12) where there was no detectable difference between PPL-004 and vehicle pretreated groups.

Activity and Pharmacokinetics of *E. coli*-Derived Recombinant PPL-003.

Figure 13:
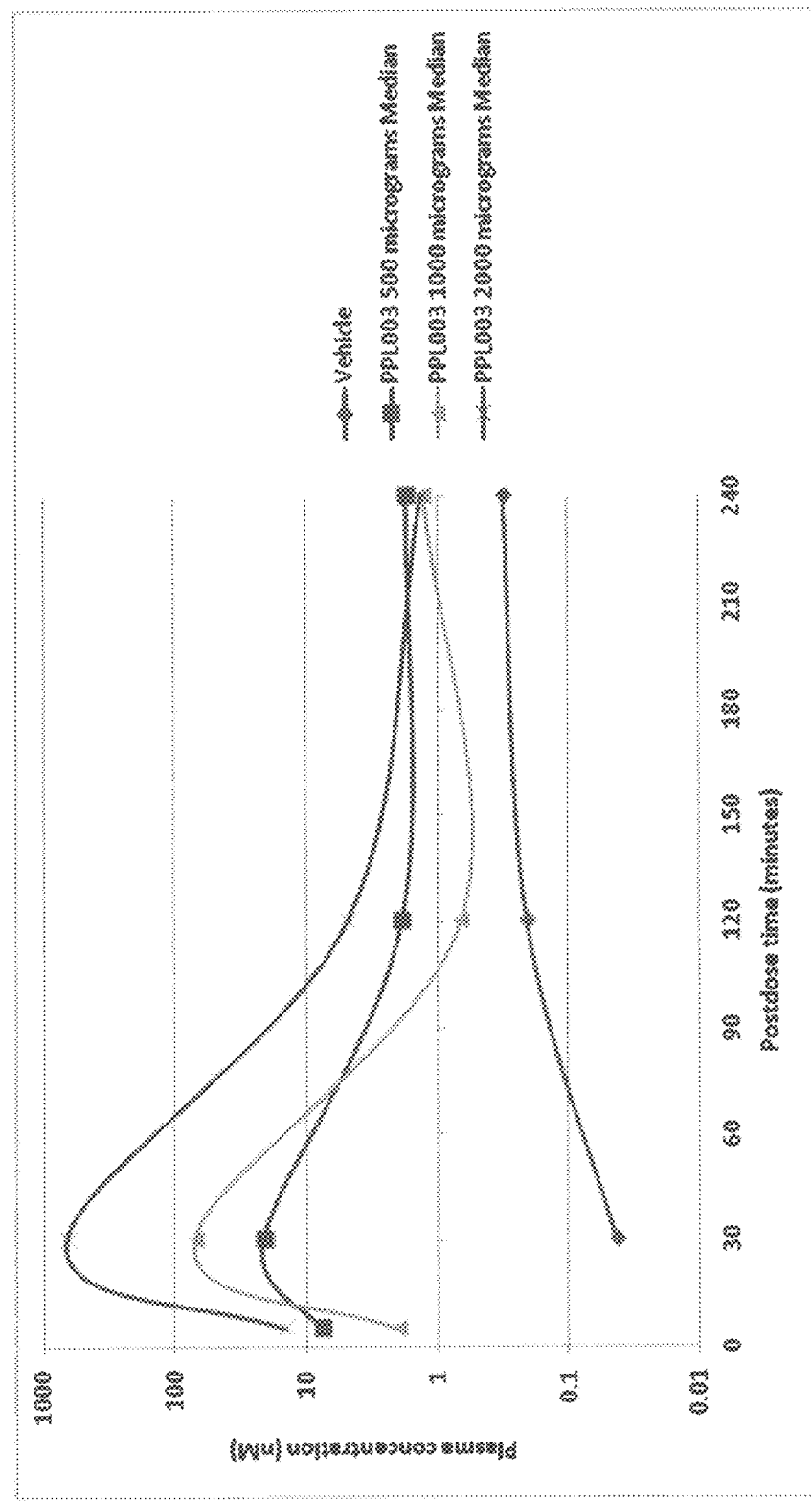
FIG. 13 shows PPL-003 concentration in plasma following dosing at 500, 1000, and 2000 microgram.
Figure 14:
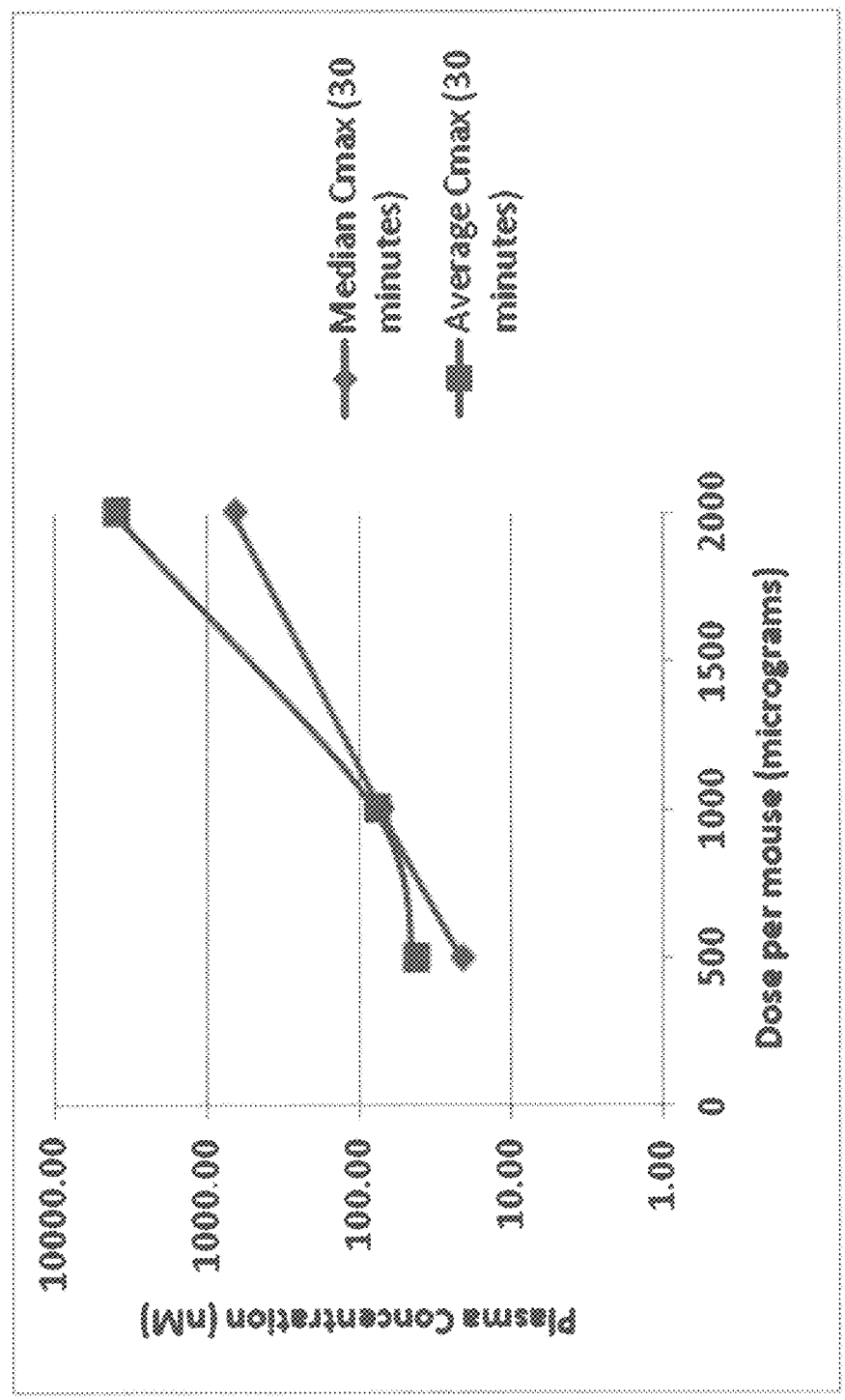
FIG. 14 shows PPL-003 $C_{max}$ in plasma by dose, showing average and median at $C_{max}$ (30 min.).
Figure 15B:
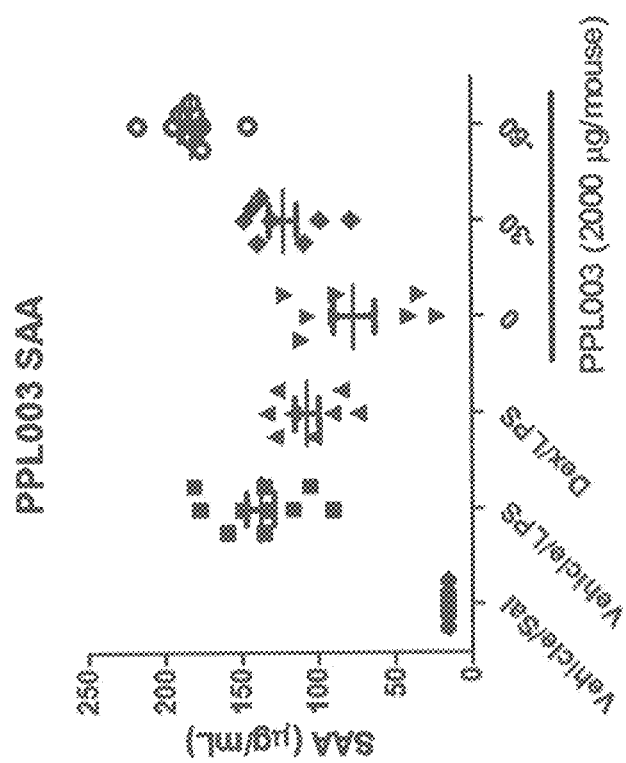
FIGS. 15a and 15b show amyloid A protein (SAA) response at 2 hours following LPS challenge with pretreatment of 2000 microgram of PPL-003 at 0, 30- and 60-minutes prior to LPS stimulation. Error bars represent SEM in FIG. 15a and data points in FIG. 15b are individual mice, horizontal lines are median values.
Figure 15A:
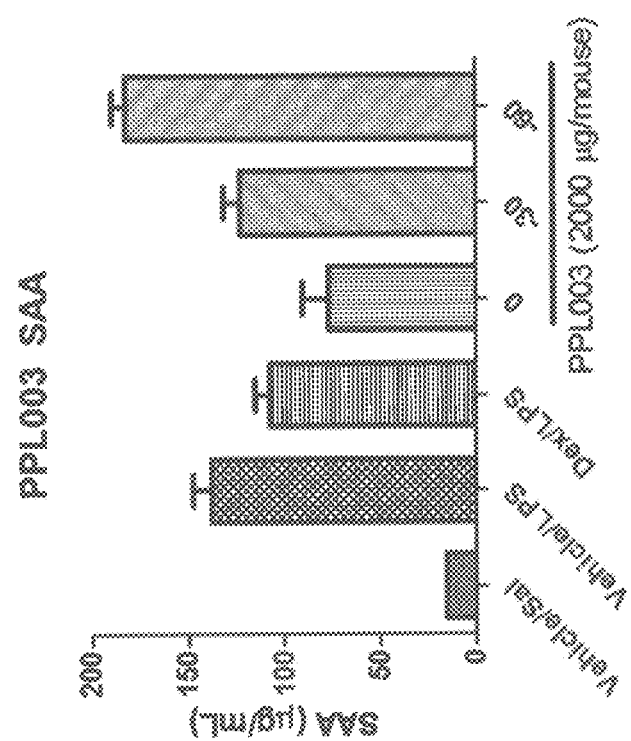
Figure 16A:
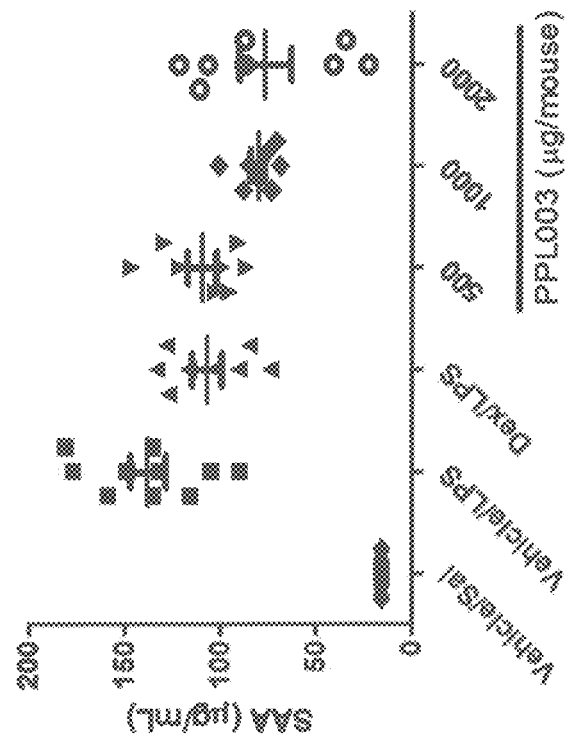
FIGS. 16a and 16b show amyloid A protein (SAA) response to LPS following PPL-003 pretreatment at doses of 500, 1000, and 2000 micrograms. Error bars represent SEM in FIG. 16a, and data points in FIG. 16b are individual mice, horizontal lines are median values. Percentages are percent inhibition relative to vehicle/LPS.
Figure 16B:
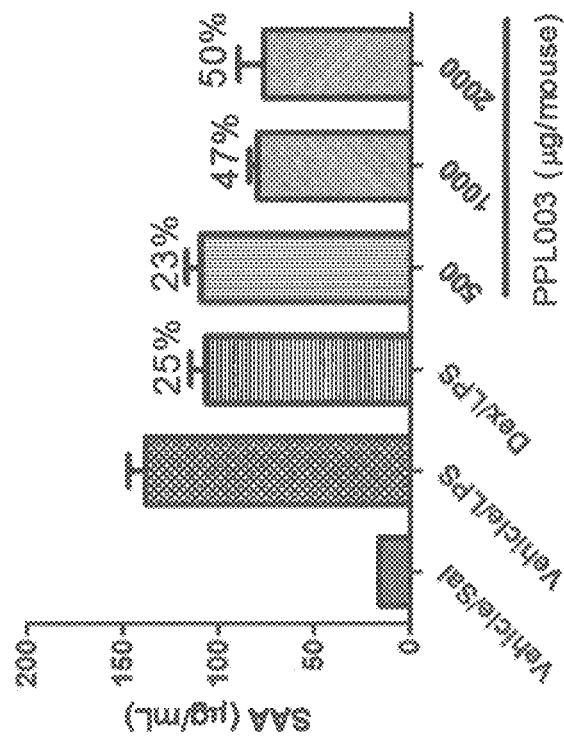

A recombinant PPL-003 (SEQ ID No. 22) embodiment produced in *E. coli* and purified as described above (see Upstream Production of SEQ ID No. 21 and SEQ ID No. 22) was administered by intra-peritoneal injection in a 10 mM Tris buffered physiological saline solution, pH 7.4, to mice, and the plasma concentration of PPL-003 was measured by ELISA assay that utilized an affinity purified rabbit antibody to SEQ ID No. 20, the NBD cargo. Mice were injected with 500 µg [micrograms], 1,000 µg or 2,000 µg of PPL-003 and blood was sampled at the indicated time points (FIG. 13). Blood was anti-coagulated with EDTA and plasma separated by centrifugation. PPL-003 levels were measured by ELISA and calculated using a standard curve of chemically synthesized pure PPL-003. Plasma PPL-003 was measurable at 5 minutes post-dose and Cmax was at about 30 minutes with levels reaching the lower limit of detection at about 240 minutes after dosing (FIGS. 13-14).

As before mice were challenged with LPS after dosing with recombinant PPL-003 and multiple cytokine responses to the LPS injection were measured 2 hours after the LPS challenge. Dosing with PPL-003 was at the same time as LPS challenge, 30 minutes prior to LPS challenge or 60 minutes prior to LPS challenge. For comparison, dexamethasone was injected 30 minutes prior to LPS challenge.

Figure 17B:
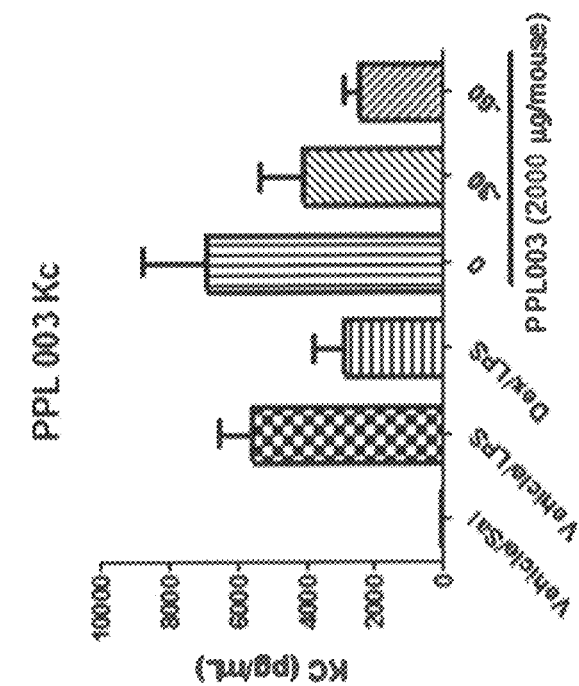
FIGS. 17a and 17b show IL-10 and Mouse Kc responses, respectively, following 2000 microgram PPL-003 dose at 0, 30- and 60-minutes prior to LPS stimulation. Error bars represent SEM.
Figure 17A:
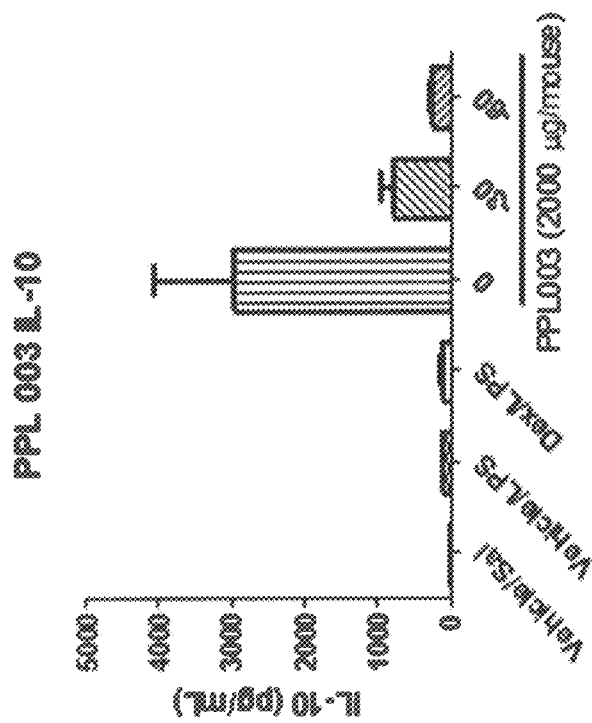

LPS-stimulated plasma levels of amyloid A protein (SAA), TNFα, IP-10, GM-CSF, IL-6, KC (equivalent of human IL-8, CXCL1) and MCP-1 were reduced to levels lower than achieved with dexamethasone pre-treatment while anti-inflammatory cytokine IL-10 levels were significantly elevated. In general the greatest inhibition was with dosing 30 minutes prior to LPS challenge although SAA inhibition was greatest with simultaneous injection of PPL-003 and LPS (FIGS. 15a, 15b, 16a and 16b). The average percent reductions in SAA concentration are indicated above the bars in FIG. 16a. IL-10 increases and Kc decreases were greatest with dosing 60 minutes prior to LPS injection. (FIGS. 17a and 17b)

Figure 18A:
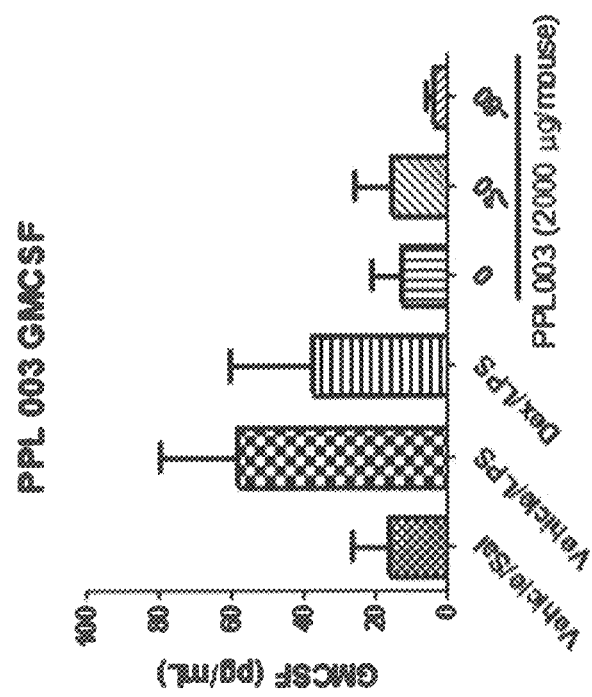
FIGS. 18a and 18b show inhibition of GM-CSF response following 2000 microgram PPL-003 or PPL-004 dose, respectively, at 0, 30- and 60-minutes prior to LPS stimulation. Error bars represent SEM.
Figure 18B:
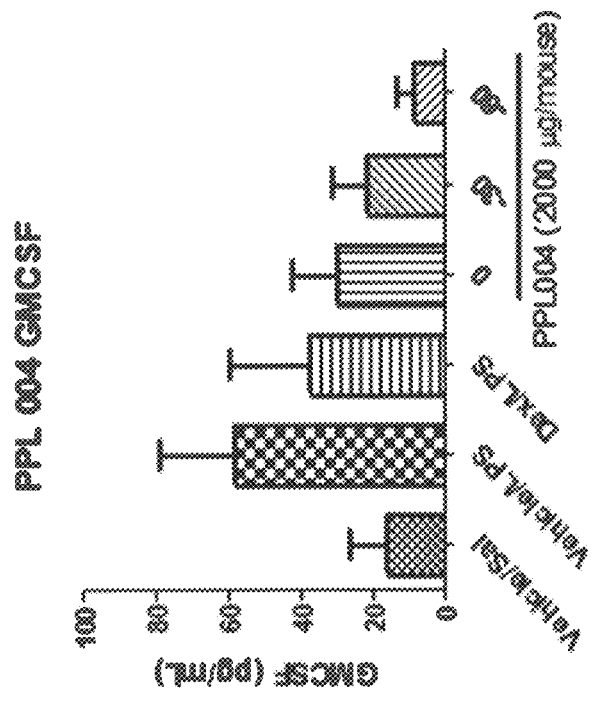

FIGS. 18a and 18b. show inhibition of the GM-CSF response to the i.v. LPS (endotoxin) challenge in mice when PPL-003 was injected (i.p.). 60- and 30-minutes before LPS was administered, and at the same time LPS was administered (0 min.). GM-CSF reduction is greater than seen after pretreatment with dexamethasone, which provides only modest inhibition. PPL-003 is more potent than PPL-004 at the same microgram dosage, although the molar dosage of PPL-004 was about three times higher than that of PPL-003 at equivalent microgram doses.

Local delivery or topical delivery will prevent unwanted systemic activity that could result in susceptibility to infections in the case of the NBD peptide containing fusion protein. As an inhaled formulation for the treatment of inflammatory airway diseases such as chronic obstructive pulmonary disease (COPD), one or more of the human HOX C12 or HOX D12 homeodomain-NBD conjugate or fusion protein embodiments disclosed (SEQ ID Nos. 21 or 22, or a portion thereof) will be evaluated for their ability to inhibit the airway inflammatory response in a well-described model in rodents (mice and rats) following pretreatment by inhalation of these compounds prior to inhalation of endotoxin. Specifically, we will conduct a study utilizing one or more human homeodomain-NBD fusion protein or conjugate embodiments at various concentrations, for example between about 1 µM to about 115 µM, and evaluate the corresponding maximal inhibition of the endotoxin-stimulated cellular and cytokine responses in BALF. In addition, studies are planned in humans challenged with small doses of inhaled endotoxin to evaluate (i) liquid formulation embodiments delivered by nebulizer; and (ii) dry powder formulation embodiments, each such formulation comprising SEQ ID Nos. 21 and/or 22, or a portion thereof. These formulation and delivery system embodiments will have efficacy in patients with inflammatory airway diseases such as COPD.

In the rodent-inhaled endotoxin challenge, administered to mice through an inhaled formulation, an embodiment comprising the NBD cargo peptide conjugated to a human HOX C12 or HOX D12 homeodomain (for example, SEQ ID Nos. 21 and/or 22, or a portion thereof) at a dose per mouse of at least 1 µg to at least about 200 µg or more. TNF-α and IL-6 concentrations in bronchoalveolar lavage fluid (BALF) fluid will be measured by known methods and results compared to the control group.

Also in the rodent-inhaled endotoxin challenge, administered to mice through an inhaled formulation, another embodiment comprising the NBD cargo peptide conjugated to the human HOX C12 or HOX D12 homeodomain or variant or portion thereof (for example, SEQ ID Nos. 21 and/or 22, or a portion thereof) at a dose per mouse of at least 1 µg to at least about 200 µg or more. Bronchoalveolar lavage fluid (BALF) inflammatory cell numbers will be measured by known methods, and results compared to the control group.

In the human-inhaled endotoxin challenge, an inhaled formulation embodiment will be administered to healthy volunteers comprising the NBD cargo peptide conjugated to the human homeodomain or variant or portion thereof (for example, SEQ ID Nos. 21 and/or 22, or a portion thereof), at a dose per 70 kg person of at least 1 µg to at least about 600 mg or more. TNF-α, IL-6, and IL-1 concentrations and inflammatory cell numbers in bronchoalveolar lavage fluid (BALF) will be measured by known methods, and results compared to the control group.

Dry eyes, keratoconjunctivitis sicca, is a medical condition in which local inflammation leads to reduced tear production. In its extreme case, corneal damage occurs. Symptoms of dry eyes such as burning, pain, excess tearing reflex in dry air or windy conditions are very common and mild cases are treated with "artificial tears." However, topical immunosuppressive therapy is required for moderate to severe cases, for example, cyclosporine eye drops (Restasis®) made by Allergan. Recently the importance of Toll-like receptor (TLR) signaling has been implicated, and murine models have been developed (Redfern et. al. "Toll-Like Receptor Expression and Activation in Mice with Experimental Dry Eye" that appeared in Invest. *Ophthalmol. Vis. Sci.* 54(2):1554-63, Feb. 28, 2013). Initially, we will conduct a study in the murine experimental dry eye (EDE) model in which inflammatory biomarkers and pathological changes can be evaluated. For example, we will evaluate the effect of one or more embodiments of the NBD peptide-containing fusion protein or conjugate administered in a topical formulation on (1) goblet cell infiltration in epithelial cornea and loss in the conjunctiva; (2) tear secretion and (3) lymph-angiogenesis. and/or (4) inflammatory cell accumulation in lachrymal tissues.

In the EDE rodent model, chronically administered daily, every other day, or weekly with a topical formulation, another embodiment comprising the NBD cargo peptide conjugated to the human HOX C12 or HOX D12 homeodomain or variant or portion thereof (SEQ ID Nos. 21 and/or 22, or a portion thereof), at a dose per mouse of at least 1 µg to at least about 500 µg or more if solubility permits. Tear production, goblet cell infiltration in epithelial cornea and loss of goblet cells in the conjunctiva will be assessed by known methods and the results compared to controls.

In more severe dry eye rodent models, administered daily, every other day, or weekly with a topical formulation, another embodiment comprising the NBD cargo peptide conjugated to the human HOX C12 or HOX D2 homeodomain or variant or portion thereof (for example, SEQ ID Nos. 21 and/or 22, or a portion thereof) at a dose per 20 g mouse of at least 1 µg to at least about 500 µg or more if solubility permits. Lymph-angiogenesis and corneal pathology will be assessed by known methods, and the results compared to controls.

In humans, chronic daily, every other day, or weekly administration with a topical formulation, another embodiment comprising the NBD cargo peptide conjugated to the human HOX C12 or HOX D12 homeodomain or variant or portion thereof (for example, SEQ ID Nos. 21 and/or 22, or a portion thereof) at dose per 70 kg person of less than 1 µg to about 100 µg changes in tear secretion towards normal levels compared to control subjects receiving a placebo treatment will be measured by the Schirmer test.

Alopecia areata is a common autoimmune skin disease resulting in the loss of hair on the scalp and elsewhere on the body. It usually starts with one or more small, round, smooth patches on the scalp and can progress to total scalp hair loss (alopecia totalis) or complete body hair loss (alopecia universalis). Alopecia areata affects approximately two percent of the population overall, including more than 5 million people in the United States alone. This common skin disease is highly unpredictable and cyclical. Hair can grow back in or fall out again at any time, and the disease course is different for each person.

Formulated in an appropriate shampoo or topical formulation for application to the scalp and other involved areas, we will evaluate the human HOX C12 or HOX D12 homeodomain-NBD fusion protein embodiment or alternative NBD protein-containing conjugate embodiments to affect (1) the downstream inflammatory response to T-cell derived cytokines by skin biopsy, (2) hair loss, and (3) hair regrowth. In this double-blind study in alopecia areata patients, paired signal lesions at the same stage of hair loss development will be treated with placebo (topical formulation alone) and with the human HOX C12 or HOX D12 homeodomain-NBD peptide-containing formulation. Hair growth and hair follicle inflammation will be measured in both lesions and compared in untreated lesions. In other parallel group studies hair loss and growth of signal lesions and numbers of new lesions will be measured and compared between treatment groups.

In rodent models of alopecia areata, for example, the Dundee Experimental Bald Rat (DEBR) model, and in alopecia areata patients, chronic administration daily, every other day, or weekly with a topical formulation, an embodiment comprising the NBD cargo peptide conjugated to the human HOX C12 or HOX D12 homeodomain or variant or portion thereof (SEQ ID Nos. 21 and/or 22, or a portion thereof) at a dosage of less than about 0.01% wt/vol to less than about 5% wt/vol. Hair loss and hair growth will be assessed by known methods in treated versus untreated lesions.

Administered as an i.v. or i.p. formulation, we will evaluate the effect of pretreatment of rodents with embodiments of the human gene-derived permeabilizing NBD fusion protein or conjugate described (SEQ ID Nos. 21 and/or 22, or a portion thereof) on ischemia-reperfusion injury in well described animal models, including a stroke model. Specifically, we will examine by known histopathology techniques in this stroke model the area of necrotic tissue, an indicator of ischemia-reperfusion injury.

In the rodent stroke model, sub-acute administration beginning within 1 hour of the ischemic event and continued at intervals such as every 6 hours, 12 hours or daily for one to three days) through an i.v. or i.p. formulation, another embodiment comprising the NBD cargo peptide conjugated to the human HOX C12 or HOX D12 homeodomain or variant or portion thereof (SEQ ID Nos. 21 and/or 22, or a portion thereof) at a dosage of less than about 0.1 mg/kg to less than about 100 mg/kg. The area of necrotic brain tissue in the treatment group will be assessed using known histopathology methods.

Uveitis is a common inflammatory condition of the eye. The many versions of uveitis can be sight-threatening, ocular inflammatory diseases. Experimental auto-immune uveoretinitis (EAU) is thought to be an animal model of human uveitis. Immunosuppressants used to treat human uveitis are effective in such an animal model. Furthermore, the NF-κB inflammatory pathway, a target of HOX C12 and HOX D12 homeodomain-NBD fusion proteins, is reported to be involved in EAU pathogenesis. Additionally, there is a particular form of familial granulomatous uveitis, Blau syndrome, which can be caused by specific mutations in the human NOD2 gene and is directly associated with NF-κB inflammation.

Formulated as a topical administration to the eye, a human HOX D12 homeodomain-NBD fusion protein embodiment will be evaluated for its ability to reduce inflammation of an animal model of uveitis. Mice deficient in NOD2 are given an intravitreal injection of muramyl dipeptide (MDP) and the intravascular response can be measured within the iris and cellular infiltration can be assessed by intrvital microscopy and histology. Or, as a preliminary test of topical efficacy, the fusion proteins can be evaluated for their ability in mice to reduce ocular inflammation caused the administration of the LPS endotoxin. It is anticipated that following indication of effectiveness in animal models of uveitis, human trials could be considered in more common types of uveitis. Clinical endpoints used on uveitis clinical trials include mean change from baseline in graded vitreous haze and mean change from baseline in graded anterior chamber cells after 16 weeks of therapy. Prevention of deterioration shown by not observing an increase in vitreous haze of greater than or equal to 2 grades, shown by preventing an increase in anterior chamber cells greater than or equal to 2 grades or preventing deterioration of visual acuity of greater than or equal to 0.3 log MAR from baseline.

In one embodiment, the effect of treatment in human subjects with an intravenous formulation of the human-derived permeabilizing NBD conjugate described (SEQ ID Nos. 21 and/or 22, or a portion thereof) can be evaluated with respect to the clinical consequences of atherosclerotic plaque instability that that lead to intravascular thrombosis and unstable angina, acute myocardial infarction and acute stroke. In human subjects with symptoms of unstable angina, acute MI and/or acute stroke, the underlying pathology is associated with inflammatory atherosclerotic plaque instability with production of prothrombotic factors by macrophages within the atherosclerotic lesion that lead to thrombus formation and partial or complete vascular occlusion. Specifically, evaluation may begin at presentation to an acute care facility. Further evaluation can include observing/measuring the effects of acute and subacute treatment for one to five days on biomarkers of inflammation such as C-reactive protein (CRP) at 24 hours post presentation. Clinical outcomes, such as mortality, cardiac function (ejection fraction in the case of acute MI) and neurological function (in the case of acute stroke) measured with the National Institutes of Health Stroke Scale (NIHSS) can be assessed at approximately one month following presentation. The NIHSS is a systematic assessment tool that provides a quantitative measure of stroke-related neurologic deficit. For example, a stroke patient with a NIHSS value below 12-14 will have an 80% chance for a good or excellent outcome while a NIHSS value above 20-26 has less than a 20% chance for a good or excellent outcome. Therefore, in these studies, the percent of human subjects with a NIHSS score below 17 at one month may be used as an endpoint for neurological function.

In another embodiment, daily intravenous therapy of a human gene-derived cell-permeabilizing NBD conjugate (SEQ ID Nos. 21 and/or 22, or a portion thereof), at daily doses of about 0.1 mg/kg to less than about 100 mg/kg, can be evaluated. CRP concentrations at 24 hours will be assessed in serum by known methods. In addition, we will assess at one month post presentation: (1) post-stroke neurological function as measured by the percent of patients with a NIHSS of less than 17; (2) post-MI cardiac output as measured by ultrasound; and (3) acute mortality levels. Results will be compared to controls.

Alternative embodiments comprising any of SEQ ID Nos. 1 through 19, or variants or portions thereof, conjugated to the NBD peptide include a variety of fusion proteins or conjugates comprising any one or more linkers known in the art, provided the function of the fusion protein or conjugate is not compromised by its addition.

Example 2

PC1 Cytoplasmic C-Terminal Tail Peptide for Polycystic Kidney Disease

Another embodiment of a human HOX C12 or HOX D12 homeodomain (or variant or portion thereof) fusion protein that inhibits protein-protein interactions is one in which the second region is composed of a 200 amino acid peptide whose sequence is derived from the cytoplasmic C-terminal tail region of the PC1 protein (PC1 CTT), also referred to as p200 (Lal et al. "Polycystin-1 C-terminal tail associates with 1-catenin and inhibits canonical Wnt Signaling" *Hum. Mol. Genet.* 17(20):3105-17, Oct. 15, 2008, including supplemental materials). The PC1 gene and/or the PC2 gene are commonly mutated in polycystic kidney disease (PKD). These mutations are inherited or result from somatic mutation or a combination of these events and result in unregulated activation of genes by a transcription factor cleaved from the c-terminal cytoplasmic tail region of the PC1 protein. The p200 protein blocks the action of this transcription factor and may be able to restore normal renal tubular development in patients with PKD if it can be effectively delivered to its site of action inside renal tubular cells.

In one embodiment, the first region human HOX C12 homeodomain 60-amino acid sequence is:

SEQ ID No. 1 (Table 3):
SRKKRKPYSKLQLAELEGEFLVNEFITRQRRRELSDRLNLSDQQVKIWFQ
NRRMKKKRLL In another embodiment the first region human HOX D12 homeodomain 60-amino acid sequence is:

SEQ ID No. 2 (Table 3):
ARKKRKPYTKQQIAELENEFLVNEFINRQKRKELSNRLNLSDQQVKIWFQ
NRRMKKKRVV and the linked second region is the p200 peptide derived from the PC1 CTT sequence; the amino acid sequence of this second portion is:

SEQ ID No. 23 (Table 3):
VILRWRYHALRGELYRPAWEPQDYEMVELFLRRLRLWMGLSKVKEFRHKV

RFEGMEPLPSRSSRGSKVSPDVPPPSAGSDASHPSTSSSQLDGLSVSLGR

LGTRCEPEPSRLQAVFEALLTQFDRLNQATEDVYQLEQQLHSLQGRRSSR

APAGSSRGPSPGLRPALPSRLARASRGVDLATGPSRTPLRAKNKVHPSST

In yet other embodiments, the second region is a variation on the cargo sequence shown here. With the addition of an initiating methionine, the entire fusion protein sequence embodiment containing HOX C12 is shown as SEQ ID No. 24 (Table 3):

MSRKKRKPYSKLQLAELEGEFLVNEFITRQRRRELSDRLNLSDQQVKIWF

QNRRMKKKRLLVILRWRYHALRGELYRPAWEPQDYEMVELFLRRLRLWMG

LSKVKEFRHKVRFEGMEPLPSRSSRGSKVSPDVPPPSAGSDASHPSTSSS

QLDGLSVSLGRLGTRCEPEPSRLQAVFEALLTQFDRLNQATEDVYQLEQQ

LHSLQGRRSSRAPAGSSRGPSPGLRPALPSRLARASRGVDLATGPSRTPL

RAKNKVHPSST and with the addition of an initiating methionine, the entire fusion protein sequence embodiment containing HOX D12 is shown as SEQ ID No. 25 (Table 3):

MARKKRKPYTKQQIAELENEFLVNEFINRQKRKELSNRLNLSDQQVKIWF

QNRRMKKKRVVVILRWRYHALRGELYRPAWEPQDYEMVELFLRRLRLWMG

LSKVKEFRHKVRFEGMEPLPSRSSRGSKVSPDVPPPSAGSDASHPSTSSS

QLDGLSVSLGRLGTRCEPEPSRLQAVFEALLTQFDRLNQATEDVYQLEQQ

LHSLQGRRSSRAPAGSSRGPSPGLRPALPSRLARASRGVDLATGPSRTPL

RAKNKVHPSST

Linkers are not required for function but linkers may be included between SEQ ID Nos. 1 and 23 or a portion thereof or between SEQ ID Nos. 2 and 23, or a portion thereof, without compromising function. A linker known in the art may be used, and SEQ ID Nos. 24 and 25 embodiments would be altered, at least in part, to the extent that the linker sequence would bridge the first and second regions of each conjugate.

In other embodiments, the p200 peptide may be conjugated to any of SEQ ID Nos. 3 through 19.

In still further embodiments, additional amino acid sequences can be added to either the amino or carboxy termini in order to facilitate purification. Such sequences may include FLAG-tags (DYKDDDDK) (SEQ ID No. 102), myc-tags (EQKLISEEDL) (SEQ ID No. 103), His-tags (HHHHHH) (SEQ ID No. 80), and other similar tags known to those in the art. Such tags may or may not include linkers. In addition, ligands such as the biotin-acceptor protein (GLNDIFEAQKIEWHE) (SEQ ID No. 105), together with the active BirA protein may be used. For sequences that include an N-terminal initiating methionine, if a N-terminal purification domain is added the methionine will be on the N-terminal of the purification domain instead of at the N-terminal of the human HOX C12 or HOX D12 homeodomain.

The fusion protein embodiment that includes the 60-amino acid human HOX C12 or HOX D12 homeodomain or variant or portion thereof with the PC1 CTT p200 peptide in the second region will be included in systemic formulations including intravenous, subcutaneous, intramuscular and injectable implant formulations for sustained release. They may also be formulated to include specific structures that target them for reuptake by renal tubular cells after they are filtered by the glomerulus and enter the nephron or via specific receptors such as the vasopressin 2 receptor (V2R, see below) that can target renal cyst cells via the blood. See, e.g., FIG. 3, showing a third region representing such a structure. As noted the biological activity of the fusion protein can be demonstrated in vitro in renal tubule cell cultures with PKD mutations where cyst-like structure formation is inhibited, and also in rodent models of PKD where the progression of cyst formation and kidney growth is inhibited. (Lal et. al. 2008). We will evaluate the effect of the fusion protein embodiments (SEQ ID Nos. 24 or 25, or a portion thereof without the initiating methionine, or an alternative PC1 CTT p200 peptide-containing conjugate embodiment) on cyst formation in vitro in these renal tubular cell cultures and also in animal models of PKD (e.g., Pkd1 transgenic mice (Pkd2W525/−)). In this PKD-1 transgenic mouse model we will measure by ultrasound inhibition of increase in kidney size (i.e., inhibition of kidney growth). In patients with PKD, using pharmaceutical formulations of one or more of the disclosed fusion protein and/or conjugate embodiments comprising the PC1 CTT p200 peptide in the second region, we will evaluate by MRI total kidney volume and the progression of cyst size and number.

In another embodiment of a PC1 CTT peptide-containing fusion protein or conjugate for treatment of PKD, the second region of the protein is p21, a portion of the p200 molecule that retains some but not all of the biological activities of p200. See Table 3, SEQ ID No. 26. The p21 peptide when genetically expressed in PKD renal tubule cell cultures described above restores the normal tubule-like phenotype to the cells in a manner similar to the effect of expressing the entire p200 peptide in these cells. Removal of the p21 amino acids from the p200 construct also eliminates the ability of p200 expression to correct the cyst-like phenotype of these cells in culture. Unlike p200, p21 does not activate the Wnt signaling pathway and hence may not induce osteoblastic activity. These differences can be measured in vivo using osteoblastic bone formation biomarkers like osteocalcin in mouse models of PKD where the beneficial effects on progression of renal cyst formation and kidney size can also be measured using ultrasound.

The amino acid sequence of the 60-amino acid human HOX C12 homeodomain first region (SEQ ID No. 1) is shown above. The amino acid sequence of this second region p21 (SEQ ID No. 26) is:

```
IRRIRLWMGLSKVKEFRHKVR.
```

In yet other embodiments, the second region is a variation on the cargo sequence shown here.

Certain embodiments such as fusion proteins containing HOX C12 and HOX D12, each with an initiating methionine, are shown in SEQ ID Nos. 27 and 28, respectively, below and in Table 3.

```
SEQ ID No. 27:
MSRKKRKPYSKLQLAELEGEFLVNEFITRQRRRELSDRLNLSDQQVKIWF
QNRRMKKKRLLIRRIRLWMGLSKVKEFRHKVR

SEQ ID No. 28:
MARKKRKPYTKQQIAELENEFLVNEFINRQKRKELSNRLNLSDQQVKIWF
QNRRMKKKRVVIRRIRLWMGLSKVKEFRHKVR
```

Linkers are not required for function but linkers may be included, for example, between SEQ ID Nos. 1 and 27 or 28, and between SEQ ID Nos. 2 and 27 or 28 without compromising function. Any linker known in the art may be used, and SEQ ID Nos. 27 and 28 embodiments would be altered, at least in part, to the extent that the linker sequence would bridge these first and second regions.

In other embodiments, the p21 peptide may be conjugated to any of SEQ ID Nos. 3 through 19.

In the PKD-1 transgenic mouse model, we will evaluate using ultrasound the effect of chronic daily i.p. or i.v. injections of formulations including (1) our human HOX C12 or HOX D12 homeodomain-p200 fusion protein or conjugate embodiment and (2) our human HOX C12 or HOX D12 homeodomain-p21 fusion protein or conjugate embodiment on kidney size.

In the PKD-1 transgenic mouse model, an embodiment comprising the PC1 CTT cargo peptide (either p200 (SEQ ID No. 23) or p21 (SEQ ID No. 26)) conjugated to the human HOX C12 or HOX D12 homeodomain (as SEQ ID Nos. 27 and 28 in the case of p21, and as SEQ ID Nos. 24 and 25 in the case of p200), or an alternative PC1 CTT peptide-containing embodiment varying by the type of linker, if any, at a dose per mouse of at least about 1 μg to at least 500 μg or more if solubility permits. Kidney size and growth rate will be assessed by ultrasound, and results from the group receiving the human HOX C12 or HOX D12 homeodomain-p21 treatment formulation will be compared to those of the control group and the group receiving the human HOX C12 or HOX D12 homeodomain-p200 fusion protein or conjugate treatment formulation.

In the PKD-1 transgenic mouse model, we will further evaluate the ability of another embodiment comprising the human HOX C12 or HOX D12 homeodomain-p21 and the human HOX C12 or HOX D12 homeodomain-p200 fusion proteins or conjugates to reduce kidney growth in comparison to the control group, and to compare effect of both human homeodomain-p21 and human homeodomain-p200 changes in osteoblastic bone biomarkers, such as osteocalcin in blood in comparison. The human HOX C12 or HOX D12 homeodomain-p21 and the human HOX C12 or HOX D12 homeodomain-p200 fusion protein or conjugate embodiments will be administered in a formulation at a dose per mouse of at least about 1 μg to at least 500 μg or more if solubility permits. Osteocalcin concentration in blood will be assessed by known methods, and results from the group receiving embodiments such as the human HOX C12 or HOX D12 homeodomain-p21 treatment formulation will be compared to those of the control group and the group receiving embodiments such as the human HOX C12 or HOX D12 homeodomain-p200 fusion protein or conjugate treatment formulation.

In patients with PKD treated systemically with chronic daily dosing of the formulations described above, embodiments comprising the PC1 CTT cargo peptide (either p200 (SEQ ID No. 23) or p21 (SEQ ID No. 26) or a portion thereof) conjugated through a peptide bond to the human HOX C12 or HOX D12 homeodomain or variant or portion thereof (with, e.g., the full sequence embodiments as SEQ ID Nos. 27-28, or variant or portion thereof, in the case of p21, and as the full sequence embodiments as SEQ ID Nos. 24-25, or variant or portion thereof, in the case of p200) or an alternative PC1 CTT peptide-containing conjugate embodiment varying by the type of linker, if any, will be administered at a dosage of less than about 0.01 mg/kg to less than about 100 mg/kg. Kidney growth rate will be assessed by known methods, and results from in the group receiving the human HOX C12 or HOX D12 homeodomain-p21 treatment formulation embodiment will be compared to those of the control group and the group receiving the human HOX C12 or HOX D12 homeodomain-p200 fusion protein or conjugate treatment formulation embodiment.

Targeting Renal Cysts:

Renal collecting ducts are thought to be the origin of some or most cysts in PKD. Collecting duct cells express the vasopressin 2 receptor (V2R). It may be possible to target fusion protein and conjugate embodiments with a human HOX C12 or HOX D12 homeodomain peptide or variant or portion thereof in the first region and p200 or p21 in the second region to the renal cysts of collecting duct origin by including in some embodiments a linked peptide V2R antagonist or by adding a peptide V2R antagonist as an additional segment of the fusion protein. In some embodiments a removable linker may be used if function of the conjugate is not compromised with its addition. An example of a non-competitive peptide V2R antagonist was reported by Rihakova, et al. "VRQ397 (CRAVKY): a novel noncompetitive V2 receptor antagonist" *Am. J. Physiol. Inteqr. Comp. Physiol.* 297:R1009-R1018, 2009. We intend to test the addition of VRQ397 (CRAVKY) (SEQ ID No. 29, shown in Table 3), a non-competitive peptide V2R antagonist, to the N-terminal or C-terminal of the human HOX C12 or HOX D12 homeodomain-p200 and/or the human HOX C12 or HOX D12 homeodomain-p21 fusion (conjugate) protein embodiments with a linker designed to unlink or dissolve once the exposed human homeodomain region has facilitated cell entry into the cytoplasm to evaluate the dosage needed for efficacy (such as change in kidney size), as well as the efficiency of delivery to the site of action. Further, we will examine whether the peptide V2R antagonist affects the efficacy of the fusion protein or conjugate embodiment via a different mechanism.

SEQ ID No. 29 (Table 3): Peptide V2R six amino acid antagonist: CRAVKY.

In various embodiments, targeted peptides for the treatment of PKD may be any of the following: CRAVKY-(linker)-p200-human homeodomain; CRAVKY-(linker)-p21-human homeodomain; human homeodomain-p200-(linker)-CRAVKY; human homeodomain-p21-(linker)-CRAVKY where the CRAVKY sequence is at the N-terminal of the protein in the first two examples and at the C-terminal of the protein in the second two examples.

The relative activity of embodiments comprising, for example, p21 and p200 peptides with and without the linked CRAVKY peptide can be evaluated in vitro in PKD cyst cell cultures as described above provided these cells are engineered to also express V2R on their surface. The in vitro dose response to the various CRAVKY-containing fusion protein or conjugate embodiments described, for example, above can be compared to the same fusion protein or conjugate embodiments without CRAVKY for their ability to change the in vitro phenotype of the cell cultures from cyst-like to tubule-like. In addition, these constructs can also be tested in the murine PKD model described above for their relative ability to reduce the growth in kidney size.

If (1) the efficacy of the human HOX C12 or HOX D12 homeodomain-p21 and/or human HOX C12 or HOX D12 homeodomain-p200 fusion protein or conjugate formulation embodiments in the PKD cyst cell cultures is observed, and (2) greater potency (i.e., a shift in the dose-response curve to the left) in the PDK-1 transgenic mouse model described above is observed when targeted using the CRAVKY peptide, at least one of the sequence embodiments described above that comprises SEQ ID No. 29 will be tested in the PDK-1 transgenic mouse model as well as in affected patients instead of SEQ ID Nos. 24, 25, 27 and/or 28 (or variant or portion thereof), or their conjugate counterparts. Kidney growth rate will be assessed by known methods.

Alternative embodiments, including those comprising any of SEQ ID Nos. 1 through 19, or variants or portions thereof, conjugated to the (1) the p200 peptide or (2) the p21 peptide include a variety of fusion proteins or conjugates comprising any one or more linkers known in the art provided function is not compromised, and may further comprise the CRAVKY peptide.

Example 3

Cell Permeable Peptide Enzyme Replacement Therapy for Lysosomal Storage Disease

There is strong evidence that cell permeable peptides can enable large "cargo" peptides or proteins such as antibodies to enter cells. Embodiments of conjugates or fusion proteins comprising a HOX-derived peptide or other human homeodomain cell permeable peptides such as those disclosed similarly can chaperone larger molecules across cell membranes to intracellular sites of action. They also reduce the immunogenicity of the otherwise antigenic cargo peptides and proteins, and allow them to cross the blood brain barrier and enter the CNS. The embodiments disclosed and their modifications therefore also include embodiments in which the first region of the conjugate or fusion protein is the 60-amino acid human homeodomain or variant or portion thereof, and the second region is an active enzyme. These compounds will restore enzymatic function in patients with inherited enzyme deficiencies such as in lysosomal storage diseases. We include three examples of lysosomal storage disease and associated "cargo" structures ((1) glucocerebrosidase (GCase), for example, as shown in SEQ ID No. 30, for Gaucher Disease, (2), alpha-L-iduronidase, for example, as shown in SEQ ID No. 45, for Hurler Syndrome; and (3) iduronate-2-sulfatase, for example, as shown in SEQ ID No. 48, for Hunter Syndrome), the same principles apply to human homeodomain fusion proteins or conjugates with other "cargo" enzymes that are absent or defective in the other lysosomal storage diseases.

The lysosomal storage diseases are generally classified by the nature of the primary stored material involved, and can be broadly broken into the following: (ICD-10 codes are provided where available).

(E75) lipid storage disorders, mainly sphingolipidoses (including Gaucher's and Niemann-Pick diseases (E75.0-E75.1) gangliosidosis (including Tay-Sachs disease (E75.2) leukodystrophies.

(E76.0) mucopolysaccharidoses (including Hunter syndrome and Hurler disease)

(E77) glycoprotein storage disorders (E77.0-E77.1) mucolipidoses

Also, Glycogen storage disease type II (Pompe disease) is also a defect in lysosomal metabolism, although it is otherwise classified into E74.0 in ICD-10.

Gaucher Disease

Gaucher Disease is an inherited lysosomal storage disorder caused by the absence or mutation of the gene GBA 1, which in turn leads to a deficiency in the GBA1 product, glucocerebrosidase (GCase). Intravenous administration of GCase relieves some symptoms of Gaucher in patients. A GCase deficiency also contributes to some inherited forms of Parkinson's Disease.

In one embodiment, the first region human HOX C12 homeodomain 60-amino acid sequence is:

SEQ ID No. 1 (Table 3):
SRKKRKPYSKLQLAELEGEFLVNEFITRQRRRELSDRLNLSDQQVKIWFQ
NRRMKKKRLL In another embodiment the first region human HOX D12 homeodomain 60-amino acid sequence is:

SEQ ID No. 2 (Table 3):
ARKKRKPYTKQQIAELENEFLVNEFINRQKRKELSNRLNLSDQQVKIWFQ
NRRMKKKRVV and in some embodiments, the linked second portion is the GCase amino acid sequence:

SEQ ID No. 30 (Table 3):
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPVVTSPTWLKTNGAVNGKGSLKG

QPGDIYHQTWARYFVKFLDAYAEHKLQFWAVTAENEPSAGLLSGYPFQCL

GFTPEHQRDFIARDLGPTLANSTHHNVRLLMLDDQRLLLPHWAKVVLTDP

EAAKYVHGIAVHWYLDFLAPAKATLGETHRLFPNTMLFASEACVGSKFWE

QSVRLGSWDRGMQYSHSIITNLLYHVVGWTDWNLALNPEGGPNWVRNFVD

SPIIVDITKDTFYKQPMFYHLGHFSKFIPEGSQRVGLVASQKNDLDAVAL

MHPDGSAVVVVLNRSSKDVPLTIKDPAVGFLETISPGYSIHTYLWRRQ

In yet other embodiments, the second region is a variation on the cargo sequence shown here. In another embodiment with the addition of an initiating methionine, the entire peptide sequence of the fusion protein with HOX C12 is SEQ ID No. 31 (Table 3):
MSRKKRKPYSKLQLAELEGEFLVNEFITRQRRRELSDRLNLSDQQVKIWF

QNRRMKKKRLLARPCIPKSFGYSSWCVCNATYCDSFDPPTFPALGTFSRY

ESTRSGRRMELSMGPIQANHTGTGLLLTLQPEQKFQKVKGFGGAMTDAA

LNILALSPPAQNLLLKSYFSEEGIGYNIIRVPMASCDFSIRTYTYADTPD

DFQLHNFSLPEEDTKLKIPLIHRALQLAQRPVSLLASPWTSPTWLKTNGA

VNGKGSLKGQPGDIYHQTWARYFVKFLDAYAEHKLQFWAVTAENEPSAGL

LSGYPFQCLGFTPEHQRDFIARDLGPTLANSTHHNVRLLMLDDQRLLLPH

WAKVVLTDPEAAKYVHGIAVHWYLDFLAPAKATLGETHRLFPNTMLFASE

ACVGSKFWEQSVRLGSWDRGMQYSHSIITNLLYHVVGWTDWNLALNPEGG

PNWVRNFVDSPIIVDITKDTFYKQPMFYHLGHFSKFIPEGSQRVGLVASQ

KNDLDAVALMHPDGSAVVVVLNRSSKDVPLTIKDPAVGFLETISPGYSIH

TYLWRRQ

With the addition of an initiating methionine in yet another embodiment, the entire peptide sequence of the fusion protein with HOX D12 is SEQ ID No. 32 (Table 3):
MARKKRKPYTKQQIAELENEFLVNEFINRQKRKELSNRLNLSDQQVKIWF

QNRRMKKKRVVARPCIPKSFGYSSVVCVCNATYCDSFDPPTFPALGTFSR

YESTRSGRRMELSMGPIQANHTGTGLLLTLQPEQKFQKVKGFGGAMTDAA

ALNILALSPPAQNLLLKSYFSEEGIGYNIIRVPMASCDFSIRTYTYADTP

DDFQLHNFSLPEEDTKLKIPLIHRALQLAQRPVSLLASPWTSPTWLKTNG

AVNGKGSLKGQPGDIYHQTWARYFVKFLDAYAEHKLQFWAVTAENEPSAG

LLSGYPFQCLGFTPEHQRDFIARDLGPTLANSTHHNVRLLMLDDQRLLLP

HWAKVVLTDPEAAKYVHGIAVHWYLDFLAPAKATLGETHRLFPNTMLFAS

EACVGSKFWEQSVRLGSWDRGMQYSHSIITNLLYHVVGWTDWNLALNPEG

GPNWVRNFVDSPIIVDITKDTFYKQPMFYHLGHFSKFIPEGSQRVGLVAS

QKNDLDAVALMHPDGSAVVVVLNRSSKDVPLTIKDPAVGFLETISPGYSI

HTYLWRRQ

Linkers may not be required for function but linkers may be included in certain embodiments, for example, between SEQ ID Nos. 1 and 30 or between SEQ ID Nos. 2 and 30 without compromising function. Any linker known in the art may be used provided the function of the conjugate is not compromised with its addition. SEQ ID Nos. 31 and 32 embodiments, or variants or portions thereof would be altered, at least in part, to the extent that the linker sequence would bridge the first and second regions in each.

Protein glycosylation may be altered in the final structure as well. Exposure of mannose at several glycosylation sites may enhance lysosomal targeting of embodiments including, for example, SEQ ID Nos. 31 and/or 32 or variants or portions thereof.

In still further embodiments, additional amino acid sequences can be added to either the amino or carboxy termini in order to facilitate purification. Such sequences may include FLAG-tags (DYKDDDDK) (SEQ ID No. 102), myc-tags (EQKLISEEDL) (SEQ ID No. 103), His-tags (HHHHHH) (SEQ ID No. 80), and other similar tags known to those in the art. Such tags may or may not include linkers. In addition, ligands such as the biotin-acceptor protein (GLNDIFEAQKIEWHE) (SEQ ID No. 105), together with the active BirA protein may be used. For sequences that include an N-terminal initiating methionine, if a N-terminal purification domain is added the methionine will be on the N-terminal of the purification domain instead of at the N-terminal of the human homeodomain or HOX peptide first region.

Conjugate or fusion protein embodiments that include a human homeodomain or variant or portion thereof and, for example, the GCase sequence in the second region will be included in systemic formulations including intravenous, subcutaneous, intramuscular and injectable implant formulations for sustained release. In murine models of Gaucher Disease where human mutations are incorporated into the mouse GCase sequence, these fusion proteins prevent the accumulation of substrate in various tissues and prevent neurological manifestations of Gaucher Disease.

We will examine immunogenicity of the 60-amino acid human HOX C12 or HOX D12 homeodomain (or variant or portion thereof) conjugate or fusion protein embodiments using lymphocyte proliferation assays that are well known in the art. To study the general ability of, for example, the 60-amino acid human homeodomain or variant or portion thereof to eliminate the immunogenicity of otherwise immunogenic proteins, isolated human mononuclear cells from subjects immune to tetanus toxoid are incubated in vitro for three days with tetanus toxoid or human homeodomain (or variant or portion thereof) peptide-tetanus toxoid conjugates at various concentrations to be determined, ranging from about 1 µM to about 115 µM. 3H-thymidine incorporation by lymphocytes in the cultures will then be determined.

In addition, we will evaluate immunogenicity of the enzyme fusion proteins or conjugate embodiments in vitro. Specifically, mononuclear leukocytes will be isolated from patients with known infusion reactions and antibody formation to the enzyme. Using techniques well known in the art these cells will be incubated in vitro with media alone and with various concentrations of the standard enzyme formulation and with various concentrations of the human HOX C12 or HOX D12 homeodomain peptide fusion protein and/or conjugate embodiments such as the GCase sequence or variant or portion thereof, for example, between 1 µM and about 115 µM. The incorporation of 3H-thymidine by lymphocytes will be determined as a measure of the lymphocyte immune response.

For example, in vitro testing of the fusion protein embodiments comprising the GCase cargo peptide conjugated to the 60-amino acid human HOX C12 or HOX D12 homeodomain or variant or portion thereof (e.g., embodiments comprising SEQ ID Nos. 24, 25, 27 and/or 28, or variants or portions thereof) will be evaluated. In one embodiment we will compare immunogenicity of the 60-amino acid human homeodomain conjugates or fusion proteins containing the GCase peptide with the immunogenicity of the enzyme alone using lymphocyte proliferation assays of isolated human mononuclear leukocytes from patients with known immune-mediated infusion reactions when treated with enzyme alone. Following incubation in vitro for three to five days at an optimal micromolar concentration to be determined. Immunogenicity of embodiments comprising the 60-amino acid human HOX C12 or HOX D12 homeodomain (or variant or portion thereof) conjugates or fusion proteins will be assessed by examining incorporation of 3H-thymidine by lymphocytes, and results compared to controls.

Later in clinical testing, various embodiments comprising human HOX C12 or HOX D12 homeodomain peptide fusion proteins or conjugates that include the GCase sequence will be evaluated on the basis of their abilities to restore function without either clinically significant infusion reactions or functionally important anti-GCase antibody production.

There are two examples of cellular assays that can be used to determine that an human homeodomain-GCase conjugate embodiment is effective, and at what concentration. In normal cells, for example, to fibroblasts in culture, the addition of the substrate for GCase results in activation of the enzyme and reduction of the substrate (which accumulates in Gaucher Disease). In fibroblasts with defective or absent GBA 1 genes, the addition of the substrate for GCase does not lead to substrate turnover. However in cultures with these cells, the addition of increasing amounts of human homeodomain-GCase with exposed mannose residues or human homeodomain-GCase conjugates delivers more enzyme to the cell and decreases, for example, radio-labeled substrate. Alternatively, in cells taken from Gaucher patients, for example, leukocytes, a fluorometric beta-glucosidase assay determines relative GCase activity as a diagnosis of the disease, and is also usable as human cell assay to demonstrate the effectiveness of embodiments such as human homeodomain-GCase fusion protein or conjugate in restoring enzyme activity.

In the fibroblast cell cultures with Gba1 gene mutations, GCase cargo peptide (for example, SEQ ID No. 30) conjugated as a fusion protein to the human HOX C12 or HOX D12 homeodomain (for example, any of SEQ ID Nos. 1 and/or 2 or a portion thereof) will be active in this in vitro assay at various concentrations between about 1 μM to about 115 μM. We will measure the accumulation of the GCase substrate, glycosylceramide, compared to that in control cultures.

Point mutations in the GBA1 gene of mice have produced a reliable model of Gaucher Disease. We will evaluate for up to two months of daily i.v. or i.p. administration of an embodiment comprising the human homeodomain-GCase fusion protein or conjugate to reduce glucosylceramide (the GCase substrate) accumulation in this murine model. The GCase cargo peptide (for example, SEQ ID No. 30) conjugated as a fusion protein to the human HOX C12 or HOX D12 homeodomain (for example, any of SEQ ID Nos. 1 and/or 2 or a portion thereof) will be administered at a dose per mouse of between at least about 1 μg to at least about 500 μg or more. Again, we will assess the accumulation of the GCase substrate, glucosylceramide, compared to that in control group.

In another mouse model of Gaucher Disease with central nervous system involvement, accumulation of α-synuclein and tau inclusions occur in regions of the brain and are hallmarks of neurodegenerative diseases, such as Parkinson's Disease. For example, single point mutations in the murine Gba1 locus (Gba1 D409V/D409V) result in accumulation of α-synuclein/ubiquitin aggregates in the CNS and a measurable deficit in hippocampal memory. In this mouse model we will evaluate the ability of embodiments comprising the human HOX C12 or HOX D12 homeodomain-GCase fusion protein or conjugate to cross the blood brain barrier and deliver enzyme capable of preventing the structural associations of Parkinson's Disease, with the goal of reducing accumulation of α-synuclein/ubiquitin aggregates in the brain, compared to the administration of the pure enzyme systemically. In this mouse model of Gaucher disease, the GCase cargo peptide (for example, SEQ ID No. 30) conjugated as a fusion protein to the human homeodomain (for example, any of SEQ ID Nos. 1 through 19, or a portion thereof) will be administered intravenously or intraperitoneally for up to two months at a dose per mouse of between at least about 1 μg to at least about 500 μg. We will assess the accumulation of the α-synuclein/ubiquitin aggregates in the brain by known methods compared to that in control group.

Alternative embodiments such as any of SEQ ID Nos. 1 through 19, or variants or portions thereof, conjugated to the GCase peptide include a variety of fusion proteins or conjugates comprising one or more linkers known in the art, provided the function of the conjugate is not compromised.

Hurler Syndrome

Another lysosomal storage disease, Hurler Syndrome, mucopolysaccharidosis I (MPS I), is one of the mucopolysaccharidoses, a group of inherited disorders caused by a lack of specific lysosomal enzymes involved in the degradation of glycosaminoglycans (GAGs), or mucopolysaccharides. The accumulation of partially degraded GAGs causes interference with cell, tissue, and organ function. Hurler Syndrome is due to an inherited deficiency of alpha-L-iduronidase due to abnormal IDUA gene structure or IDUA gene regulation and can result in a wide range of phenotypic involvement with 3 major recognized clinical entities: Hurler (MPS IH), Scheie (MPS IS; 607016), and Hurler-Scheie (MPS IH/S) syndromes. Hurler and Scheie syndromes represent phenotypes at the severe and mild ends of the MPS I clinical spectrum, respectively, and the Hurler-Scheie syndrome is intermediate in phenotypic expression.

Mucopolysaccharidosis 1H (MPS1H) is a severe form of mucopolysaccharidosis type 1 characterized by progressive physical deterioration with urinary excretion of dermatan sulfate and heparan sulfate. Patients with MPS1H usually present, within the first year of life, a combination of hepatosplenomegaly, skeletal deformities, corneal clouding and severe mental retardation. Obstructive airways disease, respiratory infection and cardiac complications usually result in death before 10 years of age.

Mucopolysaccharidosis 1H/S (MPS1H/S) is a form of mucopolysaccharidosis type 1 characterized by progressive physical deterioration with urinary excretion of dermatan sulfate and heparan sulfate. MPS1H/S represents an intermediate phenotype of the MPS1 clinical spectrum. It is characterized by relatively little neurological involvement, but most of the somatic symptoms described for severe MPS1 develop in the early to mid-teens, causing considerable loss of mobility.

Mucopolysaccharidosis 1S (MPS1S) is a mild form of mucopolysaccharidosis type 1 characterized by progressive physical deterioration with urinary excretion of dermatan sulfate and heparan sulfate. Patients with MPS1S may have little or no neurological involvement, normal stature and life span, but present development of joints stiffness, mild hepatosplenomegaly, aortic valve disease and corneal clouding.

Here we refer to all of these clinical phenotypes as Hurler syndrome or MPS I. It is more frequent than MPS II (Hunter syndrome), which has no corneal clouding and pursues a slower course (see below).

In one embodiment, the HOX C12 amino acid sequence first region is SEQ ID No. 1:

SRKKRKPYSKLQLAELEGEFLVNEFITRQRRRELSDRLNLSDQQVKIWFQ

NRRMKKKRLL

In another embodiment, the HOX D12 amino acid sequence first region is SEQ ID No. 2:

ARKKRKPYTKQQIAELENEFLVNEFINRQKRKELSNRLNLSDQQVKIWFQ

NRRMKKKRVV

The second region may be, for example, SEQ ID No. 45 (Table 3), the 653 amino acid Alpha-L-iduronidase sequence (including the 27 amino acid signal peptide):

MRPLRPRAALLALLASLLAAPPVAPAEAPHLVHVDAARALWPLRRFWRST

GFCPPLPHSQADQYVLSWDQQLNLAYVGAVPHRGIKQVRTHWLLELVTTR

GSTGRGLSYNFTHLDGYLDLLRENQLLPGFELMGSASGHFTDFEDKQQVF

-continued

EWKDLVSSLARRYIGRYGLAHVSKWNFETWNEPDHHDFDNVSMTMQGFLN

YYDACSEGLRAASPALRLGGPGDSFHTPPRSPLSWGLLRHCHDGTNFFTG

EAGVRLDYISLHRKGARSSISILEQEKVVAQQIRQLFPKFADTPIYNDEA

DPLVGWSLPQPWRADVTYAAMVVKVIAQHQNLLLANTTSAFPYALLSNDN

AFLSYHPHPFAQRTLTARFQVNNTRPPHVQLLRKPVLTAMGLLALLDEEQ

LWAEVSQAGTVLDSNHTVGVLASAHRPQGPADAWRAAVLIYASDDTRAHP

NRSVAVTLRLRGVPPGPGLVYVTRYLDNGLCSPDGEWRRLGRPVFPTAEQ

FRRMRAAEDPVAAAPRPLPAGGRLTLRPALRLPSLLLVHVCARPEKPPGQ

VTRLRALPLTQGQLVLVWSDEHVGSKCLWTYEIQFSQDGKAYTPVSRKPS

TFNLFVFSPDTGAVSGSYRVRALDYWARPGPFSDPVPYLEVPVPRGPPSP

GNP

In yet other embodiments, the second region is a variation on the cargo sequence shown here. And the complete sequence of this embodiment including the HOX C12 homeodomain with an initiating methionine may be, for example, SEQ ID No. 46 (Table 3):

MSRKKRKPYSKLQLAELEGEFLVNEFITRQRRRELSDRLNLSDQQVKIWF

QNRRMKKKRLLMRPLRPRAALLALLASLLAAPPVAPAEAPHLVHVDAARA

LWPLRRFWRSTGFCPPLPHSQADQYVLSWDQQLNLAYVGAVPHRGIKQVR

THWLLELVTTRGSTGRGLSYNFTHLDGYLDLLRENQLLPGFELMGSASGH

FTDFEDKQQVFEWKDLVSSLARRYIGRYGLAHVSKWNFETWNEPDHHDFD

NVSMTMQGFLNYYDACSEGLRAASPALRLGGPGDSFHTPPRSPLSWGLLR

HCHDGTNFFTGEAGVRLDYISLHRKGARSSISILEQEKVVAQQIRQLFPK

FADTPIYNDEADPLVGWSLPQPWRADVTYAAMVVKVIAQHQNLLLANTTS

AFPYALLSNDNAFLSYHPHPFAQRTLTARFQVNNTRPPHVQLLRKPVLTA

MGLLALLDEEQLWAEVSQAGTVLDSNHTVGVLASAHRPQGPADAWRAAVL

IYASDDTRAHPNRSVAVTLRLRGVPPGPGLVYVTRYLDNGLCSPDGEWRR

LGRPVFPTAEQFRRMRAAEDPVAAAPRPLPAGGRLTLRPALRLPSLLLVH

VCARPEKPPGQVTRLRALPLTQGQLVLVWSDEHVGSKCLWTYEIQFSQDG

KAYTPVSRKPSTFNLFVFSPDTGAVSGSYRVRALDYWARPGPFSDPVPYL

EVPVPRGPPSPGNP

The complete sequence of another embodiment including the HOX D12 homeodomain with an initiating methionine may be, for example, SEQ ID No. 47 (Table 3):

MARKKRKPYTKQQIAELENEFLVNEFINRQKRKELSNRLNLSDQQVKIWF

QNRRMKKKRVVMRPLRPRAALLALLASLLAAPPVAPAEAPHLVHVDAARA

LWPLRRFWRSTGFCPPLPHSQADQYVLSWDQQLNLAYVGAVPHRGIKQVR

THWLLELVTTRGSTGRGLSYNFTHLDGYLDLLRENQLLPGFELMGSASGH

FTDFEDKQQVFEWKDLVSSLARRYIGRYGLAHVSKWNFETWNEPDHHDFD

NVSMTMQGFLNYYDACSEGLRAASPALRLGGPGDSFHTPPRSPLSWGLLR

HCHDGTNFFTGEAGVRLDYISLHRKGARSSISILEQEKVVAQQIRQLFPK

```
-continued
FADTPIYNDEADPLVGWSLPQPWRADVTYAAMVVKVIAQHQNLLLANTTS

AFPYALLSNDNAFLSYHPHPFAQRTLTARFQVNNTRPPHVQLLRKPVLTA

MGLLALLDEEQLWAEVSQAGTVLDSNHTVGVLASAHRPQGPADAWRAAVL

IYASDDTRAHPNRSVAVTLRLRGVPPGPGLVYVTRYLDNGLCSPDGEWRR

LGRPVFPTAEQFRRMRAAEDPVAAAPRPLPAGGRLTLRPALRLPSLLLVH

VCARPEKPPGQVTRLRALPLTQGQLVLVWSDEHVGSKCLWTYEIQFSQDG

KAYTPVSRKPSTFNLFVFSPDTGAVSGSYRVRALDYWARPGPFSDPVPYL

EVPVPRGPPSPGNP
```

In some embodiments, protein glycosylation may be altered in the final structure as well. Exposure of mannose at several glycosylation sites may enhance lysosomal targeting of an alpha-L-iduronidase-containing fusion protein or conjugate embodiment.

Fusion protein and conjugate embodiments comprised of the 60-amino acid human homeodomain or variant or portion thereof and the active alpha-L-iduronidase enzyme or an alternative alpha-L-iduronidase-containing fusion protein or conjugate embodiment with one or more linkers will be evaluated in a mouse model for their abilities to reach (1) sites of accumulated GAGs in (1) brain tissue, (2) chondrocytes within articular cartilage, and (3) the growth plate cartilage of long bones.

The MPS 1-H knock-in mouse model of Hurler Syndrome carries a mutation that is analogous to the mutation found in the Hurler Syndrome patients (IDUA-W402X); the MPS 1-H mice exhibit a phenotype of biochemical, metabolic and morphological abnormalities that correlate with abnormalities in previously utilized Hurler Syndrome animal models, and with abnormalities in the most severe form of alpha-L-iduronidase deficiency in these patients. Wang et al. "Characterization of an MPS 1-K knock-in mouse that carries a nonsense mutation analogous to the human IDUA-W402X mutation" *Molecular Genetics and Metabolism* 99:62-71, 2010.

In this model we will administer i.v. or i.p. injections of a formulation embodiment comprising the alpha-L-iduronidase enzyme conjugated to the human homeodomain or variant or portion thereof, or an alternative alpha-L-iduronidase-containing fusion protein or conjugate embodiment with one or more linkers at a dose per mouse of 1 µg to at least 500 µg, if solubility permits. We will assess the accumulation of GAGs (heparan sulfate and dermatan sulfate) using histopathology techniques, and compare these results to a control group's results.

In patients with Hurler Syndrome, we will evaluate the effects of fusion protein or conjugate embodiments comprising the active alpha-L-iduronidase enzyme on GAG accumulation by measuring the reduction of urinary excretion of GAGs, including heparan sulfate and dermatan sulfate. Specifically, patients with Hurler Syndrome will be treated systemically with chronic daily dosing of the formulation embodiments comprising alpha-L-iduronidase enzyme conjugated to a 60-amino acid human HOX C12 or HOX D12 homeodomain or variant or portion thereof, or an alternative alpha-L-iduronidase-containing fusion protein or conjugate embodiment with one or more linkers at a dose of less than about 0.01 mg/kg to less than about 100 mg/kg. GAG excretion in urine (heparan sulfate and dermatan sulfate) will be assessed by known methods, and results will be compared to patients who received a formulation embodiment comprising the alpha-L-iduronidase enzyme not in fusion protein or conjugate form. Further, we will evaluate skeletal and brain development assessed by standard growth and development pediatric techniques.

Various embodiments comprising the human HOX C12 or HOX D12 homeodomain-alpha-L-iduronidase fusion protein or conjugate will be tested in vitro in cultures of fibroblast cell lines with homozygous mutations of the IDUA gene as occurs in patients born with Hurler Syndrome. In these cultures, GAG turnover with and without a fusion protein or conjugate embodiment will be measured to confirm active enzyme and reduced lysosomal accumulation of dermatan sulfate and heparan sulfate.

In the fibroblast cell cultures with homozygous mutations of the IDUA gene, one embodiment comprising the human HOX C12 or HOX D12 homeodomain-alpha-L-iduronidase fusion protein, or alternative alpha-L-iduronidase-containing fusion protein or conjugate embodiment comprising one or more linkers, will be active in this in vitro assay at an optimal concentration between about 1 µM to about 115 µM. Again, we will measure the accumulation of GAG substrates, dermatan sulfate and heparin sulfate, and compare our results to control cultures.

We will further evaluate the immunogenicity of the human HOX C12 or HOX D12 homeodomain-alpha-L-iduronidase fusion protein or conjugate embodiments in lymphocyte cultures using peripheral blood mononuclear cells from MPS I patients with documented infusion reactions while receiving replacement enzyme therapy.

In one embodiment we will compare immunogenicity of the 60-amino acid human HOX C12 or HOX D12 homeodomain (or variant or portion thereof) conjugates or fusion proteins containing the alpha-L-iduronidase peptide with the immunogenicity of the enzyme alone using lymphocyte proliferation assays in isolated human mononuclear leukocytes from patients with known allergic (infusion) reactions when receiving standard alpha-L-iduronidase enzyme replacement therapy. 3H-thymidine incorporation is measured following incubation in vitro for three to five days at an optimal enzyme concentration between about 1 µM to about 115 µM. Immunogenicity of an embodiment comprising the 60-amino acid human HOX C12 or HOX D12 homeodomain (or variant or portion thereof) conjugate or fusion protein will be assessed by examining incorporation of 3H-thymidine by lymphocytes, and results will be compared to those of the treatment group receiving only the enzyme.

Immunogenicity of human HOX C12 or HOX D12 homeodomain-enzyme fusion protein and/or conjugate embodiments in the clinic will be compared to that of standard enzyme replacement proteins by comparing the occurrence of allergic infusion reactions and the production of IgG anti-enzyme antibody.

Alternative embodiments comprising, for example, any of SEQ ID Nos. 1 through 19, or variants or portions thereof, conjugated to the α-L-iduronidase peptide include a variety of fusion protein or conjugate embodiments, and can further comprise any one or more linkers known in the art provided the function of the conjugate is not compromised with the addition of one or more linker(s).

Hunter Syndrome

Hunter Syndrome or mucopolysaccharidosis II (MPS II) is a rare X-linked recessive disorder caused by deficiency of the lysosomal enzyme iduronate-2-sulfatase, leading to progressive accumulation of glycosaminoglycans in nearly all cell types, tissues, and organs. Patients with MPS II excrete excessive amounts of chondroitin sulfate B (dermatan sulfate) and heparitin sulfate (heparan sulfate) in the urine.

MPS II is a multisystem disorder. Most children with MPS2 have a severe form with early somatic abnormalities including skeletal deformities, hepatosplenomegaly, and progressive cardiopulmonary deterioration. A prominent feature is neurological damage that presents as developmental delay and hyperactivity but progresses to mental retardation and dementia. They die before 15 years of age, usually as a result of obstructive airway disease or cardiac failure. In contrast, those with a mild form of MPS2 may survive into adulthood, with attenuated somatic complications and often without mental retardation (Wraith, J. E. et al. "Mucopolysaccharidosis type II (Hunter syndrome): a clinical review and recommendations for treatment in the era of enzyme replacement therapy" Europ. J. Pediat. 167: 267-277, 2008).

In one embodiment, the first region human HOX C12 homeodomain 60-amino acid sequence is:

SEQ ID No. 1 (Table 3):
SRKKRKPYSKLQLAELEGEFLVNEFITRQRRRELSDRLNLSDQQVKIWFQ
NRRMKKKRLL In another embodiment the first region human HOX D12 homeodomain 60-amino acid sequence is:

SEQ ID No. 2 (Table 3):
ARKKRKPYTKQQIAELENEFLVNEFINRQKRKELSNRLNLSDQQVKIWFQ
NRRMKKKRVV And the second region may be, for example, SEQ ID No. 48, the Iduronate-2-sulfatase enzyme (550 amino acids including 25 amino acid signal sequence):

MPPPRTGRGLLWLGLVLSSVCVALGSETQANSTTDALNVLLIIVDDLRPS

LGCYGDKLVRSPNIDQLASHSLLFQNAFAQQAVCAPSRVSFLTGRRPDTT

RLYDFNSYWRVHAGNFSTIPQYFKENGYVTMSVGKVFHPGISSNHTDDSP

YSWSFPPYHPSSEKYENTKTCRGPDGELHANLLCPVDVLDVPEGTLPDKQ

STEQAIQLLEKMKTSASPFFLAVGYHKPHIPFRYPKEFQKLYPLENITLA

PDPEVPDGLPPVAYNPWMDIRQREDVQALNISVPYGPIPVDFQRKIRQSY

FASVSYLDTQVGRLLSALDDLQLANSTIIAFTSDHGWALGEHGEWAKYSN

FDVATHVPLIFYVPGRTASLPEAGEKLFPYLDPFDSASQLMEPGRQSMDL

VELVSLFPTLAGLAGLQVPPRCPVPSFHVELCREGKNLLKHFRFRDLEED

PYLPGNPRELIAYSQYPRPSDIPQWNSDKPSLKDIKIMGYSIRTIDYRYT

VWVGFNPDEFLANFSDIHAGELYFVDSDPLQDHNMYNDSQGGDLFQLLMP

In yet other embodiments, the second region is a variation on the cargo sequence shown here. The complete amino acid sequence embodiment of the combined first (HOX C12) and second region with an initiating methionine is, for example, SEQ ID No. 49:

MSRKKRKPYSKLQLAELEGEFLVNEFITRQRRRELSDRLNLSDQQVKIWF

QNRRMKKKRLLMPPPRTGRGLLWLGLVLSSVCVALGSETQANSTTDALNV

LLIIVDDLRPSLGCYGDKLVRSPNIDQLASHSLLFQNAFAQQAVCAPSRV

SFLTGRRPDTTRLYDFNSYWRVHAGNFSTIPQYFKENGYVTMSVGKVFHP

GISSNHTDDSPYSWSFPPYHPSSEKYENTKTCRGPDGELHANLLCPVDVL

DVPEGTLPDKQSTEQAIQLLEKMKTSASPFFLAVGYHKPHIPFRYPKEFQ

KLYPLENITLAPDPEVPDGLPPVAYNPWMDIRQREDVQALNISVPYGPIP

VDFQRKIRQSYFASVSYLDTQVGRLLSALDDLQLANSTIIAFTSDHGWAL

GEHGEWAKYSNFDVATHVPLIFYVPGRTASLPEAGEKLFPYLDPFDSASQ

LMEPGRQSMDLVELVSLFPTLAGLAGLQVPPRCPVPSFHVELCREGKNLL

KHFRFRDLEEDPYLPGNPRELIAYSQYPRPSDIPQWNSDKPSLKDIKIMG

YSIRTIDYRYTVWVGFNPDEFLANFSDIHAGELYFVDSDPLQDHNMYNDS

QGGDLFQLLMP

The complete amino acid sequence embodiment of the combined first (HOX D12) and second region with an initiating methionine is, for example SEQ ID No. 50:

MARKKRKPYTKQQIAELENEFLVNEFINRQKRKELSNRLNLSDQQVKIWF

QNRRMKKKRVVMPPPRTGRGLLWLGLVLSSVCVALGSETQANSTTDALNV

LLIIVDDLRPSLGCYGDKLVRSPNIDQLASHSLLFQNAFAQQAVCAPSRV

SFLTGRRPDTTRLYDFNSYWRVHAGNFSTIPQYFKENGYVTMSVGKVFHP

GISSNHTDDSPYSWSFPPYHPSSEKYENTKTCRGPDGELHANLLCPVDVL

DVPEGTLPDKQSTEQAIQLLEKMKTSASPFFLAVGYHKPHIPFRYPKEFQ

KLYPLENITLAPDPEVPDGLPPVAYNPWMDIRQREDVQALNISVPYGPIP

VDFQRKIRQSYFASVSYLDTQVGRLLSALDDLQLANSTIIAFTSDHGWAL

GEHGEWAKYSNFDVATHVPLIFYVPGRTASLPEAGEKLFPYLDPFDSASQ

LMEPGRQSMDLVELVSLFPTLAGLAGLQVPPRCPVPSFHVELCREGKNLL

KHFRFRDLEEDPYLPGNPRELIAYSQYPRPSDIPQWNSDKPSLKDIKIMG

YSIRTIDYRYTVWVGFNPDEFLANFSDIHAGELYFVDSDPLQDHNMYNDS

QGGDLFQLLMP

In some embodiments, protein glycosylation may be altered in the final structure as well. Exposure of mannose at several glycosylation sites may enhance lysosomal targeting of the human HOX C12 or HOX D12 homeodomain-iduronate-2-sulfatase fusion protein or conjugate embodiments.

In the fibroblast cell cultures with homozygous mutations of the IDS gene, an embodiment such as the human HOX C12 or HOX D12 homeodomain-iduronate-2-sulfatase fusion protein, or alternative iduronate-2-sulfatase-containing fusion protein or conjugate embodiment comprising one or more linkers, will be active in this in vitro assay at various concentrations between about 1 µM to about 115 µM. Again, we will measure the accumulation of GAG substrates, and compare our results to control cultures.

In a murine model (idsy/−) of MPSII (Hunter Syndrome) that has also been used to evaluate experimental gene therapy approaches, the onset of the gross morphological phenotype is manifest at 3-4 months of age, and becomes progressively more severe until death at age 60 to 70 weeks. This phenotype includes reduced weight gain, craniofacial and other skeletal abnormalities, with a short cranium and alopecia and thickening of the digits. Further, these mice show irregular gait, abnormal walking pattern and poor locomotor and exploratory abilities in the open-field test. IDS activity in this mouse model is undetectable in liver, spleen, lung, heart, kidney, skeletal muscle, brain and eye when compared with the activities of this enzyme in the wild-type tissues. However, IDS initiates the catabolism of the dermatan and heparan sulfate GAGs. The loss of IDS activity causes GAG accumulation within all tissues after just several days of life, with a dramatic increase seen during adult life stages; it leads to progressive cellular vacuolization and the consequent cell death. MPSII mice at 3 and 9 months of age show high levels of GAG storage within the cells and, as shown in radiographic assays, progressive GAG accumulation caused skeletal deformation as well, which affected the performance in locomotor tests. (Polito, V A et al. "Correction of Hunter syndrome in the MPSII mouse model by AAV2/8-mediated gene delivery." Hum. Mol. Genet. 15(7):1225-36, Apr. 1, 2006).

We will examine IDS activity by visualizing and quantifying GAG accumulation in protein extracts prepared from tissue homogenates of these MPSII mice using the fluorescent substrate 4-methylumbelliferyl-α-iduronate-2-sulfate. GAGs can be visualized in tissues by Alcian-blue staining of the paraffin-embedded sections of liver, spleen, lung, heart, kidney and skeletal muscle in these mice. In addition, GAG concentrations will be determined using a dimethyl-methylene blue assay with protein.

We will administer to male idsy/– mice i.v. or i.p. injections of a formulation embodiment comprising the iduronate-2-sulfatase peptide conjugated to the human HOX C12 or HOX D12 homeodomain (or variant or portion thereof) at a dose per mouse of 1 µg to at least 500 µg or more, if solubility permits. We will assess the accumulation of GAGs (heparan sulfate and dermatan sulfate) using histopathology techniques, and compare these results to those of a control group.

In patients with Hunter Syndrome, we intend to evaluate the effect of treatment with formulation embodiments comprising the human HOX C12 or HOX D12 homeodomain-iduronate-2-sulfatase fusion protein or conjugate on systemic manifestations of the disease, including those in the CNS, in bone, and in joints, in relation to normal development. Patients with Hunter Syndrome will be treated systemically with chronic daily dosing of the formulation embodiments comprising, for example, iduronate-2-sulfatase enzyme conjugated to the human HOX C12 or HOX D12 homeodomain or variant or portion thereof, or an alternative fusion protein or conjugate embodiment comprising the iduronate-2-sulfatase sequence and one or more linkers at a dose of less than about 0.01 mg/kg to less than about 100 mg/kg. GAG excretion in urine (heparan sulfate and dermatan sulfate) will be assessed by known methods, and results will be compared to patients who received a formulation comprising the iduronate-2-sulfatase enzyme not in fusion protein or conjugate form. Further, we will evaluate skeletal and brain development assessed by standard growth and development pediatric techniques.

We will further evaluate the in vitro immunogenicity of human HOX C12 or HOX D12 homeodomain-iduronate-2-sulfatase fusion protein or conjugate embodiments by comparing the proliferative responses in the treatment versus control (placebo) groups. Lymphocyte cultures will be prepared using peripheral blood mononuclear cells from MPS II patients in whom there have been documented infusion reactions while receiving replacement enzyme therapy. Proliferative responses will be determined by measuring incorporation of 3H-thymidine in these cells after three to five days of culture. In one embodiment we will compare immunogenicity of the 60-amino acid human HOX C12 or HOX D12 homeodomain (or variant or portion thereof) conjugates or fusion proteins containing the human homeodomain-iduronate-2-sulfatase peptide with the immunogenicity of the enzyme alone using lymphocyte proliferation assays in isolated human mononuclear leukocytes following incubation in vitro for three to five days at an optimal concentration to be determined, in the range of about 1 µM to about 115 µM. Immunogenicity of embodiments comprising the 60-amino acid human HOX C12 or HOX D12 homeodomain (or variant or portion thereof) conjugates or fusion proteins will be assessed by examining incorporation of 3H-thymidine by lymphocytes.

Alternative embodiments comprising, for example, any of SEQ ID Nos. 1 through 19, or variants or portions thereof, conjugated to the iduronate-2-sulfatase peptide include a variety of fusion proteins or conjugates, and can comprise any one or more linkers known in the art provided the function of the conjugate is not compromised by the addition of one or more linker(s).

Example 4

Retinal Membrane Guanylyl Cyclase (RetGC-1) Replacement Therapy in Congenital Blindness Leber Congenital Amourosis type 1 (LCA1): Human RetGC-1 is an 1103 amino acid protein, including amino acids 52-1103 coding the enzyme alone without the signal peptide. RetGC-1 is the gene product of RPE65 which, when absent or mutated, causes blindness. In this disease residual cone-photoreceptor vision correlates with biochemical properties of the mutants implying that vision restoration can be achieved if RetGC-1 enzyme activity in the retinal can be restored. Embodiments and their modifications disclosed herein therefore include fusion proteins or conjugates comprising the 60-amino acid human HOX C12 or HOX D12 homeodomain (or variant or portion thereof) cell permeable peptides and the RetGC-1 enzyme as a cargo peptide, and can be administered in any number or formulation embodiments for periodic intraocular injection or topical administration.

In one embodiment, the first region human HOX C12 homeodomain 60-amino acid sequence is:

SEQ ID No. 1 (Table 3):
SRKKRKPYSKLQLAELEGEFLVNEFITRQRRRELSDRLNLSDQQVKIWFQ

NRRMKKKRLL

In another embodiment the first region human HOX D12 homeodomain 60-amino acid sequence is:

SEQ ID No. 2 (Table 3):
ARKKRKPYTKQQIAELENEFLVNEFINRQKRKELSNRLNLSDQQVKIWFQ

NRRMKKKRVV and the linked second region is, for example, a RetGC-1 enzyme sequence such as:

SEQ ID No. 33 (Table 3):
AVFTVGVLGPWACDPIFSRARPDLAARLAAARLNRDPGLAGGPRFEVALL

PEPCRTPGSLGAVSSALARVSGLVGPVNPAACRPAELLAEEAGIALVPWG

CPWTQAEGTTAPAVTPAADALYALLRAFGWARVALVTAPQDLWVEAGRSL

STALRARGLPVASVTSMEPLDLSGAREALRKVRDGPRVTAVIMVMHSVLL

```
GGEEQRYLLEAAEELGLTDGSLVFLPFDTIHYALSPGPEALAALANSSQL

RRAHDAVLTLTRHCPSEGSVLDSLRRAQERRELPSDLNLQQVSPLFGTIY

DAVFLLARGVAEARAAAGGRWVSGAAVARHIRDAQVPGFCGDLGGDEEPP

FVLLDTDAAGDRLFATYMLDPARGSFLSAGTRMHFPRGGSAPGPDPSCWF

DPNNICGGGLEPGLVFLGFLLVVGMGLAGAFLAHYVRHRLLHMQMVSGPN

KIILTVDDITFLHPHGGTSRKVAQGSRSSLGARSMSDIRSGPSQHLDSPN

IGVYEGDRVWLKKFPGDQHIAIRPATKTAFSKLQELRHENVALYLGLFLA

RGAEGPAALWEGNLAVVSEHCTRGSLQDLLAQREIKLDWMFKSSLLLDLI

KGIRYLHHRGVAHGRLKSRNCIVDGRFVLKITDHGHGRLLEAQKVLPEPP

RAEDQLWTAPELLRDPALERRGTLAGDVFSLAIIMQEVVCRSAPYAMLEL

TPEEVVQRVRSPPPLCRPLVSMDQAPVECILLMKQCWAEQPELRPSMDHT

FDLFKNINKGRKTNIIDSMLRMLEQYSSNLEDLIRERTEELELEKQKTDR

LLTQMLPPSVAEALKTGTPVEPEYFEQVTLYFSDIVGFTTISAMSEPIEV

VDLLNDLYTLFDAIIGSHDVYKVETIGDAYMVASGLPQRNGQRHAAEIAN

MSLDILSAVGTFRMRHMPEVPVRIRIGLHSGPCVAGVVGLTMPRYCLFGD

TVNTASRMESTGLPYRIHVNLSTVGILRALDSGYQVELRGRTELKGKGAE

DTFWLVGRRGFNKPIPKPPDLQPGSSNHGISLQEIPPERRRKLEKARPGQ

FS.
```

In yet other embodiments, the second region is a variation on the cargo sequence shown here. And in another embodiment with the addition of an initiating methionine, the entire peptide sequence of the fusion protein including HOX C12 is, for example:

```
SEQ ID No. 34 (Table 3):
MSRKKRKPYSKLQLAELEGEFLVNEFITRQRRRELSDRLNLSDQQVKIWF

QNRRMKKKRLLAVFTVGVLGPWACDPIFSRARPDLAARLAAARLNRDPGL

AGGPRFEVALLPEPCRTPGSLGAVSSALARVSGLVGPVNPAACRPAELLA

EEAGIALVPWGCPWTQAEGTTAPAVTPAADALYALLRAFGWARVALVTAP

QDLWVEAGRSLSTALRARGLPVASVTSMEPLDLSGAREALRKVRDGPRVT

AVIMVMHSVLLGGEEQRYLLEAAEELGLTDGSLVFLPFDTIHYALSPGPE

ALAALANSSQLRRAHDAVLTLTRHCPSEGSVLDSLRRAQERRELPSDLNL

QQVSPLFGTIYDAVFLLARGVAEARAAAGGRWVSGAAVARHIRDAQVPGF

CGDLGGDEEPPFVLLDTDAAGDRLFATYMLDPARGSFLSAGTRMHFPRGG

SAPGPDPSCWFDPNNICGGGLEPGLVFLGFLLVVGMGLAGAFLAHYVRHR

LLHMQMVSGPNKIILTVDDITFLHPHGGTSRKVAQGSRSSLGARSMSDIR

SGPSQHLDSPNIGVYEGDRVWLKKFPGDQHIAIRPATKTAFSKLQELRHE

NVALYLGLFLARGAEGPAALWEGNLAVVSEHCTRGSLQDLLAQREIKLDW

MFKSSLLLDLIKGIRYLHHRGVAHGRLKSRNCIVDGRFVLKITDHGHGRL

LEAQKVLPEPPRAEDQLWTAPELLRDPALERRGTLAGDVFSLAIIMQEVV

CRSAPYAMLELTPEEVVQRVRSPPPLCRPLVSMDQAPVECILLMKQCWAE

QPELRPSMDHTFDLFKNINKGRKTNIIDSMLRMLEQYSSNLEDLIRERTE

ELELEKQKTDRLLTQMLPPSVAEALKTGTPVEPEYFEQVTLYFSDIVGFT

TISAMSEPIEVVDLLNDLYTLFDAIIGSHDVYKVETIGDAYMVASGLPQR

NGQRHAAEIANMSLDILSAVGTFRMRHMPEVPVRIRIGLHSGPCVAGVVG

LTMPRYCLFGDTVNTASRMESTGLPYRIHVNLSTVGILRALDSGYQVELR

GRTELKGKGAEDTFWLVGRRGFNKPIPKPPDLQPGSSNHGISLQEIPPER

RRKLEKARPGQFS
```

And in yet another embodiment with the addition of an initiating methionine, the entire peptide sequence of the fusion protein including HOX D12 is, for example:

```
SEQ ID No. 35 (Table 3):
MARKKRKPYTKQQIAELENEFLVNEFINRQKRKELSNRLNLSDQQVKIWF

QNRRMKKKRVVAVFTVGVLGPWACDPIFSRARPDLAARLAAARLNRDPGL

AGGPRFEVALLPEPCRTPGSLGAVSSALARVSGLVGPVNPAACRPAELLA

EEAGIALVPWGCPWTQAEGTTAPAVTPAADALYALLRAFGWARVALVTAP

QDLWVEAGRSLSTALRARGLPVASVTSMEPLDLSGAREALRKVRDGPRVT

AVIMVMHSVLLGGEEQRYLLEAAEELGLTDGSLVFLPFDTIHYALSPGPE

ALAALANSSQLRRAHDAVLTLTRHCPSEGSVLDSLRRAQERRELPSDLNL

QQVSPLFGTIYDAVFLLARGVAEARAAAGGRWVSGAAVARHIRDAQVPGF

CGDLGGDEEPPFVLLDTDAAGDRLFATYMLDPARGSFLSAGTRMHFPRGG

SAPGPDPSCWFDPNNICGGGLEPGLVFLGFLLVVGMGLAGAFLAHYVRHR

LLHMQMVSGPNKIILTVDDITFLHPHGGTSRKVAQGSRSSLGARSMSDIR

SGPSQHLDSPNIGVYEGDRVWLKKFPGDQHIAIRPATKTAFSKLQELRHE

NVALYLGLFLARGAEGPAALWEGNLAVVSEHCTRGSLQDLLAQREIKLDW

MFKSSLLLDLIKGIRYLHHRGVAHGRLKSRNCIVDGRFVLKITDHGHGRL

LEAQKVLPEPPRAEDQLWTAPELLRDPALERRGTLAGDVFSLAIIMQEVV

CRSAPYAMLELTPEEVVQRVRSPPPLCRPLVSMDQAPVECILLMKQCWAE

QPELRPSMDHTFDLFKNINKGRKTNIIDSMLRMLEQYSSNLEDLIRERTE

ELELEKQKTDRLLTQMLPPSVAEALKTGTPVEPEYFEQVTLYFSDIVGFT

TISAMSEPIEVVDLLNDLYTLFDAIIGSHDVYKVETIGDAYMVASGLPQR

NGQRHAAEIANMSLDILSAVGTFRMRHMPEVPVRIRIGLHSGPCVAGVVG

LTMPRYCLFGDTVNTASRMESTGLPYRIHVNLSTVGILRALDSGYQVELR

GRTELKGKGAEDTFWLVGRRGFNKPIPKPPDLQPGSSNHGISLQEIPPER

RRKLEKARPGQFS
```

Linkers may not be required for function but linkers may be included in a variety of embodiments, for example, between SEQ ID Nos. 1 and 33, or between SEQ ID Nos. 2 and 33, or variants or portions thereof, without compromising function. Any linker known in the art may be used, provided the function of the conjugate is not compromised by its addition. Embodiments, for example, such as SEQ ID Nos. 34 and/or 35 or variants or portions thereof would be altered, at least in part, to the extent that the linker sequence would bridge these first and second regions.

In still further embodiments, additional amino acid sequences can be added to either the amino or carboxy termini in order to facilitate purification. Such sequences may include FLAG-tags (DYKDDDDK) (SEQ ID No. 102), myc-tags (EQKLISEEDL) (SEQ ID No. 103), His-tags (HHHHHH) (SEQ ID No. 80), and other similar tags known to those in the art. Such tags may or may not include linkers. In addition, ligands such as the biotin-acceptor protein (GLNDIFEAQKIEWHE) (SEQ ID No. 105), together with the active BirA protein may be used. For sequences that include an N-terminal initiating methionine, if a N-terminal purification domain is added the methionine will be on the N-terminal of the purification domain instead of at the N-terminal of the human homeodomain or HOX peptide first region.

Successful functional translocation of the enzyme into cells in which the enzyme is usually low or absent, for example, enzyme translocation in HEK293 cells can be determined by providing the enzyme's substrate and measuring guanylyl cyclase activity by standard methods. Evidence of increased guanylyl cyclase activity would be taken as experimental evidence that an embodiment such as a human HOX C12 or HOX D12 homeodomain with cell permeabilizing capabilities can deliver functional enzyme to human cells.

We will evaluate embodiments comprising, for example, a human HOX C12 or HOX D12 homeodomain-RetGC-1 enzyme fusion protein or conjugate in a mouse knock-out model. The animal model that best approximates LCA1 is a mouse knock-out of Gucy2e, a gene that encodes RetGC-1. This mouse exhibits nonresponsive cone photoreceptors and demonstrates the LCA1 phenotype. Jacobson et al. "Determining consequences of retinal membrane guanylyl cyclase (RetGC1) deficiency in human Leber congenital amaurosis en route to therapy: residual cone-photoreceptor vision correlates with biochemical properties of the mutants." *Human Molecular Genetics* 22(1):168-83, 2013.

We will administer an embodiment of a human homeodomain-RetGC-1 conjugate or fusion protein by retinal (retrobulbar) injection or by eye drops (i.e., topically) to the knock-out mice with evaluation of restored electroretinogram (ERG) function as a measure of returned vision. Results will be compared to those in a control group administered a buffer without the human HOX C12 or HOX D12 homeodomain-RetGC-1. In one embodiment, proteins will be administered to mice by retinal (retrobulbar) injection or by eye drops a formulation comprising the RetGC-1 peptide conjugated to the human HOX C12 or HOX D12 homeodomain or variant or portion thereof, or alternative RetGC-1-containing fusion protein or conjugate embodiments comprising one or more linkers at a dose per 20 g mouse of at least about 1 µg to at least about 500 µg. We will examine restoration of ERG function compared to that of an untreated control group.

In children with Leber Congenital Amourosis type 1 (LCA1), changes in visual acuity and electroretinogram function will be evaluated after chronic (daily, every other day, twice per week, weekly or less frequent) treatment with an ophthalmic formulation embodiment comprising the RetGC-1 peptide conjugated to the human HOX C12 or HOX D12 homeodomain or variant or portion thereof or alternative fusion protein or conjugate embodiments comprising the RetGC-1 sequence and one or more linkers at a dose of less than about 0.01 mg/kg to less than about 100 mg/kg. After various treatment durations such as 1 day, 3 days, 1 week, 2 weeks, 3 weeks or 4 weeks or longer, Patients receiving the fusion protein or conjugate treatment will be compared to their pretreatment values to evaluate clinically meaningful improvements in visual function using standard clinical methods to assess visual acuity, including, without limitation, ERG function.

Alternative embodiments comprising any of SEQ ID Nos. 1 through 19, or variants or portions thereof, conjugated to the RetGC-1 peptide include a variety of fusion proteins or conjugates comprising any one or more linkers known in the art, provided the function of the conjugate is not compromised by the addition.

Example 5

A Regulatory Peptide for Huntington's Disease (HD)

Huntington's Disease (HD), a neurodegenerative genetic disorder that affects muscle coordination and leads to cognitive decline, is caused by the expression of a mutant Huntingtin gene (HTT). It often manifests in the mid-30s to early 40s, but may begin earlier with both physical and mental abilities declining over time; gradually coordinated movement becomes very difficult. Clinically, there are also a number of subtle defects seen in patients with HD, including oculomotor, speech and cognitive problems. Mutant HTT expression is specific to the striatum, a part of the brain which controls movements, and neuronal loss and/or inflammation here is thought to underlie the clinical signs of HD.

ZF6×Hunt-Kox-1 is a specifically designed zinc finger protein which binds longer CAG repeats and represses mutant HTT gene expression. Other lengths of zinc finger proteins are also possible including but not limited to ZF12×Hunt-Kox-1 and ZF18×Hunt-Kox-1. Fusion protein or conjugate embodiments with the human HOX C12 or HOX D12 homeodomain cell permeable peptide will enable ZF6×Hunt-Kox-1, ZF12×Hunt-Kox-1, ZF18×Hunt-Kox-1, and related proteins to enter cells and the nucleus to effectively and selectively down regulate mutant HTT gene expression. We will evaluate the effect of a variety of embodiments comprising the 60-amino acid human HOX C12 or HOX D12 homeodomain-zinc finger fusion proteins or conjugates on neurological pathology. To this end we will administer intravenous formulations comprising the human homeodomain-zinc finger embodiments to Huntington's Disease patients. Specifically, we will evaluate the ability of the human HOX C12 or HOX D12 homeodomain peptide to cross the blood brain barrier and enter the central nervous system.

In one embodiment, the first region human HOX C12 homeodomain 60-amino acid sequence is:

SEQ ID No. 1 (Table 3):
SRKKRKPYSKLQLAELEGEFLVNEFITRQRRRELSDRLNLSDQQVKIWFQ

NRRMKKKRLL

In another embodiment the first region human HOX D12 homeodomain 60-amino acid sequence is:

SEQ ID No. 2 (Table 3):
ARKKRKPYTKQQIAELENEFLVNEFINRQKRKELSNRLNLSDQQVKIWFQ

NRRMKKKRVV and the linked second region is, for example, a ZF6×Hunt-Kox-1 sequence;

SEQ ID No. 36 (Table 3):
TGAERPFQCRICMRNFSQRATLQRHIRTHTGEKPFACDICGRKFAQRATL

QRHTKIHTGSERPFQCRICMRNFSQRATLQRHIRTHTGEKPFACDICGRK

-continued
```
FAQRATLQRHTKIHTGSERPFQCRICMRNFSQRATLQRHIRTHTGEKPFA
CDICGRKFAQRATLQRHTKIHLRQKDGGGGSGGGGSGGGGSQLVSSLSPQ
HSAVTQGIIKNKEGMDAKSLTAWSRTLVTFKDVFVDFTREEWKLLDTAQQ
IVYRNVMLENYKNLVSLGYQLTKPDVILRLEKGEEPWLVEREIHQETHPD
SETAFEIKSSV
```

In yet other embodiments, the second region is a variation on the cargo sequence shown here. And, in another embodiment with the addition of an initiating methionine, the entire peptide sequence of the fusion protein including the HOX C12 peptide is, for example:

```
SEQ ID No. 37 (Table 3):
MSRKKRKPYSKLQLAELEGEFLVNEFITRQRRRELSDRLNLSDQQVKIWF
QNRRMKKKRLLTGAERPFQCRICMRNFSQRATLQRHIRTHTGEKPFACDI
CGRKFAQRATLQRHTKIHTGSERPFQCRICMRNFSQRATLQRHIRTHTGE
KPFACDICGRKFAQRATLQRHTKIHTGSERPFQCRICMRNFSQRATLQRH
IRTHTGEKPFACDICGRKFAQRATLQRHTKIHLRQKDGGGGSGGGGSGGG
GSQLVSSLSPQHSAVTQGIIKNKEGMDAKSLTAWSRTLVTFKDVFVDFTR
EEWKLLDTAQQIVYRNVMLENYKNLVSLGYQLTKPDVILRLEKGEEPWLV
EREIHQETHPDSETAFEIKSSV
``` and in yet another embodiment with the addition of an initiating methionine, the entire peptide sequence of the fusion protein including the HOX D12 peptide is, for example:

```
SEQ ID No. 38 (Table 3):
MARKKRKPYTKQQIAELENEFLVNEFINRQKRKELSNRLNLSDQQVKIWF
QNRRMKKKRVVTGAERPFQCRICMRNFSQRATLQRHIRTHTGEKPFACDI
CGRKFAQRATLQRHTKIHTGSERPFQCRICMRNFSQRATLQRHIRTHTGE
KPFACDICGRKFAQRATLQRHTKIHTGSERPFQCRICMRNFSQRATLQRH
IRTHTGEKPFACDICGRKFAQRATLQRHTKIHLRQKDGGGGSGGGGSGGG
GSQLVSSLSPQHSAVTQGIIKNKEGMDAKSLTAWSRTLVTFKDVFVDFTR
EEWKLLDTAQQIVYRNVMLENYKNLVSLGYQLTKPDVILRLEKGEEPWLV
EREIHQETHPDSETAFEIKSSV
```

In a further embodiment or embodiments, additional numbers of zinc finger repeats may be included as shown in these examples of the second component with 12 and 18 repeats respectively:

ZF12×Hunt-Kox-1, for example:

```
SEQ ID No. 39 (Table 3):
TGAERPFQCRICMRNFSQRATLQRHIRTHTGEKPFACDICGRKFAQRATL
QRHTKIHTGSERPFQCRICMRNFSQRATLQRHIRTHTGEKPFACDICGRK
FAQRATLQRHTKIHTGSERPFQCRICMRNFSQRATLQRHIRTHTGEKPFA
CDICGRKFAQRATLQRHTKIHLRQKDGGGGSGGGGSGGGGSQLVGTAERP
FQCRICMRNFSQRATLQRHIRTHTGEKPFACDICGRKFAQRATLQRHTKI
HTGSERPFQCRICMRNFSQRATLQRHIRTHTGEKPFACDICGRKFAQRAT
LQRHTKIHTGSERPFQCRICMRNFSQRATLQRHIRTHTGEKPFACDICGR
KFAQRATLQRHTKIHLRQKDGGGGSGGGGSGGGGSQLVSSLSPQHSAVTQ
GIIKNKEGMDAKSLTAWSRTLVTFKDVFVDFTREEWKLLDTAQQIVYRNV
MLENYKNLVSLGYQLTKPDVILRLEKGEEPWLVEREIHQETHPDSETAFE
IKSSV
```

ZF18×Hunt-Kox-1, for example:

```
SEQ ID No. 42 (Table 3):
TGAERPFQCRICMRNFSQRATLQRHIRTHTGEKPFACDICGRKFAQRATL
QRHTKIHTGSERPFQCRICMRNFSQRATLQRHIRTHTGEKPFACDICGRK
FAQRATLQRHTKIHTGSERPFQCRICMRNFSQRATLQRHIRTHTGEKPFA
CDICGRKFAQRATLQRHTKIHLRQKDGGGGSGGGGSGGGGSQLVGTAERP
FQCRICMRNFSQRATLQRHIRTHTGEKPFACDICGRKFAQRATLQRHTKI
HTGSERPFQCRICMRNFSQRATLQRHIRTHTGEKPFACDICGRKFAQRAT
LQRHTKIHTGSERPFQCRICMRNFSQRATLQRHIRTHTGEKPFACDICGR
KFAQRATLQRHTKIHLRQKDGGGGSGGGGSGGGGSQLVGTAERPFQCRIC
MRNFSQRATLQRHIRTHTGEKPFACDICGRKFAQRATLQRHTKIHTGSER
PFQCRICMRNFSQRATLQRHIRTHTGEKPFACDICGRKFAQRATLQRHTK
IHTGSERPFQCRICMRNFSQRATLQRHIRTHTGEKPFACDICGRKFAQRA
TLQRHTKIHLRQKDGGGGSGGGGSGGGGSQLVSSLSPQHSAVTQGIIKNK
EGMDAKSLTAWSRTLVTFKDVFVDFTREEWKLLDTAQQIVYRNVMLENYK
NLVSLGYQLTKPDVILRLEKGEEPWLVEREIHQETHPDSETAFEIKSSV
```

In further embodiments, these sequences with additional numbers of zinc finger repeats are shown with the human homeodomain peptide included, for example, in an embodiment comprising the sequence with an initiating methionine residue:

Human HOX C12-ZF12×Hunt-Kox-1, for example:

```
SEQ ID No. 40 (Table 3):
MSRKKRKPYSKLQLAELEGEFLVNEFITRQRRRELSDRLNLSDQQVKIWF
QNRRMKKKRLLTGAERPFQCRICMRNFSQRATLQRHIRTHTGEKPFACDI
CGRKFAQRATLQRHTKIHTGSERPFQCRICMRNFSQRATLQRHIRTHTGE
KPFACDICGRKFAQRATLQRHTKIHTGSERPFQCRICMRNFSQRATLQRH
IRTHTGEKPFACDICGRKFAQRATLQRHTKIHLRQKDGGGGSGGGGSGGG
GSQLVGTAERPFQCRICMRNFSQRATLQRHIRTHTGEKPFACDICGRKFA
QRATLQRHTKIHTGSERPFQCRICMRNFSQRATLQRHIRTHTGEKPFACD
ICGRKFAQRATLQRHTKIHTGSERPFQCRICMRNFSQRATLQRHIRTHTG
EKPFACDICGRKFAQRATLQRHTKIHLRQKDGGGGSGGGGSGGGGSQLVS
SLSPQHSAVTQGIIKNKEGMDAKSLTAWSRTLVTFKDVFVDFTREEWKLL
DTAQQIVYRNVMLENYKNLVSLGYQLTKPDVILRLEKGEEPWLVEREIHQ
ETHPDSETAFEIKSSV
```

Human HOX D12-ZF12×Hunt-Kox-1, for example:

SEQ ID No. 41 (Table 3):
MARKKRKPYTKQQIAELENEFLVNEFINRQKRKELSNRLNLSDQQVKIWF
QNRRMKKKRVVTGAERPFQCRICMRNFSQRATLQRHIRTHTGEKPFACDI
CGRKFAQRATLQRHTKIHTGSERPFQCRICMRNFSQRATLQRHIRTHTGE
KPFACDICGRKFAQRATLQRHTKIHTGSERPFQCRICMRNFSQRATLQRH
IRTHTGEKPFACDICGRKFAQRATLQRHTKIHLRQKDGGGGSGGGGSGGG
GSQLVGTAERPFQCRICMRNFSQRATLQRHIRTHTGEKPFACDICGRKFA
QRATLQRHTKIHTGSERPFQCRICMRNFSQRATLQRHIRTHTGEKPFACD
ICGRKFAQRATLQRHTKIHTGSERPFQCRICMRNFSQRATLQRHIRTHTG
EKPFACDICGRKFAQRATLQRHTKIHLRQKDGGGGSGGGGSGGGGSQLVS
SLSPQHSAVTQGIIKNKEGMDAKSLTAWSRTLVTFKDVFVDFTREEWKLL
DTAQQIVYRNVMLENYKNLVSLGYQLTKPDVILRLEKGEEPWLVEREIHQ
ETHPDSETAFEIKSSV Human HOX C12-ZF18×Hunt-Kox-1, for example:

SEQ ID No. 43 (Table 3):
MSRKKRKPYSKLQLAELEGEFLVNEFITRQRRRELSDRLNLSDQQVKIWF
QNRRMKKKRLLTGAERPFQCRICMRNFSQRATLQRHIRTHTGEKPFACDI
CGRKFAQRATLQRHTKIHTGSERPFQCRICMRNFSQRATLQRHIRTHTGE
KPFACDICGRKFAQRATLQRHTKIHTGSERPFQCRICMRNFSQRATLQRH
IRTHTGEKPFACDICGRKFAQRATLQRHTKIHLRQKDGGGGSGGGGSGGG
GSQLVGTAERPFQCRICMRNFSQRATLQRHIRTHTGEKPFACDICGRKFA
QRATLQRHTKIHTGSERPFQCRICMRNFSQRATLQRHIRTHTGEKPFACD
ICGRKFAQRATLQRHTKIHTGSERPFQCRICMRNFSQRATLQRHIRTHTG
EKPFACDICGRKFAQRATLQRHTKIHLRQKDGGGGSGGGGSGGGGSQLVG
TAERPFQCRICMRNFSQRATLQRHIRTHTGEKPFACDICGRKFAQRATLQ
RHTKIHTGSERPFQCRICMRNFSQRATLQRHIRTHTGEKPFACDICGRKF
AQRATLQRHTKIHTGSERPFQCRICMRNFSQRATLQRHIRTHTGEKPFAC
DICGRKFAQRATLQRHTKIHLRQKDGGGGSGGGGSGGGGSQLVSSLSPQH
SAVTQGIIKNKEGMDAKSLTAWSRTLVTFKDVFVDFTREEWKLLDTAQQI
VYRNVMLENYKNLVSLGYQLTKPDVILRLEKGEEPWLVEREIHQETHPDS
ETAFEIKSSV Human HOX D12-ZF18×Hunt-Kox-1, for example:

SEQ ID No. 44 (Table 3):
MARKKRKPYTKQQIAELENEFLVNEFINRQKRKELSNRLNLSDQQVKIWF
QNRRMKKKRVVTGAERPFQCRICMRNFSQRATLQRHIRTHTGEKPFACDI
CGRKFAQRATLQRHTKIHTGSERPFQCRICMRNFSQRATLQRHIRTHTGE
KPFACDICGRKFAQRATLQRHTKIHTGSERPFQCRICMRNFSQRATLQRH
IRTHTGEKPFACDICGRKFAQRATLQRHTKIHLRQKDGGGGSGGGGSGGG
GSQLVGTAERPFQCRICMRNFSQRATLQRHIRTHTGEKPFACDICGRKFA -continued
QRATLQRHTKIHTGSERPFQCRICMRNFSQRATLQRHIRTHTGEKPFACD
ICGRKFAQRATLQRHTKIHTGSERPFQCRICMRNFSQRATLQRHIRTHTG
EKPFACDICGRKFAQRATLQRHTKIHLRQKDGGGGSGGGGSGGGGSQLVG
TAERPFQCRICMRNFSQRATLQRHIRTHTGEKPFACDICGRKFAQRATLQ
RHTKIHTGSERPFQCRICMRNFSQRATLQRHIRTHTGEKPFACDICGRKF
AQRATLQRHTKIHTGSERPFQCRICMRNFSQRATLQRHIRTHTGEKPFAC
DICGRKFAQRATLQRHTKIHLRQKDGGGGSGGGGSGGGGSQLVSSLSPQH
SAVTQGIIKNKEGMDAKSLTAWSRTLVTFKDVFVDFTREEWKLLDTAQQI
VYRNVMLENYKNLVSLGYQLTKPDVILRLEKGEEPWLVEREIHQETHPDS
ETAFEIKSSV In other embodiments, the second region may be a variation on any of the cargo sequences shown above.

Linkers may not be required for function but linkers may be included in a variety of embodiments, for example, between SEQ ID Nos. 1 and 36, 39, or 42 or between SEQ ID Nos. 2 and 36, 39, or 42 or a portion thereof without compromising function. Any linker known in the art may be used provided the function of the conjugate is not compromised by its addition; see, e.g., Table 2. Embodiments such as SEQ ID nos. 37, 38, 40, 41, 43 and/or 44 would be altered, at least in part, to the extent that the linker sequence would bridge these first and second regions.

In still further embodiments, additional amino acid sequences can be added to either the amino or carboxy termini in order to facilitate purification. Such sequences may include FLAG-tags (DYKDDDDK) (SEQ ID No. 102), myc-tags (EQKLISEEDL) (SEQ ID No. 103), His-tags (HHHHHH) (SEQ ID No. 80), and other similar tags known to those in the art. In addition, ligands such as the biotin-acceptor protein (GLNDIFEAQKIEWHE) (SEQ ID No. 105), together with the active BirA protein may be used. For sequences that include an N-terminal initiating methionine, if a N-terminal purification domain is added the methionine will be on the N-terminal of the purification domain instead of at the N-terminal of the human homeodomain or HOX peptide first region. Embodiments of the human HOX C12 or HOX D12 homeodomain-zinc finger fusion protein or conjugate will be tested in an appropriate cell line to determine that the constructs are functionally translocated and that the mutant HTT gene is repressed. Knock-in STHdh cells, where the first exon of the mouse HTT gene has been replaced by a human exon with 111 CAG repeats (STHdhQ111/HdhQ111 or STHdhQ7/HdhQ111) will be used.

In one embodiment, we will examine the translocation of the zinc finger cargo protein using the 60-amino acid human HOX C12 or HOX D12 homeodomain (or variant or portion thereof) containing fusion protein or conjugate present following incubation of knock-in STHdh cells in culture for various periods of time such as 1 hour, 2 hours, 3 hours, 4 hours, 6 hours, or 24 hours at an optimal micromolar concentration to be determined, likely between about 1 µM to about 115 µM. We will evaluate expression of the mutant HTT gene by known methods and compare the results to control cultures.

R6/2 mice are the most widely used animal model of HD. This knock-in mouse model for HD overexpresses the human HTT gene in the brain at a location known to be effected in human patients, the striatum. R6/2 mice demonstrate motor deficits phenotypically that are analogous to the signs and symptoms in HD patients, for example, the R6/2 mice lack the ability to grasp with their front claws.

In one embodiment, beginning at three or four weeks of age we will evaluate motor skills in R6/2 mice; half will be treated and the others will serve as a control group. We will administer to mice through i.v. or i.p. injections a formulation daily, every other day or every third day, a human HOX C12 or HOX D12 homeodomain-zinc finger fusion protein or conjugate embodiment comprising, for example, any of SEQ ID Nos. 37, 38, 40, 41, 42, or 43 or any portion thereof, for one to two weeks. At four to six weeks of age we will reevaluate motor skills just prior to sacrifice for histological analysis. Histological analysis will be in two parts. Firstly, using rtPCR, mutant HTT expression will be evaluated in each striatum of treated and control groups of mice. Secondly, evidence of striatal neuronal loss will be evaluated in the striata of treated vs. non-treated control mice. The reduction in neuronal loss and/or striatal cell volume will be assessed using techniques well known in neurohistology laboratories, and will be reported as density of neurons per standard microscope field at common magnification. Thus, we will evaluate both the expression of the mutant HTT gene and evidence of neuronal loss in the striatum of the brain by known methods, and after assessing motor deficits, compare the results of treated R6/2 mice to those of the untreated R6/2 controls; we will further compare each group's post-treatment motor deficits score to its own baseline score.

In clinical trials with Huntington's Disease patients motor deficits will be evaluated by using the Unified Huntington's Disease Rating Scale (UHDRS) Total Motor Score, a clinical tool used to evaluate patients in HD therapy trials. It provides a quantitative assessment of treatment benefits in HD, providing a composite score based on a number of motor deficits. Huntington Study Group authors, "Unified Huntington's Disease Rating Scale: Reliability and Consistency" *Movement Disorders* 11(2):136-142, 1996. A change from pre- to post-treatment overall motor score of one point or more is considered clinically significant.

We will evaluate the progression of the disease as reflected in the change in motor skills in HD patients following administration of a formulation embodiment comprising an human HOX C12 or HOX D12 homeodomain-zinc finger fusion protein or conjugate comprising. For example, any of SEQ ID Nos. 37, 38, 40, 41, 42, or 43, or a portion thereof. First we will assess UHDRS scores in this treatment group of these patients and then, over the course of six to eight weeks, administer the fusion protein or conjugate formulation embodiment by intravenous or subcutaneous injection on a daily basis as an optimal dose to be determined, ranging from at least 0.01 mg/kg to at least about 500 mg/kg body weight. Motor function and other HD scored deficits will be evaluated post-treatment based on the Unified Huntington's Disease Rating Scale (UHDRS) Total Motor Score; results will be compared to the baseline score. We will assess percent improvement in UHDRS relative to non-treated controls or historical controls followed for the same period.

Alternative embodiments comprising any of SEQ ID Nos. 1 through 19, or variants or portions thereof, conjugated to any of the zinc finger peptides discussed above include a variety of fusion proteins or conjugates comprising any one or more linkers known in the art, provided the function of the conjugate is not compromised with the addition.

Example 6

Cell-Penetrating Peptides and Vaccine Applications.

Cell penetrating peptides have been shown to facilitate the delivery of antigenic epitopes into the cytoplasm of antigen-presenting cells, such as dendritic cells, enabling antigen processing and presentation in a major histocompatiblity complex (MHC) class I or class II dependent manner to CD8 and CD4 T-cells respectively and provoke an effective immune response (Brooks, et al. Cell-penetrating peptides: Application in vaccine delivery, *Biochimica et Biophysica Acta* 1805:25-34, 2010). CPPs utilizing a furin-sensitive linker for conjugation with antigenic epitopes have been shown effective at provoking antigen specific cytolytic CD8 T-cell responses when administered with oligodeoxynucleotides containing CpG motifs (Lu et al. TAP-independent presentation of CTL epitopes by Trojan antigens, *J. Immunol.* 166:7063-7071, 2001.). Other methods of conjugation that allow for release of the antigenic cargo in antigen presenting cells include use of a disulfide linkage that is cleaved by cytoplasmic glutathione (Kim et al. Introduction of soluble proteins into the MHC class I pathway by conjugation to an HIV tat peptide, *J. Immunol.* 159:1666-68, 1997) and use of antigenic peptides treated with sulfosuccinimidyl 4-maleimidomethylcyclohexane carboxylate (SMCC) followed by reaction with a C-terminal cysteine modified CPP (Apostolopoulos et. al. Delivery of tumor associated antigens to antigen presenting cells using penetratin induces potent immune responses, *Vaccine* 24:3191-202, 2006). CPP fusion proteins without linkers have also been successfully used to generate specific T-cell responses to tumor antigens (Batchu et. al. Protein transduction of dendritic cells for NY-ESO-1-based immunotherapy of myeloma, *Cancer Res.* 65:10041-49, 2005, Scheller et. al. Human cytomegalovirus protein pp65: an efficient protein carrier system into human dendritic cells, *Gene Ther.* 15:318-325, 2008, Viehl et. al. Tat mammaglobin fusion protein transduced dendritic cells stimulate mammaglobin-specific CD4 and CD8 T cells, *Breast Cancer Res. Treat.* 91:271-78, 2005).

Traditionally vaccines have relied on adjuvants that are often ligands for toll-like receptors (TLRs) to target antigens to dendritic cells for enhanced immune responses. This approach has not worked well in the case of vaccines to prevent or improve outcomes in tuberculosis. Perhaps one reason is a TLR2-dependent inhibition of MHC class II dependent antigen presentation that has also been reported to be an important mechanism allowing persistent infection of mycobacteria in macrophages (Harding, C. V and Boom, W. H., Regulation of antigen presentation by Mycobacterim tuberculosis: a roll for Toll-like receptors. *Nat Rev Microbiol.* 8(4):296-307, 2010). Thus the use of CPPs may promote efficient dendritic cell antigen processing and presentation and avoid this undesirable effect of TLR2 agonists while many of the current tuberculosis vaccine candidates such as those that rely on adenovirus vectors (Appledorn et. al. Adenovirus Vector-Induced Innate Inflammatory Mediators, MAPK Signaling, As Well As Adaptive Immune Responses Are Dependent upon Both TLR2 and TLR9 In Vivo. *J Immunol* 181:2134-44, 2008) and adjuvants do not (Frick, M. The Tuberculosis Vaccines Pipeline, "Where are we going, where have we been?" June 2013 and Rowland, R. and McShane. *Expert Rev Vaccines* 10(5):645-58, 2011).

In one vaccine embodiment, the conjugate comprises a first region, the human homeodomain or variant or portion thereof having a sequence described in, for example, any of SEQ ID Nos. 1-19 or variant or portion thereof conjugated to a second region not naturally associated with the first region, wherein the second region is a peptide antigen or portion of the antigen that is an antigenic epitope. In a variety of embodiments, conjugation may be as a fusion protein (peptide linkage) or may utilize a linker such as the furin-sensitive linker (RVKR), a disulfide linkage, or other types of protein to protein conjugation known in the art.

Tuberculosis Vaccine Antigen 85A and its Epitopes.

The antigen 85 complex is a multigene family encoding several closely related major secreted proteins in mycobacteria. The signal peptide is cleaved in mature Ag85 proteins. Ag85A is a peptide of 338 amino acids with a molecular mass of 35.7 kDa and a predicted pI of 6.5. It is also called extracellular α-antigen and has mycolyltransferase activity important in cell wall synthesis. Analysis of the immunogenicity and protective activity of smaller peptide epitopes in Balb/c mice (Tchilian et. al. Immunization with different formulations of *Mycobacterium tuberculosis* antigen 85A induces immune responses with different specificity and protective efficacy. *Vaccine* 31:4624-31, 2013) after intranasal and systemic immunization of mice using a recombinant adenoviral vector, recombinant Ag85A itself or as a set of overlapping 15 mer peptides (single Balb/c H-2D restricted epitopes) demonstrated superior protection against *mycobacterium tuberculosis* (Mtb) challenge after intranasal immunization. CD4 85A99-118 and CD8 85A70-78 responses were protective while response to CD8 85A145-152 was not protective.

Human vaccine trials using the adenovirus Ag85A vaccine to enhance the effectiveness of BCG vaccine in infants induced only modest immune responses and did not have any clinical efficacy (Tameris et. al. Safety and efficacy of MVA85A, a new tuberculosis vaccine, in infants previously vaccinated with BCG: a randomised, placebo-controlled phase 2b trial. *The Lancet* 381:1021-1028, 2013). This could be due to the inhibitory effects of TLR2 agonist properties of the adenovirus component shown to provoke IL-10 responses that down-regulate the immune response or due to non-protective responses to some Ag85A epitopes.

Tuberculosis Vaccine.

The current embodiments for a protective human tuberculosis vaccine are conjugates or a mixture of conjugates administered by the inhaled, intranasal or parenteral injection route. In one embodiment the inhaled route provides local immunity in the lung.

In Balb/c mice the concept will be tested where a conjugate or conjugate mixture is composed of a first region, the human homeodomain or variant or portion thereof including but not limited to sequences described in any of SEQ ID Nos. 1-19 or variant or portion thereof conjugated to a second region not naturally associated with the first region. In certain embodiments, the second region is one or more of four peptides that span the Ag85A 99-118 epitope (See Table 3):

Peptide one of four of the Ag85A 99-118 epitope is SEQ ID No. 51: ETFLTSELPGWLQAN;
Peptide two of four of the Ag85A 99-118 epitope is SEQ ID No. 54: SELPGWLQANRHVKP;
Peptide three of four of the Ag85A 99-118 epitope is SEQ ID No. 57: WLQANRHVKPTGSA; and
Peptide four of four of the Ag85A 99-118 epitope is SEQ ID No. 60: RHVKPTGSAVVGLSM.

In yet other embodiments, the second region is a variation on one or more of these four peptides. The sequence ID numbers for several of these conjugates are shown in Table 3. For example, in one embodiment, the complete amino acid sequence of the combined first (HOX C12) and second region SEQ ID No. 51 of the Ag85A 99-118 epitope is SEQ ID No. 52: SRKKRKPYSKLQLAEL-EGEFLVNEFITRQRRRELSDRLNLSDQQVKIW-FQNRRM KKKRLLETFLTSELPGWLQAN. Likewise, in another embodiment, the complete amino acid sequence of the combined first (HOX D12) and second region SEQ ID No. 51 of the Ag85A 99-118 epitope is SEQ ID No. 53: ARKKRKPYTKQQIAELENEFLVN-EFINRQKRKELSNRLNLSDQQVKIWFQNRRM KKKRVVETFLTSELPGWLQAN.

The second conjugate or conjugate mixture for testing in Balb/c mice is composed of a first region, the human homeodomain or variant or portion thereof having a sequence described in any of SEQ ID Nos. 1-19 or variant or portion thereof conjugated to a second region not naturally associated with the first region. In certain embodiments, the second region is one or more of three peptides that span the Ag85A 70-78 epitope (See Table 3):

Peptide one of three of the Ag85A 70-78 epitope is SEQ ID No. 63: QSGLSWMPVGGQSS;
Peptide two of three of the Ag85A 70-78 epitope is SEQ ID No. 66: VVMPVGGQSSFYSDW; and
Peptide three of three of the Ag85A 70-78 epitope is SEQ ID No. 69: GGQSSFYSDWYQPAC.

In yet other embodiments, the second region is a variation on one or more of these three peptides. The sequence ID numbers for several of these conjugates are also shown in Table 3. For example, in one embodiment the complete amino acid sequence of the combined first (HOX C12) and second region SEQ ID No. 63 of the Ag85A 70-78 epitope is SEQ ID No. 64: SRKKRK-PYSKLQLAELEGEFLVNEFITRQRRRELSDRLN-LSDQQVKIWFQNRRM KKKRLLQSGLSWV-VMPVGGQSS. Likewise, in another embodiment the complete amino acid sequence of the combined first (HOX D12) and second region SEQ ID No. 63 of the Ag85A 70-78 epitope is SEQ ID No. 65: ARKKRK-PYTKQQIAELENEFLVNEFINRQKRKELSNRLN-LSDQQVKIWFQNRRM KKKRWQSGLSWMPVG-GQSS.

Thus, the entire vaccine to be tested in mice and later in humans is composed of mixtures of conjugates where each conjugate has, as its cargo in a variety of embodiments, one or more of these smaller peptides or variations thereof, and together they provide for a robust CD4 response to Ag85A 99-118 and a robust CD8 response to Ag85A 70-78.

In one human vaccine embodiment the vaccine will be composed of a first region, the human homeodomain or variant or portion thereof including but not limited to a sequence described in any of SEQ ID Nos. 1-19 or variant or portion thereof conjugated to a second region not naturally associated with the first region, wherein the second region is, in one embodiment, the entire Ag85A 338-amino acid peptide or an HLA-restricted epitope of Ag85A such as one or more specific HLA-restricted epitopes of Ag85A shown to provoke immune responses in appropriate human subjects (see Table 3). The Ag85A peptide, or its human epitopes, may be linked to the first region as described above. In another embodiment, the entire Ag85A sequence is linked to the first region to provide a single vaccine construct for subjects with different HLA class I and class II genotypes. The Ag85A sequence is:

(SEQ ID NO: 106)
<u>MQLVDRVRGA VTGMSRRLVV GAVGAALVSG LVGAVGGTAT</u>

<u>AGAFSRPGLP</u> VEYLQVPSPS MGRDIKVQFQ SGGANSPALY

LLDGLRAQDD FSGWDINTPA *FEWYDQSGLS* VMPVGGQSS

-continued

FYSDWYQPAC GKAGCQTYKW ETFLTSELPG WLQANRHVKP

TGSAVVGLSM AASSALTLAI YHPQQFVYAG AMSGLLDPSQ

AMGPTLIGLA MGDAGGYKAS DMWGPKEDPA WQRNDPLLNV

GKLIANNTRV WVYCGNGKPS DLGGNNLPAK FL_E_GFVRTSN

IKFQDAYNAG GGHNGVFDFP DSGT_H_SWEYW GAQLNAMKPD

LQRALGATPN TGPAPQGA.

Here the longer region of the sequence in bold and underlined font above is the signal peptide that is cleaved when the mature Ag85A sequence is produced (the remaining 296 amino acid peptide). The fibronectin binding domain is shown in bold and italicized font just below it, and the three amino acids below that in bold, underlined and italicized font are in the catalytic domain.

In one embodiment, the second region amino acid sequence for Ag85A (without the signal peptide) would be: AFSRPGLP VEYLQVPSPS MGRDIKVQFQ SGGANSPALY LLDGLRAQDD FSGWDINTPA FEWYDQSGLS WMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA The sequence ID number (SEQ. ID No. 72) for this Ag85A cargo peptide is shown in Table 3, along with two of many possible embodiments in which the Ag85A cargo peptide or a variation comprises the second region of the conjugate or fusion protein: those containing the first region HOX C12 (SEQ. ID No. 73) or HOX D12 (SEQ. ID No. 74) sequences. A person of ordinary skill in the molecular biology/biotechnology art would appreciate that numerous variations on any of these and other sequences shown in Table 3 would fall within the embodiments disclosed herein.

Measurement of the Vaccine-Induced Immune Response.

In vitro whole blood cultures with specific antigens and measurement of type I cytokine responses was successfully used to measure the immune response to the adenovirus vector Ag85A vaccine in a phase I clinical trial (Smaill et. al. A Human Type 5 Adenovirus-Based Tuberculosis Vaccine Induces Robust T Cell Responses in Humans Despite Preexisting Anti-Adenovirus Immunity. Sci. Transl. Med. 5, 205: 1-11, 2013). This technique can be used to measure the immune response in humans to CPP-based Ag85A epitope vaccine mixtures. In murine models similar methods can be used with post-treatment cultures of splenic lymphocytes and measurement of cytokine responses in Balb/c mice using the epitopes described.

The number of responsive CD4 T-cells to specific antigenic epitopes can be quantitated by IFN-gamma ELISPOT assays and both CD4 and CD8 T-cell responses can be measured by intracellular cytokine staining together with T-cell subtype classification in peripheral blood lymphocyte cultures (Smaill et. al. 2013).

Example 7

Human-derived CPP structures can include, but are not limited to, the first region, which can comprise the HOX D12 homeodomain, the HOX C12 homeodomain, or other first region structures, such as those described in Table 3 (SEQ ID Nos. 1-19). The first region can be conjugated to a second region such that the first region can be used to carry 'cargo' to intracellular and/or intranuclear targets that may be abnormally expressed in disease states. Such targets may include nucleic acid structures such as genes, mRNA and miRNA. Here DNA, RNA, LNA, PNA, γPNA, other standard or modified nucleic acid or a combination of these components can be designed to bind to these intracellular and/or intranuclear targets and reduce abnormal expression or activation characteristic of the disease state. Table 4 shows nucleotide sequences, and three examples are described below.

TABLE 4

Nucleotide Sequence Identities

| SEQ. ID No. | Descriptor | Nucleotide Sequence |
|---|---|---|
| 75 | miRNA132 target sequence to which cargo binds | 5'-UAACAGUCUACAGCCAUGGUCG-3' |
| 76 | Cargo sequence that binds to miRNA21 | 5'-TCAACATCAGTCTGATAAGCTA-3' |
| 77 | miRNA21 target sequence to which the cargo binds | 5'-TAGCTTATCAGACTGATGTTGA-3' |
| 78 | Cargo sequence that binds to miRNA132 | 5'-CGACCATGGCTGTAGACTGTTA-3' |
| 79 | Cargo sequence that binds to DYRK1b | 5'-GTGGTGAAAGCCTATGATCAT-3' |

Affecting the Ras Pathway:

In one or more embodiments, a second region cargo binds to an miRNA132 target sequence to affect the Ras pathway.

The Ras pathway is abnormally expressed in many types of cancer and constructs that affect the pathway would reduce the growth of tumors dependent on it. Diagnostic tests would identify those patients whose tumors would be most likely to respond to this treatment. Tumor cell lines known to have an activated Ras pathway can be used to demonstrate the biological activity of Ras-inhibiting constructs described below. They will reduce the growth of these tumor cells in vitro and reduce the growth of tumors in murine xenograft models that use these cells following systemic treatment.

In one embodiment, the HOX C12 amino acid sequence first region is SEQ ID No. 1:

SRKKRKPYSKLQLAELEGEFLVNEFITRQRRRELSDRLNLSDQQVKIWFQ

NRRMKKKRLL

In another embodiment, the HOX D12 amino acid sequence first region is SEQ ID No. 2:

ARKKRKPYTKQQIAELENEFLVNEFINRQKRKELSNRLNLSDQQVKIWFQ

NRRMKKKRVV

In another embodiment, the second region cargo may be, for example, nucleic acid SEQ ID No. 76 (Table 4) (or a variation thereof):

5'-TCAACATCAGTCTGATAAGCTA-3' In yet another embodiment, for example, the complete conjugate comprises SEQ ID Nos. 1 and 76.

Affecting Tumor Suppressor Pathways in Many Cancers:

The second region cargo binds to miRNA21 target sequence to affect tumor suppressor pathways found in many types of cancers. As in the Ras pathway example described above, in a variety of embodiments the first region homeodomain sequence may be, for example, HOX C12 (SEQ ID No. 1) or HOX D12 (SEQ ID No. 2) (see Table 3). In one or more embodiments, the conjugate's second region cargo binds to an miRNA21 target sequence, which sequence includes but is not limited to SEQ. ID No. 77 (Table 4), or any variation thereof. Thus, in one embodiment the second region cargo, for example, 5'-CGACCATGGCT-GTAGACTGTTA-3' (SEQ. ID No. 76), binds to the miRNA21 target sequence, for example, 5'-TAGCTTATCA-GACTGATGTTGA-3' (SEQ. ID No. 77) to affect tumor suppressor pathways found in many types of cancers.

Testing these constructs in vitro and in murine xenograft tumor models can confirm their activity by measuring reduced tumor cell growth and tumor growth. Treatment of cancer patients found to have tumors that have abnormal expression of this miRNA will have clinical benefit. In one embodiment, the second region cargo sequence (SEQ. ID No. 79) binds to target sequence DYRK1b. In other embodiments variations to SEQ. ID No. 79 bind to DYRK1b, or a functional variation thereof.

Affecting Gene Expression:

In one or more embodiments, the second region cargo binds to DYRK1 b to reduce gene expression.

Over expression of this gene is present in many cancers including lung and pancreatic cancers. Mutations in DYRK1b that result in increased expression also are associated with familial inheritance of type II diabetes, central obesity and early coronary artery disease, all features of the metabolic syndrome. It is likely that this pathway is also contributing to the pathogenesis of type II diabetes and obesity in the general population. Thus systemic treatment with inhibitors of DYRK1b such as those described below will have efficacy in cancers with abnormal high expression of DYRK1b and also in patients with type II diabetes and other features of metabolic syndrome. It will be especially effective in those patients with identified mutations in DYRK1b that lead to over expression. As in the Ras and tumor suppressor pathways examples discussed above, a variety of embodiments the first region homeodomain sequence may be, for example HOX C12 (SEQ ID No. 1) or HOX D12 (SEQ ID No. 2) (see Table 3). In one embodiment, the sequence 5'-GTGGTGAAAGCCTATGATCAT-3' (SEQ. ID No. 79, see Table 4) or variation thereof, binds to DYRK1b. In other embodiments variations to SEQ. ID No. 79 bind to DYRK1 b, or a functional variation thereof.

For certain comparisons between groups reported in the studies described in the examples above, significance was tested at $p<0.05$.

From the foregoing, it will be appreciated that specific embodiments have been described herein for purposes of illustration, but that various modifications may be made without deviating from the spirit and scope of the disclosure. Accordingly, the disclosure is not limited except as by the appended claims.

We claim:

1. A cell-penetrating peptide conjugate consisting of SEQ ID No. 22.

2. The conjugate of claim 1 wherein the conjugate interacts with an intracellular target and/or an intranuclear target.

3. A composition comprising the conjugate of claim 1 and a pharmaceutically acceptable carrier.

* * * * *

SEQUENCE LISTING

```
<160> NUMBER OF SEQ ID NOS: 117

<210> SEQ ID NO 1
<211> LENGTH: 60
<212> TYPE: PRT
<213> ORGANISM: Homo sapiens

<400> SEQUENCE: 1

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
            20                  25                  30

Glu Leu Ser Asp Arg Leu Asn Leu Ser Asp Gln Gln Val Lys Ile Trp
        35                  40                  45

Phe Gln Asn Arg Arg Met Lys Lys Lys Arg Leu Leu
    50                  55                  60

<210> SEQ ID NO 2
<211> LENGTH: 60
<212> TYPE: PRT
<213> ORGANISM: Homo sapiens

<400> SEQUENCE: 2

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
            20                  25                  30

Glu Leu Ser Asn Arg Leu Asn Leu Ser Asp Gln Gln Val Lys Ile Trp
```

```
                    35                  40                  45

Phe Gln Asn Arg Arg Met Lys Lys Arg Val Val
    50                  55                  60

<210> SEQ ID NO 3
<211> LENGTH: 60
<212> TYPE: PRT
<213> ORGANISM: Homo sapiens

<400> SEQUENCE: 3

Gln Lys Arg His Arg Thr Arg Phe Thr Pro Ala Gln Leu Asn Glu Leu
1               5                   10                  15

Glu Arg Ser Phe Ala Lys Thr His Tyr Pro Asp Ile Phe Met Arg Glu
                20                  25                  30

Glu Leu Ala Leu Arg Ile Gly Leu Thr Glu Ser Arg Val Gln Val Trp
            35                  40                  45

Phe Gln Asn Arg Arg Ala Lys Trp Lys Lys Arg Lys
    50                  55                  60

<210> SEQ ID NO 4
<211> LENGTH: 60
<212> TYPE: PRT
<213> ORGANISM: Homo sapiens

<400> SEQUENCE: 4

Lys Lys Lys Pro Arg Thr Ser Phe Thr Arg Leu Gln Ile Cys Glu Leu
1               5                   10                  15

Glu Lys Arg Phe His Arg Gln Lys Tyr Leu Ala Ser Ala Glu Arg Ala
                20                  25                  30

Ala Leu Ala Lys Ala Leu Lys Met Thr Asp Ala Gln Val Lys Thr Trp
            35                  40                  45

Phe Gln Asn Arg Arg Thr Lys Trp Arg Arg Gln Thr
    50                  55                  60

<210> SEQ ID NO 5
<211> LENGTH: 60
<212> TYPE: PRT
<213> ORGANISM: Homo sapiens

<400> SEQUENCE: 5

Arg Lys Lys Pro Arg Thr Ser Phe Ser Arg Val Gln Ile Cys Glu Leu
1               5                   10                  15

Glu Lys Arg Phe His Arg Gln Lys Tyr Leu Ala Ser Ala Glu Arg Ala
                20                  25                  30

Ala Leu Ala Lys Ser Leu Lys Met Thr Asp Ala Gln Val Lys Thr Trp
            35                  40                  45

Phe Gln Asn Arg Arg Thr Lys Trp Arg Arg Gln Thr
    50                  55                  60

<210> SEQ ID NO 6
<211> LENGTH: 60
<212> TYPE: PRT
<213> ORGANISM: Homo sapiens

<400> SEQUENCE: 6

Arg Lys Lys Pro Arg Thr Ser Phe Ser Arg Ser Gln Val Leu Glu Leu
1               5                   10                  15

Glu Arg Arg Phe Leu Arg Gln Lys Tyr Leu Ala Ser Ala Glu Arg Ala
                20                  25                  30
```

Ala Leu Ala Lys Ala Leu Arg Met Thr Asp Ala Gln Val Lys Thr Trp
                35                  40                  45

Phe Gln Asn Arg Arg Thr Lys Trp Arg Arg Gln Thr
        50                  55                  60

<210> SEQ ID NO 7
<211> LENGTH: 60
<212> TYPE: PRT
<213> ORGANISM: Homo sapiens

<400> SEQUENCE: 7

Arg Lys His Thr Arg Pro Thr Phe Ser Gly Gln Gln Ile Phe Ala Leu
1               5                   10                  15

Glu Lys Thr Phe Glu Gln Thr Lys Tyr Leu Ala Gly Pro Glu Arg Ala
                20                  25                  30

Arg Leu Ala Tyr Ser Leu Gly Met Thr Glu Ser Gln Val Lys Val Trp
                35                  40                  45

Phe Gln Asn Arg Arg Thr Lys Trp Arg Lys Lys His
        50                  55                  60

<210> SEQ ID NO 8
<211> LENGTH: 60
<212> TYPE: PRT
<213> ORGANISM: Homo sapiens

<400> SEQUENCE: 8

Lys Lys His Ser Arg Pro Thr Phe Ser Gly Gln Gln Ile Phe Ala Leu
1               5                   10                  15

Glu Lys Thr Phe Glu Gln Thr Lys Tyr Leu Ala Gly Pro Glu Arg Ala
                20                  25                  30

Arg Leu Ala Tyr Ser Leu Gly Met Thr Glu Ser Gln Val Lys Val Trp
                35                  40                  45

Phe Gln Asn Arg Arg Thr Lys Trp Arg Lys Arg His
        50                  55                  60

<210> SEQ ID NO 9
<211> LENGTH: 60
<212> TYPE: PRT
<213> ORGANISM: Homo sapiens

<400> SEQUENCE: 9

Lys Lys His Thr Arg Pro Thr Phe Thr Gly His Gln Ile Phe Ala Leu
1               5                   10                  15

Glu Lys Thr Phe Glu Gln Thr Lys Tyr Leu Ala Gly Pro Glu Arg Ala
                20                  25                  30

Arg Leu Ala Tyr Ser Leu Gly Met Thr Glu Ser Gln Val Lys Val Trp
                35                  40                  45

Phe Gln Asn Arg Arg Thr Lys Trp Arg Lys Lys Ser
        50                  55                  60

<210> SEQ ID NO 10
<211> LENGTH: 60
<212> TYPE: PRT
<213> ORGANISM: Homo sapiens

<400> SEQUENCE: 10

Lys Lys Arg Ser Arg Ala Ala Phe Ser His Ala Gln Val Phe Glu Leu
1               5                   10                  15

Glu Arg Arg Phe Asn His Gln Arg Tyr Leu Ser Gly Pro Glu Arg Ala
                20                  25                  30

Asp Leu Ala Ala Ser Leu Lys Leu Thr Glu Thr Gln Val Lys Ile Trp
        35                  40                  45

Phe Gln Asn Arg Arg Tyr Lys Thr Lys Arg Arg Gln
    50                  55                  60

<210> SEQ ID NO 11
<211> LENGTH: 60
<212> TYPE: PRT
<213> ORGANISM: Homo sapiens

<400> SEQUENCE: 11

Pro Arg Lys Ala Arg Thr Ala Phe Thr Asp His Gln Leu Ala Gln Leu
1               5                   10                  15

Glu Arg Ser Phe Glu Arg Gln Lys Tyr Leu Ser Val Gln Asp Arg Met
            20                  25                  30

Glu Leu Ala Ala Ser Leu Asn Leu Thr Asp Thr Gln Val Lys Thr Trp
        35                  40                  45

Tyr Gln Asn Arg Arg Thr Lys Trp Lys Arg Gln Thr
    50                  55                  60

<210> SEQ ID NO 12
<211> LENGTH: 60
<212> TYPE: PRT
<213> ORGANISM: Homo sapiens

<400> SEQUENCE: 12

Pro Arg Lys Ala Arg Thr Ala Phe Ser Asp His Gln Leu Asn Gln Leu
1               5                   10                  15

Glu Arg Ser Phe Glu Arg Gln Lys Tyr Leu Ser Val Gln Asp Arg Met
            20                  25                  30

Asp Leu Ala Ala Ala Leu Asn Leu Thr Asp Thr Gln Val Lys Thr Trp
        35                  40                  45

Tyr Gln Asn Arg Arg Thr Lys Trp Lys Arg Gln Thr
    50                  55                  60

<210> SEQ ID NO 13
<211> LENGTH: 60
<212> TYPE: PRT
<213> ORGANISM: Homo sapiens

<400> SEQUENCE: 13

Gly Arg Arg Ser Arg Thr Val Phe Thr Glu Leu Gln Leu Met Gly Leu
1               5                   10                  15

Glu Lys Arg Phe Glu Lys Gln Lys Tyr Leu Ser Thr Pro Asp Arg Ile
            20                  25                  30

Asp Leu Ala Glu Ser Leu Gly Leu Ser Gln Leu Gln Val Lys Thr Trp
        35                  40                  45

Tyr Gln Asn Arg Arg Met Lys Trp Lys Lys Ile Val
    50                  55                  60

<210> SEQ ID NO 14
<211> LENGTH: 60
<212> TYPE: PRT
<213> ORGANISM: Homo sapiens

<400> SEQUENCE: 14

Pro Arg Arg Ser Arg Thr Ile Phe Thr Glu Leu Gln Leu Met Gly Leu
1               5                   10                  15

Glu Lys Lys Phe Gln Lys Gln Lys Tyr Leu Ser Thr Pro Asp Arg Leu

```
                    20                  25                  30

Asp Leu Ala Gln Ser Leu Gly Leu Thr Gln Leu Gln Val Lys Thr Trp
            35                  40                  45

Tyr Gln Asn Arg Arg Met Lys Trp Lys Lys Met Val
    50                  55                  60

<210> SEQ ID NO 15
<211> LENGTH: 60
<212> TYPE: PRT
<213> ORGANISM: Homo sapiens

<400> SEQUENCE: 15

Arg Arg Lys Ala Arg Thr Val Phe Ser Asp Ser Gln Leu Ser Gly Leu
1               5                   10                  15

Glu Lys Arg Phe Glu Ile Gln Arg Tyr Leu Ser Thr Pro Glu Arg Val
            20                  25                  30

Glu Leu Ala Thr Ala Leu Ser Leu Ser Glu Thr Gln Val Lys Thr Trp
            35                  40                  45

Phe Gln Asn Arg Arg Met Lys His Lys Lys Gln Leu
    50                  55                  60

<210> SEQ ID NO 16
<211> LENGTH: 60
<212> TYPE: PRT
<213> ORGANISM: Homo sapiens

<400> SEQUENCE: 16

Val Arg Lys Pro Arg Thr Ile Tyr Ser Ser Phe Gln Leu Ala Ala Leu
1               5                   10                  15

Gln Arg Arg Phe Gln Lys Thr Gln Tyr Leu Ala Leu Pro Glu Arg Ala
            20                  25                  30

Glu Leu Ala Ala Ser Leu Gly Leu Thr Gln Thr Gln Val Lys Ile Trp
            35                  40                  45

Phe Gln Asn Arg Arg Ser Lys Phe Lys Lys Met Trp
    50                  55                  60

<210> SEQ ID NO 17
<211> LENGTH: 60
<212> TYPE: PRT
<213> ORGANISM: Homo sapiens

<400> SEQUENCE: 17

Val Arg Lys Pro Arg Thr Ile Tyr Ser Ser Tyr Gln Leu Ala Ala Leu
1               5                   10                  15

Gln Arg Arg Phe Gln Lys Ala Gln Tyr Leu Ala Leu Pro Glu Arg Ala
            20                  25                  30

Glu Leu Ala Ala Gln Leu Gly Leu Thr Gln Thr Gln Val Lys Ile Trp
            35                  40                  45

Phe Gln Asn Arg Arg Ser Lys Phe Lys Lys Leu Tyr
    50                  55                  60

<210> SEQ ID NO 18
<211> LENGTH: 60
<212> TYPE: PRT
<213> ORGANISM: Homo sapiens

<400> SEQUENCE: 18

Gly Met Leu Arg Arg Ala Val Phe Ser Asp Val Gln Arg Lys Ala Leu
1               5                   10                  15
```

```
Glu Lys Met Phe Gln Lys Gln Lys Tyr Ile Ser Lys Pro Asp Arg Lys
                20                  25                  30

Lys Leu Ala Ala Lys Leu Gly Leu Lys Asp Ser Gln Val Lys Ile Trp
            35                  40                  45

Phe Gln Asn Arg Arg Met Lys Trp Arg Asn Ser Lys
        50                  55                  60

<210> SEQ ID NO 19
<211> LENGTH: 60
<212> TYPE: PRT
<213> ORGANISM: Homo sapiens

<400> SEQUENCE: 19

Gly Ile Leu Arg Arg Ala Val Phe Ser Glu Asp Gln Arg Lys Ala Leu
1               5                   10                  15

Glu Lys Met Phe Gln Lys Gln Lys Tyr Ile Ser Lys Thr Asp Arg Lys
                20                  25                  30

Lys Leu Ala Ile Asn Leu Gly Leu Lys Glu Ser Gln Val Lys Ile Trp
            35                  40                  45

Phe Gln Asn Arg Arg Met Lys Trp Arg Asn Ser Lys
        50                  55                  60

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ala Leu Asp Trp Ser Trp Leu Gln Thr Glu
1               5                   10

<210> SEQ ID NO 21
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
                20                  25                  30

Glu Leu Ser Asp Arg Leu Asn Leu Ser Asp Gln Gln Val Lys Ile Trp
            35                  40                  45

Phe Gln Asn Arg Arg Met Lys Lys Lys Arg Leu Leu Thr Ala Leu Asp
        50                  55                  60

Trp Ser Trp Leu Gln Thr Glu
65                  70

<210> SEQ ID NO 22
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
            20                  25                  30

Glu Leu Ser Asn Arg Leu Asn Leu Ser Asp Gln Val Lys Ile Trp
        35                  40                  45

Phe Gln Asn Arg Arg Met Lys Lys Arg Val Val Thr Ala Leu Asp
    50                  55                  60

Trp Ser Trp Leu Gln Thr Glu
65                  70

<210> SEQ ID NO 23
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Ile Leu Arg Trp Arg Tyr His Ala Leu Arg Gly Glu Leu Tyr Arg
1               5                   10                  15

Pro Ala Trp Glu Pro Gln Asp Tyr Glu Met Val Glu Leu Phe Leu Arg
            20                  25                  30

Arg Leu Arg Leu Trp Met Gly Leu Ser Lys Val Lys Glu Phe Arg His
        35                  40                  45

Lys Val Arg Phe Glu Gly Met Glu Pro Leu Pro Ser Arg Ser Ser Arg
    50                  55                  60

Gly Ser Lys Val Ser Pro Asp Val Pro Pro Ser Ala Gly Ser Asp
65                  70                  75                  80

Ala Ser His Pro Ser Thr Ser Ser Gln Leu Asp Gly Leu Ser Val
                85                  90                  95

Ser Leu Gly Arg Leu Gly Thr Arg Cys Glu Pro Glu Pro Ser Arg Leu
                100                 105                 110

Gln Ala Val Phe Glu Ala Leu Leu Thr Gln Phe Asp Arg Leu Asn Gln
            115                 120                 125

Ala Thr Glu Asp Val Tyr Gln Leu Glu Gln Gln Leu His Ser Leu Gln
    130                 135                 140

Gly Arg Arg Ser Ser Arg Ala Pro Ala Gly Ser Ser Arg Gly Pro Ser
145                 150                 155                 160

Pro Gly Leu Arg Pro Ala Leu Pro Ser Arg Leu Ala Arg Ala Ser Arg
                165                 170                 175

Gly Val Asp Leu Ala Thr Gly Pro Ser Arg Thr Pro Leu Arg Ala Lys
            180                 185                 190

Asn Lys Val His Pro Ser Ser Thr
            195                 200

<210> SEQ ID NO 24
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ser Arg Lys Lys Arg Lys Pro Tyr Ser Lys Leu Gln Leu Ala Glu
1               5                   10                  15

```
Leu Glu Gly Glu Phe Leu Val Asn Glu Phe Ile Thr Arg Gln Arg Arg
         20                  25                  30

Arg Glu Leu Ser Asp Arg Leu Asn Leu Ser Asp Gln Gln Val Lys Ile
         35                  40                  45

Trp Phe Gln Asn Arg Arg Met Lys Lys Arg Leu Leu Val Ile Leu
 50                  55                  60

Arg Trp Arg Tyr His Ala Leu Arg Gly Glu Leu Tyr Arg Pro Ala Trp
 65                  70                  75                  80

Glu Pro Gln Asp Tyr Glu Met Val Glu Leu Phe Leu Arg Arg Leu Arg
                 85                  90                  95

Leu Trp Met Gly Leu Ser Lys Val Lys Glu Phe Arg His Lys Val Arg
            100                 105                 110

Phe Glu Gly Met Glu Pro Leu Pro Ser Arg Ser Ser Arg Gly Ser Lys
            115                 120                 125

Val Ser Pro Asp Val Pro Pro Ser Ala Gly Ser Asp Ala Ser His
130                 135                 140

Pro Ser Thr Ser Ser Ser Gln Leu Asp Gly Leu Ser Val Ser Leu Gly
145                 150                 155                 160

Arg Leu Gly Thr Arg Cys Glu Pro Glu Pro Ser Arg Leu Gln Ala Val
                165                 170                 175

Phe Glu Ala Leu Leu Thr Gln Phe Asp Arg Leu Asn Gln Ala Thr Glu
            180                 185                 190

Asp Val Tyr Gln Leu Glu Gln Gln Leu His Ser Leu Gln Gly Arg Arg
            195                 200                 205

Ser Ser Arg Ala Pro Ala Gly Ser Ser Arg Gly Pro Ser Pro Gly Leu
210                 215                 220

Arg Pro Ala Leu Pro Ser Arg Leu Ala Arg Ala Ser Arg Gly Val Asp
225                 230                 235                 240

Leu Ala Thr Gly Pro Ser Arg Thr Pro Leu Arg Ala Lys Asn Lys Val
                245                 250                 255

His Pro Ser Ser Thr
            260

<210> SEQ ID NO 25
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala Arg Lys Lys Arg Lys Pro Tyr Thr Lys Gln Gln Ile Ala Glu
 1               5                  10                  15

Leu Glu Asn Glu Phe Leu Val Asn Glu Phe Ile Asn Arg Gln Lys Arg
                 20                  25                  30

Lys Glu Leu Ser Asn Arg Leu Asn Leu Ser Asp Gln Gln Val Lys Ile
            35                  40                  45

Trp Phe Gln Asn Arg Arg Met Lys Lys Arg Val Val Ile Leu
 50                  55                  60

Arg Trp Arg Tyr His Ala Leu Arg Gly Glu Leu Tyr Arg Pro Ala Trp
 65                  70                  75                  80

Glu Pro Gln Asp Tyr Glu Met Val Glu Leu Phe Leu Arg Arg Leu Arg
                 85                  90                  95

Leu Trp Met Gly Leu Ser Lys Val Lys Glu Phe Arg His Lys Val Arg
```

```
                        100                 105                 110
Phe Glu Gly Met Glu Pro Leu Pro Ser Arg Ser Ser Arg Gly Ser Lys
            115                 120                 125

Val Ser Pro Asp Val Pro Pro Ser Ala Gly Ser Asp Ala Ser His
    130                 135                 140

Pro Ser Thr Ser Ser Ser Gln Leu Asp Gly Leu Ser Val Ser Leu Gly
145                 150                 155                 160

Arg Leu Gly Thr Arg Cys Glu Pro Glu Pro Ser Arg Leu Gln Ala Val
                165                 170                 175

Phe Glu Ala Leu Leu Thr Gln Phe Asp Arg Leu Asn Gln Ala Thr Glu
            180                 185                 190

Asp Val Tyr Gln Leu Glu Gln Gln Leu His Ser Leu Gln Gly Arg Arg
        195                 200                 205

Ser Ser Arg Ala Pro Ala Gly Ser Ser Arg Gly Pro Ser Pro Gly Leu
    210                 215                 220

Arg Pro Ala Leu Pro Ser Arg Leu Ala Arg Ala Ser Arg Gly Val Asp
225                 230                 235                 240

Leu Ala Thr Gly Pro Ser Arg Thr Pro Leu Arg Ala Lys Asn Lys Val
                245                 250                 255

His Pro Ser Ser Thr
            260

<210> SEQ ID NO 26
<211> LENGTH: 21
<212> TYPE: PRT
<213> ORGANISM: Unknown
<220> FEATURE:
<223> OTHER INFORMATION: Description of Unknown: p21 peptide

<400> SEQUENCE: 26

Ile Arg Arg Ile Arg Leu Trp Met Gly Leu Ser Lys Val Lys Glu Phe
1               5                   10                  15

Arg His Lys Val Arg
            20

<210> SEQ ID NO 27
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ser Arg Lys Lys Arg Lys Pro Tyr Ser Lys Leu Gln Leu Ala Glu
1               5                   10                  15

Leu Glu Gly Glu Phe Leu Val Asn Glu Phe Ile Thr Arg Gln Arg Arg
            20                  25                  30

Arg Glu Leu Ser Asp Arg Leu Asn Leu Ser Asp Gln Gln Val Lys Ile
        35                  40                  45

Trp Phe Gln Asn Arg Arg Met Lys Lys Arg Leu Leu Ile Arg Arg
    50                  55                  60

Ile Arg Leu Trp Met Gly Leu Ser Lys Val Lys Glu Phe Arg His Lys
65                  70                  75                  80

Val Arg

<210> SEQ ID NO 28
<211> LENGTH: 82
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
            20                  25                  30

Lys Glu Leu Ser Asn Arg Leu Asn Leu Ser Asp Gln Gln Val Lys Ile
        35                  40                  45

Trp Phe Gln Asn Arg Arg Met Lys Lys Arg Val Val Ile Arg Arg
    50                  55                  60

Ile Arg Leu Trp Met Gly Leu Ser Lys Val Lys Glu Phe Arg His Lys
65                  70                  75                  80

Val Arg

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Arg Ala Val Lys Tyr
1               5

<210> SEQ ID NO 30
<211> LENGTH: 497
<212> TYPE: PRT
<213> ORGANISM: Homo sapiens

<400> SEQUENCE: 30

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175
```

```
Ser Pro Trp Thr Ser Pro Thr Trp Leu Lys Thr Asn Gly Ala Val Asn
                180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
        210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln
```

<210> SEQ ID NO 31
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Met Ser Arg Lys Lys Arg Lys Pro Tyr Ser Lys Leu Gln Leu Ala Glu
1               5                   10                  15

Leu Glu Gly Glu Phe Leu Val Asn Glu Phe Ile Thr Arg Gln Arg Arg
                20                  25                  30
```

```
Arg Glu Leu Ser Asp Arg Leu Asn Leu Ser Asp Gln Gln Val Lys Ile
         35                  40                  45

Trp Phe Gln Asn Arg Arg Met Lys Lys Lys Arg Leu Leu Ala Arg Pro
 50                  55                  60

Cys Ile Pro Lys Ser Phe Gly Tyr Ser Val Val Cys Val Cys Asn
 65                  70                  75                  80

Ala Thr Tyr Cys Asp Ser Phe Asp Pro Pro Thr Phe Pro Ala Leu Gly
                 85                  90                  95

Thr Phe Ser Arg Tyr Glu Ser Thr Arg Ser Gly Arg Arg Met Glu Leu
                100                 105                 110

Ser Met Gly Pro Ile Gln Ala Asn His Thr Gly Thr Gly Leu Leu Leu
            115                 120                 125

Thr Leu Gln Pro Glu Gln Lys Phe Gln Lys Val Lys Gly Phe Gly Gly
        130                 135                 140

Ala Met Thr Asp Ala Ala Leu Asn Ile Leu Ala Leu Ser Pro Pro
145                 150                 155                 160

Ala Gln Asn Leu Leu Leu Lys Ser Tyr Phe Ser Glu Glu Gly Ile Gly
                165                 170                 175

Tyr Asn Ile Ile Arg Val Pro Met Ala Ser Cys Asp Phe Ser Ile Arg
            180                 185                 190

Thr Tyr Thr Tyr Ala Asp Thr Pro Asp Asp Phe Gln Leu His Asn Phe
        195                 200                 205

Ser Leu Pro Glu Glu Asp Thr Lys Leu Lys Ile Pro Leu Ile His Arg
    210                 215                 220

Ala Leu Gln Leu Ala Gln Arg Pro Val Ser Leu Leu Ala Ser Pro Trp
225                 230                 235                 240

Thr Ser Pro Thr Trp Leu Lys Thr Asn Gly Ala Val Asn Gly Lys Gly
                245                 250                 255

Ser Leu Lys Gly Gln Pro Gly Asp Ile Tyr His Gln Thr Trp Ala Arg
            260                 265                 270

Tyr Phe Val Lys Phe Leu Asp Ala Tyr Ala Glu His Lys Leu Gln Phe
        275                 280                 285

Trp Ala Val Thr Ala Glu Asn Glu Pro Ser Ala Gly Leu Leu Ser Gly
    290                 295                 300

Tyr Pro Phe Gln Cys Leu Gly Phe Thr Pro Glu His Gln Arg Asp Phe
305                 310                 315                 320

Ile Ala Arg Asp Leu Gly Pro Thr Leu Ala Asn Ser Thr His His Asn
                325                 330                 335

Val Arg Leu Leu Met Leu Asp Asp Gln Arg Leu Leu Leu Pro His Trp
            340                 345                 350

Ala Lys Val Val Leu Thr Asp Pro Glu Ala Ala Lys Tyr Val His Gly
        355                 360                 365

Ile Ala Val His Trp Tyr Leu Asp Phe Leu Ala Pro Ala Lys Ala Thr
    370                 375                 380

Leu Gly Glu Thr His Arg Leu Phe Pro Asn Thr Met Leu Phe Ala Ser
385                 390                 395                 400

Glu Ala Cys Val Gly Ser Lys Phe Trp Glu Gln Ser Val Arg Leu Gly
                405                 410                 415

Ser Trp Asp Arg Gly Met Gln Tyr Ser His Ser Ile Ile Thr Asn Leu
            420                 425                 430

Leu Tyr His Val Val Gly Trp Thr Asp Trp Asn Leu Ala Leu Asn Pro
        435                 440                 445
```

```
Glu Gly Gly Pro Asn Trp Val Arg Asn Phe Val Asp Ser Pro Ile Ile
            450                 455                 460

Val Asp Ile Thr Lys Asp Thr Phe Tyr Lys Gln Pro Met Phe Tyr His
465                 470                 475                 480

Leu Gly His Phe Ser Lys Phe Ile Pro Glu Gly Ser Gln Arg Val Gly
                485                 490                 495

Leu Val Ala Ser Gln Lys Asn Asp Leu Asp Ala Val Ala Leu Met His
            500                 505                 510

Pro Asp Gly Ser Ala Val Val Val Leu Asn Arg Ser Ser Lys Asp
            515                 520                 525

Val Pro Leu Thr Ile Lys Asp Pro Ala Val Gly Phe Leu Glu Thr Ile
530                 535                 540

Ser Pro Gly Tyr Ser Ile His Thr Tyr Leu Trp Arg Arg Gln
545                 550                 555
```

<210> SEQ ID NO 32
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
            20                  25                  30

Lys Glu Leu Ser Asn Arg Leu Asn Leu Ser Asp Gln Gln Val Lys Ile
        35                  40                  45

Trp Phe Gln Asn Arg Arg Met Lys Lys Lys Arg Val Val Ala Arg Pro
    50                  55                  60

Cys Ile Pro Lys Ser Phe Gly Tyr Ser Ser Val Val Cys Val Cys Asn
65                  70                  75                  80

Ala Thr Tyr Cys Asp Ser Phe Asp Pro Pro Thr Phe Pro Ala Leu Gly
                85                  90                  95

Thr Phe Ser Arg Tyr Glu Ser Thr Arg Ser Gly Arg Arg Met Glu Leu
            100                 105                 110

Ser Met Gly Pro Ile Gln Ala Asn His Thr Gly Thr Gly Leu Leu Leu
        115                 120                 125

Thr Leu Gln Pro Glu Gln Lys Phe Gln Lys Val Lys Gly Phe Gly Gly
    130                 135                 140

Ala Met Thr Asp Ala Ala Ala Leu Asn Ile Leu Ala Leu Ser Pro Pro
145                 150                 155                 160

Ala Gln Asn Leu Leu Leu Lys Ser Tyr Phe Ser Glu Glu Gly Ile Gly
                165                 170                 175

Tyr Asn Ile Ile Arg Val Pro Met Ala Ser Cys Asp Phe Ser Ile Arg
            180                 185                 190

Thr Tyr Thr Tyr Ala Asp Thr Pro Asp Asp Phe Gln Leu His Asn Phe
        195                 200                 205

Ser Leu Pro Glu Glu Asp Thr Lys Leu Lys Ile Pro Leu Ile His Arg
    210                 215                 220

Ala Leu Gln Leu Ala Gln Arg Pro Val Ser Leu Leu Ala Ser Pro Trp
225                 230                 235                 240

Thr Ser Pro Thr Trp Leu Lys Thr Asn Gly Ala Val Asn Gly Lys Gly
                245                 250                 255
```

```
Ser Leu Lys Gly Gln Pro Gly Asp Ile Tyr His Gln Thr Trp Ala Arg
            260                 265                 270

Tyr Phe Val Lys Phe Leu Asp Ala Tyr Ala Glu His Lys Leu Gln Phe
        275                 280                 285

Trp Ala Val Thr Ala Glu Asn Glu Pro Ser Ala Gly Leu Leu Ser Gly
290                 295                 300

Tyr Pro Phe Gln Cys Leu Gly Phe Thr Pro Glu His Gln Arg Asp Phe
305                 310                 315                 320

Ile Ala Arg Asp Leu Gly Pro Thr Leu Ala Asn Ser Thr His His Asn
                325                 330                 335

Val Arg Leu Leu Met Leu Asp Asp Gln Arg Leu Leu Leu Pro His Trp
                340                 345                 350

Ala Lys Val Val Leu Thr Asp Pro Glu Ala Ala Lys Tyr Val His Gly
                355                 360                 365

Ile Ala Val His Trp Tyr Leu Asp Phe Leu Ala Pro Ala Lys Ala Thr
370                 375                 380

Leu Gly Glu Thr His Arg Leu Phe Pro Asn Thr Met Leu Phe Ala Ser
385                 390                 395                 400

Glu Ala Cys Val Gly Ser Lys Phe Trp Glu Gln Ser Val Arg Leu Gly
                405                 410                 415

Ser Trp Asp Arg Gly Met Gln Tyr Ser His Ser Ile Ile Thr Asn Leu
                420                 425                 430

Leu Tyr His Val Val Gly Trp Thr Asp Trp Asn Leu Ala Leu Asn Pro
                435                 440                 445

Glu Gly Gly Pro Asn Trp Val Arg Asn Phe Val Asp Ser Pro Ile Ile
                450                 455                 460

Val Asp Ile Thr Lys Asp Thr Phe Tyr Lys Gln Pro Met Phe Tyr His
465                 470                 475                 480

Leu Gly His Phe Ser Lys Phe Ile Pro Glu Gly Ser Gln Arg Val Gly
                485                 490                 495

Leu Val Ala Ser Gln Lys Asn Asp Leu Asp Ala Val Ala Leu Met His
                500                 505                 510

Pro Asp Gly Ser Ala Val Val Val Leu Asn Arg Ser Ser Lys Asp
                515                 520                 525

Val Pro Leu Thr Ile Lys Asp Pro Ala Val Gly Phe Leu Glu Thr Ile
                530                 535                 540

Ser Pro Gly Tyr Ser Ile His Thr Tyr Leu Trp Arg Arg Gln
545                 550                 555

<210> SEQ ID NO 33
<211> LENGTH: 1052
<212> TYPE: PRT
<213> ORGANISM: Homo sapiens

<400> SEQUENCE: 33

Ala Val Phe Thr Val Gly Val Leu Gly Pro Trp Ala Cys Asp Pro Ile
1               5                   10                  15

Phe Ser Arg Ala Arg Pro Asp Leu Ala Ala Arg Leu Ala Ala Ala Arg
                20                  25                  30

Leu Asn Arg Asp Pro Gly Leu Gly Gly Pro Arg Phe Glu Val Ala
                35                  40                  45

Leu Leu Pro Glu Pro Cys Arg Thr Pro Gly Ser Leu Gly Ala Val Ser
                50                  55                  60

Ser Ala Leu Ala Arg Val Ser Gly Leu Val Gly Pro Val Asn Pro Ala
```

-continued

```
             65                  70                  75                  80
        Ala Cys Arg Pro Ala Glu Leu Leu Ala Glu Glu Ala Gly Ile Ala Leu
                         85                  90                  95

Val Pro Trp Gly Cys Pro Trp Thr Gln Ala Glu Gly Thr Thr Ala Pro
                        100                 105                 110

Ala Val Thr Pro Ala Ala Asp Ala Leu Tyr Ala Leu Leu Arg Ala Phe
                        115                 120                 125

Gly Trp Ala Arg Val Ala Leu Val Thr Ala Pro Gln Asp Leu Trp Val
                130                 135                 140

Glu Ala Gly Arg Ser Leu Ser Thr Ala Leu Arg Ala Arg Gly Leu Pro
        145                 150                 155                 160

Val Ala Ser Val Thr Ser Met Glu Pro Leu Asp Leu Ser Gly Ala Arg
                        165                 170                 175

Glu Ala Leu Arg Lys Val Arg Asp Gly Pro Arg Val Thr Ala Val Ile
                        180                 185                 190

Met Val Met His Ser Val Leu Leu Gly Gly Glu Glu Gln Arg Tyr Leu
                        195                 200                 205

Leu Glu Ala Ala Glu Glu Leu Gly Leu Thr Asp Gly Ser Leu Val Phe
                210                 215                 220

Leu Pro Phe Asp Thr Ile His Tyr Ala Leu Ser Pro Gly Pro Glu Ala
        225                 230                 235                 240

Leu Ala Ala Leu Ala Asn Ser Ser Gln Leu Arg Arg Ala His Asp Ala
                        245                 250                 255

Val Leu Thr Leu Thr Arg His Cys Pro Ser Glu Gly Ser Val Leu Asp
                        260                 265                 270

Ser Leu Arg Arg Ala Gln Glu Arg Glu Leu Pro Ser Asp Leu Asn
                275                 280                 285

Leu Gln Gln Val Ser Pro Leu Phe Gly Thr Ile Tyr Asp Ala Val Phe
                290                 295                 300

Leu Leu Ala Arg Gly Val Ala Glu Ala Arg Ala Ala Gly Gly Arg
        305                 310                 315                 320

Trp Val Ser Gly Ala Ala Val Ala Arg His Ile Arg Asp Ala Gln Val
                        325                 330                 335

Pro Gly Phe Cys Gly Asp Leu Gly Gly Asp Glu Glu Pro Pro Phe Val
                        340                 345                 350

Leu Leu Asp Thr Asp Ala Ala Gly Asp Arg Leu Phe Ala Thr Tyr Met
                        355                 360                 365

Leu Asp Pro Ala Arg Gly Ser Phe Leu Ser Ala Gly Thr Arg Met His
                370                 375                 380

Phe Pro Arg Gly Gly Ser Ala Pro Gly Pro Asp Pro Ser Cys Trp Phe
        385                 390                 395                 400

Asp Pro Asn Asn Ile Cys Gly Gly Leu Glu Pro Gly Leu Val Phe
                        405                 410                 415

Leu Gly Phe Leu Leu Val Val Gly Met Gly Leu Ala Gly Ala Phe Leu
                        420                 425                 430

Ala His Tyr Val Arg His Arg Leu Leu His Met Gln Met Val Ser Gly
                        435                 440                 445

Pro Asn Lys Ile Ile Leu Thr Val Asp Asp Ile Thr Phe Leu His Pro
                        450                 455                 460

His Gly Gly Thr Ser Arg Lys Val Ala Gln Gly Ser Arg Ser Ser Leu
        465                 470                 475                 480

Gly Ala Arg Ser Met Ser Asp Ile Arg Ser Gly Pro Ser Gln His Leu
                        485                 490                 495
```

```
Asp Ser Pro Asn Ile Gly Val Tyr Glu Gly Asp Arg Val Trp Leu Lys
            500                 505                 510

Lys Phe Pro Gly Asp Gln His Ile Ala Ile Arg Pro Ala Thr Lys Thr
            515                 520                 525

Ala Phe Ser Lys Leu Gln Glu Leu Arg His Glu Asn Val Ala Leu Tyr
            530                 535                 540

Leu Gly Leu Phe Leu Ala Arg Gly Ala Glu Gly Pro Ala Ala Leu Trp
545                 550                 555                 560

Glu Gly Asn Leu Ala Val Val Ser Glu His Cys Thr Arg Gly Ser Leu
            565                 570                 575

Gln Asp Leu Leu Ala Gln Arg Glu Ile Lys Leu Asp Trp Met Phe Lys
            580                 585                 590

Ser Ser Leu Leu Leu Asp Leu Ile Lys Gly Ile Arg Tyr Leu His His
            595                 600                 605

Arg Gly Val Ala His Gly Arg Leu Lys Ser Arg Asn Cys Ile Val Asp
            610                 615                 620

Gly Arg Phe Val Leu Lys Ile Thr Asp His Gly His Gly Arg Leu Leu
625                 630                 635                 640

Glu Ala Gln Lys Val Leu Pro Glu Pro Pro Arg Ala Glu Asp Gln Leu
            645                 650                 655

Trp Thr Ala Pro Glu Leu Leu Arg Asp Pro Ala Leu Glu Arg Arg Gly
            660                 665                 670

Thr Leu Ala Gly Asp Val Phe Ser Leu Ala Ile Ile Met Gln Glu Val
            675                 680                 685

Val Cys Arg Ser Ala Pro Tyr Ala Met Leu Glu Leu Thr Pro Glu Glu
            690                 695                 700

Val Val Gln Arg Val Arg Ser Pro Pro Pro Leu Cys Arg Pro Leu Val
705                 710                 715                 720

Ser Met Asp Gln Ala Pro Val Glu Cys Ile Leu Leu Met Lys Gln Cys
            725                 730                 735

Trp Ala Glu Gln Pro Glu Leu Arg Pro Ser Met Asp His Thr Phe Asp
            740                 745                 750

Leu Phe Lys Asn Ile Asn Lys Gly Arg Lys Thr Asn Ile Ile Asp Ser
            755                 760                 765

Met Leu Arg Met Leu Glu Gln Tyr Ser Ser Asn Leu Glu Asp Leu Ile
            770                 775                 780

Arg Glu Arg Thr Glu Glu Leu Glu Leu Glu Lys Gln Lys Thr Asp Arg
785                 790                 795                 800

Leu Leu Thr Gln Met Leu Pro Pro Ser Val Ala Glu Ala Leu Lys Thr
            805                 810                 815

Gly Thr Pro Val Glu Pro Glu Tyr Phe Glu Gln Val Thr Leu Tyr Phe
            820                 825                 830

Ser Asp Ile Val Gly Phe Thr Thr Ile Ser Ala Met Ser Glu Pro Ile
            835                 840                 845

Glu Val Val Asp Leu Leu Asn Asp Leu Tyr Thr Leu Phe Asp Ala Ile
            850                 855                 860

Ile Gly Ser His Asp Val Tyr Lys Val Glu Thr Ile Gly Asp Ala Tyr
865                 870                 875                 880

Met Val Ala Ser Gly Leu Pro Gln Arg Asn Gly Gln Arg His Ala Ala
            885                 890                 895

Glu Ile Ala Asn Met Ser Leu Asp Ile Leu Ser Ala Val Gly Thr Phe
            900                 905                 910
```

Arg Met Arg His Met Pro Glu Val Pro Val Arg Ile Arg Ile Gly Leu
915                 920                 925

His Ser Gly Pro Cys Val Ala Gly Val Val Gly Leu Thr Met Pro Arg
930                 935                 940

Tyr Cys Leu Phe Gly Asp Thr Val Asn Thr Ala Ser Arg Met Glu Ser
945                 950                 955                 960

Thr Gly Leu Pro Tyr Arg Ile His Val Asn Leu Ser Thr Val Gly Ile
            965                 970                 975

Leu Arg Ala Leu Asp Ser Gly Tyr Gln Val Leu Arg Gly Arg Thr
            980                 985                 990

Glu Leu Lys Gly Lys Gly Ala Glu Asp Thr Phe Trp Leu Val Gly Arg
            995                 1000                1005

Arg Gly Phe Asn Lys Pro Ile Pro Lys Pro Pro Asp Leu Gln Pro
        1010                1015            1020

Gly Ser Ser Asn His Gly Ile Ser Leu Gln Glu Ile Pro Pro Glu
        1025                1030            1035

Arg Arg Arg Lys Leu Glu Lys Ala Arg Pro Gly Gln Phe Ser
        1040                1045            1050

<210> SEQ ID NO 34
<211> LENGTH: 1113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ser Arg Lys Lys Arg Lys Pro Tyr Ser Lys Leu Gln Leu Ala Glu
1               5                   10                  15

Leu Glu Gly Glu Phe Leu Val Asn Glu Phe Ile Thr Arg Gln Arg Arg
            20                  25                  30

Arg Glu Leu Ser Asp Arg Leu Asn Leu Ser Asp Gln Gln Val Lys Ile
        35                  40                  45

Trp Phe Gln Asn Arg Arg Met Lys Lys Lys Arg Leu Leu Ala Val Phe
    50                  55                  60

Thr Val Gly Val Leu Gly Pro Trp Ala Cys Asp Pro Ile Phe Ser Arg
65                  70                  75                  80

Ala Arg Pro Asp Leu Ala Ala Arg Leu Ala Ala Arg Leu Asn Arg
                85                  90                  95

Asp Pro Gly Leu Ala Gly Gly Pro Arg Phe Glu Val Ala Leu Leu Pro
            100                 105                 110

Glu Pro Cys Arg Thr Pro Gly Ser Leu Gly Ala Val Ser Ser Ala Leu
        115                 120                 125

Ala Arg Val Ser Gly Leu Val Gly Pro Val Asn Pro Ala Ala Cys Arg
    130                 135                 140

Pro Ala Glu Leu Leu Ala Glu Ala Gly Ile Ala Leu Val Pro Trp
145                 150                 155                 160

Gly Cys Pro Trp Thr Gln Ala Glu Gly Thr Thr Ala Pro Ala Val Thr
                165                 170                 175

Pro Ala Ala Asp Ala Leu Tyr Ala Leu Leu Arg Ala Phe Gly Trp Ala
            180                 185                 190

Arg Val Ala Leu Val Thr Ala Pro Gln Asp Leu Trp Val Glu Ala Gly
        195                 200                 205

Arg Ser Leu Ser Thr Ala Leu Arg Ala Arg Gly Leu Pro Val Ala Ser
    210                 215                 220

```
Val Thr Ser Met Glu Pro Leu Asp Leu Ser Gly Ala Arg Glu Ala Leu
225                 230                 235                 240

Arg Lys Val Arg Asp Gly Pro Arg Val Thr Ala Val Ile Met Val Met
            245                 250                 255

His Ser Val Leu Leu Gly Gly Glu Gln Arg Tyr Leu Leu Glu Ala
            260                 265                 270

Ala Glu Glu Leu Gly Leu Thr Asp Gly Ser Leu Val Phe Leu Pro Phe
            275                 280                 285

Asp Thr Ile His Tyr Ala Leu Ser Pro Gly Pro Glu Ala Leu Ala Ala
            290                 295                 300

Leu Ala Asn Ser Ser Gln Leu Arg Arg Ala His Asp Ala Val Leu Thr
305                 310                 315                 320

Leu Thr Arg His Cys Pro Ser Glu Gly Ser Val Leu Asp Ser Leu Arg
            325                 330                 335

Arg Ala Gln Glu Arg Glu Leu Pro Ser Asp Leu Asn Leu Gln Gln
            340                 345                 350

Val Ser Pro Leu Phe Gly Thr Ile Tyr Asp Ala Val Phe Leu Leu Ala
            355                 360                 365

Arg Gly Val Ala Glu Ala Arg Ala Ala Gly Gly Arg Trp Val Ser
370                 375                 380

Gly Ala Ala Val Ala Arg His Ile Arg Asp Ala Gln Val Pro Gly Phe
385                 390                 395                 400

Cys Gly Asp Leu Gly Gly Asp Glu Glu Pro Pro Phe Val Leu Leu Asp
            405                 410                 415

Thr Asp Ala Ala Gly Asp Arg Leu Phe Ala Thr Tyr Met Leu Asp Pro
            420                 425                 430

Ala Arg Gly Ser Phe Leu Ser Ala Gly Thr Arg Met His Phe Pro Arg
            435                 440                 445

Gly Gly Ser Ala Pro Gly Pro Asp Pro Ser Cys Trp Phe Asp Pro Asn
            450                 455                 460

Asn Ile Cys Gly Gly Gly Leu Glu Pro Gly Leu Val Phe Leu Gly Phe
465                 470                 475                 480

Leu Leu Val Val Gly Met Gly Leu Ala Gly Ala Phe Leu Ala His Tyr
            485                 490                 495

Val Arg His Arg Leu Leu His Met Gln Met Val Ser Gly Pro Asn Lys
            500                 505                 510

Ile Ile Leu Thr Val Asp Asp Ile Thr Phe Leu His Pro His Gly Gly
            515                 520                 525

Thr Ser Arg Lys Val Ala Gln Gly Ser Arg Ser Ser Leu Gly Ala Arg
            530                 535                 540

Ser Met Ser Asp Ile Arg Ser Gly Pro Ser Gln His Leu Asp Ser Pro
545                 550                 555                 560

Asn Ile Gly Val Tyr Glu Gly Asp Arg Val Trp Leu Lys Lys Phe Pro
            565                 570                 575

Gly Asp Gln His Ile Ala Ile Arg Pro Ala Thr Lys Thr Ala Phe Ser
            580                 585                 590

Lys Leu Gln Glu Leu Arg His Glu Asn Val Ala Leu Tyr Leu Gly Leu
            595                 600                 605

Phe Leu Ala Arg Gly Ala Glu Gly Pro Ala Ala Leu Trp Glu Gly Asn
            610                 615                 620

Leu Ala Val Val Ser Glu His Cys Thr Arg Gly Ser Leu Gln Asp Leu
625                 630                 635                 640
```

```
Leu Ala Gln Arg Glu Ile Lys Leu Asp Trp Met Phe Lys Ser Ser Leu
                645                 650                 655

Leu Leu Asp Leu Ile Lys Gly Ile Arg Tyr Leu His His Arg Gly Val
        660                 665                 670

Ala His Gly Arg Leu Lys Ser Arg Asn Cys Ile Val Asp Gly Arg Phe
            675                 680                 685

Val Leu Lys Ile Thr Asp His Gly His Gly Arg Leu Leu Glu Ala Gln
        690                 695                 700

Lys Val Leu Pro Glu Pro Arg Ala Glu Asp Gln Leu Trp Thr Ala
705                 710                 715                 720

Pro Glu Leu Leu Arg Asp Pro Ala Leu Glu Arg Gly Thr Leu Ala
                725                 730                 735

Gly Asp Val Phe Ser Leu Ala Ile Ile Met Gln Glu Val Val Cys Arg
            740                 745                 750

Ser Ala Pro Tyr Ala Met Leu Glu Leu Thr Pro Glu Glu Val Val Gln
        755                 760                 765

Arg Val Arg Ser Pro Pro Leu Cys Arg Pro Leu Val Ser Met Asp
        770                 775                 780

Gln Ala Pro Val Glu Cys Ile Leu Leu Met Lys Gln Cys Trp Ala Glu
785                 790                 795                 800

Gln Pro Glu Leu Arg Pro Ser Met Asp His Thr Phe Asp Leu Phe Lys
                805                 810                 815

Asn Ile Asn Lys Gly Arg Lys Thr Asn Ile Ile Asp Ser Met Leu Arg
            820                 825                 830

Met Leu Glu Gln Tyr Ser Ser Asn Leu Glu Asp Leu Ile Arg Glu Arg
            835                 840                 845

Thr Glu Glu Leu Glu Leu Glu Lys Gln Lys Thr Asp Arg Leu Leu Thr
850                 855                 860

Gln Met Leu Pro Pro Ser Val Ala Glu Ala Leu Lys Thr Gly Thr Pro
865                 870                 875                 880

Val Glu Pro Glu Tyr Phe Glu Gln Val Thr Leu Tyr Phe Ser Asp Ile
                885                 890                 895

Val Gly Phe Thr Thr Ile Ser Ala Met Ser Glu Pro Ile Glu Val Val
            900                 905                 910

Asp Leu Leu Asn Asp Leu Tyr Thr Leu Phe Asp Ala Ile Ile Gly Ser
            915                 920                 925

His Asp Val Tyr Lys Val Glu Thr Ile Gly Asp Ala Tyr Met Val Ala
        930                 935                 940

Ser Gly Leu Pro Gln Arg Asn Gly Gln Arg His Ala Ala Glu Ile Ala
945                 950                 955                 960

Asn Met Ser Leu Asp Ile Leu Ser Ala Val Gly Thr Phe Arg Met Arg
                965                 970                 975

His Met Pro Glu Val Pro Val Arg Ile Arg Ile Gly Leu His Ser Gly
            980                 985                 990

Pro Cys Val Ala Gly Val Val Gly Leu Thr Met Pro Arg Tyr Cys Leu
        995                 1000                1005

Phe Gly Asp Thr Val Asn Thr Ala Ser Arg Met Glu Ser Thr Gly
    1010                1015                1020

Leu Pro Tyr Arg Ile His Val Asn Leu Ser Thr Val Gly Ile Leu
    1025                1030                1035

Arg Ala Leu Asp Ser Gly Tyr Gln Val Glu Leu Arg Gly Arg Thr
    1040                1045                1050

Glu Leu Lys Gly Lys Gly Ala Glu Asp Thr Phe Trp Leu Val Gly
```

```
                 1055                 1060                 1065

Arg Arg Gly Phe Asn Lys Pro Ile Pro Lys Pro Pro Asp Leu Gln
        1070                1075                1080

Pro Gly Ser Ser Asn His Gly Ile Ser Leu Gln Glu Ile Pro Pro
        1085                1090                1095

Glu Arg Arg Arg Lys Leu Glu Lys Ala Arg Pro Gly Gln Phe Ser
    1100                1105                1110
```

<210> SEQ ID NO 35
<211> LENGTH: 1113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
                20                  25                  30

Lys Glu Leu Ser Asn Arg Leu Asn Leu Ser Asp Gln Gln Val Lys Ile
            35                  40                  45

Trp Phe Gln Asn Arg Arg Met Lys Lys Lys Arg Val Val Ala Val Phe
50                  55                  60

Thr Val Gly Val Leu Gly Pro Trp Ala Cys Asp Pro Ile Phe Ser Arg
65              70                  75                  80

Ala Arg Pro Asp Leu Ala Ala Arg Leu Ala Ala Arg Leu Asn Arg
                85                  90                  95

Asp Pro Gly Leu Ala Gly Gly Pro Arg Phe Glu Val Ala Leu Leu Pro
            100                 105                 110

Glu Pro Cys Arg Thr Pro Gly Ser Leu Gly Ala Val Ser Ser Ala Leu
        115                 120                 125

Ala Arg Val Ser Gly Leu Val Gly Pro Val Asn Pro Ala Ala Cys Arg
    130                 135                 140

Pro Ala Glu Leu Leu Ala Glu Glu Ala Gly Ile Ala Leu Val Pro Trp
145                 150                 155                 160

Gly Cys Pro Trp Thr Gln Ala Glu Gly Thr Thr Ala Pro Ala Val Thr
                165                 170                 175

Pro Ala Ala Asp Ala Leu Tyr Ala Leu Leu Arg Ala Phe Gly Trp Ala
            180                 185                 190

Arg Val Ala Leu Val Thr Ala Pro Gln Asp Leu Trp Val Glu Ala Gly
        195                 200                 205

Arg Ser Leu Ser Thr Ala Leu Arg Ala Arg Gly Leu Pro Val Ala Ser
    210                 215                 220

Val Thr Ser Met Glu Pro Leu Asp Leu Ser Gly Ala Arg Glu Ala Leu
225                 230                 235                 240

Arg Lys Val Arg Asp Gly Pro Arg Val Thr Ala Val Ile Met Val Met
                245                 250                 255

His Ser Val Leu Leu Gly Gly Glu Glu Gln Arg Tyr Leu Leu Glu Ala
            260                 265                 270

Ala Glu Glu Leu Gly Leu Thr Asp Gly Ser Leu Val Phe Leu Pro Phe
        275                 280                 285

Asp Thr Ile His Tyr Ala Leu Ser Pro Gly Pro Glu Ala Leu Ala Ala
    290                 295                 300
```

```
Leu Ala Asn Ser Ser Gln Leu Arg Arg Ala His Asp Ala Val Leu Thr
305                 310                 315                 320
Leu Thr Arg His Cys Pro Ser Glu Gly Ser Val Leu Asp Ser Leu Arg
                325                 330                 335
Arg Ala Gln Glu Arg Arg Glu Leu Pro Ser Asp Leu Asn Leu Gln Gln
            340                 345                 350
Val Ser Pro Leu Phe Gly Thr Ile Tyr Asp Ala Val Phe Leu Leu Ala
        355                 360                 365
Arg Gly Val Ala Glu Ala Arg Ala Ala Gly Gly Arg Trp Val Ser
370                 375                 380
Gly Ala Ala Val Ala Arg His Ile Arg Asp Ala Gln Val Pro Gly Phe
385                 390                 395                 400
Cys Gly Asp Leu Gly Gly Asp Glu Glu Pro Pro Phe Val Leu Leu Asp
                405                 410                 415
Thr Asp Ala Ala Gly Asp Arg Leu Phe Ala Thr Tyr Met Leu Asp Pro
            420                 425                 430
Ala Arg Gly Ser Phe Leu Ser Ala Gly Thr Arg Met His Phe Pro Arg
        435                 440                 445
Gly Gly Ser Ala Pro Gly Pro Asp Pro Ser Cys Trp Phe Asp Pro Asn
450                 455                 460
Asn Ile Cys Gly Gly Gly Leu Glu Pro Gly Leu Val Phe Leu Gly Phe
465                 470                 475                 480
Leu Leu Val Val Gly Met Gly Leu Ala Gly Ala Phe Leu Ala His Tyr
                485                 490                 495
Val Arg His Arg Leu Leu His Met Gln Met Val Ser Gly Pro Asn Lys
            500                 505                 510
Ile Ile Leu Thr Val Asp Asp Ile Thr Phe Leu His Pro His Gly Gly
        515                 520                 525
Thr Ser Arg Lys Val Ala Gln Gly Ser Arg Ser Ser Leu Gly Ala Arg
530                 535                 540
Ser Met Ser Asp Ile Arg Ser Gly Pro Ser Gln His Leu Asp Ser Pro
545                 550                 555                 560
Asn Ile Gly Val Tyr Glu Gly Asp Arg Val Trp Leu Lys Lys Phe Pro
                565                 570                 575
Gly Asp Gln His Ile Ala Ile Arg Pro Ala Thr Lys Thr Ala Phe Ser
            580                 585                 590
Lys Leu Gln Glu Leu Arg His Glu Asn Val Ala Leu Tyr Leu Gly Leu
        595                 600                 605
Phe Leu Ala Arg Gly Ala Glu Gly Pro Ala Ala Leu Trp Glu Gly Asn
610                 615                 620
Leu Ala Val Val Ser Glu His Cys Thr Arg Gly Ser Leu Gln Asp Leu
625                 630                 635                 640
Leu Ala Gln Arg Glu Ile Lys Leu Asp Trp Met Phe Lys Ser Ser Leu
                645                 650                 655
Leu Leu Asp Leu Ile Lys Gly Ile Arg Tyr Leu His His Arg Gly Val
            660                 665                 670
Ala His Gly Arg Leu Lys Ser Arg Asn Cys Ile Val Asp Gly Arg Phe
        675                 680                 685
Val Leu Lys Ile Thr Asp His Gly His Gly Arg Leu Leu Glu Ala Gln
690                 695                 700
Lys Val Leu Pro Glu Pro Pro Arg Ala Glu Asp Gln Leu Trp Thr Ala
705                 710                 715                 720
Pro Glu Leu Leu Arg Asp Pro Ala Leu Glu Arg Arg Gly Thr Leu Ala
```

```
                725                 730                 735
Gly Asp Val Phe Ser Leu Ala Ile Ile Met Gln Glu Val Val Cys Arg
                740                 745                 750
Ser Ala Pro Tyr Ala Met Leu Glu Leu Thr Pro Glu Val Val Gln
            755                 760                 765
Arg Val Arg Ser Pro Pro Leu Cys Arg Pro Leu Val Ser Met Asp
770                 775                 780
Gln Ala Pro Val Glu Cys Ile Leu Leu Met Lys Gln Cys Trp Ala Glu
785                 790                 795                 800
Gln Pro Glu Leu Arg Pro Ser Met Asp His Thr Phe Asp Leu Phe Lys
            805                 810                 815
Asn Ile Asn Lys Gly Arg Lys Thr Asn Ile Ile Asp Ser Met Leu Arg
            820                 825                 830
Met Leu Glu Gln Tyr Ser Ser Asn Leu Glu Asp Leu Ile Arg Glu Arg
            835                 840                 845
Thr Glu Glu Leu Glu Leu Glu Lys Gln Lys Thr Asp Arg Leu Leu Thr
850                 855                 860
Gln Met Leu Pro Pro Ser Val Ala Glu Ala Leu Lys Thr Gly Thr Pro
865                 870                 875                 880
Val Glu Pro Glu Tyr Phe Glu Gln Val Thr Leu Tyr Phe Ser Asp Ile
                885                 890                 895
Val Gly Phe Thr Thr Ile Ser Ala Met Ser Glu Pro Ile Glu Val Val
                900                 905                 910
Asp Leu Leu Asn Asp Leu Tyr Thr Leu Phe Asp Ala Ile Ile Gly Ser
            915                 920                 925
His Asp Val Tyr Lys Val Glu Thr Ile Gly Asp Ala Tyr Met Val Ala
930                 935                 940
Ser Gly Leu Pro Gln Arg Asn Gly Gln Arg His Ala Ala Glu Ile Ala
945                 950                 955                 960
Asn Met Ser Leu Asp Ile Leu Ser Ala Val Gly Thr Phe Arg Met Arg
            965                 970                 975
His Met Pro Glu Val Pro Val Arg Ile Arg Ile Gly Leu His Ser Gly
            980                 985                 990
Pro Cys Val Ala Gly Val Val Gly Leu Thr Met Pro Arg Tyr Cys Leu
            995                 1000                1005
Phe Gly Asp Thr Val Asn Thr Ala Ser Arg Met Glu Ser Thr Gly
            1010                1015                1020
Leu Pro Tyr Arg Ile His Val Asn Leu Ser Thr Val Gly Ile Leu
            1025                1030                1035
Arg Ala Leu Asp Ser Gly Tyr Gln Val Glu Leu Arg Gly Arg Thr
            1040                1045                1050
Glu Leu Lys Gly Lys Gly Ala Glu Asp Thr Phe Trp Leu Val Gly
            1055                1060                1065
Arg Arg Gly Phe Asn Lys Pro Ile Pro Lys Pro Asp Leu Gln
            1070                1075                1080
Pro Gly Ser Ser Asn His Gly Ile Ser Leu Gln Glu Ile Pro Pro
            1085                1090                1095
Glu Arg Arg Arg Lys Leu Glu Lys Ala Arg Pro Gly Gln Phe Ser
            1100                1105                1110

<210> SEQ ID NO 36
<211> LENGTH: 311
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 36

Thr Gly Ala Glu Arg Pro Phe Gln Cys Arg Ile Cys Met Arg Asn Phe
1               5                   10                  15

Ser Gln Arg Ala Thr Leu Gln Arg His Ile Arg Thr His Thr Gly Glu
                20                  25                  30

Lys Pro Phe Ala Cys Asp Ile Cys Gly Arg Lys Phe Ala Gln Arg Ala
            35                  40                  45

Thr Leu Gln Arg His Thr Lys Ile His Thr Gly Ser Glu Arg Pro Phe
    50                  55                  60

Gln Cys Arg Ile Cys Met Arg Asn Phe Ser Gln Arg Ala Thr Leu Gln
65                  70                  75                  80

Arg His Ile Arg Thr His Thr Gly Glu Lys Pro Phe Ala Cys Asp Ile
                85                  90                  95

Cys Gly Arg Lys Phe Ala Gln Arg Ala Thr Leu Gln Arg His Thr Lys
            100                 105                 110

Ile His Thr Gly Ser Glu Arg Pro Phe Gln Cys Arg Ile Cys Met Arg
    115                 120                 125

Asn Phe Ser Gln Arg Ala Thr Leu Gln Arg His Ile Arg Thr His Thr
130                 135                 140

Gly Glu Lys Pro Phe Ala Cys Asp Ile Cys Gly Arg Lys Phe Ala Gln
145                 150                 155                 160

Arg Ala Thr Leu Gln Arg His Thr Lys Ile His Leu Arg Gln Lys Asp
                165                 170                 175

Gly Gly Gly Gly Ser Gly Gly Gly Ser Gly Gly Gly Ser Gln
            180                 185                 190

Leu Val Ser Ser Leu Ser Pro Gln His Ser Ala Val Thr Gln Gly Ile
    195                 200                 205

Ile Lys Asn Lys Glu Gly Met Asp Ala Lys Ser Leu Thr Ala Trp Ser
    210                 215                 220

Arg Thr Leu Val Thr Phe Lys Asp Val Phe Val Asp Phe Thr Arg Glu
225                 230                 235                 240

Glu Trp Lys Leu Leu Asp Thr Ala Gln Gln Ile Val Tyr Arg Asn Val
                245                 250                 255

Met Leu Glu Asn Tyr Lys Asn Leu Val Ser Leu Gly Tyr Gln Leu Thr
            260                 265                 270

Lys Pro Asp Val Ile Leu Arg Leu Glu Lys Gly Glu Glu Pro Trp Leu
    275                 280                 285

Val Glu Arg Glu Ile His Gln Glu Thr His Pro Asp Ser Glu Thr Ala
    290                 295                 300

Phe Glu Ile Lys Ser Ser Val
305             310

<210> SEQ ID NO 37
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Ser Arg Lys Lys Arg Lys Pro Tyr Ser Lys Leu Gln Leu Ala Glu
1               5                   10                  15
```

Leu Glu Gly Glu Phe Leu Val Asn Glu Phe Ile Thr Arg Gln Arg Arg
            20                  25                  30

Arg Glu Leu Ser Asp Arg Leu Asn Leu Ser Asp Gln Gln Val Lys Ile
        35                  40                  45

Trp Phe Gln Asn Arg Arg Met Lys Lys Arg Leu Leu Thr Gly Ala
50                  55                  60

Glu Arg Pro Phe Gln Cys Arg Ile Cys Met Arg Asn Phe Ser Gln Arg
65                  70                  75                  80

Ala Thr Leu Gln Arg His Ile Arg Thr His Thr Gly Glu Lys Pro Phe
                85                  90                  95

Ala Cys Asp Ile Cys Gly Arg Lys Phe Ala Gln Arg Ala Thr Leu Gln
            100                 105                 110

Arg His Thr Lys Ile His Thr Gly Ser Glu Arg Pro Phe Gln Cys Arg
        115                 120                 125

Ile Cys Met Arg Asn Phe Ser Gln Arg Ala Thr Leu Gln Arg His Ile
130                 135                 140

Arg Thr His Thr Gly Glu Lys Pro Phe Ala Cys Asp Ile Cys Gly Arg
145                 150                 155                 160

Lys Phe Ala Gln Arg Ala Thr Leu Gln Arg His Thr Lys Ile His Thr
                165                 170                 175

Gly Ser Glu Arg Pro Phe Gln Cys Arg Ile Cys Met Arg Asn Phe Ser
            180                 185                 190

Gln Arg Ala Thr Leu Gln Arg His Ile Arg Thr His Thr Gly Glu Lys
        195                 200                 205

Pro Phe Ala Cys Asp Ile Cys Gly Arg Lys Phe Ala Gln Arg Ala Thr
210                 215                 220

Leu Gln Arg His Thr Lys Ile His Leu Arg Gln Lys Asp Gly Gly
225                 230                 235                 240

Gly Ser Gly Gly Gly Ser Gly Gly Gly Ser Gln Leu Val Ser
            245                 250                 255

Ser Leu Ser Pro Gln His Ser Ala Val Thr Gln Gly Ile Ile Lys Asn
            260                 265                 270

Lys Glu Gly Met Asp Ala Lys Ser Leu Thr Ala Trp Ser Arg Thr Leu
            275                 280                 285

Val Thr Phe Lys Asp Val Phe Val Asp Phe Thr Arg Glu Glu Trp Lys
290                 295                 300

Leu Leu Asp Thr Ala Gln Gln Ile Val Tyr Arg Asn Val Met Leu Glu
305                 310                 315                 320

Asn Tyr Lys Asn Leu Val Ser Leu Gly Tyr Gln Leu Thr Lys Pro Asp
                325                 330                 335

Val Ile Leu Arg Leu Glu Lys Gly Glu Glu Pro Trp Leu Val Glu Arg
            340                 345                 350

Glu Ile His Gln Glu Thr His Pro Asp Ser Glu Thr Ala Phe Glu Ile
        355                 360                 365

Lys Ser Ser Val
    370

<210> SEQ ID NO 38
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
            20                  25                  30

Lys Glu Leu Ser Asn Arg Leu Asn Leu Ser Asp Gln Val Lys Ile
        35                  40                  45

Trp Phe Gln Asn Arg Arg Met Lys Lys Arg Val Val Thr Gly Ala
    50                  55                  60

Glu Arg Pro Phe Gln Cys Arg Ile Cys Met Arg Asn Phe Ser Gln Arg
65                  70                  75                  80

Ala Thr Leu Gln Arg His Ile Arg Thr His Thr Gly Glu Lys Pro Phe
                85                  90                  95

Ala Cys Asp Ile Cys Gly Arg Lys Phe Ala Gln Arg Ala Thr Leu Gln
                100                 105                 110

Arg His Thr Lys Ile His Thr Gly Ser Glu Arg Pro Phe Gln Cys Arg
            115                 120                 125

Ile Cys Met Arg Asn Phe Ser Gln Arg Ala Thr Leu Gln Arg His Ile
        130                 135                 140

Arg Thr His Thr Gly Glu Lys Pro Phe Ala Cys Asp Ile Cys Gly Arg
145                 150                 155                 160

Lys Phe Ala Gln Arg Ala Thr Leu Gln Arg His Thr Lys Ile His Thr
                165                 170                 175

Gly Ser Glu Arg Pro Phe Gln Cys Arg Ile Cys Met Arg Asn Phe Ser
            180                 185                 190

Gln Arg Ala Thr Leu Gln Arg His Ile Arg Thr His Thr Gly Glu Lys
        195                 200                 205

Pro Phe Ala Cys Asp Ile Cys Gly Arg Lys Phe Ala Gln Arg Ala Thr
    210                 215                 220

Leu Gln Arg His Thr Lys Ile His Leu Arg Gln Lys Asp Gly Gly
225                 230                 235                 240

Gly Ser Gly Gly Gly Ser Gly Gly Gly Ser Gln Leu Val Ser
                245                 250                 255

Ser Leu Ser Pro Gln His Ser Ala Val Thr Gln Gly Ile Ile Lys Asn
            260                 265                 270

Lys Glu Gly Met Asp Ala Lys Ser Leu Thr Ala Trp Ser Arg Thr Leu
        275                 280                 285

Val Thr Phe Lys Asp Val Phe Val Asp Phe Thr Arg Glu Glu Trp Lys
    290                 295                 300

Leu Leu Asp Thr Ala Gln Gln Ile Val Tyr Arg Asn Val Met Leu Glu
305                 310                 315                 320

Asn Tyr Lys Asn Leu Val Ser Leu Gly Tyr Gln Leu Thr Lys Pro Asp
                325                 330                 335

Val Ile Leu Arg Leu Glu Lys Gly Glu Glu Pro Trp Leu Val Glu Arg
            340                 345                 350

Glu Ile His Gln Glu Thr His Pro Asp Ser Glu Thr Ala Phe Glu Ile
        355                 360                 365

Lys Ser Ser Val
        370
```

<210> SEQ ID NO 39
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Thr Gly Ala Glu Arg Pro Phe Gln Cys Arg Ile Cys Met Arg Asn Phe
1               5                   10                  15

Ser Gln Arg Ala Thr Leu Gln Arg His Ile Arg Thr His Thr Gly Glu
            20                  25                  30

Lys Pro Phe Ala Cys Asp Ile Cys Gly Arg Lys Phe Ala Gln Arg Ala
        35                  40                  45

Thr Leu Gln Arg His Thr Lys Ile His Thr Gly Ser Glu Arg Pro Phe
    50                  55                  60

Gln Cys Arg Ile Cys Met Arg Asn Phe Ser Gln Arg Ala Thr Leu Gln
65                  70                  75                  80

Arg His Ile Arg Thr His Thr Gly Glu Lys Pro Phe Ala Cys Asp Ile
                85                  90                  95

Cys Gly Arg Lys Phe Ala Gln Arg Ala Thr Leu Gln Arg His Thr Lys
            100                 105                 110

Ile His Thr Gly Ser Glu Arg Pro Phe Gln Cys Arg Ile Cys Met Arg
        115                 120                 125

Asn Phe Ser Gln Arg Ala Thr Leu Gln Arg His Ile Arg Thr His Thr
    130                 135                 140

Gly Glu Lys Pro Phe Ala Cys Asp Ile Cys Gly Arg Lys Phe Ala Gln
145                 150                 155                 160

Arg Ala Thr Leu Gln Arg His Thr Lys Ile His Leu Arg Gln Lys Asp
                165                 170                 175

Gly Gly Gly Gly Ser Gly Gly Gly Ser Gly Gly Gly Ser Gln
            180                 185                 190

Leu Val Gly Thr Ala Glu Arg Pro Phe Gln Cys Arg Ile Cys Met Arg
        195                 200                 205

Asn Phe Ser Gln Arg Ala Thr Leu Gln Arg His Ile Arg Thr His Thr
    210                 215                 220

Gly Glu Lys Pro Phe Ala Cys Asp Ile Cys Gly Arg Lys Phe Ala Gln
225                 230                 235                 240

Arg Ala Thr Leu Gln Arg His Thr Lys Ile His Thr Gly Ser Glu Arg
                245                 250                 255

Pro Phe Gln Cys Arg Ile Cys Met Arg Asn Phe Ser Gln Arg Ala Thr
            260                 265                 270

Leu Gln Arg His Ile Arg Thr His Thr Gly Glu Lys Pro Phe Ala Cys
        275                 280                 285

Asp Ile Cys Gly Arg Lys Phe Ala Gln Arg Ala Thr Leu Gln Arg His
    290                 295                 300

Thr Lys Ile His Thr Gly Ser Glu Arg Pro Phe Gln Cys Arg Ile Cys
305                 310                 315                 320

Met Arg Asn Phe Ser Gln Arg Ala Thr Leu Gln Arg His Ile Arg Thr
                325                 330                 335

His Thr Gly Glu Lys Pro Phe Ala Cys Asp Ile Cys Gly Arg Lys Phe
            340                 345                 350

Ala Gln Arg Ala Thr Leu Gln Arg His Thr Lys Ile His Leu Arg Gln
        355                 360                 365

Lys Asp Gly Gly Gly Gly Ser Gly Gly Gly Ser Gly Gly Gly Gly
    370                 375                 380

Ser Gln Leu Val Ser Ser Leu Ser Pro Gln His Ser Ala Val Thr Gln
```

```
                385                 390                 395                 400
        Gly Ile Ile Lys Asn Lys Glu Gly Met Asp Ala Lys Ser Leu Thr Ala
                        405                 410                 415

Trp Ser Arg Thr Leu Val Thr Phe Lys Asp Val Phe Val Asp Phe Thr
                        420                 425                 430

Arg Glu Glu Trp Lys Leu Leu Asp Thr Ala Gln Gln Ile Val Tyr Arg
                        435                 440                 445

Asn Val Met Leu Glu Asn Tyr Lys Asn Leu Val Ser Leu Gly Tyr Gln
                        450                 455                 460

Leu Thr Lys Pro Asp Val Ile Leu Arg Leu Glu Lys Gly Glu Pro
        465                 470                 475                 480

Trp Leu Val Glu Arg Glu Ile His Gln Glu Thr His Pro Asp Ser Glu
                        485                 490                 495

Thr Ala Phe Glu Ile Lys Ser Ser Val
                        500                 505

<210> SEQ ID NO 40
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ser Arg Lys Lys Arg Lys Pro Tyr Ser Lys Leu Gln Leu Ala Glu
1               5                   10                  15

Leu Glu Gly Glu Phe Leu Val Asn Glu Phe Ile Thr Arg Gln Arg Arg
                20                  25                  30

Arg Glu Leu Ser Asp Arg Leu Asn Leu Ser Asp Gln Gln Val Lys Ile
                35                  40                  45

Trp Phe Gln Asn Arg Arg Met Lys Lys Lys Arg Leu Leu Thr Gly Ala
            50                  55                  60

Glu Arg Pro Phe Gln Cys Arg Ile Cys Met Arg Asn Phe Ser Gln Arg
65              70                  75                  80

Ala Thr Leu Gln Arg His Ile Arg Thr His Thr Gly Glu Lys Pro Phe
                85                  90                  95

Ala Cys Asp Ile Cys Gly Arg Lys Phe Ala Gln Arg Ala Thr Leu Gln
                100                 105                 110

Arg His Thr Lys Ile His Thr Gly Ser Glu Arg Pro Phe Gln Cys Arg
                115                 120                 125

Ile Cys Met Arg Asn Phe Ser Gln Arg Ala Thr Leu Gln Arg His Ile
            130                 135                 140

Arg Thr His Thr Gly Glu Lys Pro Phe Ala Cys Asp Ile Cys Gly Arg
145                 150                 155                 160

Lys Phe Ala Gln Arg Ala Thr Leu Gln Arg His Thr Lys Ile His Thr
                165                 170                 175

Gly Ser Glu Arg Pro Phe Gln Cys Arg Ile Cys Met Arg Asn Phe Ser
                180                 185                 190

Gln Arg Ala Thr Leu Gln Arg His Ile Arg Thr His Thr Gly Glu Lys
                195                 200                 205

Pro Phe Ala Cys Asp Ile Cys Gly Arg Lys Phe Ala Gln Arg Ala Thr
            210                 215                 220

Leu Gln Arg His Thr Lys Ile His Leu Arg Gln Lys Asp Gly Gly
225                 230                 235                 240
```

Gly Ser Gly Gly Gly Gly Ser Gly Gly Gly Ser Gln Leu Val Gly
                245                 250                 255

Thr Ala Glu Arg Pro Phe Gln Cys Arg Ile Cys Met Arg Asn Phe Ser
            260                 265                 270

Gln Arg Ala Thr Leu Gln Arg His Ile Arg Thr His Thr Gly Glu Lys
        275                 280                 285

Pro Phe Ala Cys Asp Ile Cys Gly Arg Lys Phe Ala Gln Arg Ala Thr
    290                 295                 300

Leu Gln Arg His Thr Lys Ile His Thr Gly Ser Glu Arg Pro Phe Gln
305                 310                 315                 320

Cys Arg Ile Cys Met Arg Asn Phe Ser Gln Arg Ala Thr Leu Gln Arg
                325                 330                 335

His Ile Arg Thr His Thr Gly Glu Lys Pro Phe Ala Cys Asp Ile Cys
            340                 345                 350

Gly Arg Lys Phe Ala Gln Arg Ala Thr Leu Gln Arg His Thr Lys Ile
        355                 360                 365

His Thr Gly Ser Glu Arg Pro Phe Gln Cys Arg Ile Cys Met Arg Asn
    370                 375                 380

Phe Ser Gln Arg Ala Thr Leu Gln Arg His Ile Arg Thr His Thr Gly
385                 390                 395                 400

Glu Lys Pro Phe Ala Cys Asp Ile Cys Gly Arg Lys Phe Ala Gln Arg
                405                 410                 415

Ala Thr Leu Gln Arg His Thr Lys Ile His Leu Arg Gln Lys Asp Gly
            420                 425                 430

Gly Gly Gly Ser Gly Gly Gly Ser Gly Gly Gly Ser Gln Leu
        435                 440                 445

Val Ser Ser Leu Ser Pro Gln His Ser Ala Val Thr Gln Gly Ile Ile
450                 455                 460

Lys Asn Lys Glu Gly Met Asp Ala Lys Ser Leu Thr Ala Trp Ser Arg
465                 470                 475                 480

Thr Leu Val Thr Phe Lys Asp Val Phe Val Asp Phe Thr Arg Glu Glu
                485                 490                 495

Trp Lys Leu Leu Asp Thr Ala Gln Gln Ile Val Tyr Arg Asn Val Met
            500                 505                 510

Leu Glu Asn Tyr Lys Asn Leu Val Ser Leu Gly Tyr Gln Leu Thr Lys
        515                 520                 525

Pro Asp Val Ile Leu Arg Leu Glu Lys Gly Glu Pro Trp Leu Val
    530                 535                 540

Glu Arg Glu Ile His Gln Glu Thr His Pro Asp Ser Glu Thr Ala Phe
545                 550                 555                 560

Glu Ile Lys Ser Ser Val
                565

<210> SEQ ID NO 41
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
            20                  25                  30

```
Lys Glu Leu Ser Asn Arg Leu Asn Leu Ser Asp Gln Gln Val Lys Ile
         35                  40                  45

Trp Phe Gln Asn Arg Arg Met Lys Lys Lys Arg Val Val Thr Gly Ala
     50                  55                  60

Glu Arg Pro Phe Gln Cys Arg Ile Cys Met Arg Asn Phe Ser Gln Arg
 65                  70                  75                  80

Ala Thr Leu Gln Arg His Ile Arg Thr His Thr Gly Glu Lys Pro Phe
                 85                  90                  95

Ala Cys Asp Ile Cys Gly Arg Lys Phe Ala Gln Arg Ala Thr Leu Gln
             100                 105                 110

Arg His Thr Lys Ile His Thr Gly Ser Glu Arg Pro Phe Gln Cys Arg
         115                 120                 125

Ile Cys Met Arg Asn Phe Ser Gln Arg Ala Thr Leu Gln Arg His Ile
     130                 135                 140

Arg Thr His Thr Gly Glu Lys Pro Phe Ala Cys Asp Ile Cys Gly Arg
145                 150                 155                 160

Lys Phe Ala Gln Arg Ala Thr Leu Gln Arg His Thr Lys Ile His Thr
                 165                 170                 175

Gly Ser Glu Arg Pro Phe Gln Cys Arg Ile Cys Met Arg Asn Phe Ser
             180                 185                 190

Gln Arg Ala Thr Leu Gln Arg His Ile Arg Thr His Thr Gly Glu Lys
         195                 200                 205

Pro Phe Ala Cys Asp Ile Cys Gly Arg Lys Phe Ala Gln Arg Ala Thr
     210                 215                 220

Leu Gln Arg His Thr Lys Ile His Leu Arg Gln Lys Asp Gly Gly
225                 230                 235                 240

Gly Ser Gly Gly Gly Ser Gly Gly Gly Ser Gln Leu Val Gly
             245                 250                 255

Thr Ala Glu Arg Pro Phe Gln Cys Arg Ile Cys Met Arg Asn Phe Ser
         260                 265                 270

Gln Arg Ala Thr Leu Gln Arg His Ile Arg Thr His Thr Gly Glu Lys
     275                 280                 285

Pro Phe Ala Cys Asp Ile Cys Gly Arg Lys Phe Ala Gln Arg Ala Thr
 290                 295                 300

Leu Gln Arg His Thr Lys Ile His Thr Gly Ser Glu Arg Pro Phe Gln
305                 310                 315                 320

Cys Arg Ile Cys Met Arg Asn Phe Ser Gln Arg Ala Thr Leu Gln Arg
                 325                 330                 335

His Ile Arg Thr His Thr Gly Glu Lys Pro Phe Ala Cys Asp Ile Cys
             340                 345                 350

Gly Arg Lys Phe Ala Gln Arg Ala Thr Leu Gln Arg His Thr Lys Ile
         355                 360                 365

His Thr Gly Ser Glu Arg Pro Phe Gln Cys Arg Ile Cys Met Arg Asn
     370                 375                 380

Phe Ser Gln Arg Ala Thr Leu Gln Arg His Ile Arg Thr His Thr Gly
385                 390                 395                 400

Glu Lys Pro Phe Ala Cys Asp Ile Cys Gly Arg Lys Phe Ala Gln Arg
                 405                 410                 415

Ala Thr Leu Gln Arg His Thr Lys Ile His Leu Arg Gln Lys Asp Gly
             420                 425                 430

Gly Gly Gly Ser Gly Gly Gly Ser Gly Gly Gly Ser Gln Leu
         435                 440                 445
```

```
Val Ser Ser Leu Ser Pro Gln His Ser Ala Val Thr Gln Gly Ile Ile
    450                 455                 460

Lys Asn Lys Glu Gly Met Asp Ala Lys Ser Leu Thr Ala Trp Ser Arg
465                 470                 475                 480

Thr Leu Val Thr Phe Lys Asp Val Phe Val Asp Phe Thr Arg Glu Glu
                485                 490                 495

Trp Lys Leu Leu Asp Thr Ala Gln Gln Ile Val Tyr Arg Asn Val Met
                500                 505                 510

Leu Glu Asn Tyr Lys Asn Leu Val Ser Leu Gly Tyr Gln Leu Thr Lys
                515                 520                 525

Pro Asp Val Ile Leu Arg Leu Glu Lys Gly Glu Pro Trp Leu Val
530                 535                 540

Glu Arg Glu Ile His Gln Glu Thr His Pro Asp Ser Glu Thr Ala Phe
545                 550                 555                 560

Glu Ile Lys Ser Ser Val
                565

<210> SEQ ID NO 42
<211> LENGTH: 699
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Thr Gly Ala Glu Arg Pro Phe Gln Cys Arg Ile Cys Met Arg Asn Phe
1               5                   10                  15

Ser Gln Arg Ala Thr Leu Gln Arg His Ile Arg Thr His Thr Gly Glu
                20                  25                  30

Lys Pro Phe Ala Cys Asp Ile Cys Gly Arg Lys Phe Ala Gln Arg Ala
            35                  40                  45

Thr Leu Gln Arg His Thr Lys Ile His Thr Gly Ser Glu Arg Pro Phe
    50                  55                  60

Gln Cys Arg Ile Cys Met Arg Asn Phe Ser Gln Arg Ala Thr Leu Gln
65                  70                  75                  80

Arg His Ile Arg Thr His Thr Gly Glu Lys Pro Phe Ala Cys Asp Ile
                85                  90                  95

Cys Gly Arg Lys Phe Ala Gln Arg Ala Thr Leu Gln Arg His Thr Lys
            100                 105                 110

Ile His Thr Gly Ser Glu Arg Pro Phe Gln Cys Arg Ile Cys Met Arg
        115                 120                 125

Asn Phe Ser Gln Arg Ala Thr Leu Gln Arg His Ile Arg Thr His Thr
130                 135                 140

Gly Glu Lys Pro Phe Ala Cys Asp Ile Cys Gly Arg Lys Phe Ala Gln
145                 150                 155                 160

Arg Ala Thr Leu Gln Arg His Thr Lys Ile His Leu Arg Gln Lys Asp
                165                 170                 175

Gly Gly Gly Gly Ser Gly Gly Gly Ser Gly Gly Gly Ser Gln
                180                 185                 190

Leu Val Gly Thr Ala Glu Arg Pro Phe Gln Cys Arg Ile Cys Met Arg
            195                 200                 205

Asn Phe Ser Gln Arg Ala Thr Leu Gln Arg His Ile Arg Thr His Thr
210                 215                 220

Gly Glu Lys Pro Phe Ala Cys Asp Ile Cys Gly Arg Lys Phe Ala Gln
225                 230                 235                 240
```

```
Arg Ala Thr Leu Gln Arg His Thr Lys Ile His Thr Gly Ser Glu Arg
                245                 250                 255
Pro Phe Gln Cys Arg Ile Cys Met Arg Asn Phe Ser Gln Arg Ala Thr
                260                 265                 270
Leu Gln Arg His Ile Arg Thr His Thr Gly Glu Lys Pro Phe Ala Cys
                275                 280                 285
Asp Ile Cys Gly Arg Lys Phe Ala Gln Arg Ala Thr Leu Gln Arg His
                290                 295                 300
Thr Lys Ile His Thr Gly Ser Glu Arg Pro Phe Gln Cys Arg Ile Cys
305                 310                 315                 320
Met Arg Asn Phe Ser Gln Arg Ala Thr Leu Gln Arg His Ile Arg Thr
                325                 330                 335
His Thr Gly Glu Lys Pro Phe Ala Cys Asp Ile Cys Gly Arg Lys Phe
                340                 345                 350
Ala Gln Arg Ala Thr Leu Gln Arg His Thr Lys Ile His Leu Arg Gln
                355                 360                 365
Lys Asp Gly Gly Gly Ser Gly Gly Gly Ser Gly Gly Gly Gly
                370                 375                 380
Ser Gln Leu Val Gly Thr Ala Glu Arg Pro Phe Gln Cys Arg Ile Cys
385                 390                 395                 400
Met Arg Asn Phe Ser Gln Arg Ala Thr Leu Gln Arg His Ile Arg Thr
                405                 410                 415
His Thr Gly Glu Lys Pro Phe Ala Cys Asp Ile Cys Gly Arg Lys Phe
                420                 425                 430
Ala Gln Arg Ala Thr Leu Gln Arg His Thr Lys Ile His Thr Gly Ser
                435                 440                 445
Glu Arg Pro Phe Gln Cys Arg Ile Cys Met Arg Asn Phe Ser Gln Arg
                450                 455                 460
Ala Thr Leu Gln Arg His Ile Arg Thr His Thr Gly Glu Lys Pro Phe
465                 470                 475                 480
Ala Cys Asp Ile Cys Gly Arg Lys Phe Ala Gln Arg Ala Thr Leu Gln
                485                 490                 495
Arg His Thr Lys Ile His Thr Gly Ser Glu Arg Pro Phe Gln Cys Arg
                500                 505                 510
Ile Cys Met Arg Asn Phe Ser Gln Arg Ala Thr Leu Gln Arg His Ile
                515                 520                 525
Arg Thr His Thr Gly Glu Lys Pro Phe Ala Cys Asp Ile Cys Gly Arg
                530                 535                 540
Lys Phe Ala Gln Arg Ala Thr Leu Gln Arg His Thr Lys Ile His Leu
545                 550                 555                 560
Arg Gln Lys Asp Gly Gly Gly Ser Gly Gly Gly Ser Gly Gly
                565                 570                 575
Gly Gly Ser Gln Leu Val Ser Ser Leu Ser Pro Gln His Ser Ala Val
                580                 585                 590
Thr Gln Gly Ile Ile Lys Asn Lys Glu Gly Met Asp Ala Lys Ser Leu
                595                 600                 605
Thr Ala Trp Ser Arg Thr Leu Val Thr Phe Lys Asp Val Phe Val Asp
                610                 615                 620
Phe Thr Arg Glu Glu Trp Lys Leu Leu Asp Thr Ala Gln Gln Ile Val
625                 630                 635                 640
Tyr Arg Asn Val Met Leu Glu Asn Tyr Lys Asn Leu Val Ser Leu Gly
                645                 650                 655
```

```
Tyr Gln Leu Thr Lys Pro Asp Val Ile Leu Arg Leu Glu Lys Gly Glu
                660                 665                 670

Glu Pro Trp Leu Val Glu Arg Glu Ile His Gln Glu Thr His Pro Asp
            675                 680                 685

Ser Glu Thr Ala Phe Glu Ile Lys Ser Ser Val
        690                 695

<210> SEQ ID NO 43
<211> LENGTH: 760
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Ser Arg Lys Lys Arg Lys Pro Tyr Ser Lys Leu Gln Leu Ala Glu
1               5                   10                  15

Leu Glu Gly Glu Phe Leu Val Asn Glu Phe Ile Thr Arg Gln Arg Arg
            20                  25                  30

Arg Glu Leu Ser Asp Arg Leu Asn Leu Ser Asp Gln Gln Val Lys Ile
        35                  40                  45

Trp Phe Gln Asn Arg Arg Met Lys Lys Arg Leu Leu Thr Gly Ala
    50                  55                  60

Glu Arg Pro Phe Gln Cys Arg Ile Cys Met Arg Asn Phe Ser Gln Arg
65                  70                  75                  80

Ala Thr Leu Gln Arg His Ile Arg Thr His Thr Gly Glu Lys Pro Phe
                85                  90                  95

Ala Cys Asp Ile Cys Gly Arg Lys Phe Ala Gln Arg Ala Thr Leu Gln
            100                 105                 110

Arg His Thr Lys Ile His Thr Gly Ser Glu Arg Pro Phe Gln Cys Arg
        115                 120                 125

Ile Cys Met Arg Asn Phe Ser Gln Arg Ala Thr Leu Gln Arg His Ile
    130                 135                 140

Arg Thr His Thr Gly Glu Lys Pro Phe Ala Cys Asp Ile Cys Gly Arg
145                 150                 155                 160

Lys Phe Ala Gln Arg Ala Thr Leu Gln Arg His Thr Lys Ile His Thr
                165                 170                 175

Gly Ser Glu Arg Pro Phe Gln Cys Arg Ile Cys Met Arg Asn Phe Ser
            180                 185                 190

Gln Arg Ala Thr Leu Gln Arg His Ile Arg Thr His Thr Gly Glu Lys
        195                 200                 205

Pro Phe Ala Cys Asp Ile Cys Gly Arg Lys Phe Ala Gln Arg Ala Thr
    210                 215                 220

Leu Gln Arg His Thr Lys Ile His Leu Arg Gln Lys Asp Gly Gly Gly
225                 230                 235                 240

Gly Ser Gly Gly Gly Gly Ser Gly Gly Gly Gly Ser Gln Leu Val Gly
                245                 250                 255

Thr Ala Glu Arg Pro Phe Gln Cys Arg Ile Cys Met Arg Asn Phe Ser
            260                 265                 270

Gln Arg Ala Thr Leu Gln Arg His Ile Arg Thr His Thr Gly Glu Lys
        275                 280                 285

Pro Phe Ala Cys Asp Ile Cys Gly Arg Lys Phe Ala Gln Arg Ala Thr
    290                 295                 300

Leu Gln Arg His Thr Lys Ile His Thr Gly Ser Glu Arg Pro Phe Gln
305                 310                 315                 320
```

```
Cys Arg Ile Cys Met Arg Asn Phe Ser Gln Arg Ala Thr Leu Gln Arg
                325                 330                 335

His Ile Arg Thr His Thr Gly Glu Lys Pro Phe Ala Cys Asp Ile Cys
            340                 345                 350

Gly Arg Lys Phe Ala Gln Arg Ala Thr Leu Gln Arg His Thr Lys Ile
        355                 360                 365

His Thr Gly Ser Glu Arg Pro Phe Gln Cys Arg Ile Cys Met Arg Asn
    370                 375                 380

Phe Ser Gln Arg Ala Thr Leu Gln Arg His Ile Arg Thr His Thr Gly
385                 390                 395                 400

Glu Lys Pro Phe Ala Cys Asp Ile Cys Gly Arg Lys Phe Ala Gln Arg
                405                 410                 415

Ala Thr Leu Gln Arg His Thr Lys Ile His Leu Arg Gln Lys Asp Gly
            420                 425                 430

Gly Gly Ser Gly Gly Gly Ser Gly Gly Gly Ser Gln Leu
        435                 440                 445

Val Gly Thr Ala Glu Arg Pro Phe Gln Cys Arg Ile Cys Met Arg Asn
        450                 455                 460

Phe Ser Gln Arg Ala Thr Leu Gln Arg His Ile Arg Thr His Thr Gly
465                 470                 475                 480

Glu Lys Pro Phe Ala Cys Asp Ile Cys Gly Arg Lys Phe Ala Gln Arg
                485                 490                 495

Ala Thr Leu Gln Arg His Thr Lys Ile His Thr Gly Ser Glu Arg Pro
            500                 505                 510

Phe Gln Cys Arg Ile Cys Met Arg Asn Phe Ser Gln Arg Ala Thr Leu
                515                 520                 525

Gln Arg His Ile Arg Thr His Thr Gly Glu Lys Pro Phe Ala Cys Asp
        530                 535                 540

Ile Cys Gly Arg Lys Phe Ala Gln Arg Ala Thr Leu Gln Arg His Thr
545                 550                 555                 560

Lys Ile His Thr Gly Ser Glu Arg Pro Phe Gln Cys Arg Ile Cys Met
            565                 570                 575

Arg Asn Phe Ser Gln Arg Ala Thr Leu Gln Arg His Ile Arg Thr His
        580                 585                 590

Thr Gly Glu Lys Pro Phe Ala Cys Asp Ile Cys Gly Arg Lys Phe Ala
    595                 600                 605

Gln Arg Ala Thr Leu Gln Arg His Thr Lys Ile His Leu Arg Gln Lys
610                 615                 620

Asp Gly Gly Gly Ser Gly Gly Gly Ser Gly Gly Gly Ser
625                 630                 635                 640

Gln Leu Val Ser Ser Leu Ser Pro Gln His Ser Ala Val Thr Gln Gly
            645                 650                 655

Ile Ile Lys Asn Lys Glu Gly Met Asp Ala Lys Ser Leu Thr Ala Trp
        660                 665                 670

Ser Arg Thr Leu Val Thr Phe Lys Asp Val Phe Val Asp Phe Thr Arg
    675                 680                 685

Glu Glu Trp Lys Leu Leu Asp Thr Ala Gln Gln Ile Val Tyr Arg Asn
690                 695                 700

Val Met Leu Glu Asn Tyr Lys Asn Leu Val Ser Leu Gly Tyr Gln Leu
705                 710                 715                 720

Thr Lys Pro Asp Val Ile Leu Arg Leu Glu Lys Gly Glu Glu Pro Trp
                725                 730                 735
```

-continued

```
Leu Val Glu Arg Glu Ile His Gln Glu Thr His Pro Asp Ser Glu Thr
                740                 745                 750

Ala Phe Glu Ile Lys Ser Ser Val
        755                 760

<210> SEQ ID NO 44
<211> LENGTH: 760
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
            20                  25                  30

Lys Glu Leu Ser Asn Arg Leu Asn Leu Ser Asp Gln Gln Val Lys Ile
        35                  40                  45

Trp Phe Gln Asn Arg Arg Met Lys Lys Lys Arg Val Val Thr Gly Ala
    50                  55                  60

Glu Arg Pro Phe Gln Cys Arg Ile Cys Met Arg Asn Phe Ser Gln Arg
65                  70                  75                  80

Ala Thr Leu Gln Arg His Ile Arg Thr His Thr Gly Glu Lys Pro Phe
                85                  90                  95

Ala Cys Asp Ile Cys Gly Arg Lys Phe Ala Gln Arg Ala Thr Leu Gln
            100                 105                 110

Arg His Thr Lys Ile His Thr Gly Ser Glu Arg Pro Phe Gln Cys Arg
        115                 120                 125

Ile Cys Met Arg Asn Phe Ser Gln Arg Ala Thr Leu Gln Arg His Ile
    130                 135                 140

Arg Thr His Thr Gly Glu Lys Pro Phe Ala Cys Asp Ile Cys Gly Arg
145                 150                 155                 160

Lys Phe Ala Gln Arg Ala Thr Leu Gln Arg His Thr Lys Ile His Thr
                165                 170                 175

Gly Ser Glu Arg Pro Phe Gln Cys Arg Ile Cys Met Arg Asn Phe Ser
            180                 185                 190

Gln Arg Ala Thr Leu Gln Arg His Ile Arg Thr His Thr Gly Glu Lys
        195                 200                 205

Pro Phe Ala Cys Asp Ile Cys Gly Arg Lys Phe Ala Gln Arg Ala Thr
    210                 215                 220

Leu Gln Arg His Thr Lys Ile His Leu Arg Gln Lys Asp Gly Gly Gly
225                 230                 235                 240

Gly Ser Gly Gly Gly Ser Gly Gly Gly Ser Gln Leu Val Gly
                245                 250                 255

Thr Ala Glu Arg Pro Phe Gln Cys Arg Ile Cys Met Arg Asn Phe Ser
            260                 265                 270

Gln Arg Ala Thr Leu Gln Arg His Ile Arg Thr His Thr Gly Glu Lys
        275                 280                 285

Pro Phe Ala Cys Asp Ile Cys Gly Arg Lys Phe Ala Gln Arg Ala Thr
    290                 295                 300

Leu Gln Arg His Thr Lys Ile His Thr Gly Ser Glu Arg Pro Phe Gln
305                 310                 315                 320

Cys Arg Ile Cys Met Arg Asn Phe Ser Gln Arg Ala Thr Leu Gln Arg
                325                 330                 335
```

```
His Ile Arg Thr His Thr Gly Glu Lys Pro Phe Ala Cys Asp Ile Cys
                340                 345                 350

Gly Arg Lys Phe Ala Gln Arg Ala Thr Leu Gln Arg His Thr Lys Ile
                355                 360                 365

His Thr Gly Ser Glu Arg Pro Phe Gln Cys Arg Ile Cys Met Arg Asn
                370                 375                 380

Phe Ser Gln Arg Ala Thr Leu Gln Arg His Ile Arg Thr His Thr Gly
385                 390                 395                 400

Glu Lys Pro Phe Ala Cys Asp Ile Cys Gly Arg Lys Phe Ala Gln Arg
                405                 410                 415

Ala Thr Leu Gln Arg His Thr Lys Ile His Leu Arg Gln Lys Asp Gly
                420                 425                 430

Gly Gly Gly Ser Gly Gly Gly Ser Gly Gly Gly Ser Gln Leu
                435                 440                 445

Val Gly Thr Ala Glu Arg Pro Phe Gln Cys Arg Ile Cys Met Arg Asn
                450                 455                 460

Phe Ser Gln Arg Ala Thr Leu Gln Arg His Ile Arg Thr His Thr Gly
465                 470                 475                 480

Glu Lys Pro Phe Ala Cys Asp Ile Cys Gly Arg Lys Phe Ala Gln Arg
                485                 490                 495

Ala Thr Leu Gln Arg His Thr Lys Ile His Thr Gly Ser Glu Arg Pro
                500                 505                 510

Phe Gln Cys Arg Ile Cys Met Arg Asn Phe Ser Gln Arg Ala Thr Leu
                515                 520                 525

Gln Arg His Ile Arg Thr His Thr Gly Glu Lys Pro Phe Ala Cys Asp
                530                 535                 540

Ile Cys Gly Arg Lys Phe Ala Gln Arg Ala Thr Leu Gln Arg His Thr
545                 550                 555                 560

Lys Ile His Thr Gly Ser Glu Arg Pro Phe Gln Cys Arg Ile Cys Met
                565                 570                 575

Arg Asn Phe Ser Gln Arg Ala Thr Leu Gln Arg His Ile Arg Thr His
                580                 585                 590

Thr Gly Glu Lys Pro Phe Ala Cys Asp Ile Cys Gly Arg Lys Phe Ala
                595                 600                 605

Gln Arg Ala Thr Leu Gln Arg His Thr Lys Ile His Leu Arg Gln Lys
                610                 615                 620

Asp Gly Gly Gly Gly Ser Gly Gly Gly Gly Ser Gly Gly Gly Gly Ser
625                 630                 635                 640

Gln Leu Val Ser Ser Leu Ser Pro Gln His Ser Ala Val Thr Gln Gly
                645                 650                 655

Ile Ile Lys Asn Lys Glu Gly Met Asp Ala Lys Ser Leu Thr Ala Trp
                660                 665                 670

Ser Arg Thr Leu Val Thr Phe Lys Asp Val Phe Val Asp Phe Thr Arg
                675                 680                 685

Glu Glu Trp Lys Leu Leu Asp Thr Ala Gln Gln Ile Val Tyr Arg Asn
                690                 695                 700

Val Met Leu Glu Asn Tyr Lys Asn Leu Val Ser Leu Gly Tyr Gln Leu
705                 710                 715                 720

Thr Lys Pro Asp Val Ile Leu Arg Leu Glu Lys Gly Glu Glu Pro Trp
                725                 730                 735

Leu Val Glu Arg Glu Ile His Gln Glu Thr His Pro Asp Ser Glu Thr
                740                 745                 750
```

```
Ala Phe Glu Ile Lys Ser Ser Val
        755                 760

<210> SEQ ID NO 45
<211> LENGTH: 653
<212> TYPE: PRT
<213> ORGANISM: Homo sapiens

<400> SEQUENCE: 45

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365
```

Phe Gln Val Asn Asn Thr Arg Pro Pro His Val Gln Leu Leu Arg Lys
            370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650

<210> SEQ ID NO 46
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Ser Arg Lys Lys Arg Lys Pro Tyr Ser Leu Gln Leu Ala Glu
1               5                   10                  15

Leu Glu Gly Glu Phe Leu Val Asn Glu Phe Ile Thr Arg Gln Arg Arg
            20                  25                  30

Arg Glu Leu Ser Asp Arg Leu Asn Leu Ser Asp Gln Val Lys Ile
        35                  40                  45

Trp Phe Gln Asn Arg Arg Met Lys Lys Lys Arg Leu Leu Met Arg Pro
    50                  55                  60

Leu Arg Pro Arg Ala Ala Leu Leu Ala Leu Leu Ala Ser Leu Leu Ala

-continued

```
             65                  70                  75                  80
Ala Pro Pro Val Ala Pro Ala Glu Ala Pro His Leu Val His Val Asp
                     85                  90                  95
Ala Ala Arg Ala Leu Trp Pro Leu Arg Arg Phe Trp Arg Ser Thr Gly
                    100                 105                 110
Phe Cys Pro Pro Leu Pro His Ser Gln Ala Asp Gln Tyr Val Leu Ser
                    115                 120                 125
Trp Asp Gln Gln Leu Asn Leu Ala Tyr Val Gly Ala Val Pro His Arg
            130                 135                 140
Gly Ile Lys Gln Val Arg Thr His Trp Leu Leu Glu Leu Val Thr Thr
145                 150                 155                 160
Arg Gly Ser Thr Gly Arg Gly Leu Ser Tyr Asn Phe Thr His Leu Asp
                    165                 170                 175
Gly Tyr Leu Asp Leu Leu Arg Glu Asn Gln Leu Leu Pro Gly Phe Glu
                180                 185                 190
Leu Met Gly Ser Ala Ser Gly His Phe Thr Asp Phe Glu Asp Lys Gln
                195                 200                 205
Gln Val Phe Glu Trp Lys Asp Leu Val Ser Ser Leu Ala Arg Arg Tyr
            210                 215                 220
Ile Gly Arg Tyr Gly Leu Ala His Val Ser Lys Trp Asn Phe Glu Thr
225                 230                 235                 240
Trp Asn Glu Pro Asp His His Asp Phe Asp Asn Val Ser Met Thr Met
                    245                 250                 255
Gln Gly Phe Leu Asn Tyr Tyr Asp Ala Cys Ser Glu Gly Leu Arg Ala
                260                 265                 270
Ala Ser Pro Ala Leu Arg Leu Gly Gly Pro Gly Asp Ser Phe His Thr
            275                 280                 285
Pro Pro Arg Ser Pro Leu Ser Trp Gly Leu Leu Arg His Cys His Asp
            290                 295                 300
Gly Thr Asn Phe Phe Thr Gly Glu Ala Gly Val Arg Leu Asp Tyr Ile
305                 310                 315                 320
Ser Leu His Arg Lys Gly Ala Arg Ser Ser Ile Ser Ile Leu Glu Gln
                    325                 330                 335
Glu Lys Val Val Ala Gln Gln Ile Arg Gln Leu Phe Pro Lys Phe Ala
                340                 345                 350
Asp Thr Pro Ile Tyr Asn Asp Glu Ala Asp Pro Leu Val Gly Trp Ser
                355                 360                 365
Leu Pro Gln Pro Trp Arg Ala Asp Val Thr Tyr Ala Ala Met Val Val
            370                 375                 380
Lys Val Ile Ala Gln His Gln Asn Leu Leu Leu Ala Asn Thr Thr Ser
385                 390                 395                 400
Ala Phe Pro Tyr Ala Leu Leu Ser Asn Asp Asn Ala Phe Leu Ser Tyr
                    405                 410                 415
His Pro His Pro Phe Ala Gln Arg Thr Leu Thr Ala Arg Phe Gln Val
                420                 425                 430
Asn Asn Thr Arg Pro Pro His Val Gln Leu Leu Arg Lys Pro Val Leu
            435                 440                 445
Thr Ala Met Gly Leu Leu Ala Leu Leu Asp Glu Gln Leu Trp Ala
            450                 455                 460
Glu Val Ser Gln Ala Gly Thr Val Leu Asp Ser Asn His Thr Val Gly
465                 470                 475                 480
Val Leu Ala Ser Ala His Arg Pro Gln Gly Pro Ala Asp Ala Trp Arg
                    485                 490                 495
```

```
Ala Ala Val Leu Ile Tyr Ala Ser Asp Asp Thr Arg Ala His Pro Asn
            500                 505                 510

Arg Ser Val Ala Val Thr Leu Arg Leu Arg Gly Val Pro Pro Gly Pro
            515                 520                 525

Gly Leu Val Tyr Val Thr Arg Tyr Leu Asp Asn Gly Leu Cys Ser Pro
            530                 535                 540

Asp Gly Glu Trp Arg Arg Leu Gly Arg Pro Val Phe Pro Thr Ala Glu
545                 550                 555                 560

Gln Phe Arg Arg Met Arg Ala Ala Glu Asp Pro Val Ala Ala Ala Pro
                565                 570                 575

Arg Pro Leu Pro Ala Gly Gly Arg Leu Thr Leu Arg Pro Ala Leu Arg
            580                 585                 590

Leu Pro Ser Leu Leu Val His Val Cys Ala Arg Pro Glu Lys Pro
            595                 600                 605

Pro Gly Gln Val Thr Arg Leu Arg Ala Leu Pro Leu Thr Gln Gly Gln
            610                 615                 620

Leu Val Leu Val Trp Ser Asp Glu His Val Gly Ser Lys Cys Leu Trp
625                 630                 635                 640

Thr Tyr Glu Ile Gln Phe Ser Gln Asp Gly Lys Ala Tyr Thr Pro Val
                645                 650                 655

Ser Arg Lys Pro Ser Thr Phe Asn Leu Phe Val Phe Ser Pro Asp Thr
            660                 665                 670

Gly Ala Val Ser Gly Ser Tyr Arg Val Arg Ala Leu Asp Tyr Trp Ala
            675                 680                 685

Arg Pro Gly Pro Phe Ser Asp Pro Val Pro Tyr Leu Glu Val Pro Val
            690                 695                 700

Pro Arg Gly Pro Pro Ser Pro Gly Asn Pro
705                 710

<210> SEQ ID NO 47
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
            20                  25                  30

Lys Glu Leu Ser Asn Arg Leu Asn Leu Ser Asp Gln Gln Val Lys Ile
            35                  40                  45

Trp Phe Gln Asn Arg Arg Met Lys Lys Lys Arg Val Val Met Arg Pro
    50                  55                  60

Leu Arg Pro Arg Ala Ala Leu Leu Ala Leu Leu Ala Ser Leu Leu Ala
65                  70                  75                  80

Ala Pro Pro Val Ala Pro Ala Glu Ala Pro His Leu Val His Val Asp
                85                  90                  95

Ala Ala Arg Ala Leu Trp Pro Leu Arg Arg Phe Trp Arg Ser Thr Gly
            100                 105                 110

Phe Cys Pro Pro Leu Pro His Ser Gln Ala Asp Gln Tyr Val Leu Ser
            115                 120                 125

Trp Asp Gln Gln Leu Asn Leu Ala Tyr Val Gly Ala Val Pro His Arg
```

-continued

```
        130                 135                 140
Gly Ile Lys Gln Val Arg Thr His Trp Leu Leu Glu Leu Val Thr Thr
145                 150                 155                 160
Arg Gly Ser Thr Gly Arg Gly Leu Ser Tyr Asn Phe Thr His Leu Asp
                165                 170                 175
Gly Tyr Leu Asp Leu Leu Arg Glu Asn Gln Leu Leu Pro Gly Phe Glu
            180                 185                 190
Leu Met Gly Ser Ala Ser Gly His Phe Thr Asp Phe Glu Asp Lys Gln
        195                 200                 205
Gln Val Phe Glu Trp Lys Asp Leu Val Ser Ser Leu Ala Arg Arg Tyr
    210                 215                 220
Ile Gly Arg Tyr Gly Leu Ala His Val Ser Lys Trp Asn Phe Glu Thr
225                 230                 235                 240
Trp Asn Glu Pro Asp His His Asp Phe Asp Asn Val Ser Met Thr Met
                245                 250                 255
Gln Gly Phe Leu Asn Tyr Tyr Asp Ala Cys Ser Glu Gly Leu Arg Ala
            260                 265                 270
Ala Ser Pro Ala Leu Arg Leu Gly Gly Pro Gly Asp Ser Phe His Thr
        275                 280                 285
Pro Pro Arg Ser Pro Leu Ser Trp Gly Leu Leu Arg His Cys His Asp
    290                 295                 300
Gly Thr Asn Phe Phe Thr Gly Glu Ala Gly Val Arg Leu Asp Tyr Ile
305                 310                 315                 320
Ser Leu His Arg Lys Gly Ala Arg Ser Ser Ile Ser Ile Leu Glu Gln
                325                 330                 335
Glu Lys Val Val Ala Gln Gln Ile Arg Gln Leu Phe Pro Lys Phe Ala
            340                 345                 350
Asp Thr Pro Ile Tyr Asn Asp Glu Ala Asp Pro Leu Val Gly Trp Ser
        355                 360                 365
Leu Pro Gln Pro Trp Arg Ala Asp Val Thr Tyr Ala Ala Met Val Val
    370                 375                 380
Lys Val Ile Ala Gln His Gln Asn Leu Leu Leu Ala Asn Thr Thr Ser
385                 390                 395                 400
Ala Phe Pro Tyr Ala Leu Leu Ser Asn Asp Asn Ala Phe Leu Ser Tyr
                405                 410                 415
His Pro His Pro Phe Ala Gln Arg Thr Leu Thr Ala Arg Phe Gln Val
            420                 425                 430
Asn Asn Thr Arg Pro Pro His Val Gln Leu Leu Arg Lys Pro Val Leu
        435                 440                 445
Thr Ala Met Gly Leu Leu Ala Leu Leu Asp Glu Gln Leu Trp Ala
    450                 455                 460
Glu Val Ser Gln Ala Gly Thr Val Leu Asp Ser Asn His Thr Val Gly
465                 470                 475                 480
Val Leu Ala Ser Ala His Arg Pro Gln Gly Pro Ala Asp Ala Trp Arg
                485                 490                 495
Ala Ala Val Leu Ile Tyr Ala Ser Asp Asp Thr Arg Ala His Pro Asn
            500                 505                 510
Arg Ser Val Ala Val Thr Leu Arg Leu Arg Gly Val Pro Pro Gly Pro
        515                 520                 525
Gly Leu Val Tyr Val Thr Arg Tyr Leu Asp Asn Gly Leu Cys Ser Pro
    530                 535                 540
Asp Gly Glu Trp Arg Arg Leu Gly Arg Pro Val Phe Pro Thr Ala Glu
545                 550                 555                 560
```

```
Gln Phe Arg Arg Met Arg Ala Ala Glu Asp Pro Val Ala Ala Pro
                565                 570                 575

Arg Pro Leu Pro Ala Gly Gly Arg Leu Thr Leu Arg Pro Ala Leu Arg
            580                 585                 590

Leu Pro Ser Leu Leu Leu Val His Val Cys Ala Arg Pro Glu Lys Pro
            595                 600                 605

Pro Gly Gln Val Thr Arg Leu Arg Ala Leu Pro Leu Thr Gln Gly Gln
            610                 615                 620

Leu Val Leu Val Trp Ser Asp Glu His Val Gly Ser Lys Cys Leu Trp
625                 630                 635                 640

Thr Tyr Glu Ile Gln Phe Ser Gln Asp Gly Lys Ala Tyr Thr Pro Val
                645                 650                 655

Ser Arg Lys Pro Ser Thr Phe Asn Leu Phe Val Phe Ser Pro Asp Thr
            660                 665                 670

Gly Ala Val Ser Gly Ser Tyr Arg Val Arg Ala Leu Asp Tyr Trp Ala
            675                 680                 685

Arg Pro Gly Pro Phe Ser Asp Pro Val Pro Tyr Leu Glu Val Pro Val
            690                 695                 700

Pro Arg Gly Pro Pro Ser Pro Gly Asn Pro
705                 710

<210> SEQ ID NO 48
<211> LENGTH: 550
<212> TYPE: PRT
<213> ORGANISM: Homo sapiens

<400> SEQUENCE: 48

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
```

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
                260                 265                 270

Arg Glu Asp Val Gln Ala Leu Asn Ile Ser Val Pro Tyr Gly Pro Ile
            275                 280                 285

Pro Val Asp Phe Gln Arg Lys Ile Arg Gln Ser Tyr Phe Ala Ser Val
        290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
                340                 345                 350

Val Ala Thr His Val Pro Leu Ile Phe Tyr Val Pro Gly Arg Thr Ala
                355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
                420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
        530                 535                 540

Phe Gln Leu Leu Met Pro
545                 550

<210> SEQ ID NO 49
<211> LENGTH: 611
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ser Arg Lys Lys Arg Lys Pro Tyr Ser Lys Leu Gln Leu Ala Glu
1               5                   10                  15

-continued

```
Leu Glu Gly Glu Phe Leu Val Asn Glu Phe Ile Thr Arg Gln Arg Arg
         20                  25                  30
Arg Glu Leu Ser Asp Arg Leu Asn Leu Ser Asp Gln Gln Val Lys Ile
         35                  40              45
Trp Phe Gln Asn Arg Arg Met Lys Lys Lys Arg Leu Leu Met Pro Pro
     50                  55                  60
Pro Arg Thr Gly Arg Gly Leu Leu Trp Leu Gly Leu Val Leu Ser Ser
 65                  70                  75                  80
Val Cys Val Ala Leu Gly Ser Glu Thr Gln Ala Asn Ser Thr Thr Asp
                 85                  90                  95
Ala Leu Asn Val Leu Leu Ile Ile Val Asp Asp Leu Arg Pro Ser Leu
             100                 105                 110
Gly Cys Tyr Gly Asp Lys Leu Val Arg Ser Pro Asn Ile Asp Gln Leu
         115                 120                 125
Ala Ser His Ser Leu Leu Phe Gln Asn Ala Phe Ala Gln Gln Ala Val
     130                 135                 140
Cys Ala Pro Ser Arg Val Ser Phe Leu Thr Gly Arg Arg Pro Asp Thr
145                 150                 155                 160
Thr Arg Leu Tyr Asp Phe Asn Ser Tyr Trp Arg Val His Ala Gly Asn
                 165                 170                 175
Phe Ser Thr Ile Pro Gln Tyr Phe Lys Glu Asn Gly Tyr Val Thr Met
             180                 185                 190
Ser Val Gly Lys Val Phe His Pro Gly Ile Ser Ser Asn His Thr Asp
         195                 200                 205
Asp Ser Pro Tyr Ser Trp Ser Phe Pro Pro Tyr His Pro Ser Ser Glu
     210                 215                 220
Lys Tyr Glu Asn Thr Lys Thr Cys Arg Gly Pro Asp Gly Glu Leu His
225                 230                 235                 240
Ala Asn Leu Leu Cys Pro Val Asp Val Leu Asp Val Pro Glu Gly Thr
                 245                 250                 255
Leu Pro Asp Lys Gln Ser Thr Glu Gln Ala Ile Gln Leu Leu Glu Lys
             260                 265                 270
Met Lys Thr Ser Ala Ser Pro Phe Phe Leu Ala Val Gly Tyr His Lys
         275                 280                 285
Pro His Ile Pro Phe Arg Tyr Pro Lys Glu Phe Gln Lys Leu Tyr Pro
     290                 295                 300
Leu Glu Asn Ile Thr Leu Ala Pro Asp Pro Glu Val Pro Asp Gly Leu
305                 310                 315                 320
Pro Pro Val Ala Tyr Asn Pro Trp Met Asp Ile Arg Gln Arg Glu Asp
                 325                 330                 335
Val Gln Ala Leu Asn Ile Ser Val Pro Tyr Gly Pro Ile Pro Val Asp
             340                 345                 350
Phe Gln Arg Lys Ile Arg Gln Ser Tyr Phe Ala Ser Val Ser Tyr Leu
         355                 360                 365
Asp Thr Gln Val Gly Arg Leu Leu Ser Ala Leu Asp Asp Leu Gln Leu
     370                 375                 380
Ala Asn Ser Thr Ile Ile Ala Phe Thr Ser Asp His Gly Trp Ala Leu
385                 390                 395                 400
Gly Glu His Gly Glu Trp Ala Lys Tyr Ser Asn Phe Asp Val Ala Thr
                 405                 410                 415
His Val Pro Leu Ile Phe Tyr Val Pro Gly Arg Thr Ala Ser Leu Pro
             420                 425                 430
Glu Ala Gly Glu Lys Leu Phe Pro Tyr Leu Asp Pro Phe Asp Ser Ala
```

```
                    435                 440                 445

Ser Gln Leu Met Glu Pro Gly Arg Gln Ser Met Asp Leu Val Glu Leu
    450                 455                 460

Val Ser Leu Phe Pro Thr Leu Ala Gly Leu Ala Gly Leu Gln Val Pro
465                 470                 475                 480

Pro Arg Cys Pro Val Pro Ser Phe His Val Glu Leu Cys Arg Glu Gly
                    485                 490                 495

Lys Asn Leu Leu Lys His Phe Arg Phe Arg Asp Leu Glu Glu Asp Pro
                500                 505                 510

Tyr Leu Pro Gly Asn Pro Arg Glu Leu Ile Ala Tyr Ser Gln Tyr Pro
            515                 520                 525

Arg Pro Ser Asp Ile Pro Gln Trp Asn Ser Asp Lys Pro Ser Leu Lys
        530                 535                 540

Asp Ile Lys Ile Met Gly Tyr Ser Ile Arg Thr Ile Asp Tyr Arg Tyr
545                 550                 555                 560

Thr Val Trp Val Gly Phe Asn Pro Asp Glu Phe Leu Ala Asn Phe Ser
                    565                 570                 575

Asp Ile His Ala Gly Glu Leu Tyr Phe Val Asp Ser Asp Pro Leu Gln
                580                 585                 590

Asp His Asn Met Tyr Asn Asp Ser Gln Gly Gly Asp Leu Phe Gln Leu
            595                 600                 605

Leu Met Pro
    610

<210> SEQ ID NO 50
<211> LENGTH: 611
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Ala Arg Lys Lys Arg Lys Pro Tyr Thr Lys Gln Gln Ile Ala Glu
1               5                   10                  15

Leu Glu Asn Glu Phe Leu Val Asn Glu Phe Ile Asn Arg Gln Lys Arg
                20                  25                  30

Lys Glu Leu Ser Asn Arg Leu Asn Leu Ser Asp Gln Gln Val Lys Ile
            35                  40                  45

Trp Phe Gln Asn Arg Arg Met Lys Lys Lys Arg Val Val Met Pro Pro
        50                  55                  60

Pro Arg Thr Gly Arg Gly Leu Leu Trp Leu Gly Leu Val Leu Ser Ser
65                  70                  75                  80

Val Cys Val Ala Leu Gly Ser Glu Thr Gln Ala Asn Ser Thr Thr Asp
                85                  90                  95

Ala Leu Asn Val Leu Leu Ile Ile Val Asp Asp Leu Arg Pro Ser Leu
                100                 105                 110

Gly Cys Tyr Gly Asp Lys Leu Val Arg Ser Pro Asn Ile Asp Gln Leu
            115                 120                 125

Ala Ser His Ser Leu Leu Phe Gln Asn Ala Phe Ala Gln Gln Ala Val
        130                 135                 140

Cys Ala Pro Ser Arg Val Ser Phe Leu Thr Gly Arg Arg Pro Asp Thr
145                 150                 155                 160

Thr Arg Leu Tyr Asp Phe Asn Ser Tyr Trp Arg Val His Ala Gly Asn
                165                 170                 175
```

```
Phe Ser Thr Ile Pro Gln Tyr Phe Lys Glu Asn Gly Tyr Val Thr Met
            180                 185                 190
Ser Val Gly Lys Val Phe His Pro Gly Ile Ser Ser Asn His Thr Asp
        195                 200                 205
Asp Ser Pro Tyr Ser Trp Ser Phe Pro Pro Tyr His Pro Ser Ser Glu
    210                 215                 220
Lys Tyr Glu Asn Thr Lys Thr Cys Arg Gly Pro Asp Gly Glu Leu His
225                 230                 235                 240
Ala Asn Leu Leu Cys Pro Val Asp Val Leu Asp Val Pro Glu Gly Thr
                245                 250                 255
Leu Pro Asp Lys Gln Ser Thr Glu Gln Ala Ile Gln Leu Leu Glu Lys
            260                 265                 270
Met Lys Thr Ser Ala Ser Pro Phe Phe Leu Ala Val Gly Tyr His Lys
        275                 280                 285
Pro His Ile Pro Phe Arg Tyr Pro Lys Glu Phe Gln Lys Leu Tyr Pro
    290                 295                 300
Leu Glu Asn Ile Thr Leu Ala Pro Asp Pro Glu Val Pro Asp Gly Leu
305                 310                 315                 320
Pro Pro Val Ala Tyr Asn Pro Trp Met Asp Ile Arg Gln Arg Glu Asp
                325                 330                 335
Val Gln Ala Leu Asn Ile Ser Val Pro Tyr Gly Pro Ile Pro Val Asp
            340                 345                 350
Phe Gln Arg Lys Ile Arg Gln Ser Tyr Phe Ala Ser Val Ser Tyr Leu
        355                 360                 365
Asp Thr Gln Val Gly Arg Leu Leu Ser Ala Leu Asp Asp Leu Gln Leu
    370                 375                 380
Ala Asn Ser Thr Ile Ile Ala Phe Thr Ser Asp His Gly Trp Ala Leu
385                 390                 395                 400
Gly Glu His Gly Glu Trp Ala Lys Tyr Ser Asn Phe Asp Val Ala Thr
                405                 410                 415
His Val Pro Leu Ile Phe Tyr Val Pro Gly Arg Thr Ala Ser Leu Pro
            420                 425                 430
Glu Ala Gly Glu Lys Leu Phe Pro Tyr Leu Asp Pro Phe Asp Ser Ala
        435                 440                 445
Ser Gln Leu Met Glu Pro Gly Arg Gln Ser Met Asp Leu Val Glu Leu
    450                 455                 460
Val Ser Leu Phe Pro Thr Leu Ala Gly Leu Ala Gly Leu Gln Val Pro
465                 470                 475                 480
Pro Arg Cys Pro Val Pro Ser Phe His Val Glu Leu Cys Arg Glu Gly
                485                 490                 495
Lys Asn Leu Leu Lys His Phe Arg Phe Arg Asp Leu Glu Glu Asp Pro
            500                 505                 510
Tyr Leu Pro Gly Asn Pro Arg Glu Leu Ile Ala Tyr Ser Gln Tyr Pro
        515                 520                 525
Arg Pro Ser Asp Ile Pro Gln Trp Asn Ser Asp Lys Pro Ser Leu Lys
    530                 535                 540
Asp Ile Lys Ile Met Gly Tyr Ser Ile Arg Thr Ile Asp Tyr Arg Tyr
545                 550                 555                 560
Thr Val Trp Val Gly Phe Asn Pro Asp Glu Phe Leu Ala Asn Phe Ser
                565                 570                 575
Asp Ile His Ala Gly Glu Leu Tyr Phe Val Asp Ser Asp Pro Leu Gln
            580                 585                 590
Asp His Asn Met Tyr Asn Asp Ser Gln Gly Gly Asp Leu Phe Gln Leu
```

```
                595                 600                 605

Leu Met Pro
    610

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Thr Phe Leu Thr Ser Glu Leu Pro Gly Trp Leu Gln Ala Asn
1               5                   10                  15

<210> SEQ ID NO 52
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
            20                  25                  30

Glu Leu Ser Asp Arg Leu Asn Leu Ser Asp Gln Gln Val Lys Ile Trp
        35                  40                  45

Phe Gln Asn Arg Arg Met Lys Lys Lys Arg Leu Leu Glu Thr Phe Leu
    50                  55                  60

Thr Ser Glu Leu Pro Gly Trp Leu Gln Ala Asn
65                  70                  75

<210> SEQ ID NO 53
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
            20                  25                  30

Glu Leu Ser Asn Arg Leu Asn Leu Ser Asp Gln Gln Val Lys Ile Trp
        35                  40                  45

Phe Gln Asn Arg Arg Met Lys Lys Lys Arg Val Val Glu Thr Phe Leu
    50                  55                  60

Thr Ser Glu Leu Pro Gly Trp Leu Gln Ala Asn
65                  70                  75

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 54

Ser Glu Leu Pro Gly Trp Leu Gln Ala Asn Arg His Val Lys Pro
1               5                   10                  15

<210> SEQ ID NO 55
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
                20                  25                  30

Glu Leu Ser Asp Arg Leu Asn Leu Ser Asp Gln Gln Val Lys Ile Trp
            35                  40                  45

Phe Gln Asn Arg Arg Met Lys Lys Lys Arg Leu Leu Ser Glu Leu Pro
        50                  55                  60

Gly Trp Leu Gln Ala Asn Arg His Val Lys Pro
65                  70                  75

<210> SEQ ID NO 56
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
                20                  25                  30

Glu Leu Ser Asn Arg Leu Asn Leu Ser Asp Gln Gln Val Lys Ile Trp
            35                  40                  45

Phe Gln Asn Arg Arg Met Lys Lys Lys Arg Val Val Ser Glu Leu Pro
        50                  55                  60

Gly Trp Leu Gln Ala Asn Arg His Val Lys Pro
65                  70                  75

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Leu Gln Ala Asn Arg His Val Lys Pro Thr Gly Ser Ala Val
1               5                   10                  15

<210> SEQ ID NO 58
<211> LENGTH: 75
<212> TYPE: PRT
<213> ORGANISM: Artificial Sequence
<220> FEATURE:
<223> OTHER INFORMATION: Description of Artificial Sequence: Synthetic

```
            polypeptide

<400> SEQUENCE: 58

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
            20                  25                  30

Glu Leu Ser Asp Arg Leu Asn Leu Ser Asp Gln Gln Val Lys Ile Trp
        35                  40                  45

Phe Gln Asn Arg Arg Met Lys Lys Arg Leu Leu Trp Leu Gln Ala
    50                  55                  60

Asn Arg His Val Lys Pro Thr Gly Ser Ala Val
65                  70                  75

<210> SEQ ID NO 59
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
            20                  25                  30

Glu Leu Ser Asn Arg Leu Asn Leu Ser Asp Gln Gln Val Lys Ile Trp
        35                  40                  45

Phe Gln Asn Arg Arg Met Lys Lys Arg Val Val Trp Leu Gln Ala
    50                  55                  60

Asn Arg His Val Lys Pro Thr Gly Ser Ala Val
65                  70                  75

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg His Val Lys Pro Thr Gly Ser Ala Val Val Gly Leu Ser Met
1               5                   10                  15

<210> SEQ ID NO 61
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
            20                  25                  30

Glu Leu Ser Asp Arg Leu Asn Leu Ser Asp Gln Gln Val Lys Ile Trp
        35                  40                  45
```

Phe Gln Asn Arg Arg Met Lys Lys Arg Leu Leu Arg His Val Lys
    50                  55                  60

Pro Thr Gly Ser Ala Val Val Gly Leu Ser Met
65                  70                  75

<210> SEQ ID NO 62
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
                20                  25                  30

Glu Leu Ser Asn Arg Leu Asn Leu Ser Asp Gln Gln Val Lys Ile Trp
            35                  40                  45

Phe Gln Asn Arg Arg Met Lys Lys Arg Val Val Arg His Val Lys
    50                  55                  60

Pro Thr Gly Ser Ala Val Val Gly Leu Ser Met
65                  70                  75

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ser Gly Leu Ser Val Val Met Pro Val Gly Gly Gln Ser Ser
1               5                   10                  15

<210> SEQ ID NO 64
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
                20                  25                  30

Glu Leu Ser Asp Arg Leu Asn Leu Ser Asp Gln Gln Val Lys Ile Trp
            35                  40                  45

Phe Gln Asn Arg Arg Met Lys Lys Arg Leu Leu Gln Ser Gly Leu
    50                  55                  60

Ser Val Val Met Pro Val Gly Gly Gln Ser Ser
65                  70                  75

<210> SEQ ID NO 65
<211> LENGTH: 75
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
            20                  25                  30

Glu Leu Ser Asn Arg Leu Asn Leu Ser Asp Gln Gln Val Lys Ile Trp
        35                  40                  45

Phe Gln Asn Arg Arg Met Lys Lys Lys Arg Val Val Gln Ser Gly Leu
    50                  55                  60

Ser Val Val Met Pro Val Gly Gly Gln Ser Ser
65                  70                  75

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Val Met Pro Val Gly Gly Gln Ser Ser Phe Tyr Ser Asp Trp
1               5                   10                  15

<210> SEQ ID NO 67
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
            20                  25                  30

Glu Leu Ser Asp Arg Leu Asn Leu Ser Asp Gln Gln Val Lys Ile Trp
        35                  40                  45

Phe Gln Asn Arg Arg Met Lys Lys Lys Arg Leu Leu Val Val Met Pro
    50                  55                  60

Val Gly Gly Gln Ser Ser Phe Tyr Ser Asp Trp
65                  70                  75

<210> SEQ ID NO 68
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Arg Lys Lys Arg Lys Pro Tyr Thr Lys Gln Gln Ile Ala Glu Leu
1               5                   10                  15

Glu Asn Glu Phe Leu Val Asn Glu Phe Ile Asn Arg Gln Lys Arg Lys
            20                  25                  30

Glu Leu Ser Asn Arg Leu Asn Leu Ser Asp Gln Gln Val Lys Ile Trp
        35                  40                  45

```
Phe Gln Asn Arg Arg Met Lys Lys Arg Val Val Val Met Pro
    50                  55                  60

Val Gly Gly Gln Ser Ser Ph

Ala Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Ala
            20                  25                  30

Asn Ser Pro Ala Leu Tyr Leu Leu Asp Gly Leu Arg Ala Gln Asp Asp
        35                  40                  45

Phe Ser Gly Trp Asp Ile Asn Thr Pro Ala Phe Glu Trp Tyr Asp Gln
    50                  55                  60

Ser Gly Leu Ser Val Val Met Pro Val Gly Gly Gln Ser Ser Phe Tyr
65                  70                  75                  80

Ser Asp Trp Tyr Gln Pro Ala Cys Gly Lys Ala Gly Cys Gln Thr Tyr
                85                  90                  95

Lys Trp Glu Thr Phe Leu Thr Ser Glu Leu Pro Gly Trp Leu Gln Ala
            100                 105                 110

Asn Arg His Val Lys Pro Thr Gly Ser Ala Val Val Gly Leu Ser Met
        115                 120                 125

Ala Ala Ser Ser Ala Leu Thr Leu Ala Ile Tyr His Pro Gln Gln Phe
    130                 135                 140

Val Tyr Ala Gly Ala Met Ser Gly Leu Leu Asp Pro Ser Gln Ala Met
145                 150                 155                 160

Gly Pro Thr Leu Ile Gly Leu Ala Met Gly Asp Ala Gly Gly Tyr Lys
                165                 170                 175

Ala Ser Asp Met Trp Gly Pro Lys Glu Asp Pro Ala Trp Gln Arg Asn
            180                 185                 190

Asp Pro Leu Leu Asn Val Gly Lys Leu Ile Ala Asn Asn Thr Arg Val
        195                 200                 205

Trp Val Tyr Cys Gly Asn Gly Lys Pro Ser Asp Leu Gly Gly Asn Asn
210                 215                 220

Leu Pro Ala Lys Phe Leu Glu Gly Phe Val Arg Thr Ser Asn Ile Lys
225                 230                 235                 240

Phe Gln Asp Ala Tyr Asn Ala Gly Gly Gly His Asn Gly Val Phe Asp
                245                 250                 255

Phe Pro Asp Ser Gly Thr His Ser Trp Glu Tyr Trp Gly Ala Gln Leu
            260                 265                 270

Asn Ala Met Lys Pro Asp Leu Gln Arg Ala Leu Gly Ala Thr Pro Asn
        275                 280                 285

Thr Gly Pro Ala Pro Gln Gly Ala
    290                 295

<210> SEQ ID NO 73
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ser Arg Lys Lys Arg Lys Pro Tyr Ser Lys Leu Gln Leu Ala Glu Leu
1               5                   10                  15

Glu Gly Glu Phe Leu Val Asn Glu Phe Ile Thr Arg Gln Arg Arg Arg
            20                  25                  30

Glu Leu Ser Asp Arg Leu Asn Leu Ser Asp Gln Gln Val Lys Ile Trp
        35                  40                  45

Phe Gln Asn Arg Arg Met Lys Lys Lys Arg Leu Leu Ala Phe Ser Arg

```
                50                  55                  60
Pro Gly Leu Pro Val Glu Tyr Leu Gln Val Pro Ser Pro Ser Met Gly
 65                  70                  75                  80

Arg Asp Ile Lys Val Gln Phe Gln Ser Gly Ala Asn Ser Pro Ala
                 85                  90                  95

Leu Tyr Leu Leu Asp Gly Leu Arg Ala Gln Asp Phe Ser Gly Trp
                100                 105                 110

Asp Ile Asn Thr Pro Ala Phe Glu Trp Tyr Asp Gln Ser Gly Leu Ser
                115                 120                 125

Val Val Met Pro Val Gly Gly Gln Ser Ser Phe Tyr Ser Asp Trp Tyr
                130                 135                 140

Gln Pro Ala Cys Gly Lys Ala Gly Cys Gln Thr Tyr Lys Trp Glu Thr
145                 150                 155                 160

Phe Leu Thr Ser Glu Leu Pro Gly Trp Leu Gln Ala Asn Arg His Val
                165                 170                 175

Lys Pro Thr Gly Ser Ala Val Val Gly Leu Ser Met Ala Ala Ser Ser
                180                 185                 190

Ala Leu Thr Leu Ala Ile Tyr His Pro Gln Gln Phe Val Tyr Ala Gly
                195                 200                 205

Ala Met Ser Gly Leu Leu Asp Pro Ser Gln Ala Met Gly Pro Thr Leu
                210                 215                 220

Ile Gly Leu Ala Met Gly Asp Ala Gly Gly Tyr Lys Ala Ser Asp Met
225                 230                 235                 240

Trp Gly Pro Lys Glu Asp Pro Ala Trp Gln Arg Asn Asp Pro Leu Leu
                245                 250                 255

Asn Val Gly Lys Leu Ile Ala Asn Asn Thr Arg Val Trp Val Tyr Cys
                260                 265                 270

Gly Asn Gly Lys Pro Ser Asp Leu Gly Gly Asn Asn Leu Pro Ala Lys
                275                 280                 285

Phe Leu Glu Gly Phe Val Arg Thr Ser Asn Ile Lys Phe Gln Asp Ala
                290                 295                 300

Tyr Asn Ala Gly Gly His Asn Gly Val Phe Asp Phe Pro Asp Ser
305                 310                 315                 320

Gly Thr His Ser Trp Glu Tyr Trp Gly Ala Gln Leu Asn Ala Met Lys
                325                 330                 335

Pro Asp Leu Gln Arg Ala Leu Gly Ala Thr Pro Asn Thr Gly Pro Ala
                340                 345                 350

Pro Gln Gly Ala
            355

<210> SEQ ID NO 74
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ala Arg Lys Lys Arg Lys Pro Tyr Thr Lys Gln Gln Ile Ala Glu Leu
 1               5                  10                  15

Glu Asn Glu Phe Leu Val Asn Glu Phe Ile Asn Arg Gln Lys Arg Lys
                20                  25                  30

Glu Leu Ser Asn Arg Leu Asn Leu Ser Asp Gln Gln Val Lys Ile Trp
            35                  40                  45
```

Phe Gln Asn Arg Arg Met Lys Lys Arg Val Val Ala Phe Ser Arg
 50                  55                  60

Pro Gly Leu Pro Val Glu Tyr Leu Gln Val Pro Ser Pro Ser Met Gly
 65                  70                  75                  80

Arg Asp Ile Lys Val Gln Phe Gln Ser Gly Gly Ala Asn Ser Pro Ala
                 85                  90                  95

Leu Tyr Leu Leu Asp Gly Leu Arg Ala Gln Asp Asp Phe Ser Gly Trp
            100                 105                 110

Asp Ile Asn Thr Pro Ala Phe Glu Trp Tyr Asp Gln Ser Gly Leu Ser
        115                 120                 125

Val Val Met Pro Val Gly Gly Gln Ser Ser Phe Tyr Ser Asp Trp Tyr
130                 135                 140

Gln Pro Ala Cys Gly Lys Ala Gly Cys Gln Thr Tyr Lys Trp Glu Thr
145                 150                 155                 160

Phe Leu Thr Ser Glu Leu Pro Gly Trp Leu Gln Ala Asn Arg His Val
                165                 170                 175

Lys Pro Thr Gly Ser Ala Val Val Gly Leu Ser Met Ala Ala Ser Ser
            180                 185                 190

Ala Leu Thr Leu Ala Ile Tyr His Pro Gln Gln Phe Val Tyr Ala Gly
        195                 200                 205

Ala Met Ser Gly Leu Leu Asp Pro Ser Gln Ala Met Gly Pro Thr Leu
210                 215                 220

Ile Gly Leu Ala Met Gly Asp Ala Gly Gly Tyr Lys Ala Ser Asp Met
225                 230                 235                 240

Trp Gly Pro Lys Glu Asp Pro Ala Trp Gln Arg Asn Asp Pro Leu Leu
                245                 250                 255

Asn Val Gly Lys Leu Ile Ala Asn Asn Thr Arg Val Trp Val Tyr Cys
            260                 265                 270

Gly Asn Gly Lys Pro Ser Asp Leu Gly Gly Asn Asn Leu Pro Ala Lys
        275                 280                 285

Phe Leu Glu Gly Phe Val Arg Thr Ser Asn Ile Lys Phe Gln Asp Ala
290                 295                 300

Tyr Asn Ala Gly Gly Gly His Asn Gly Val Phe Asp Phe Pro Asp Ser
305                 310                 315                 320

Gly Thr His Ser Trp Glu Tyr Trp Gly Ala Gln Leu Asn Ala Met Lys
                325                 330                 335

Pro Asp Leu Gln Arg Ala Leu Gly Ala Thr Pro Asn Thr Gly Pro Ala
            340                 345                 350

Pro Gln Gly Ala
        355

<210> SEQ ID NO 75
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uaacagucua cagccauggu cg                                              22

<210> SEQ ID NO 76
<211> LENGTH: 22
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 76
tcaacatcag tctgataagc ta                                           22

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
tagcttatca gactgatgtt ga                                           22

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
cgaccatggc tgtagactgt ta                                           22

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
gtggtgaaag cctatgatca t                                            21

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 80

His His His His His His
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Glu Asn Leu Tyr Phe Gln Ser
1               5

<210> SEQ ID NO 82
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 82
cggaggacag tcctccg                                                      17

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Glu Gly Arg
1

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Asp Asp Asp Lys
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Val Pro Arg Gly
1               5

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1, 2, 3, or 4 "Gly
      Gly Gly Gly Ser" repeating units, wherein some positions may
      not be present

<400> SEQUENCE: 86

Gly Gly Gly Gly Ser Gly Gly Gly Ser Gly Gly Gly Gly Ser Gly
1               5                   10                  15

Gly Gly Gly Ser
            20

<210> SEQ ID NO 87
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 6 or 8 residues,
      wherein some positions may not be present

<400> SEQUENCE: 87

Gly Gly Gly Gly Gly Gly Gly Gly
1               5

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 "Glu Ala Ala
      Ala Lys" repeating units, wherein some positions may not be
      present

<400> SEQUENCE: 88

Glu Ala Ala Ala Lys Glu Ala Ala Ala Lys Glu Ala Ala Ala Lys
1               5                   10                  15

<210> SEQ ID NO 89
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Pro Ala Pro Ala Pro
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Glu Ala Ala Ala Lys Glu Ala Ala Ala Lys Ala
```

<210> SEQ ID NO 92
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(34)
<223> OTHER INFORMATION: This sequence may encompass 10-34 residues,
      wherein some positions may not be present

<400> SEQUENCE: 92

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val Ser Gln Thr Ser Lys Leu Thr Arg Ala Glu Thr Val Phe Pro Asp
1               5                   10                  15

Val

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Leu Gly Leu Trp Ala Cys
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Val Leu Ala Glu Ala
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 96

Glu Asp Val Val Cys Cys Ser Met Ser Tyr
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Ile Glu Gly Arg Gly Ser
1               5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Arg His Arg Gln Pro Arg Gly Trp Glu
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Gly Asn Arg Val Arg Arg Ser Val Gly
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Arg Arg Arg Arg Arg Arg Arg Arg
1               5

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Leu Gly
1

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102
```

-continued

```
Asp Tyr Lys Asp Asp Asp Lys
1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Glu Gln Lys Leu Ile Ser Glu Glu Asp Leu
1               5                   10

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

His His His His His His Gly Ser
1               5

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Leu Asn Asp Ile Phe Glu Ala Gln Lys Ile Glu Trp His Glu
1               5                   10                  15

<210> SEQ ID NO 106
<211> LENGTH: 338
<212> TYPE: PRT
<213> ORGANISM: Mycobacterium tuberculosis

<400> SEQUENCE: 106

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
                20                  25                  30

Gly Ala Val Gly Gly Thr Ala Thr Ala Gly Ala Phe Ser Arg Pro Gly
            35                  40                  45

Leu Pro Val Glu Tyr Leu Gln Val Pro Ser Pro Ser Met Gly Arg Asp
        50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160
```

Thr Gly Ser Ala Val Val Gly Leu Ser Met Ala Ala Ser Ser Ala Leu
            165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
            195                 200                 205

Leu Ala Met Gly Asp Ala Gly Gly Tyr Lys Ala Ser Asp Met Trp Gly
            210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
            245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
            275                 280                 285

Ala Gly Gly His Asn Gly Val Phe Asp Phe Pro Asp Ser Gly Thr
            290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
            325                 330                 335

Gly Ala

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Arg Lys Lys Arg Lys Pro Tyr Thr Lys Gln Gln
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Trp Phe Gln Asn Arg Arg Met Lys Lys Lys Arg Val Val
1               5                   10

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Arg Lys Lys Arg Lys Pro Tyr Ser Lys Leu Gln Leu Ala Glu Leu
1               5                   10                  15

```
<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Phe Gln Asn Arg Arg Met Lys Lys Arg Leu Leu
1               5                   10

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ser His His His His His His
1               5

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Arg Lys Lys Arg Lys Pro Tyr Thr Lys Gln Gln Ile Ala Glu
1               5                   10                  15

<210> SEQ ID NO 113
<211> LENGTH: 264
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(264)

<400> SEQUENCE: 113 atg gcc cat cac cac cac cat cac agc gct gca gaa aat ctg tac ttt      48
Met Ala His His His His His His Ser Ala Ala Glu Asn Leu Tyr Phe
1               5                   10                  15 cag agc cgt aag aag cgt aaa ccg tat tcc aaa ctg caa ctg gcg gag      96
Gln Ser Arg Lys Lys Arg Lys Pro Tyr Ser Lys Leu Gln Leu Ala Glu
                20                  25                  30 ttg gaa ggt gag ttc ctg gtt aac gaa ttc att acc cgt cag cgc cgt     144
Leu Glu Gly Glu Phe Leu Val Asn Glu Phe Ile Thr Arg Gln Arg Arg
            35                  40                  45 cgc gag ctg agc gat cgc ctg aac ctg tct gac caa caa gtg aaa atc     192
Arg Glu Leu Ser Asp Arg Leu Asn Leu Ser Asp Gln Gln Val Lys Ile
        50                  55                  60 tgg ttt cag aat cgt cgt atg aag aaa aag cgc ctg ctg acc gcg ttg     240
Trp Phe Gln Asn Arg Arg Met Lys Lys Arg Leu Leu Thr Ala Leu
65                  70                  75                  80 gac tgg agc tgg ctg cag acg gag                                     264
Asp Trp Ser Trp Leu Gln Thr Glu
                85

<210> SEQ ID NO 114
<211> LENGTH: 88
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Ala His His His His His His Ser Ala Ala Glu Asn Leu Tyr Phe
1               5                   10                  15

Gln Ser Arg Lys Lys Arg Lys Pro Tyr Ser Lys Leu Gln Leu Ala Glu
            20                  25                  30

Leu Glu Gly Glu Phe Leu Val Asn Glu Phe Ile Thr Arg Gln Arg Arg
        35                  40                  45

Arg Glu Leu Ser Asp Arg Leu Asn Leu Ser Asp Gln Gln Val Lys Ile
    50                  55                  60

Trp Phe Gln Asn Arg Arg Met Lys Lys Lys Arg Leu Leu Thr Ala Leu
65                  70                  75                  80

Asp Trp Ser Trp Leu Gln Thr Glu
                85

<210> SEQ ID NO 115
<211> LENGTH: 264
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(264)

<400> SEQUENCE: 115 atg gct cat cac cac cat cac cac agc gca gcg gag aac ttg tat ttt      48
Met Ala His His His His His His Ser Ala Ala Glu Asn Leu Tyr Phe
1               5                   10                  15 caa gcc cgt aag aaa cgt aaa ccg tac acc aag cag caa att gcg gag      96
Gln Ala Arg Lys Lys Arg Lys Pro Tyr Thr Lys Gln Gln Ile Ala Glu
            20                  25                  30 ctg gag aat gaa ttc ctg gtc aat gaa ttc atc aac cgt cag aag cgc     144
Leu Glu Asn Glu Phe Leu Val Asn Glu Phe Ile Asn Arg Gln Lys Arg
        35                  40                  45 aaa gaa ctg agc aat cgc ctg aac ctg tcc gac cag caa gtg aaa atc     192
Lys Glu Leu Ser Asn Arg Leu Asn Leu Ser Asp Gln Gln Val Lys Ile
    50                  55                  60 tgg ttt caa aac cgt cgc atg aag aag aaa cgt gtt gtt acg gcg ctg     240
Trp Phe Gln Asn Arg Arg Met Lys Lys Lys Arg Val Val Thr Ala Leu
65                  70                  75                  80 gat tgg agc tgg ctg cag acc gag                                     264
Asp Trp Ser Trp Leu Gln Thr Glu
                85

<210> SEQ ID NO 116
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Ala His His His His His His Ser Ala Ala Glu Asn Leu Tyr Phe
1               5                   10                  15

Gln Ala Arg Lys Lys Arg Lys Pro Tyr Thr Lys Gln Gln Ile Ala Glu
            20                  25                  30
```

-continued

```
Leu Glu Asn Glu Phe Leu Val Asn Glu Phe Ile Asn Arg Gln Lys Arg
         35                  40                  45
Lys Glu Leu Ser Asn Arg Leu Asn Leu Ser Asp Gln Gln Val Lys Ile
     50                  55                  60
Trp Phe Gln Asn Arg Arg Met Lys Lys Arg Val Val Thr Ala Leu
 65              70                  75                  80
Asp Trp Ser Trp Leu Gln Thr Glu
                 85

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Val Lys Arg
 1
```

UNITED STATES PATENT AND TRADEMARK OFFICE
CERTIFICATE OF CORRECTION

PATENT NO. : 10,301,629 B2
APPLICATION NO. : 14/897450
DATED : May 28, 2019
INVENTOR(S) : Bruce H. Littman et al.

Page 1 of 1

It is certified that error appears in the above-identified patent and that said Letters Patent is hereby corrected as shown below:

In the Specification

At Column 59, Lines 22-24, should read:
SEQ ID No. 22:
ARKKRKPYTKQQIAELENEFLVNEFINRQKRKELSNRLNLSDQQVKIWFQNRRM
KKKRVVTALDWSWLQTE At Column 96, Lines 34-37, should read:
SEQ ID No. 65:
ARKKRKPYTKQQIAELENEFLVNEFINRQKRKELSNRLNLSDQQVKIWFQNRRM
KKKRVVQSGLSWMPVGGQSS Signed and Sealed this
Twenty-second Day of June, 2021

Drew Hirshfeld
*Performing the Functions and Duties of the
Under Secretary of Commerce for Intellectual Property and
Director of the United States Patent and Trademark Office*